(12) United States Patent
Sim et al.

(10) Patent No.: US 10,566,545 B2
(45) Date of Patent: Feb. 18, 2020

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin-si, Gyeonggi-do (KR)

(72) Inventors: Munki Sim, Yongin-si (KR); Junha Park, Yongin-si (KR); Hyoyoung Lee, Yongin-si (KR); Eunjae Jeong, Yongin-si (KR); Youngkook Kim, Yongin-si (KR); Seokhwan Hwang, Yongin-si (KR)

(73) Assignee: SAMSUNG DISPLAY CO., LTD., Yongin-si, Gyeonggi-Do (KR)

( * ) Notice: Subject to any disclaimer, the term of this patent is extended or adjusted under 35 U.S.C. 154(b) by 192 days.

(21) Appl. No.: 15/684,582

(22) Filed: Aug. 23, 2017

(65) Prior Publication Data

US 2018/0097186 A1 Apr. 5, 2018

(30) Foreign Application Priority Data

Sep. 30, 2016 (KR) .................. 10-2016-0127147

(51) Int. Cl.
*H01L 51/00* (2006.01)
*C07D 495/04* (2006.01)
(Continued)

(52) U.S. Cl.
CPC ........ *H01L 51/0071* (2013.01); *C07D 495/04* (2013.01); *C07F 9/6561* (2013.01);
(Continued)

(58) Field of Classification Search
None
See application file for complete search history.

(56) References Cited

U.S. PATENT DOCUMENTS 4,143,142 A * 3/1979 Adhikary ............. C07D 471/04
514/287
4,863,930 A * 9/1989 Adhikary ............. A61K 31/425
514/287
(Continued)

FOREIGN PATENT DOCUMENTS

JP 10017860 1/1998
JP 11087067 3/1999
(Continued)

OTHER PUBLICATIONS

European Search report dated Jan. 8, 2018 in corresponding European Patent Application No. 17188566.8 (13 pages).
(Continued)

*Primary Examiner* — Robert S Loewe
(74) *Attorney, Agent, or Firm* — F.Chau & Associates, LLC

(57) ABSTRACT

A condensed cyclic compound and an organic light-emitting device including the same are provided. The organic light-emitting device includes a first electrode, a second electrode, and an organic layer disposed between the first electrode and the second electrode. The organic layer includes the condensed cyclic compound represented by Formula 1:

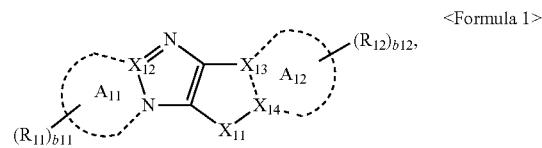

in Formula 1, $A_{11}$ is a $C_1$-$C_{60}$ heterocyclic group, $A_{12}$ is a $C_5$-$C_{60}$ carbocyclic group or a $C_1$-$C_{60}$ heterocyclic group, $X_{11}$ is O or S, $X_{12}$ is C, $X_{13}$ is selected from N, C, and
(Continued)

$C(R_{13})$, $X_{14}$ is selected from N, C, and $C(R_{14})$, and $X_{13}$ and $X_{14}$ are linked via a single bond or a double bond.

20 Claims, 2 Drawing Sheets

(51) Int. Cl.
 *C07F 9/6561* (2006.01)
 *H01L 51/50* (2006.01)
(52) U.S. Cl.
 CPC ...... *H01L 51/0067* (2013.01); *H01L 51/0072* (2013.01); *H01L 51/5012* (2013.01); *H01L 51/5016* (2013.01); *H01L 51/5072* (2013.01)

(56) References Cited

U.S. PATENT DOCUMENTS

| | | | |
|---|---|---|---|
| 5,645,948 A | 7/1997 | Shi et al. | |
| 2011/0284799 A1 | 11/2011 | Stoessel et al. | |
| 2015/0105556 A1 | 4/2015 | Li et al. | |
| 2015/0303381 A1* | 10/2015 | Kang | H01L 51/0072 257/40 |
| 2017/0141325 A1 | 5/2017 | Lee et al. | |

FOREIGN PATENT DOCUMENTS

| | | | | |
|---|---|---|---|---|
| JP | 4060669 | | 3/2008 | |
| KR | 100525408 | | 11/2005 | |
| KR | 1020110128669 | | 11/2011 | |
| KR | 1020120104067 | | 9/2012 | |
| KR | 20150017817 A | * | 2/2015 | ............ C09K 11/06 |
| KR | 1020150075169 | | 7/2015 | |
| KR | 1020160001702 | | 1/2016 | |
| KR | 1020160052398 | | 5/2016 | |
| WO | 84/03838 | | 10/1984 | |
| WO | 2010086089 | | 8/2010 | |

OTHER PUBLICATIONS

Teulade, Jean Claude et al., "Carbon-Nitrogen Bond Formation in Cyclisations by Deoxygenation, Thermolysis, or Photolysis of Phenylimidazo[1,2-a]pyridine Systems: Access to Pyrido[1',2':1,2]imidazo[4,5-b]indoles", J. Chem. Soc. Perkin Trans. I 1989, vol. 11, pp. 1895-1899.

Huang Hui, et al., "Copper-catalyzed synthesis of benzo[b]thiophene-fused imidazopyridines via the cleavage of C—H bond and C—X Bond", Tetrahedron Letters, vol. 57, No. 5, Dec. 23, 2015 (Dec. 23, 2015), pp. 574-577.

Johansson, et al., "Solid-State Amplified Spontaneous Emission in Some Spiro-Type Molecules: A New Concept for the Design of Solid-State Lasing Molecules", Adv. Mater. 1998, 10, No. 14, pp. 1136-1141.

Tao, et al., "Sharp Green Electroluminescence From 1H-pyrazolo[3,4-b]quinolne-based Light Emitting Diodes", Applied Physics Letters, 77, (2000), pp. 1575-1577.

Yan, et al., "Copper-catalyzed domino synthesis of benzo[b]thiophene/imidazo[1,2-a]pyridines by sequential Ullmann-type coupling and intramolecular c(sp2)-H thiolation", Organic Chemistry Frontiers, 2016, 3, pp. 66-70.

Cui, et al., "Benzimidazobenzothiazole-Based Bipolar Hosts to Harvest Nearly All of the Excitons from Blue Delayed Fluorescence and Phosphorescent Organic Light-Emitting Diodes", Angew. Chem. Int. Ed., 2016, 55, pp. 6864-6868.

Tang, et al., "Organic electroluminescent diodes", Applied Physics Letters, 51, (1987), pp. 913-915.

Adachi, et al., "Confinement of charge carriers and molecular excitons within 5nmthick emitter layer in organic electroluminescent devices with a double heterostructure", Applied Physics Letter, 57, (1990), pp. 531-533.

Sakamoto, et al., "Synthesis, Characterization, and Electron-Transport Property of Perfluorinated Phenylene Dendrimers", J. Am. Chem. Soc., 2000, 122, pp. 1832-1833.

Yamaguchi, et al., "Diphenylamino-Substituted 2,5-Diarylsiloles for Single-Layer Organic Electroluminescent Devices", Chemistry Letters 2001, pp. 98-99.

* cited by examiner

CONDENSED CYCLIC COMPOUND AND ORGANIC LIGHT-EMITTING DEVICE INCLUDING THE SAME

CROSS-REFERENCE TO RELATED APPLICATION

This application claims the benefit under 35 U.S.C. § 119 of Korean Patent Application No. 10-2016-0127147, filed on Sep. 30, 2016, in the Korean Intellectual Property Office, the disclosure of which is incorporated by reference herein in its entirety.

TECHNICAL FIELD

Exemplary embodiments of the present disclosure relate to a condensed cyclic compound and an organic light-emitting device including the same.

DISCUSSION OF RELATED ART

Organic light-emitting devices are self-emission devices that produce full-color images and have wide viewing angles, high contrast ratios, short response times, and excellent characteristics in terms of brightness, driving voltage, and response speed.

An example of organic light-emitting devices may include a first electrode disposed on a substrate, and a hole transport region, an emission layer, an electron transport region, and a second electrode sequentially disposed on the first electrode. Holes provided from the first electrode may move toward the emission layer through the hole transport region, electrons provided from the second electrode may move toward the emission layer through the electron transport region, and when holes and electrons meet in the emission layer, they may recombine to produce excitons. These excitons transition from an excited state to a ground state, thereby generating light.

SUMMARY

Exemplary embodiments of the present disclosure provide a condensed cyclic compound and an organic light-emitting device including the same.

According to an exemplary embodiment of the present disclosure, a condensed cyclic compound is represented by Formula 1:

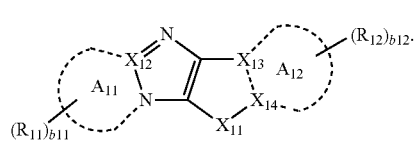

<Formula 1>

In Formula 1, $A_{11}$ may be a $C_1$-$C_{60}$ heterocyclic group, $A_{12}$ may be a $C_5$-$C_{60}$ carbocyclic group or a $C_1$-$C_{60}$ heterocyclic group, $X_{11}$ may be O or S, $X_{12}$ may be C, $X_{13}$ may be selected from N, C, and $C(R_{13})$, $X_{14}$ may be selected from N, C, and $C(R_{14})$, $X_{13}$ and $X_{14}$ may be linked via a single bond or a double bond, and $R_{11}$ and $R_{12}$ may each independently be selected from a group represented by *-$(L_{11})_{a11}$-$(Ar_{11})c_{11}$, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and at least one of $R_{11}$ and $R_{12}$ is a group represented by *-$(L_{11})_{a11}$-$(Ar_{11})c_{11}$, b11 and b12 may each independently be selected from 1, 2, 3, 4, 5, 6, 7, 8, 9, and 10.

$L_{11}$ may be selected from a single bond, a substituted or unsubstituted $C_5$-$C_{60}$ carbocyclic group, and a substituted or unsubstituted $C_1$-$C_{60}$ heterocyclic group, a11 may be selected from 0, 1, 2, 3, and 4, $Ar_{11}$ may be selected from —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), c11 may be selected from 1, 2, 3, 4, 5, and 6, $R_{13}$, $R_{14}$, and $Q_1$ to $Q_3$ may each independently be selected from hydrogen, deuterium, —F, —Cl, —Br, —I, a hydroxyl group, a cyano group, a nitro group, an amidino group, a hydrazine group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, and a substituted or unsubstituted monovalent non-aromatic condensed heteropolycyclic group, and . indicates a binding site to a neighboring atom.

According to an exemplary embodiment of the present disclosure, an organic light-emitting device includes: a first electrode; a second electrode; an organic layer disposed between the first electrode and the second electrode, the organic layer including an emission layer, in which the organic layer may include the condensed cyclic compound represented by Formula 1.

According to an exemplary embodiment of the present disclosure, an organic light-emitting device includes: a first electrode; a second electrode; an organic layer disposed between the first electrode and the second electrode, the organic layer including a condensed cyclic compound, in which the condensed cyclic compound may include a multicyclic structure including a bicyclic structure of two fused 5-member heterocyclic rings, one of the two fused 5-member heterocyclic rings may include two N atoms as hetero atoms, other one of the two fused 5-member heterocyclic rings may include O atom or S atom as a hetero atom, the multicyclic structure may include tricyclic structure, tetracyclic structure or higher order polycyclic structure, at least one hydrogen of the multicyclic structure may be substituted with F, Cl, Br, I, a hydroxyl group, a cyano group, a nitro group, an amidino group, a hydrazino group, a hydrazono group, or an organic substituent group, and the organic substituent group may include at least one C atom and optionally includes at least one of N, S, O, P, Si, B, F, Cl, Br, and I atoms.

BRIEF DESCRIPTION OF THE DRAWINGS

These and/or other aspects of the present disclosure will become apparent and more readily appreciated from the following description of the embodiments, taken in conjunction with the accompanying drawings in which.

Figure 1:
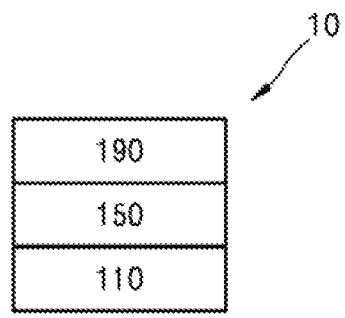
FIG. 1 is a schematic cross-sectional view of an organic light-emitting device according to an exemplary embodiment of the present disclosure.

Since the drawings in FIGS. 1-4 are intended for illustrative purposes, the elements in the drawings are not necessarily drawn to scale. For example, some of the elements may be enlarged or exaggerated for clarity purpose.

DETAILED DESCRIPTION OF THE EMBODIMENTS

The present disclosure will now be described more fully with reference to the accompanying drawings, in which exemplary embodiments of the present disclosure are shown. The disclosure may, however, be embodied in many different forms and should not be construed as being limited to the specific exemplary embodiments set forth herein; rather, these exemplary embodiments of the present disclosure are provided so that this disclosure will be thorough and complete, and will fully convey the concept of the disclosure to those skilled in the art.

Hereinafter, exemplary embodiments of the present disclosure are described in detail by referring to the accompanying drawings, and in the drawings, like reference numerals denote like elements, and a redundant explanation thereof will not be provided.

As used herein, the singular forms "a," "an," and "the" are intended to include the plural forms as well, unless the context clearly indicates otherwise.

It will be understood that the terms "comprises" and/or "comprising" used herein specify the presence of stated features and/or components, but do not preclude the presence or addition of one or more other features and/or components.

It will be further understood that when a layer, region, or component is referred to as being "on" or "onto" another layer, region, or component, it may be directly or indirectly formed on or onto the other layer, region, or component. That is, for example, intervening layers, regions, or components may be present.

A condensed cyclic compound according to an exemplary embodiment of the present disclosure is represented by Formula 1 below:

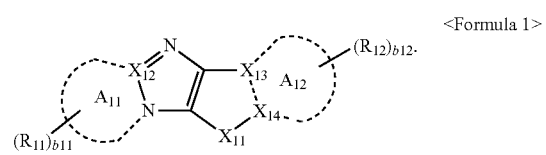

<Formula 1>

$A_{11}$ in Formula 1 may be a $C_1$-$C_{60}$ heterocyclic group.

In an exemplary embodiment of the present disclosure, $A_{11}$ in Formula 1 may be selected from a pyrrolidine group, a dihydropyrrole group, an isoindoline group, a piperidine group, a tetrahydropyridine group, a dihydropyridine group, a tetrahydroisoquinoline group, a dihydroisoquinoline group, an imidazole group, a pyrazole group, a thiazole group, an isothiazole group, an oxazole group, an isoxazole group, a pyridine group, a pyrazine group, a pyrimidine group, a quinoline group, an isoquinoline group, a benzoquinoline group, a quinoxaline group, a quinazoline group, a benzimidazole group, a benzothiazole group, a benzisothiazole group, a benzoxazole group, a benzisoxazole group, a triazine group, a tetrazine group, and an azacarbazole group, but the present disclosure is not limited thereto.

In an exemplary embodiment of the present disclosure, $A_{11}$ in Formula 1 may be selected from a piperidine group, a tetrahydropyridine group, a dihydropyridine group, a tetrahydroisoquinoline group, a dihydroisoquinoline group, a pyridine group, a pyrazine group, a pyrimidine group, a quinoline group, an isoquinoline group, a benzoquinoline group, a quinoxaline group, a quinazoline group, a triazine group, a tetrazine group, and an azacarbazole group, but the present disclosure is not limited thereto.

In an exemplary embodiment of the present disclosure, $A_{11}$ in Formula 1 may be selected from a piperidine group, a tetrahydropyridine group, a dihydropyridine group, a pyridine group, a pyrazine group, a pyrimidine group, a triazine group, and a tetrazine group, but the present disclosure is not limited thereto.

$A_{12}$ in Formula 1 may be a $C_5$-$C_{60}$ carbocyclic group or a $C_1$-$C_{60}$ heterocyclic group.

In an exemplary embodiment of the present disclosure, $A_{12}$ in Formula 1 may be selected from a pyrrolidine group, a dihydropyrrole group, an isoindoline group, a piperidine group, a tetrahydropyridine group, a dihydropyridine group, a tetrahydroisoquinoline group, a dihydroisoquinoline group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, an azacarbazole group, a benzimidazole group, a benzothiazole group, a benzisothiazole group, a benzoxazole group, a benzisoxazole group, a triazole group, a tetrazole group, a thiadiazol group, an oxadiazole group, a triazine group, a tetrazine group, a benzene group, a naphthalene group, a fluorene group, a spiro-bifluorene group, an indene group, a pyrrole group, a thiophene group, a furan group, a benzofuran group, a benzothiophene group, a dibenzofuran group, and a dibenzothiophene group, but the present disclosure is not limited thereto.

In an exemplary embodiment of the present disclosure, $A_{12}$ in Formula 1 may be selected from a piperidine group, a tetrahydropyridine group, a dihydropyridine group, a tetrahydroisoquinoline group, a dihydroisoquinoline group, a pyridine group, a pyrazine group, a pyrimidine group, a pyridazine group, a quinoline group, an isoquinoline group, a benzoquinoline group, a quinoxaline group, a quinazoline group, a carbazole group, an azacarbazole group, a triazine group, a tetrazine group, a benzene group, a naphthalene group, a fluorene group, a spiro-bifluorene group, an indene group, a benzofuran group, a benzothiophene group, a dibenzofuran group, and a dibenzothiophene group, but the present disclosure is not limited thereto.

In an exemplary embodiment of the present disclosure, $A_{12}$ in Formula 1 may be selected from a piperidine group, a tetrahydropyridine group, a dihydropyridine group, a pyridine group, a pyrazine group, a pyrimidine group, a pyridazine group, a triazine group, a tetrazine group, and a benzene group, but the present disclosure is not limited thereto.

$X_{11}$ in Formula 1 may be O or S.

$X_{12}$ in Formula 1 may be C.

$X_{13}$ in Formula 1 may be selected from N, C, and $C(R_{13})$, wherein $R_{13}$ may be the same as described below. For example, $X_{13}$ in Formula 1 may be C, but the present disclosure is not limited thereto.

$X_{14}$ in Formula 1 may be selected from N, C, and $C(R_{14})$, wherein $R_{14}$ may be the same as described below. For example, $X_{14}$ in Formula 1 may be C, but the present disclosure is not limited thereto.

In an exemplary embodiment of the present disclosure, in Formula 1, $X_{13}$ may be C and $X_{14}$ may be C, but the present disclosure is not limited thereto.

$X_{13}$ and $X_{14}$ in Formula 1 may be linked via a single bond or a double bond.

In an exemplary embodiment of the present disclosure, Formula 1 may include a multicyclic structure, and a bicyclic structure of two fused 5-member heterocyclic rings in the multicyclic structure. One of the two fused 5-member heterocyclic rings may include two N atoms as hetero atoms, and the other one of the two fused 5-member heterocyclic rings may include O atom or S atom as a hetero atom. The multicyclic structure may include tricyclic structure, tetracyclic structure or higher order polycyclic structure.

When $X_{13}$ and $X_{14}$ in Formula 1 is linked via a double bond, the two fused 5-member heterocyclic rings may become two fused 5-member heteroaryl rings. For example, an imidazole heteroaryl ring may be fused with a furan heteroaryl ring or a thiophene heteroaryl ring to form a bicyclic structure as part of the Formula 1.

$R_{11}$ and $R_{12}$ in Formula 1 may each independently be selected from a group represented by *-$(L_{11})_{a11}$-$(Ar_{11})c_{11}$, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and at least one of $R_{11}$ and $R_{12}$ may be a group represented by *-$(L_{11})_{a11}$-$(Ar_{11})c_{11}$.

$Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, and a substituted or unsubstituted monovalent non-aromatic condensed heteropolycyclic group, and $L_{11}$, a11, $Ar_{11}$, and c11 may be the same as described below.

In an exemplary embodiment of the present disclosure, $R_{11}$ and $R_{12}$ in Formula 1 may each independently be selected from:

a group represented by *-$(L_{11})_{a11}$-$(Ar_{11})c_{11}$, hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazoryl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), wherein $Q_1$ to $Q_3$ and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, but the present disclosure is not limited thereto.

In an exemplary embodiment of the present disclosure, $R_{11}$ and $R_{12}$ in Formula 1 may each independently be selected from:

a group represented by *-$(L_{11})_{a11}$-$(Ar_{11})c_{11}$, hydrogen, deuterium, —F, —Cl, —Br, —I, a cyano group, and a $C_1$-$C_{20}$ alkyl group;

a $C_1$-$C_{20}$ alkyl group, substituted with at least one selected from deuterium, —F, —Cl, —Br, —I, and a cyano group;

groups represented by Formulae 5-1 to 5-138; and

—Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), but the present disclosure is not limited thereto:

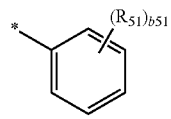

5-1

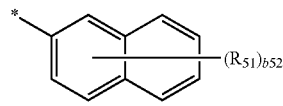

5-2

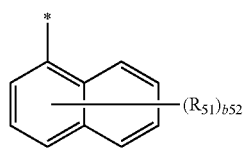

5-3

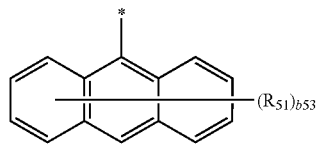

5-4

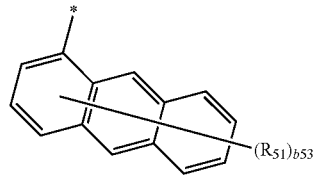

5-5

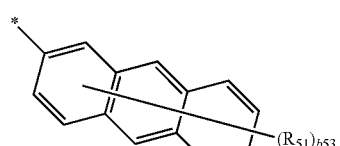

5-6

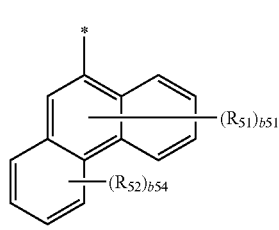

5-7

-continued

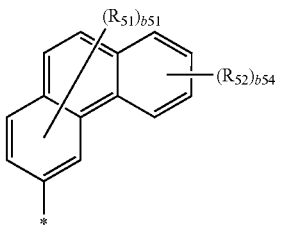

5-8

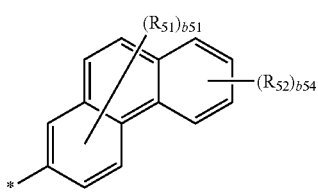

5-9

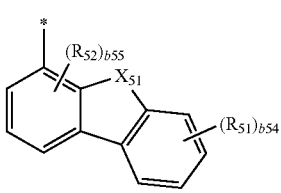

5-10

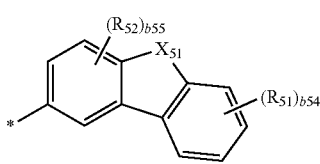

5-11

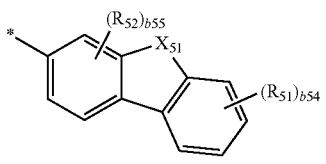

5-12

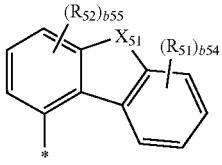

5-13

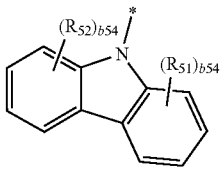

5-14

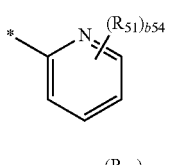

5-15

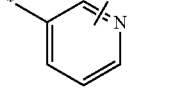

5-16

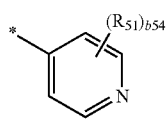 5-17
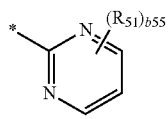 5-18
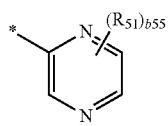 5-19
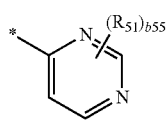 5-20
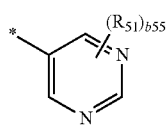 5-21
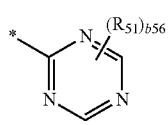 5-22
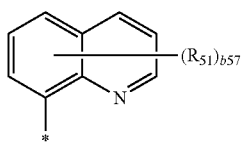 5-23
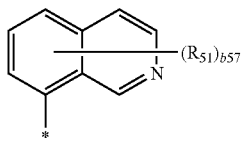 5-24
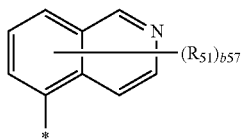 5-25
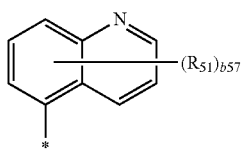 5-26
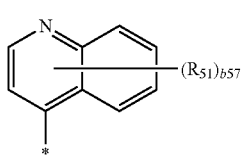 5-27
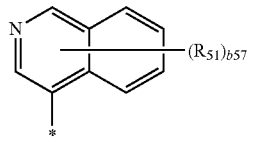 5-28
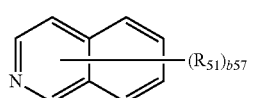 5-29
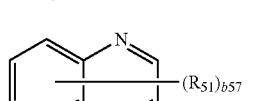 5-30
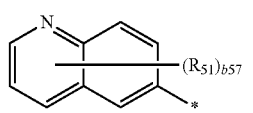 5-31
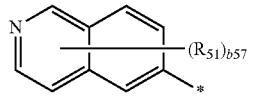 5-32
 5-33
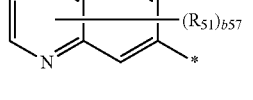 5-34
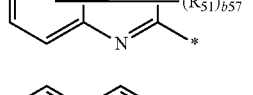 5-35
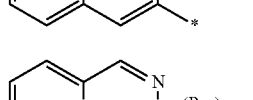 5-36
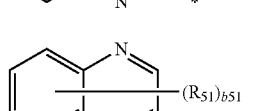 5-37
 5-38
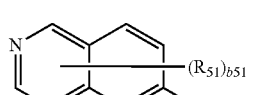 5-39
 5-40

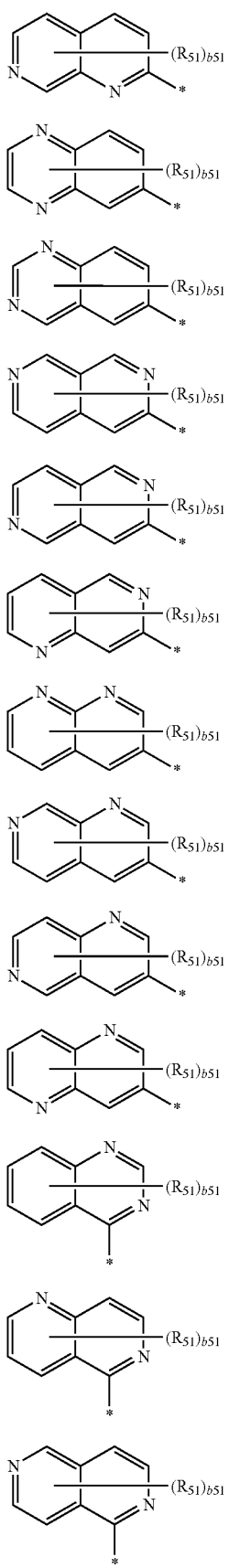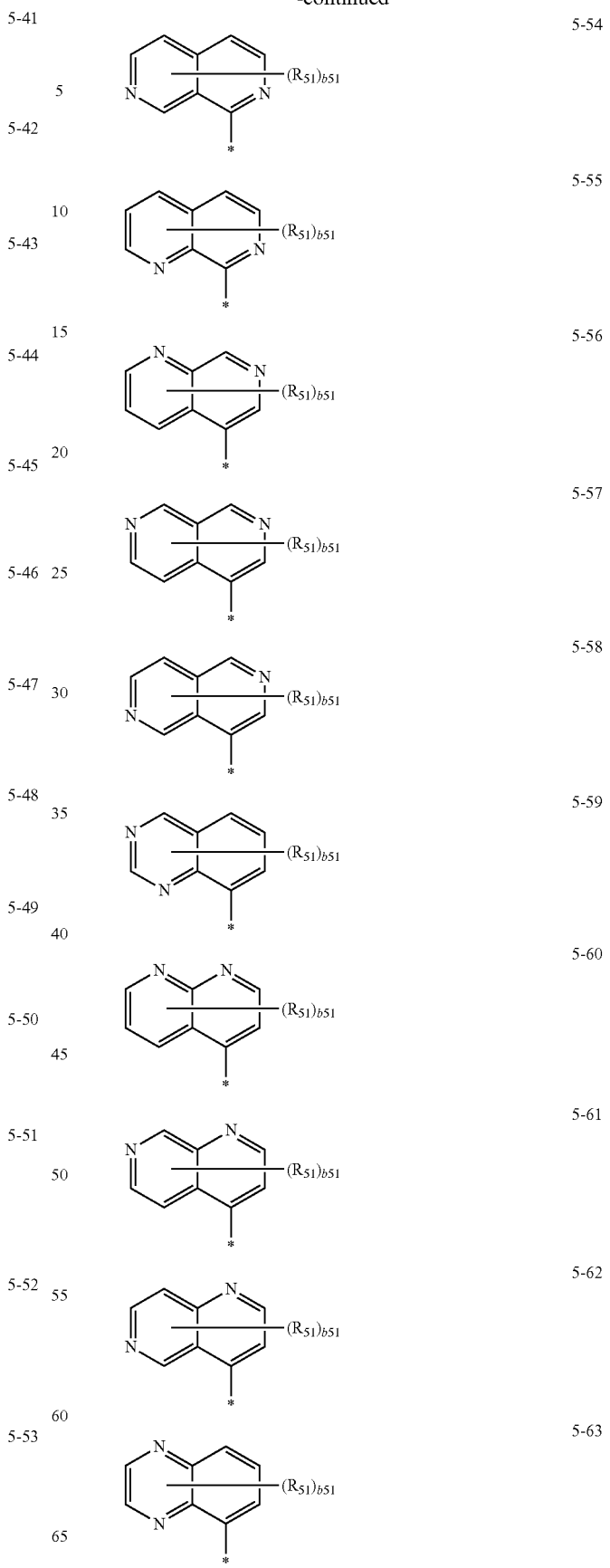

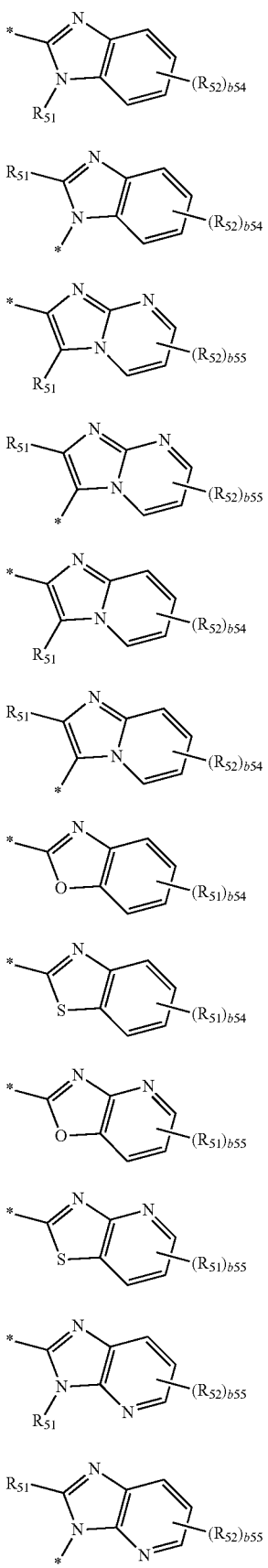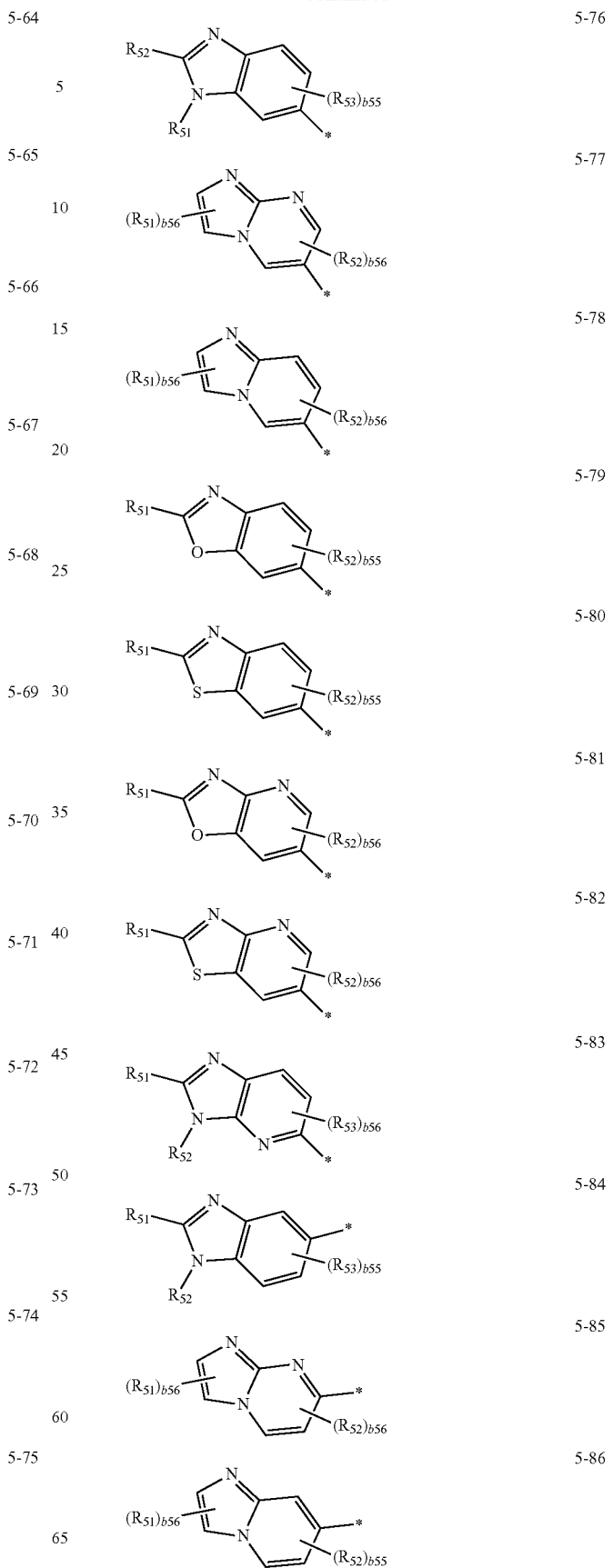

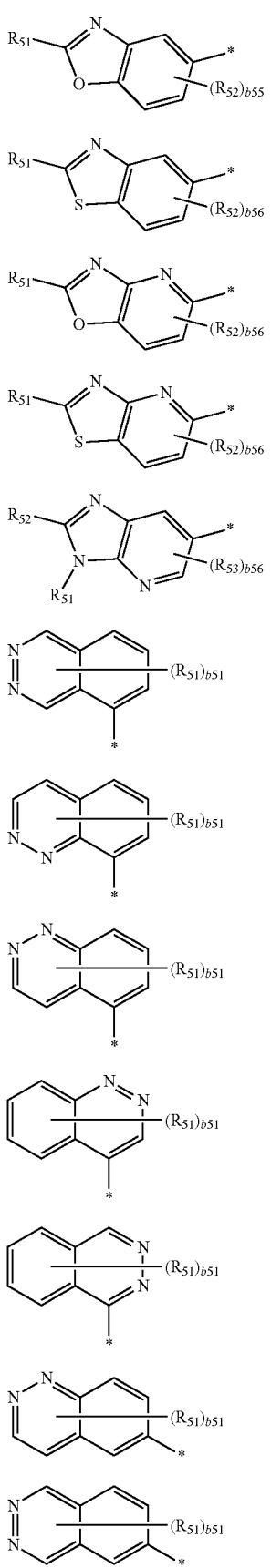
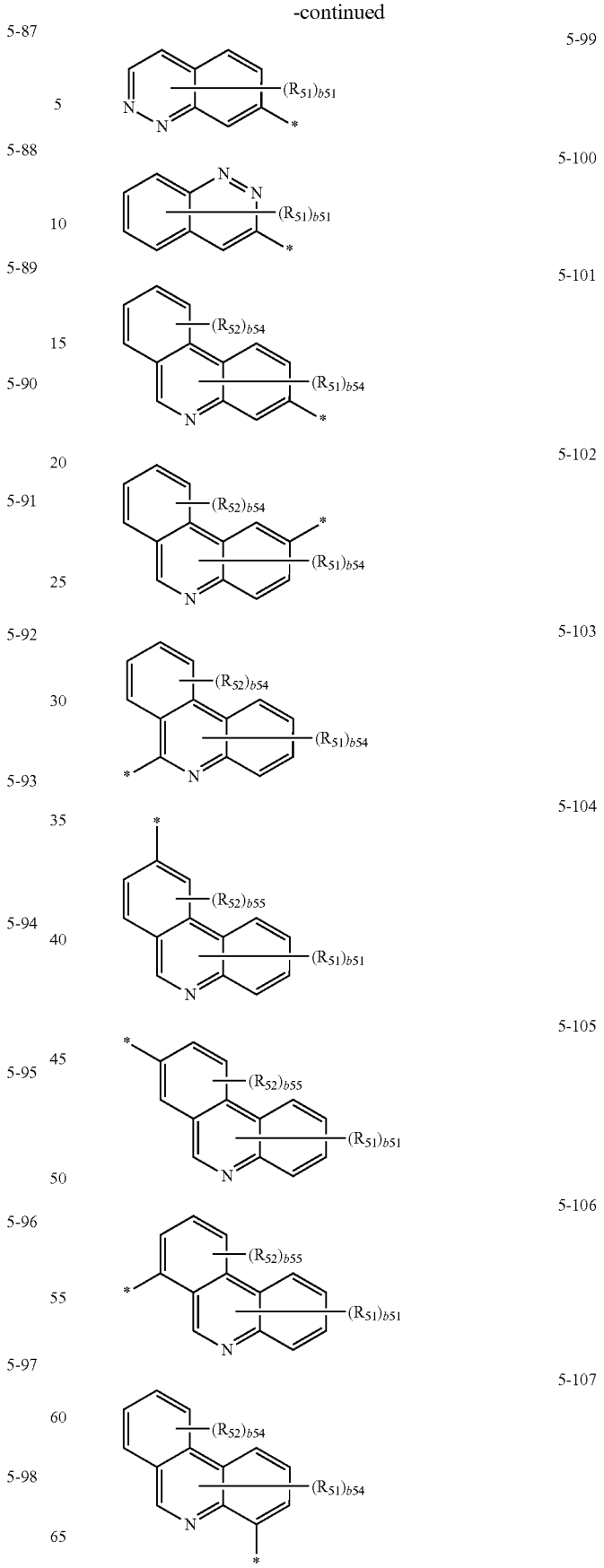

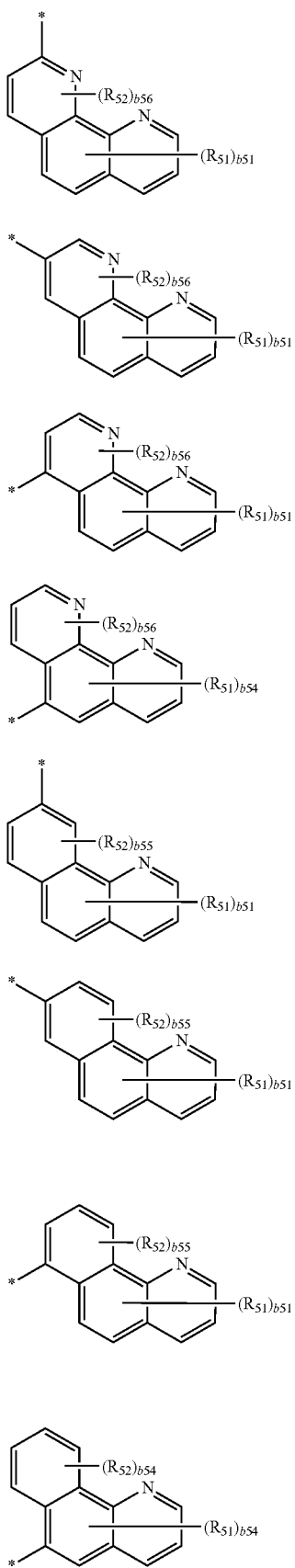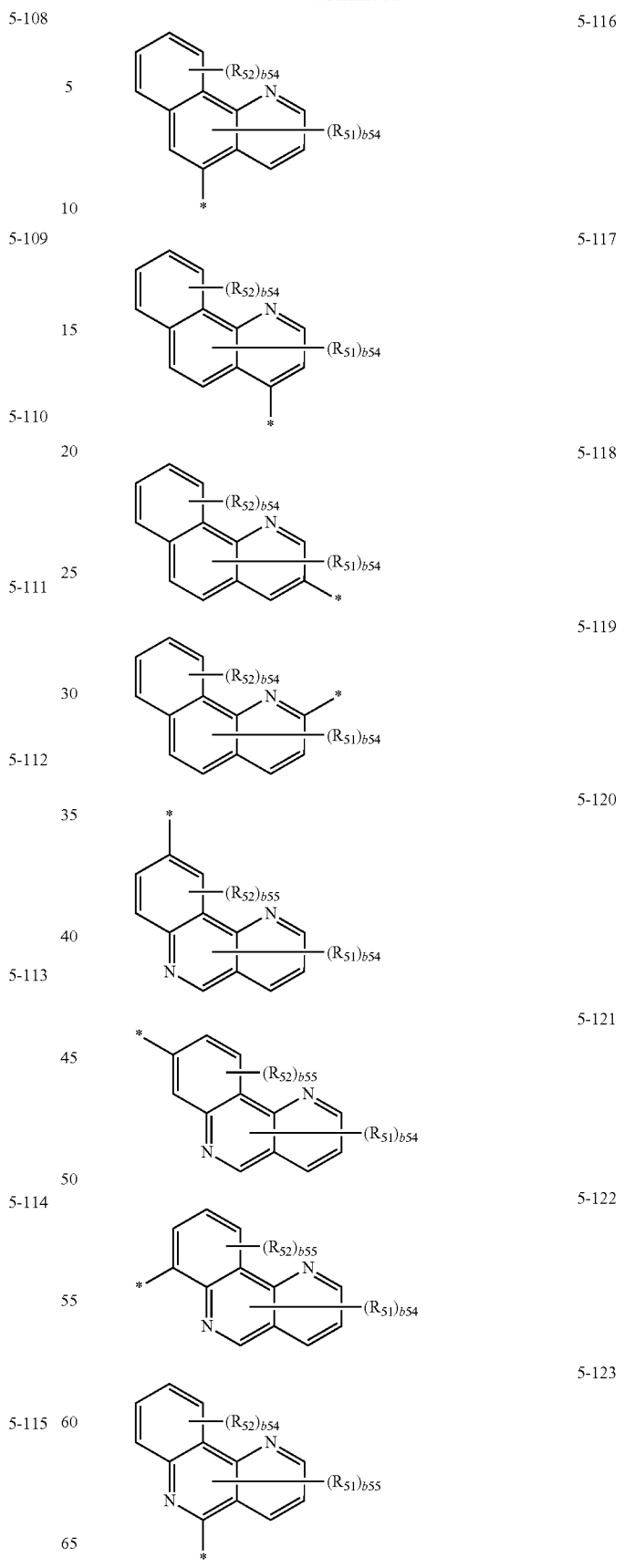

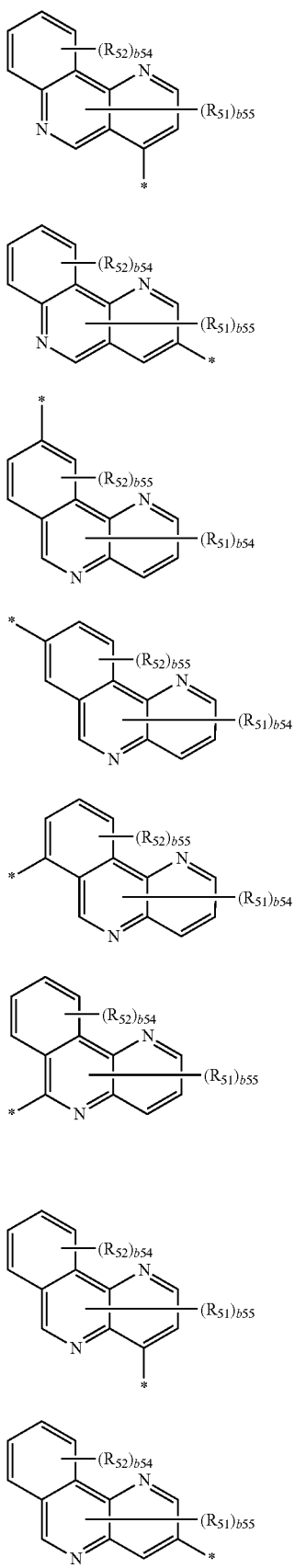
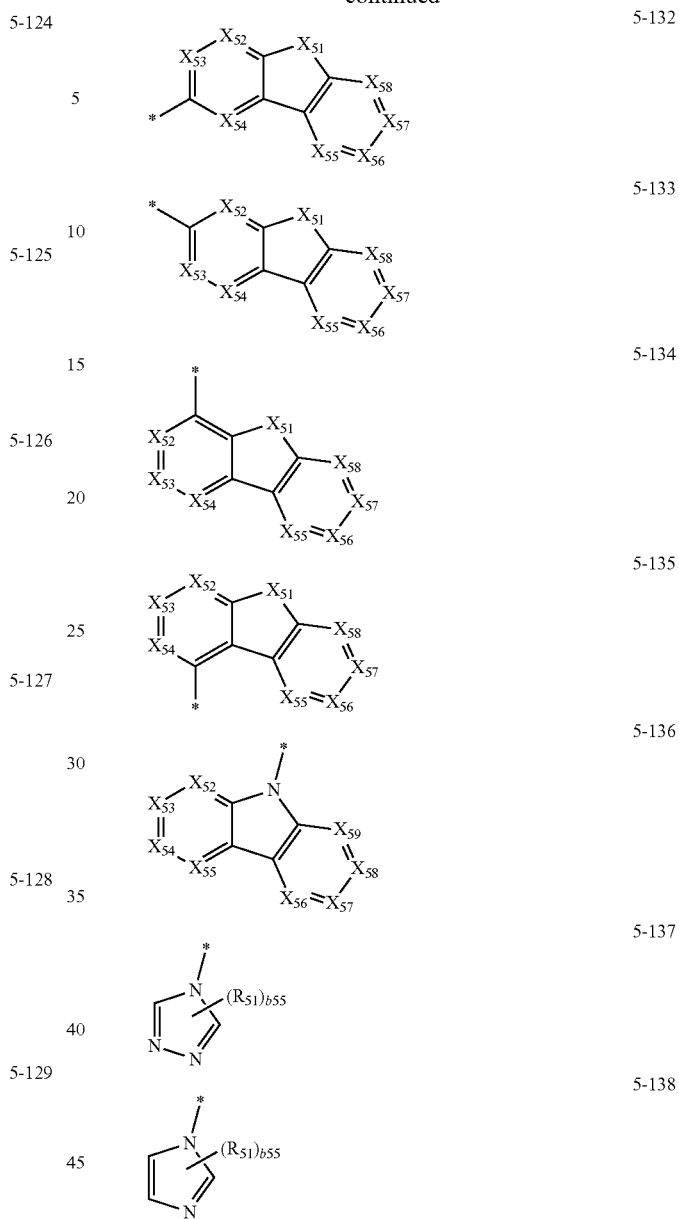

In Formulae 5-1 to 5-138.

$X_{51}$ may be selected from O, S, $N(R_{51})$, and $C(R_{51})(R_{60})$, $X_{52}$ may be N or $C(R_{52})$, $X_{53}$ may be N or $C(R_{53})$, $X_{54}$ may be N or $C(R_{54})$, $X_{55}$ may be N or $C(R_{55})$, $X_{56}$ may be N or $C(R_{56})$, $X_{57}$ may be N or $C(R_{57})$, $X_{58}$ may be N or $C(R_{58})$, and $X_{59}$ may be N or $C(R_{59})$, $R_{51}$ to $R_{60}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si(Q$_{31}$)(Q$_{32}$)(Q$_{33}$), —N(Q$_{31}$)(Q$_{32}$), —B(Q$_{31}$)(Q$_{32}$), —C(=O)(Q$_{31}$), —S(=O)(Q$_{31}$), —S(=O)$_2$(Q$_{31}$), —P(=O)(Q$_{31}$)(Q$_{32}$), and —P(=S)(Q$_{31}$)(Q$_{32}$), Q$_1$ to Q$_3$ and Q$_{31}$ to Q$_{33}$ may each independently be selected from a C$_1$-C$_{60}$ alkyl group, a phenyl group, a biphenyl group, and a terphenyl group, b51 may be selected from 1, 2, 3, 4, and 5, b52 may be selected from 1, 2, 3, 4, 5, 6, and 7, b53 may be selected from 1, 2, 3, 4, 5, 6, 7, 8, and 9, b54 may be selected from 1, 2, 3, and 4, b55 may be selected from 1, 2, and 3, b56 may be 1 or 2, b57 may be selected from 1, 2, 3, 4, 5, and 6, and

* indicates a binding site to a neighboring atom.

In Formulae 5-1 to 5-138. b51 to b57 indicate the number of sites are substituted. When any of b51 to b57 in any of Formulae 5-1 to 5-138 is two or more for any of the corresponding R$_{51}$ and R$_{52}$, two or more of the corresponding R$_{51}$(s) and R$_{52}$(s) may be identical to or different from each other. For example, in Formula 5-128, the b54 for R$_{51}$ in (R$_{51}$)b$_{54}$ may be 3, then 2 or 3 of these 3 R$_{51}$(s) may be identical, or all 3 are different from each other.

In an exemplary embodiment of the present disclosure, R$_{11}$ and R$_{12}$ in Formula 1 may each independently be selected from:

a group represented by *-(L$_{11}$)$_{a11}$-(Ar$_{11}$)c$_{11}$, hydrogen, deuterium, —F, —Cl, —Br, —I, a cyano group, a methyl group, an ethyl group, an n-propyl group, an iso-propyl group, an n-butyl group, an iso-butyl group, a sec-butyl group, and a tert-butyl group;

a methyl group, an ethyl group, an n-propyl group, an iso-propyl group, an n-butyl group, an iso-butyl group, a sec-butyl group, and a tert-butyl group, each substituted with at least one selected from deuterium, —F, —Cl, —Br, —I, and a cyano group; and a phenyl group, a naphthyl group, and a pyridinyl group, but the present disclosure is not limited thereto.

b11 and b12 in Formula 1 indicate the number of R$_{11}$(s) and the number of R$_{12}$(s), respectively. b11 and b12 in Formula 1 may each independently be selected from 1, 2, 3, 4, 5, 6, 7, 8, 9, and 10. When b11 and b12 in Formula 1 are each two or more, two or more R$_{11}$(s) may be identical to or different from each other and two or more R$_{12}$(s) may be identical to or different from each other.

L$_{11}$ in Formula 1 may be selected from a single bond, a substituted or unsubstituted C$_5$-C$_{60}$ carbocyclic group, and a substituted or unsubstituted C$_1$-C$_{60}$ heterocyclic group.

In an exemplary embodiment of the present disclosure, L$_{11}$ in Formula 1 may be selected from:

a single bond, a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a pentacene group, a rubicene group, a coronene group, an ovalene group, a pyrrole group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, a dibenzosilole group, a pyridine group, an imidazole group, a pyrazole group, a thiazole group, an isothiazole group, an oxazole group, an isoxazole group, a thiadiazol group, an oxadiazole group, a pyrazine group, a pyrimidine group, a pyridazine group, a triazine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzothiazole group, a benzisothiazole group, a benzoxazole group, a benzisoxazole group, a triazole group, a tetrazole group, an imidazopyridinyl group, an imidazopyrimidinyl group, and an azacarbazole group; and a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a pentacene group, a rubicene group, a coronene group, an ovalene group, a pyrrole group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, a dibenzosilole group, a pyridine group, an imidazole group, a pyrazole group, a thiazole group, an isothiazole group, an oxazole group, an isoxazole group, a thiadiazol group, an oxadiazole group, a pyrazine group, a pyrimidine group, a pyridazine group, a triazine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzothiazole group, a benzisothiazole group, a benzoxazole group, a benzisoxazole group, a triazole group, a tetrazole group, an imidazopyridinyl group, an imidazopyrimidinyl group, and an azacarbazole group, each substituted with at least one selected from deuterium, —F, —Cl, —Br, —I, a hydroxyl group, a cyano group, a nitro group, an amidino group, a hydrazino group, a hydrazono group, a C$_1$-C$_{20}$ alkyl group, a C$_1$-C$_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzothiazolyl group, a benzisothiazolyl group, a benzoxazolyl group, a benzisoxazolyl group, a triazolyl group, a tetrazolyl group, an imidazopyridinyl group, an imidazopyrimidinyl group, an azacarbazoryl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$), wherein $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, but the present disclosure is not limited thereto.

In an exemplary embodiment of the present disclosure, $L_{11}$ in Formula 1 may be selected from:

a single bond, a benzene group, a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a perylene group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, and a dibenzosilole group; and a benzene group, a naphthalene group, a fluorene group, a spiro-bifluorene group, a benzofluorene group, a dibenzofluorene group, a phenanthrene group, an anthracene group, a fluoranthene group, a triphenylene group, a pyrene group, a chrysene group, a perylene group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, and a dibenzosilole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), and —B($Q_{31}$)($Q_{32}$), wherein $Q_{31}$ to $Q_{33}$ may each independently be selected from a $C_1$-$C_{60}$ alkyl group, a phenyl group, a biphenyl group, and a terphenyl group, but the present disclosure is not limited thereto.

In an exemplary embodiment of the present disclosure, $L_{11}$ in Formula 1 may be selected from groups represented by Formulae 3-1 to 3-41, but the present disclosure is not limited thereto:

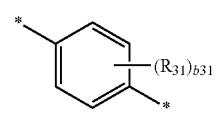
3-1

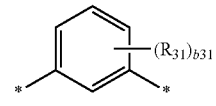
3-2

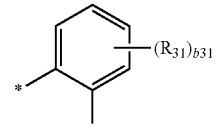
3-3

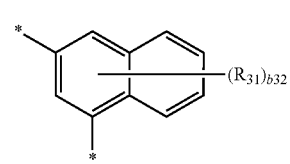
3-4

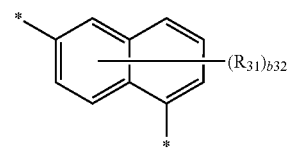
3-5

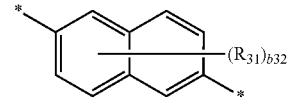
3-6

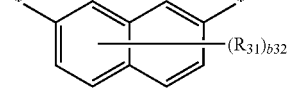
3-7

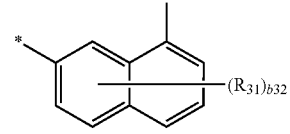
3-8

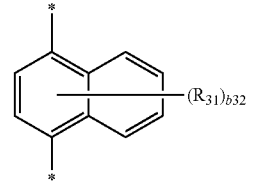
3-9

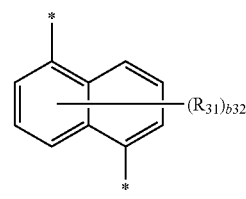
3-10

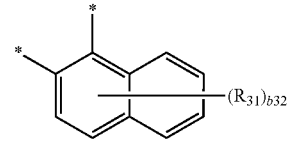
3-11

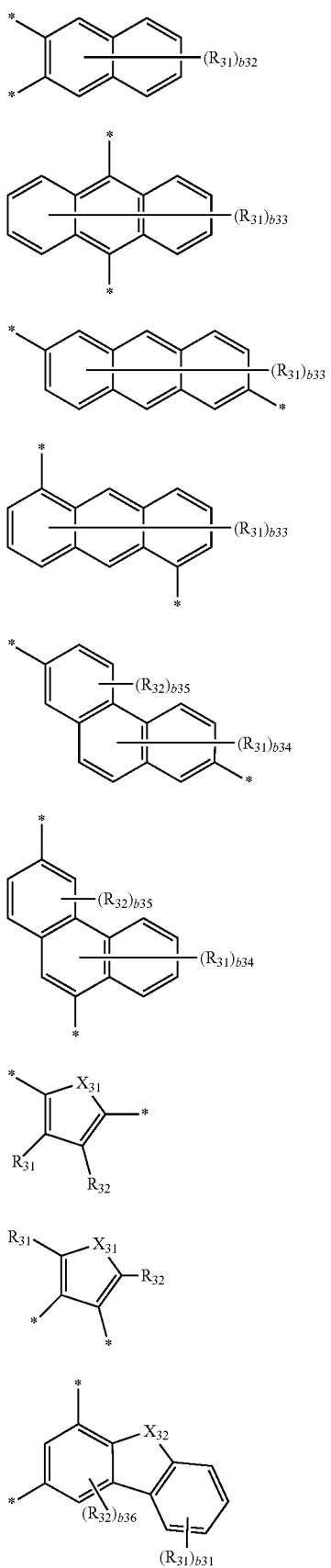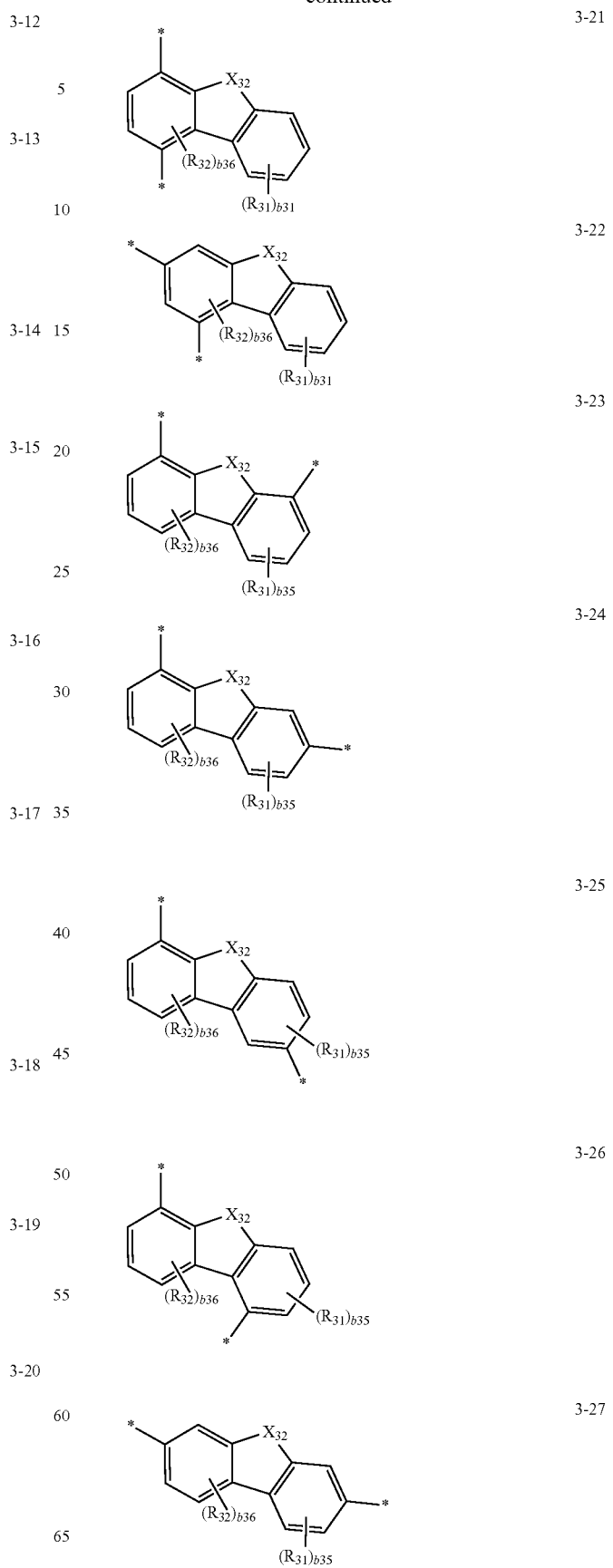

3-28
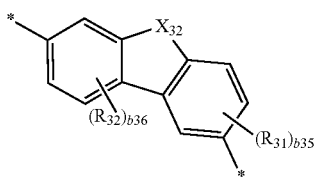
3-29
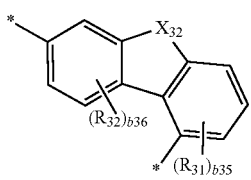
3-30
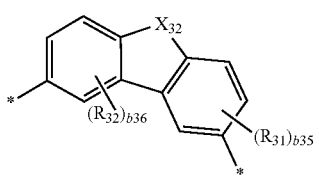
3-31
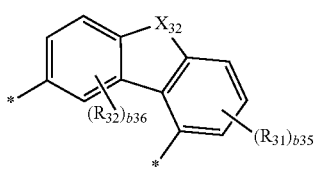
3-32
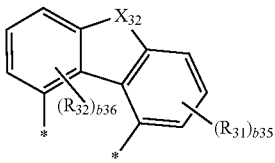
3-33
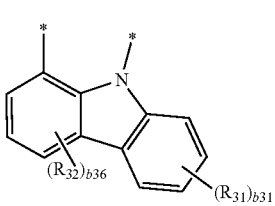
3-34
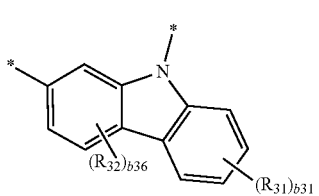
3-35
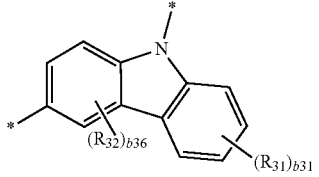
3-36
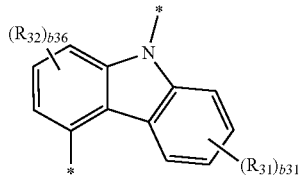
3-37
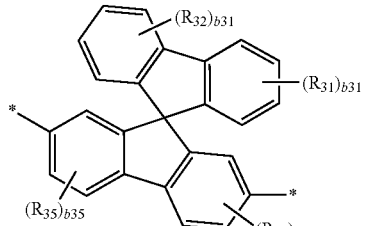
3-38
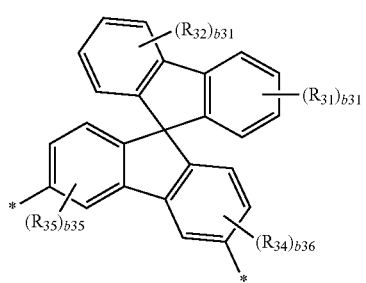
3-39
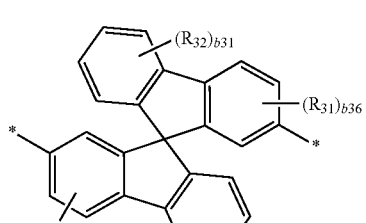
3-40
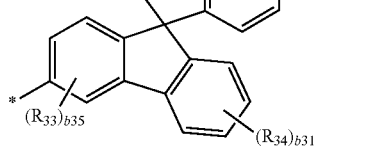
3-41
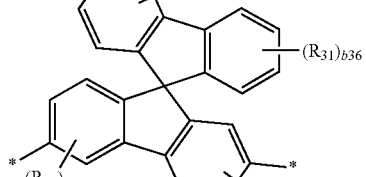
In Formulae 3-1 to 3-41,
$X_{31}$ may be O or S,
$X_{32}$ may be selected from O, S, N($R_{33}$), and C($R_{33}$)($R_{34}$),
$R_{31}$ to $R_{34}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —$Si(Q_{31})(Q_{32})(Q_{33})$, —$N(Q_{31})(Q_{32})$, and —$B(Q_{31})(Q_{32})$, $Q_{31}$ to $Q_{33}$ may each independently be selected from a $C_1$-$C_{60}$ alkyl group, a phenyl group, a biphenyl group, and a terphenyl group, b31 may be selected from 1, 2, 3, and 4,
b32 may be selected from 1, 2, 3, 4, 5, and 6,
b33 may be selected from 1, 2, 3, 4, 5, 6, 7, and 8,
b34 may be selected from 1, 2, 3, 4, and 5,
b35 may be selected from 1, 2, and 3,
b36 may be 1 or 2, and
* and *' each indicates a binding site to a neighboring atom.

a11 in Formula 1 indicates the repeating number of $L_{11}(s)$. a11 in Formula 1 may be selected from 0, 1, 2, 3, and 4. When a11 in Formula 1 is zero, $(L_{11})_{a11}$ may be a single bond. When a11 in Formula 1 is two or more, two or more $L_{11}(s)$ may be identical to or different from each other.

In Formulae 3-1 to 3-41, b31 to b36 indicate the number of sites are substituted. When any of b31 to b36 in any of Formulae 3-1 to 3-41 is two or more for any of the corresponding $R_{31}$ to $R_{34}$, two or more of the corresponding $R_{31}(s)$ to $R_{34}(s)$ may be identical to or different from each other. For example, in Formula 3-40, the b31 for $R_{32}$ in $(R_{32})b_{31}$ may be 3, then 2 or 3 of these 3 $R_{32}(s)$ may be identical, or all 3 are different from each other.

In an exemplary embodiment of the present disclosure, a11 in Formula 1 may be selected from 0, 1, and 2, but the present disclosure is not limited thereto.

$Ar_{11}$ in Formula 1 may be selected from —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_1)(Q_2)$, —$B(Q_1)(Q_2)$, —$C(=O)(Q_1)$, —$S(=O)(Q_1)$, —$S(=O)_2(Q_1)$, —$P(=O)(Q_1)(Q_2)$, and —$P(=S)(Q_1)(Q_2)$, wherein $Q_1$ to $Q_3$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, and a substituted or unsubstituted monovalent non-aromatic condensed heteropolycyclic group.

In an exemplary embodiment of the present disclosure, $Ar_{11}$ in Formula 1 may be selected from:

—F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a thazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), wherein $Q_1$ to $Q_3$ and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group, but the present disclosure is not limited thereto.

In an exemplary embodiment of the present disclosure, $Ar_{11}$ in Formula 1 may be selected from:

—F, —Cl, —Br, —I, a cyano group, and a $C_1$-$C_{20}$ alkyl group;

a $C_1$-$C_{20}$ alkyl group, substituted with at least one selected from deuterium, —F, —Cl, —Br, —I, and a cyano group;

groups represented by Formulae 5-1 to 5-138; and

—Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), wherein $Q_1$ to $Q_3$ may each independently be selected from a $C_1$-$C_{60}$ alkyl group, a phenyl group, a biphenyl group, and a terphenyl group, but the present disclosure is not limited thereto.

In an exemplary embodiment of the present disclosure, $Ar_{11}$ in Formula 1 may be selected from:

—F, —Cl, —Br, —I, a cyano group, a methyl group, an ethyl group, an n-propyl group, an iso-propyl group, an n-butyl group, an iso-butyl group, a sec-butyl group, and a tert-butyl group;

a methyl group, an ethyl group, an n-propyl group, an iso-propyl group, an n-butyl group, an iso-butyl group, a sec-butyl group, and a tert-butyl group, each substituted with at least one selected from deuterium, —F, —Cl, —Br, —I, and a cyano group;

groups represented by Formulae 6-1 to 6-257; and

—S(=O)(Ph), —S(=O)$_2$(Ph), —P(=O)(Ph)$_2$, and —P(=S)(Ph)$_2$, but the present disclosure is not limited thereto:

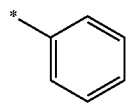

6-1

6-2 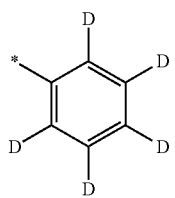
6-3 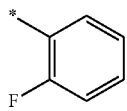
6-4 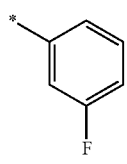
6-5 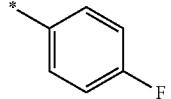
6-6 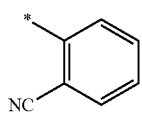
6-7 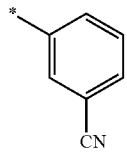
6-8 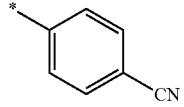
6-9 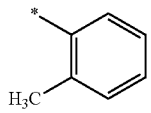
6-10 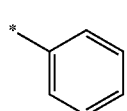
6-11 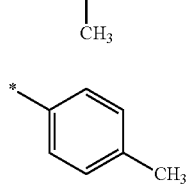
6-12 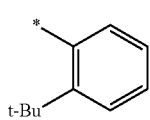

-continued
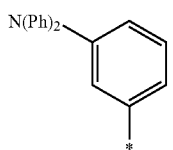
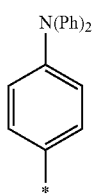
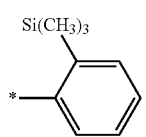
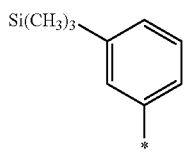
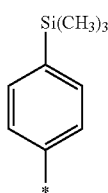
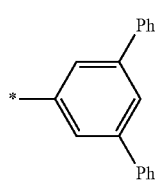
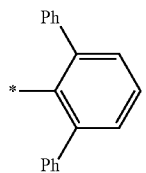
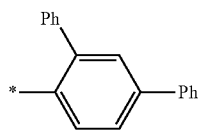
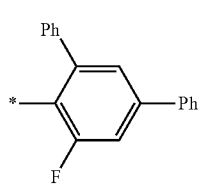
-continued
6-23 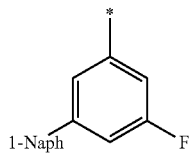
6-24 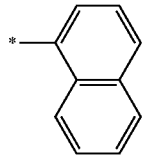
6-25 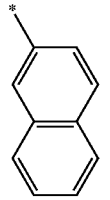
6-26
6-27 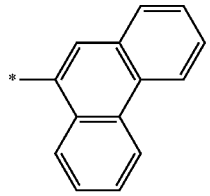
6-28 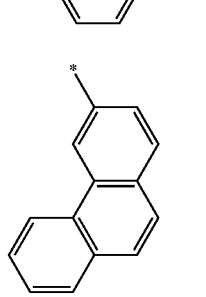
6-29
6-30 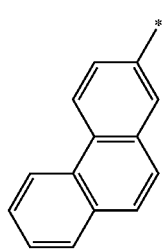
6-31 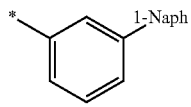
6-32
6-33
6-34
6-35
6-36
6-37
6-38
6-39
6-40 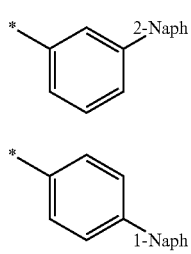

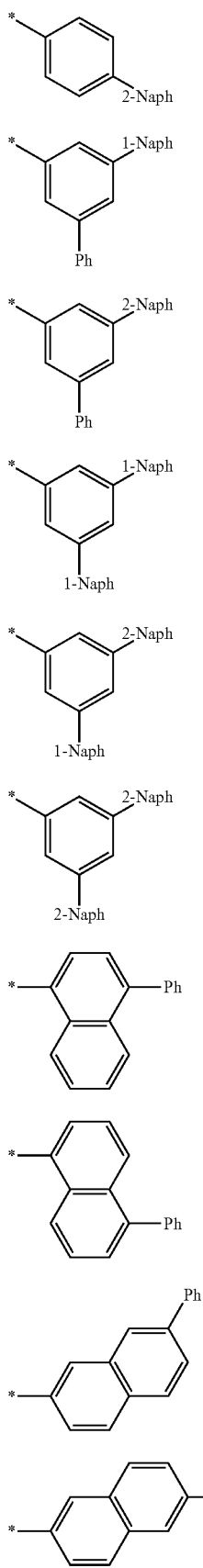
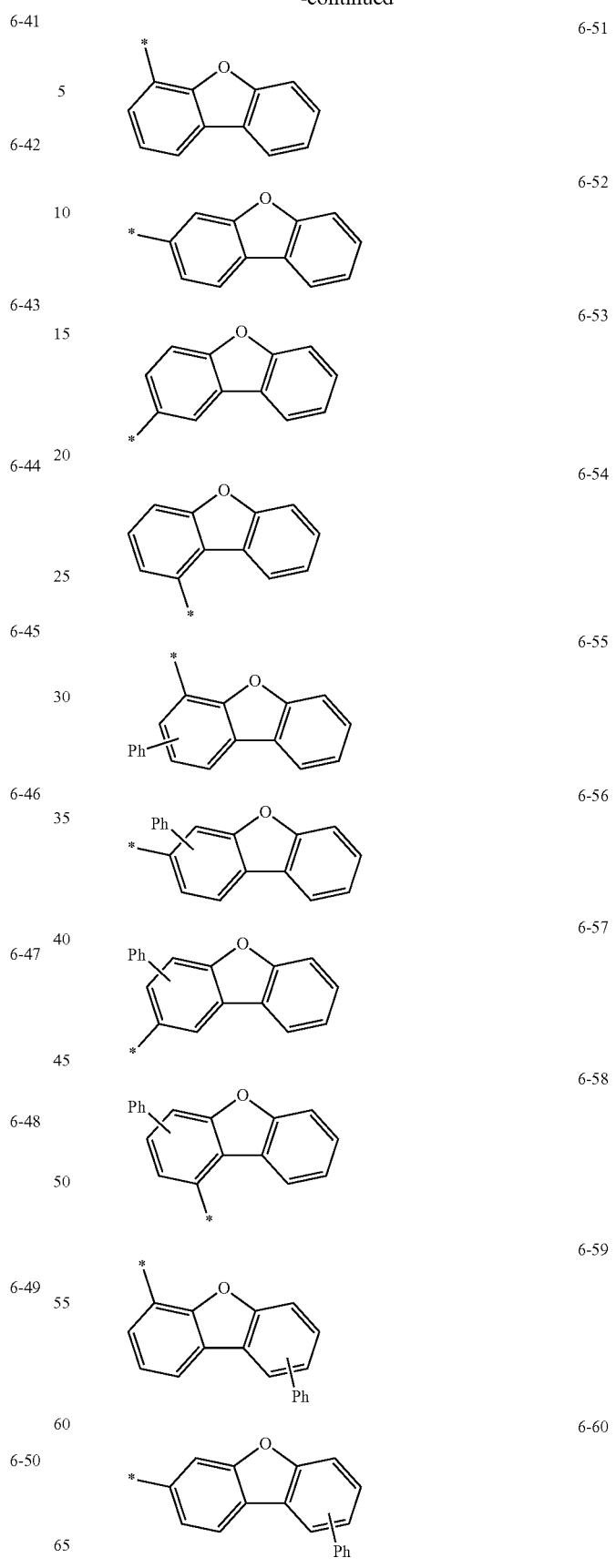

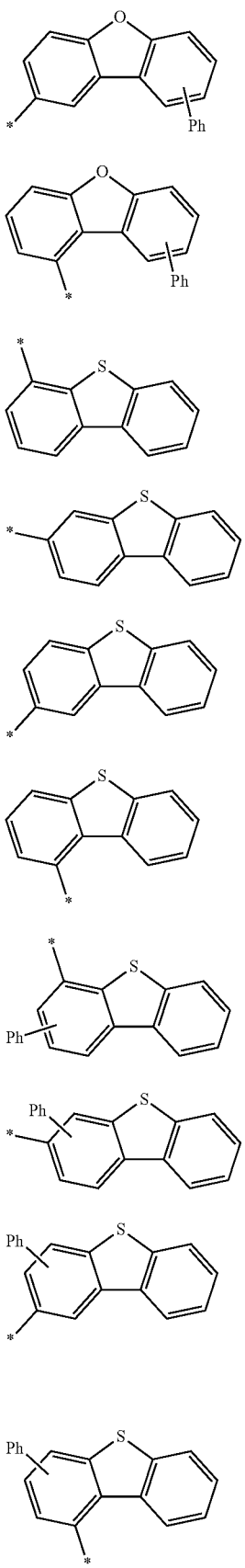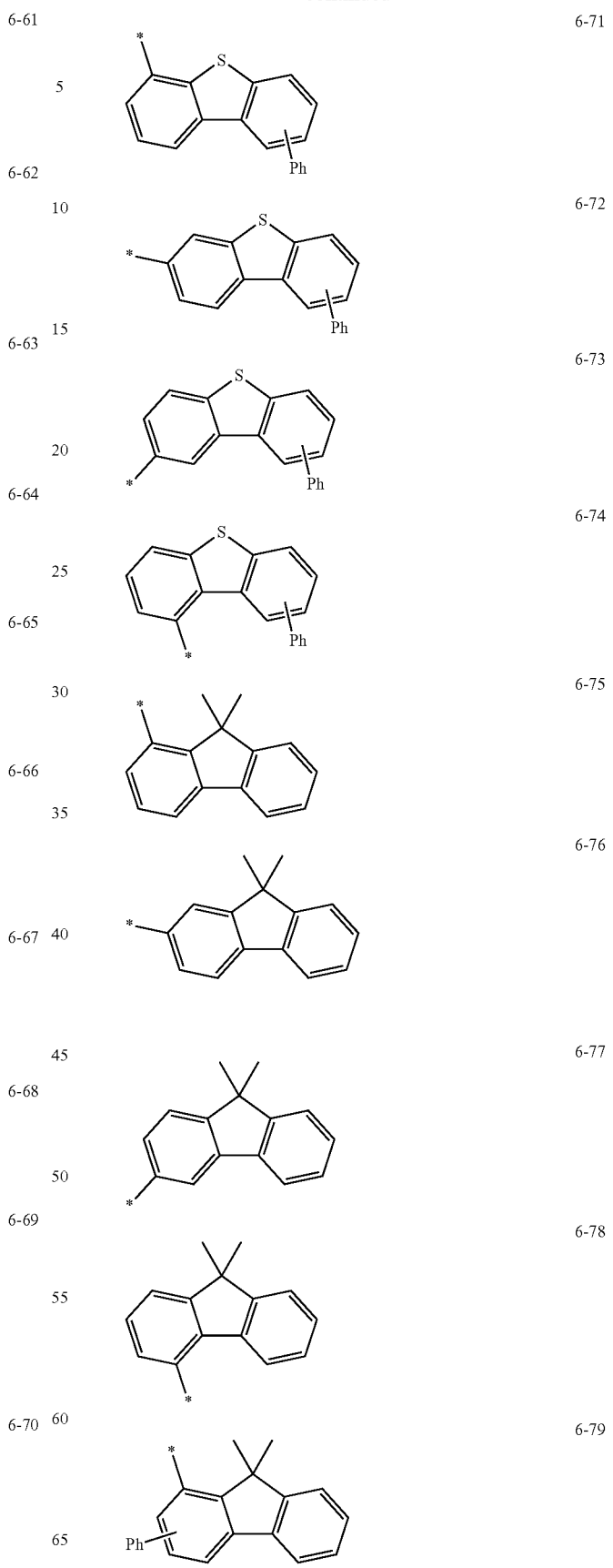

6-80 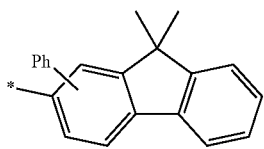
6-81 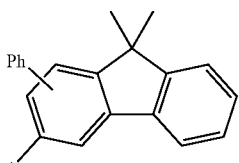
6-82 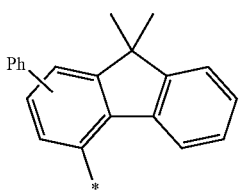
6-83 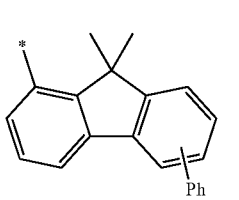
6-84 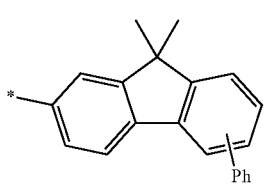
6-85 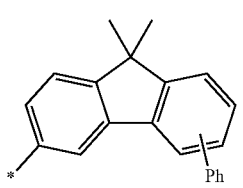
6-86 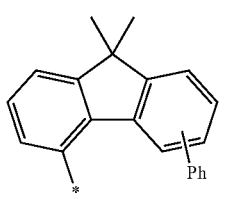
6-87 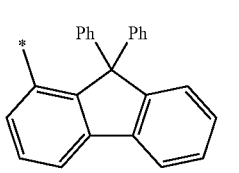
6-88 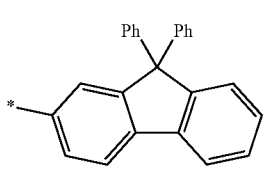
6-89 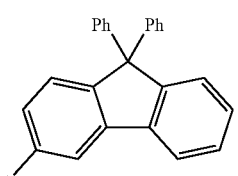
6-90 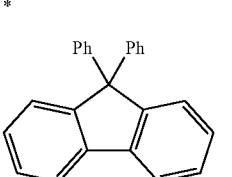
6-91 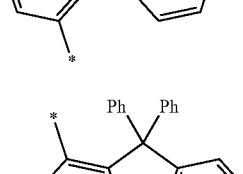
6-92 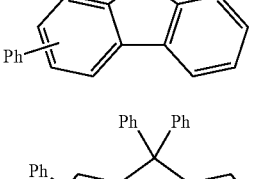
6-93 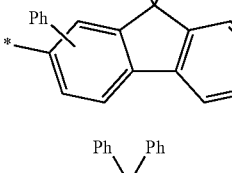
6-94 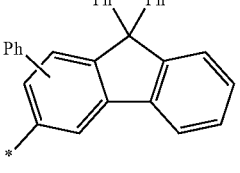
6-95 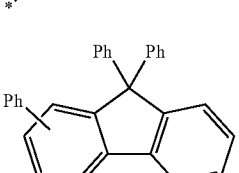
6-96 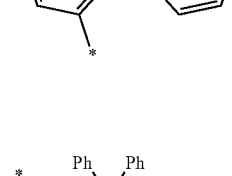

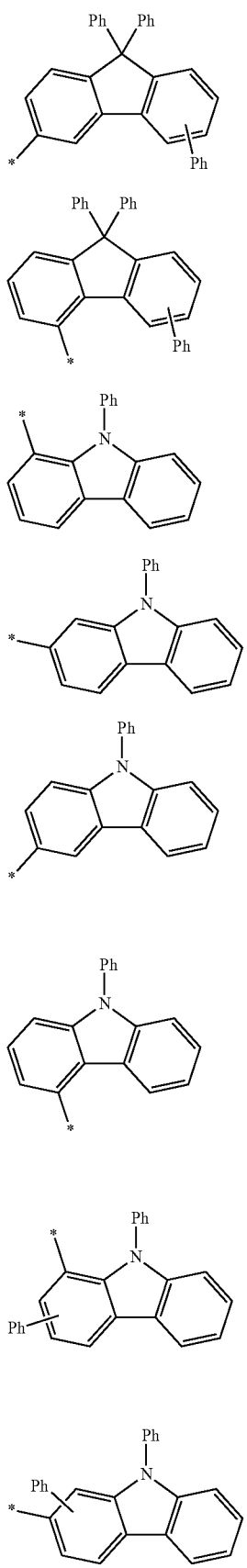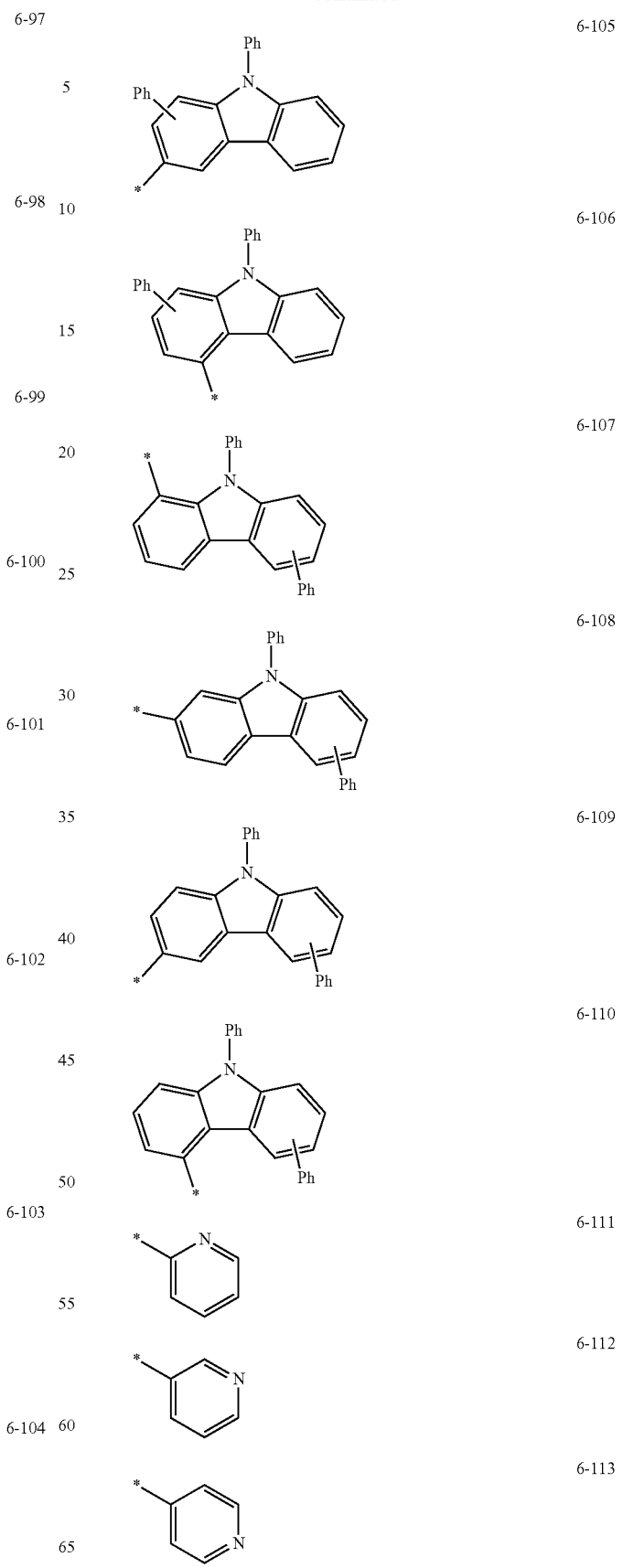

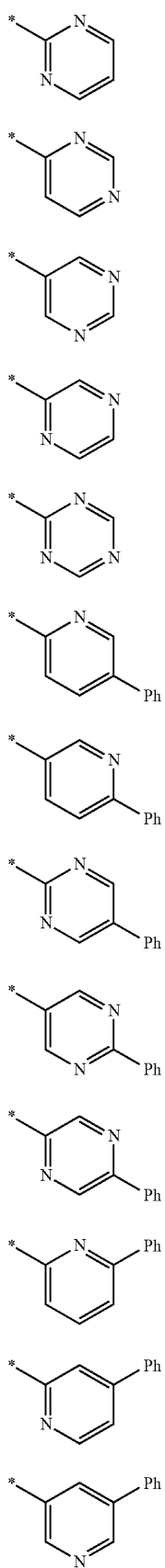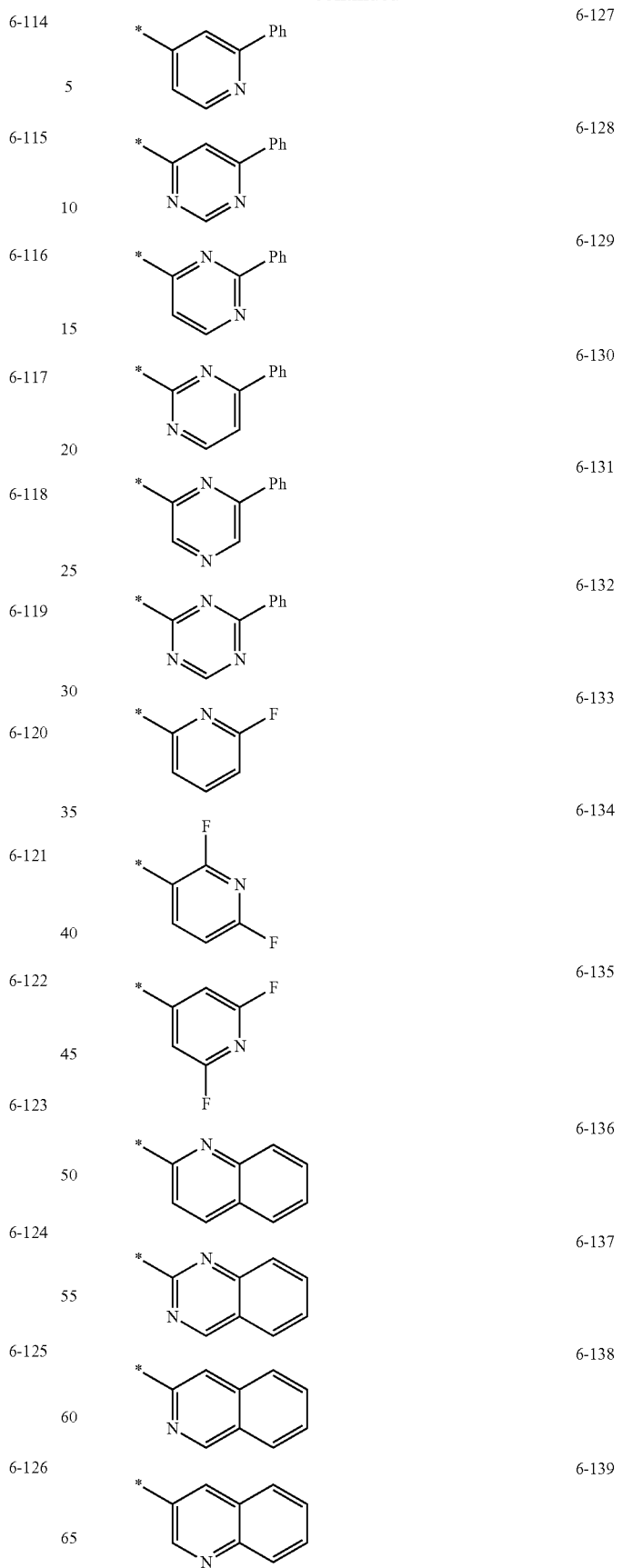

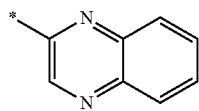
6-140
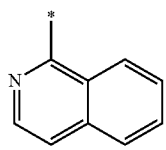
6-141
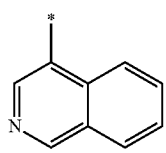
6-142
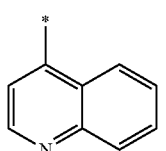
6-143
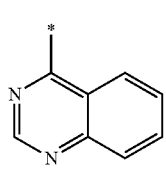
6-144
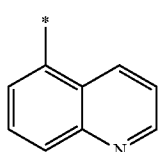
6-145
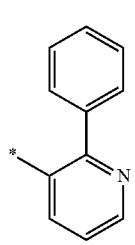
6-146
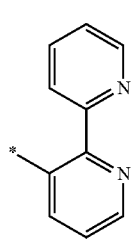
6-147
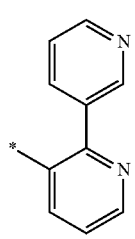
6-148
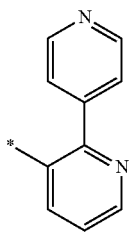
6-149
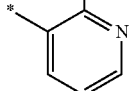
6-150
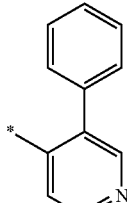
6-151
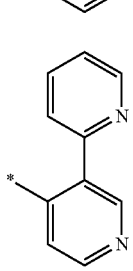
6-152
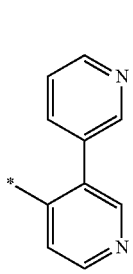
6-153
6-154

6-155 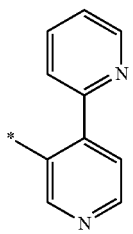
6-156 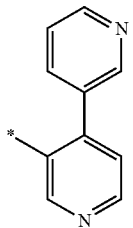
6-157 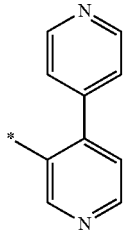
6-158 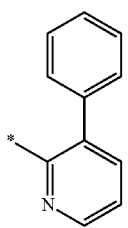
6-159 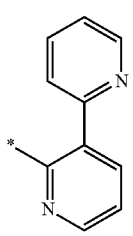
6-160 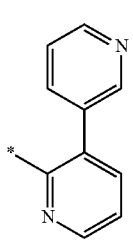
6-161 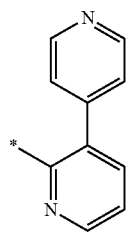
6-162 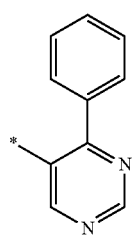
6-163 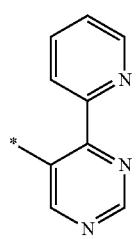
6-164 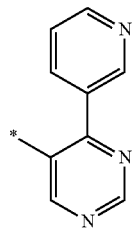
6-165 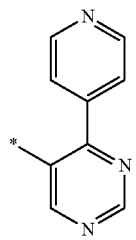
6-166 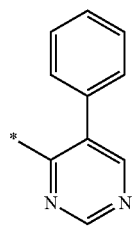

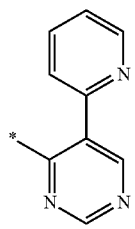
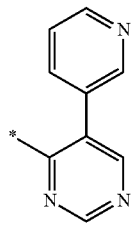
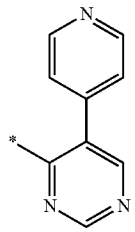
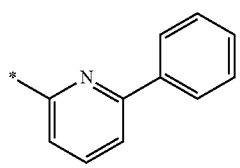
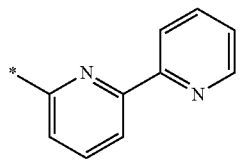
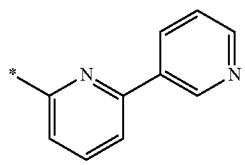
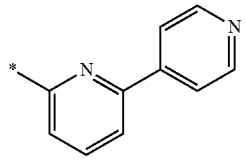

6-167
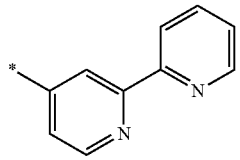
6-168
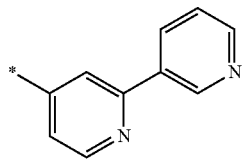
6-169
6-170
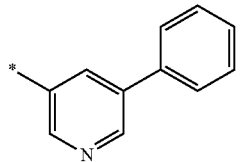
6-171
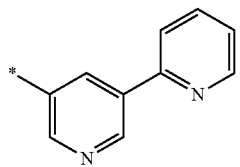
6-172
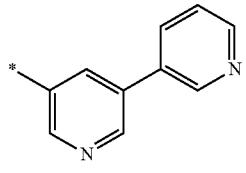
6-173
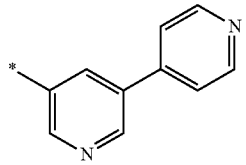
6-174
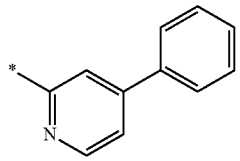
6-175
6-176
6-177
6-178
6-179
6-180
6-181
6-182
6-183
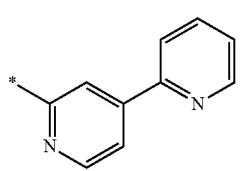

6-184 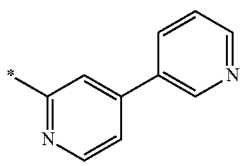
6-185 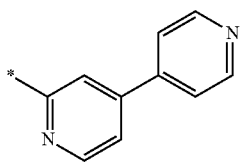
6-186 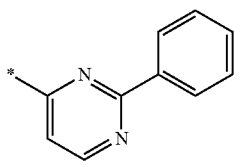
6-187 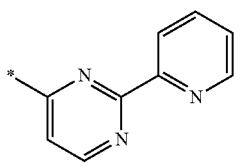
6-188 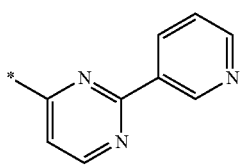
6-189 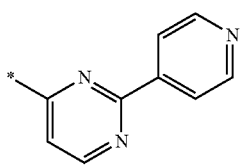
6-190 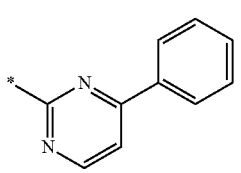
6-191 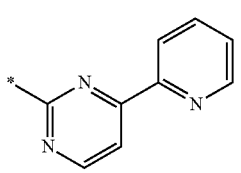
6-192 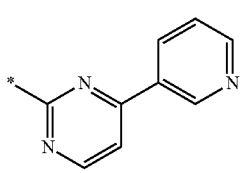
6-193 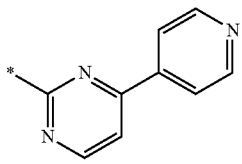
6-194 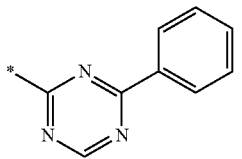
6-195 
6-196 
6-197 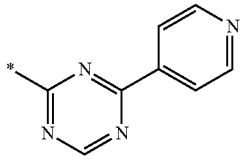
6-198 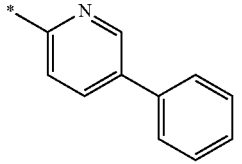
6-199 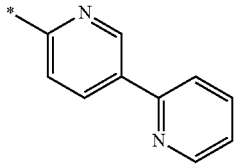
6-200 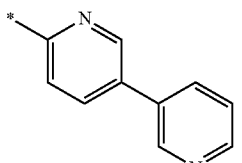
6-201 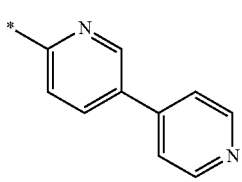

6-202 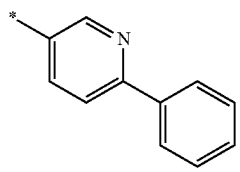
6-203 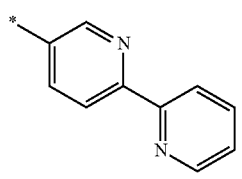
6-204 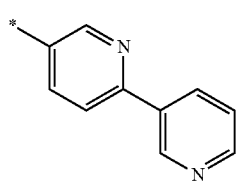
6-205 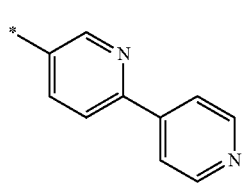
6-206 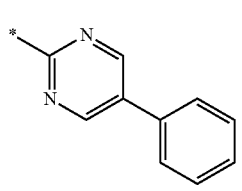
6-207 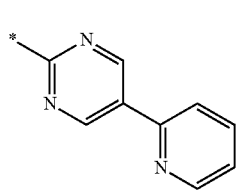
6-208 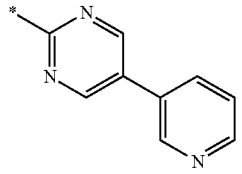
6-209 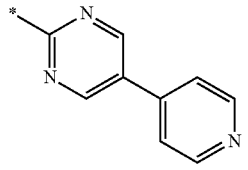
6-210 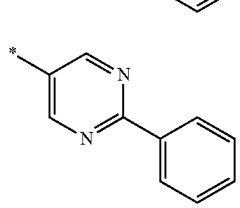
6-211 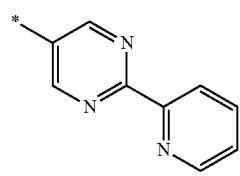
6-212 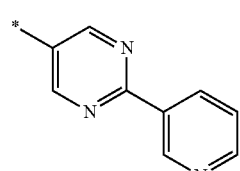
6-213 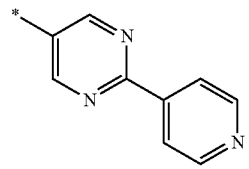
6-214 
6-215 
6-216 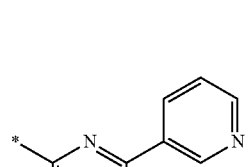

6-217 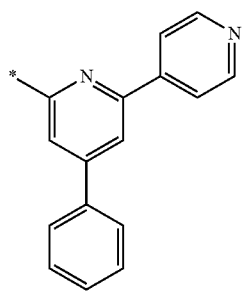
6-218 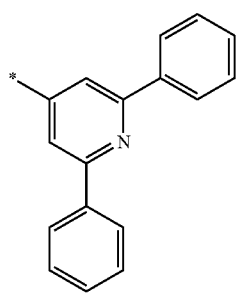
6-219 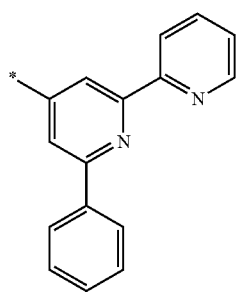
6-220 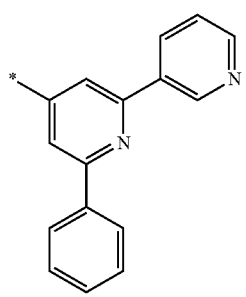
6-221 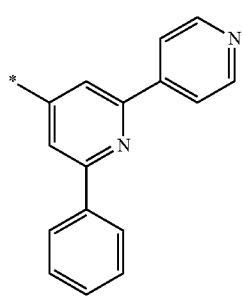
6-222 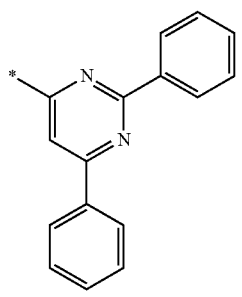
6-223 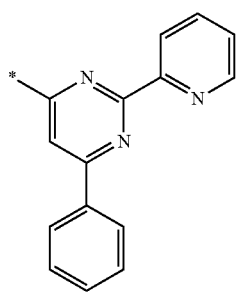
6-224 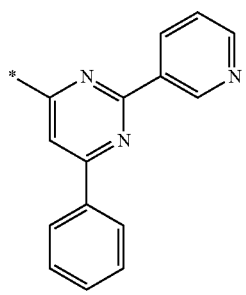
6-225 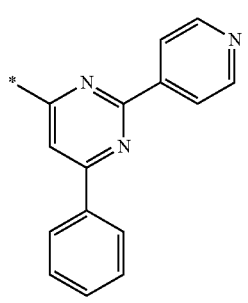
6-226 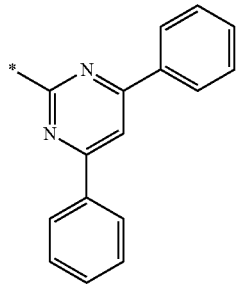

6-227 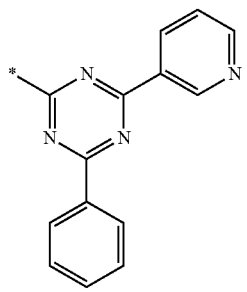
6-228 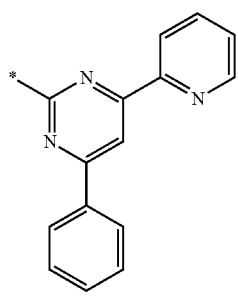
6-229 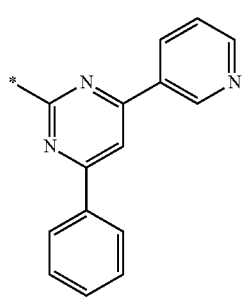
6-230 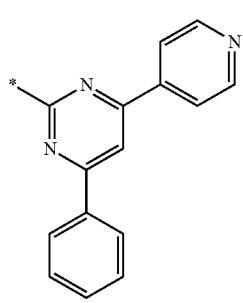
6-231 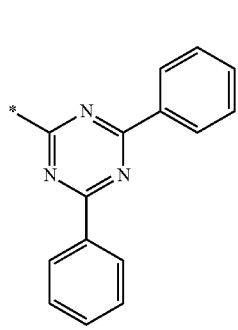
6-232 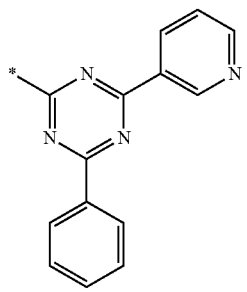
6-233 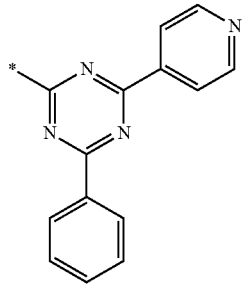
6-234 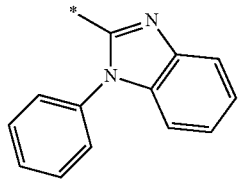
6-235 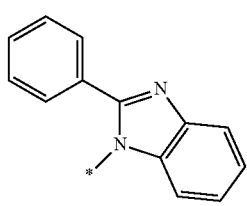
6-236 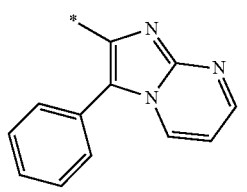
6-237 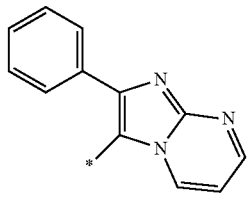
6-238 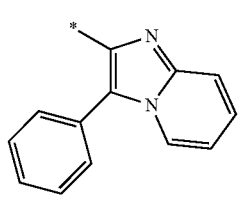

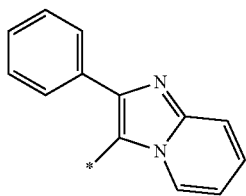
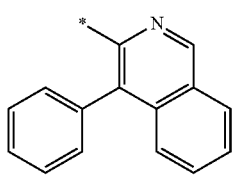

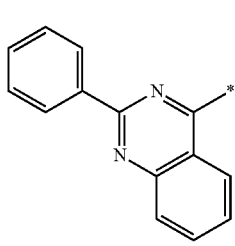
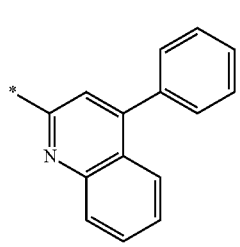
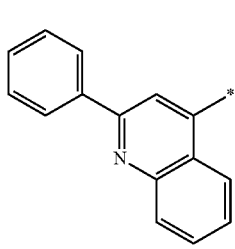
6-239
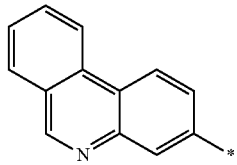
6-240
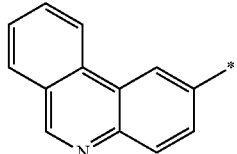
6-241
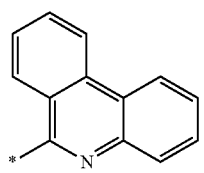
6-242
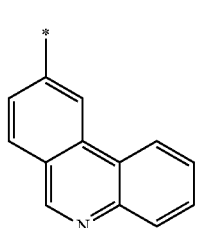
6-243
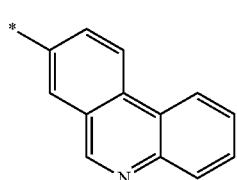
6-244
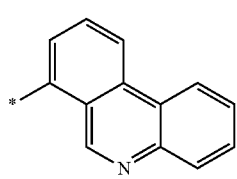
6-245
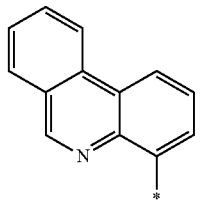
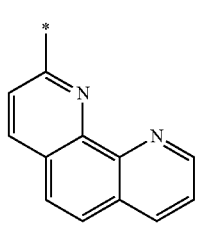
6-246
6-247
6-248
6-249
6-250
6-251
6-252
6-253

-continued

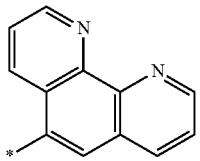
6-254

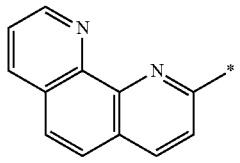
6-255

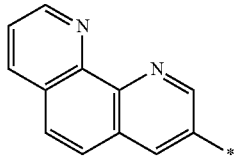
6-256

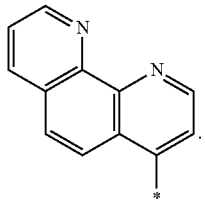
6-257

In Formulae 6-1 to 6-257,
t-Bu indicates a tert-butyl group,
Ph indicates a phenyl group,
1-Naph indicates a 1-naphthyl group,
2-Naph indicates a 2-naphthyl group, and
* indicates a binding site to a neighboring atom.

c11 in Formula 1 indicates the substitution number of $Ar_{11}(s)$. c11 in Formula 1 may be selected from 1, 2, 3, 4, 5, and 6. When c11 is two or more, two or more $Ar_{11}(s)$ may be identical to or different from each other.

In an exemplary embodiment of the present disclosure, c11 in Formula 1 may be selected from 1, 2, and 3, but the present disclosure is not limited thereto.

$R_{13}$ and $R_{14}$ in Formula 1 may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, and a substituted or unsubstituted monovalent non-aromatic condensed heteropolycyclic group.

In an exemplary embodiment of the present disclosure, $R_{13}$ and $R_{14}$ in Formula 1 may each independently be selected from:

hydrogen, deuterium, —F, —Cl, —Br, —I, a cyano group, a methyl group, an ethyl group, an n-propyl group, an iso-propyl group, an n-butyl group, an iso-butyl group, a sec-butyl group, and a tert-butyl group;

a methyl group, an ethyl group, an n-propyl group, an iso-propyl group, an n-butyl group, an iso-butyl group, a sec-butyl group, and a tert-butyl group, each substituted with at least one selected from deuterium, —F, —Cl, —Br, —I, and a cyano group; and a phenyl group, a naphthyl group, and a pyridinyl group, but the present disclosure is not limited thereto.

In an exemplary embodiment of the present disclosure, the condensed cyclic compound represented by Formula 1 may be represented by Formula 1-1, but the present disclosure is not limited thereto:

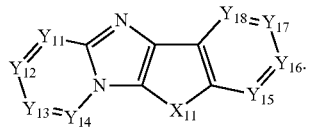

<Formula 1-1>

In Formula 1-1.

$Y_{11}$ to $Y_{18}$ may each independently be selected from N, $C(R_x)$, and $C(R_y)$, provided that at least one of $Y_{11}$ to $Y_{18}$ is $C(R_y)$, $R_x$ may be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), $R_y$ may be a group represented by *-($L_{11}$)$_{a11}$-($Ar_{11}$)$_{c11}$, $X_{11}$, $L_{11}$, a11, $Ar_{11}$, c11, and $Q_1$ to $Q_3$ may be the same as described in connection with Formula 1, and . indicates a binding site to a neighboring atom.

In an exemplary embodiment of the present disclosure, in Formula 1-1. $Y_{11}$ may be $C(R_y)$ and $Y_{12}$ to $Y_{18}$ may each independently be selected from N, $C(R_x)$, and $C(R_y)$;

$Y_{12}$ may be $C(R_y)$, and $Y_{11}$ and $Y_{13}$ to $Y_{18}$ may each independently be selected from N, $C(R_x)$, and $C(R_y)$;

$Y_{13}$ may be $C(R_y)$, and $Y_{11}$, $Y_{12}$, and $Y_{14}$ to $Y_{18}$ may each independently be selected from N, $C(R_x)$, and $C(R_y)$;

$Y_{14}$ may be $C(R_y)$, and $Y_{11}$ to $Y_{13}$ and $Y_{15}$ to $Y_{18}$ may each independently be selected from N, $C(R_x)$, and $C(R_y)$;

$Y_{15}$ may be $C(R_y)$, and $Y_{11}$ to $Y_{14}$ and $Y_{16}$ to $Y_{18}$ may each independently be selected from N, $C(R_x)$, and $C(R_y)$;

$Y_{16}$ may be $C(R_y)$, and $Y_{11}$ to $Y_{15}$, $Y_{17}$, and $Y_{18}$ may each independently be selected from N, $C(R_x)$, and $C(R_y)$;

$Y_{17}$ may be $C(R_y)$, and $Y_{11}$ to $Y_{16}$ and $Y_{18}$ may each independently be selected from N, $C(R_x)$, and $C(R_y)$; or $Y_{18}$ may be $C(R_y)$, and $Y_{11}$ to $Y_{17}$ may each independently be selected from N, $C(R_x)$, and $C(R_y)$, but the present disclosure is not limited thereto.

In an exemplary embodiment of the present disclosure, Formula 1-1 may include a tetracyclic structure including 4 fused aromatic rings. At least one hydrogen of the tetracyclic structure may be substituted with F, Cl, Br, I, a hydroxyl group, a cyano group, a nitro group, an amidino group, a hydrazino group, a hydrazono group, or an organic substituent group. The organic substituent group may include at least one C atom, and may optionally include at least one of N, S, O, P, Si, B, F, Cl, Br, and I atoms.

In an exemplary embodiment of the present disclosure, the condensed cyclic compound represented by Formula 1 may be represented by one of Formulae 1-11 to 1-18, 1-21 to 1-27, 1-31 to 1-37, 1-41 to 1-47, 1-51 to 1-57, 1-61 to 1-67, 1-71 to 1-77, and 1-81 to 1-87, but the present disclosure is not limited thereto:

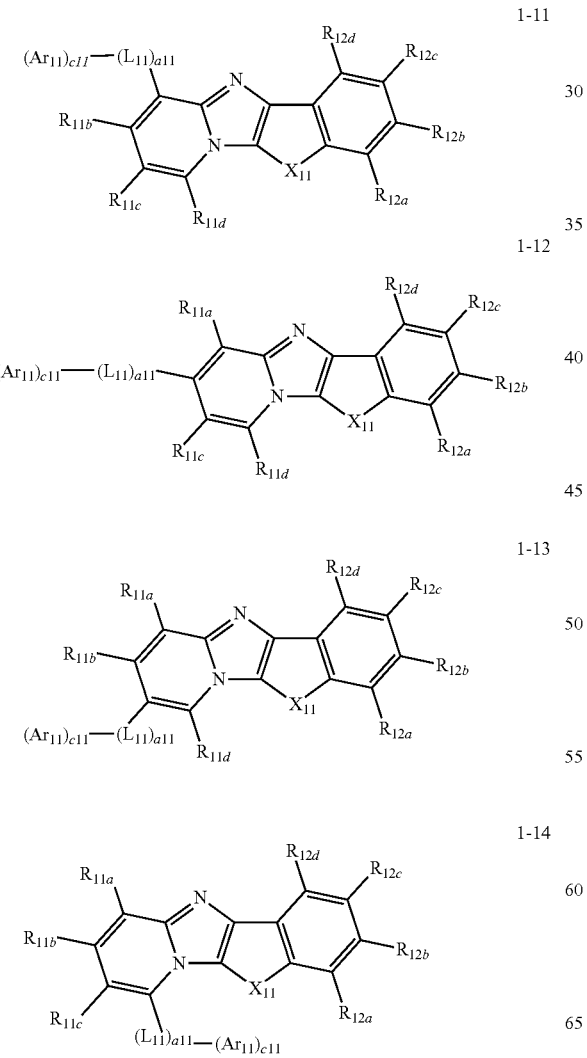

-continued

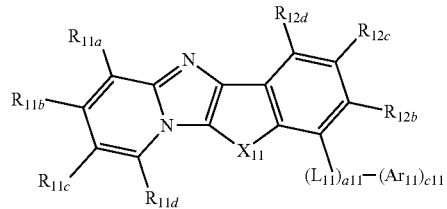

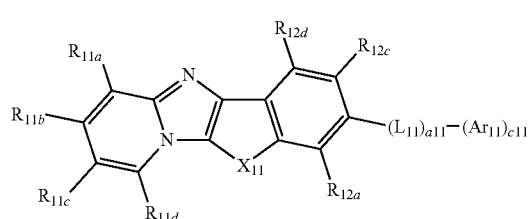

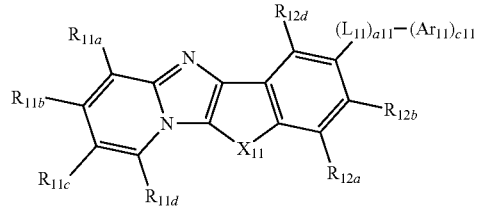

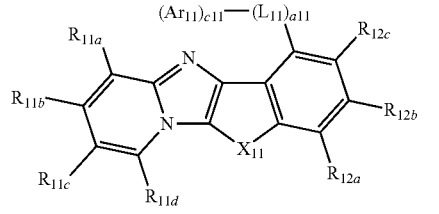

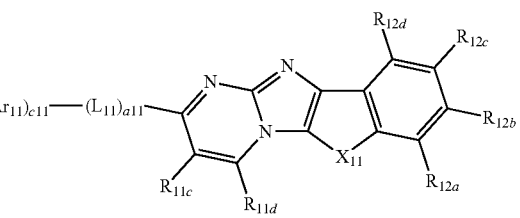

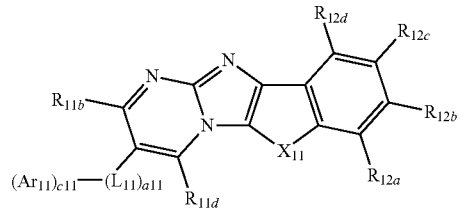

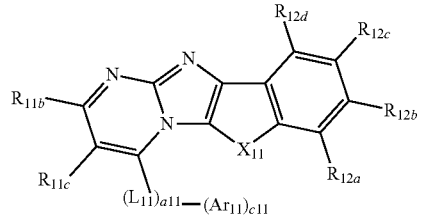

1-24
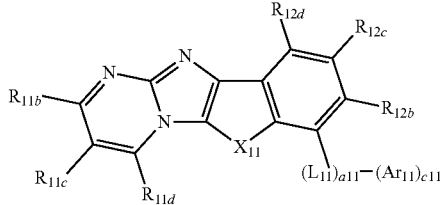
1-25
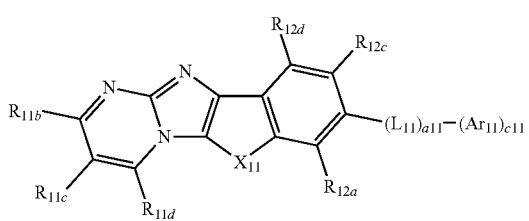
1-26
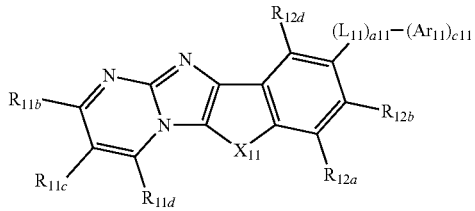
1-27
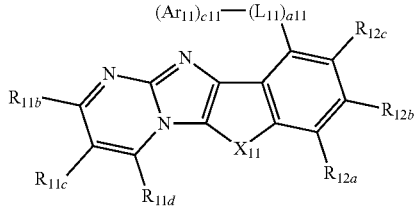
1-31
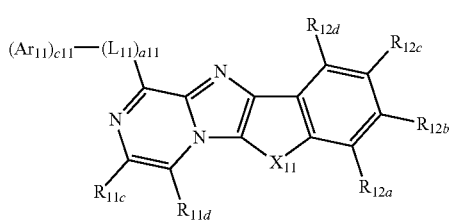
1-32
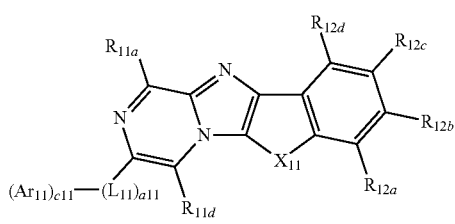
1-33
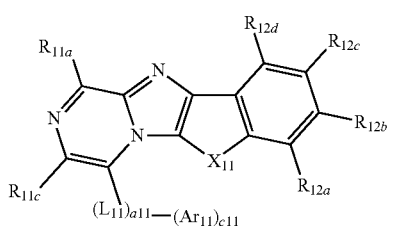
1-34
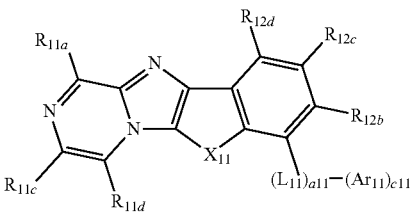
1-35
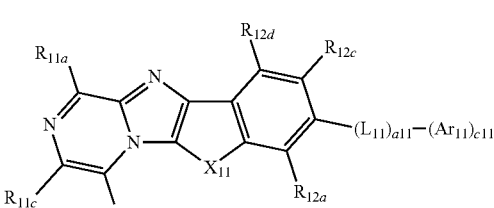
1-36
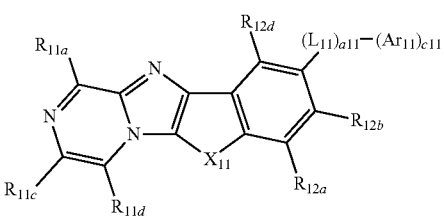
1-37
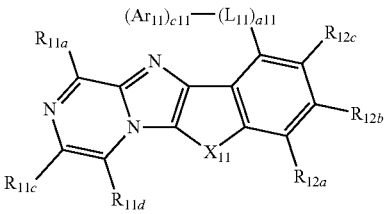
1-41
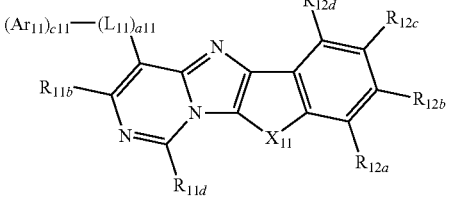
1-42
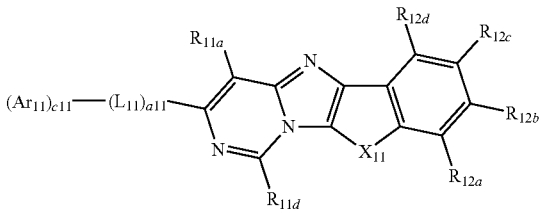
1-43
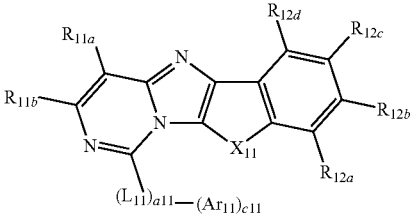

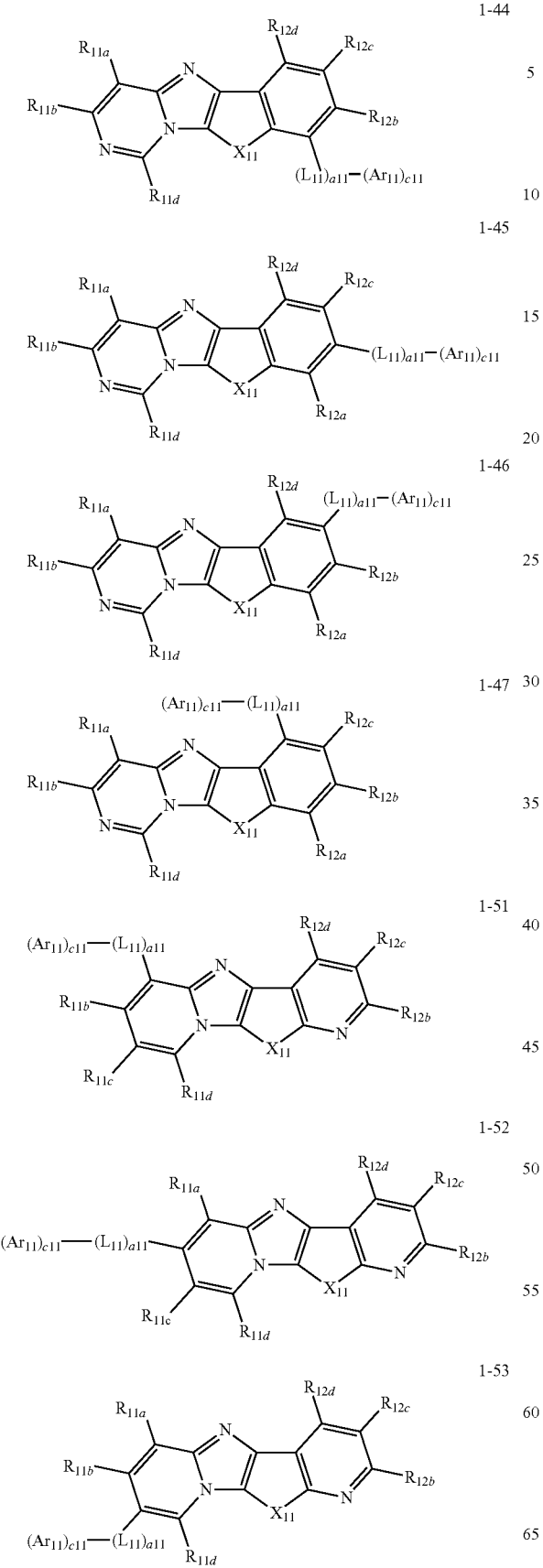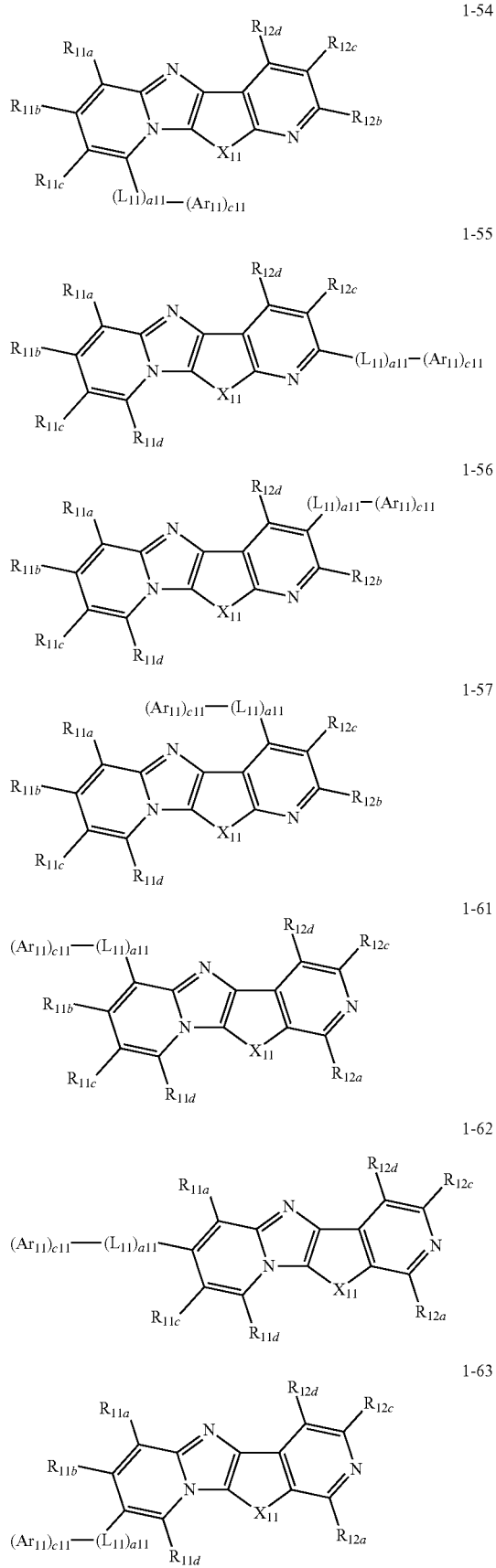

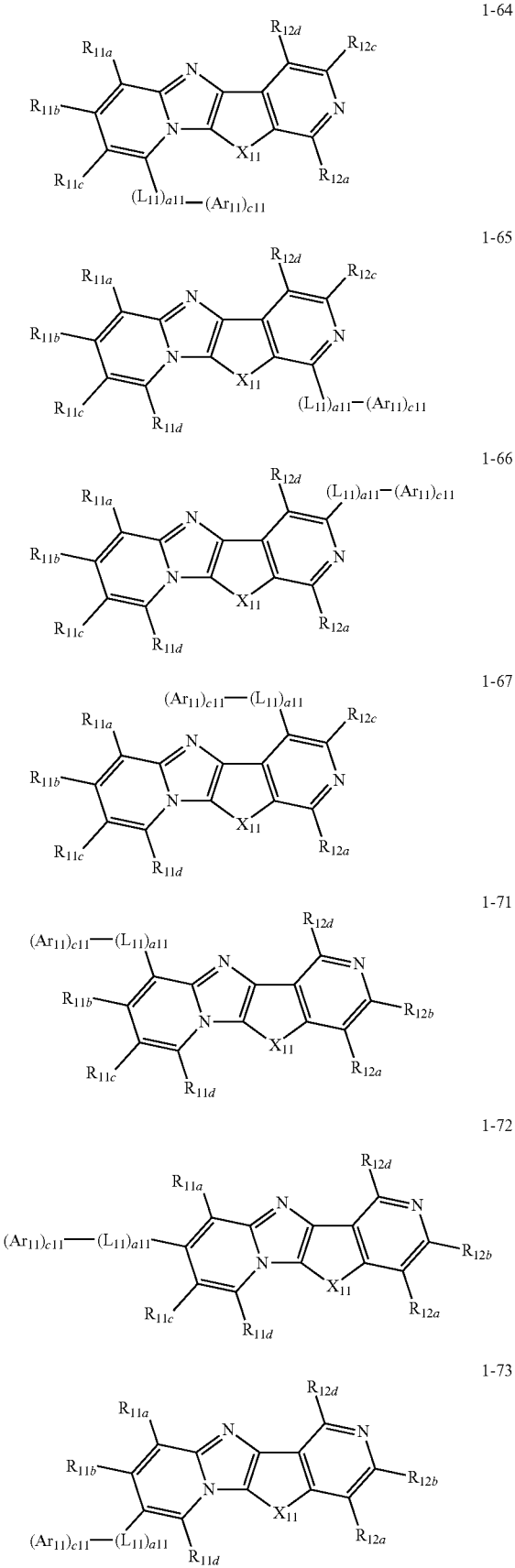
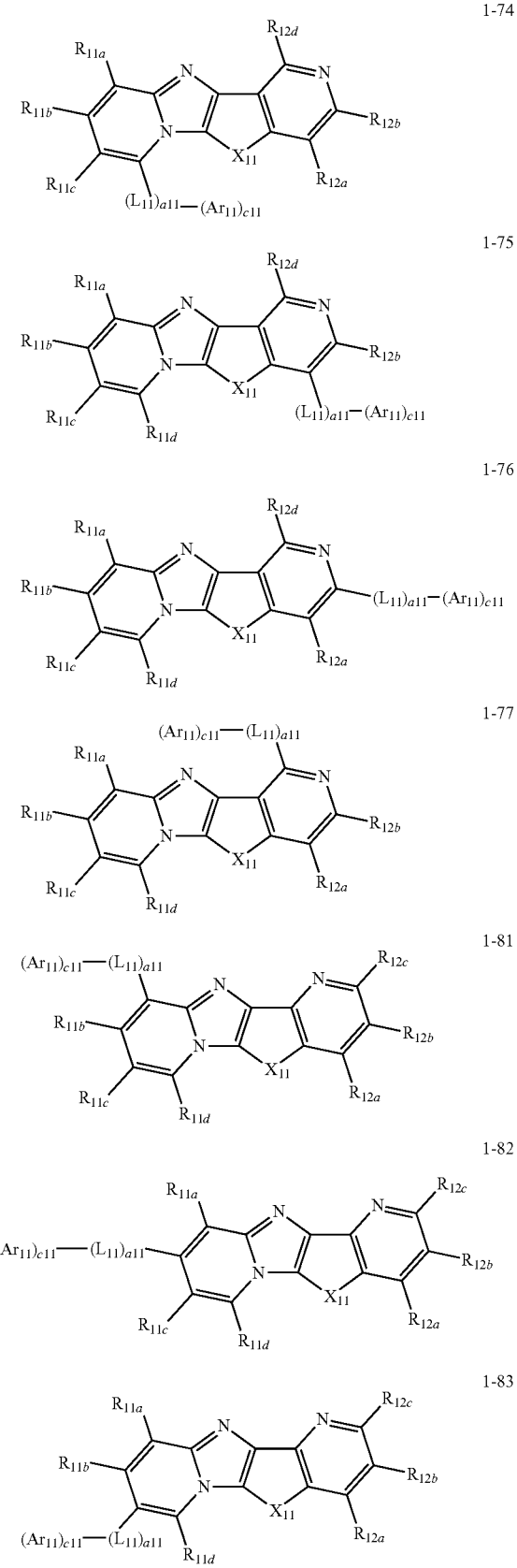

-continued 1-84 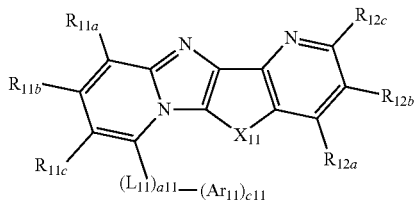

1-85 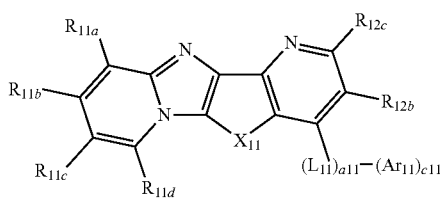

1-86 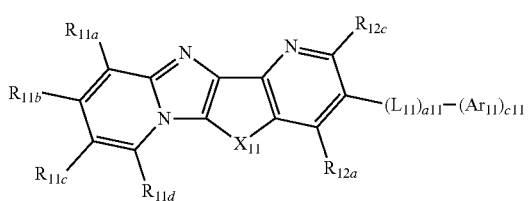

1-87 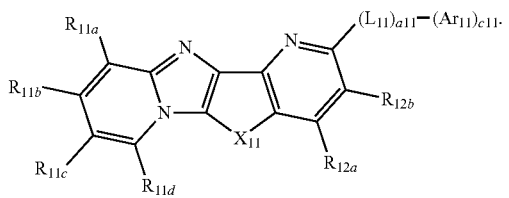

In Formulae 1-11 to 1-18, 1-21 to 1-27, 1-31 to 1-37, 1-41 to 1-47, 1-51 to 1-57, 1-61 to 1-67, 1-71 to 1-77, and 1-81 to 1-87.

$R_{11a}$, $R_{11b}$, $R_{11c}$, $R_{11d}$, $R_{12a}$, $R_{12b}$, $R_{12c}$, and $R_{12d}$ may each independently be selected from hydrogen, deuterium, —F, —Cl, —Br, —I, a hydroxyl group, a cyano group, a nitro group, an amidino group, a hydrazine group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and $X_{11}$, $L_{11}$, a11, $Ar_{11}$, c11, and $Q_1$ to $Q_3$ may be the same as described in connection with Formula 1.

In an exemplary embodiment of the present disclosure, in Formulae 1-11 to 1-18, 1-21 to 1-27, 1-31 to 1-37, 1-41 to 1-47, 1-51 to 1-57, 1-61 to 1-67, 1-71 to 1-77, and 1-81 to 1-87, $R_{11a}$, $R_{11b}$, $R_{11c}$, $R_{11d}$, $R_{12a}$, $R_{12b}$, $R_{12c}$, and $R_{12d}$ may each independently be selected from:

hydrogen, deuterium, —F, —Cl, —Br, —I, a cyano group, a methyl group, an ethyl group, an n-propyl group, an iso-propyl group, an n-butyl group, an iso-butyl group, a sec-butyl group, and a tert-butyl group;

a methyl group, an ethyl group, an n-propyl group, an iso-propyl group, an n-butyl group, an iso-butyl group, a sec-butyl group, and a tert-butyl group, each substituted with at least one selected from deuterium, —F, —Cl, —Br, —I, and a cyano group; and a phenyl group, a naphthyl group, and a pyridinyl group, but the present disclosure is not limited thereto.

In an exemplary embodiment of the present disclosure, the condensed cyclic compound represented by Formula 1 may be represented by one of Formulae 1-12, 1-13, 1-14, 1-17, and 1-22, but the present disclosure is not limited thereto.

In an exemplary embodiment of the present disclosure, the condensed cyclic compound represented by Formula 1 may be selected from Compounds 1 to 211, but the present disclosure is not limited thereto:

1

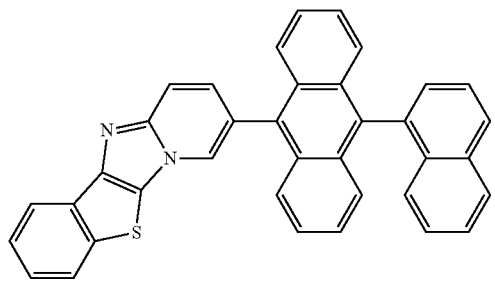

2

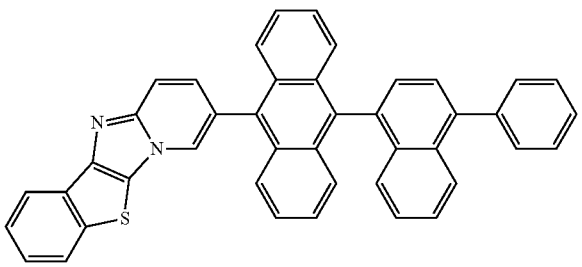

-continued
3
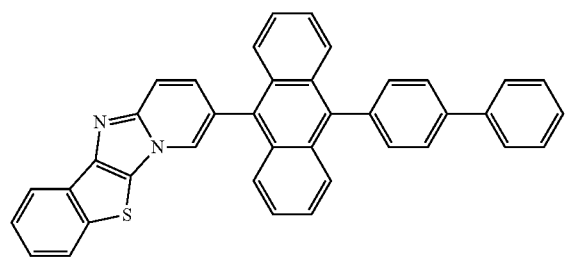
4
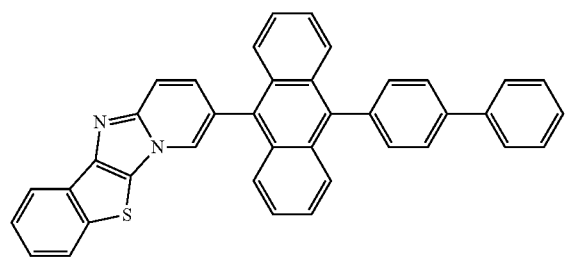
5
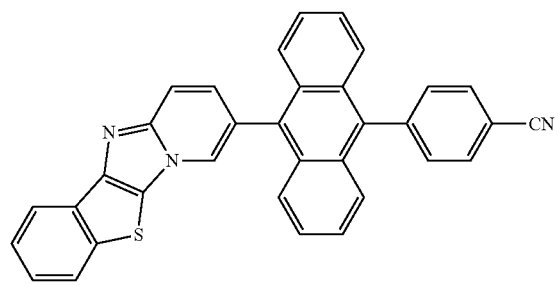
6
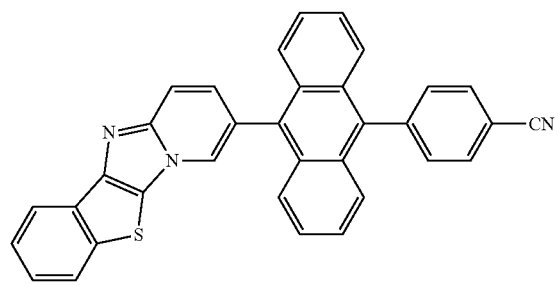
7
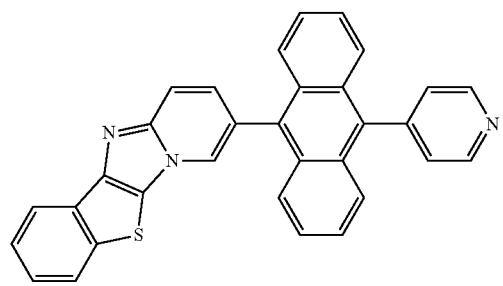
8
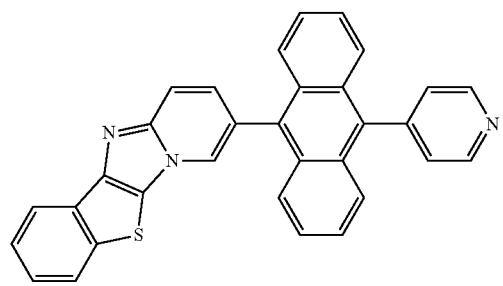
9
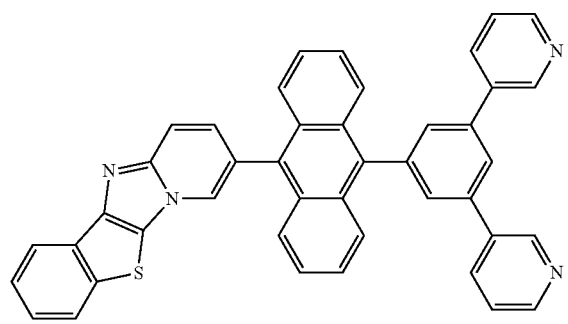
10
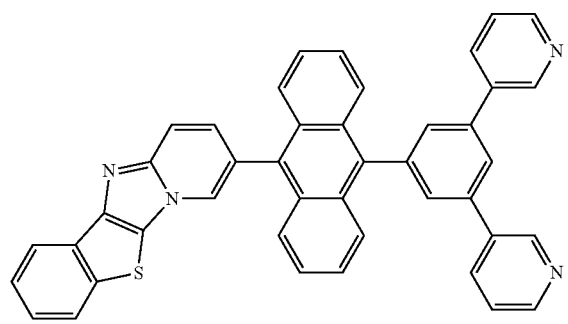
11
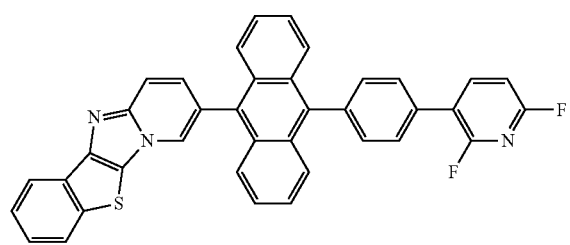
12
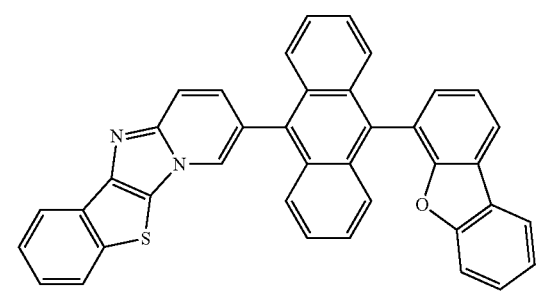

-continued
13
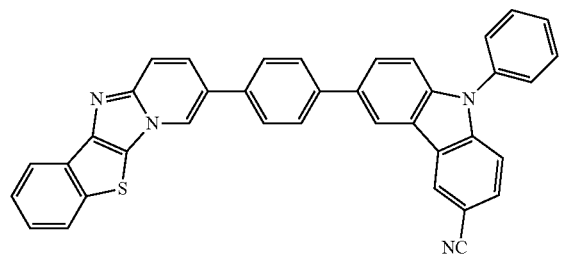
14
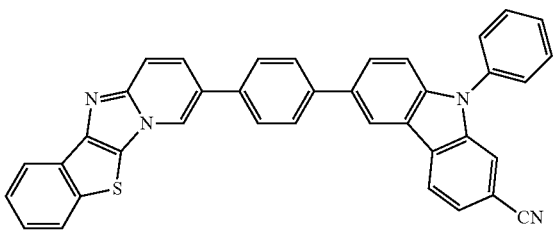
15
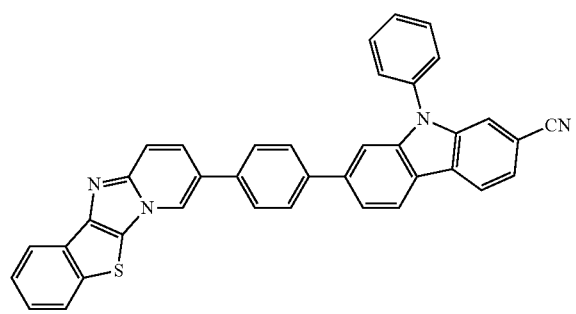
16
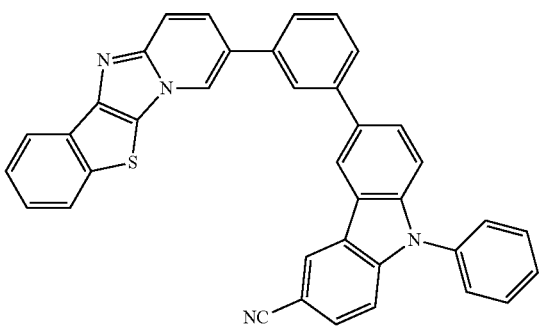
17
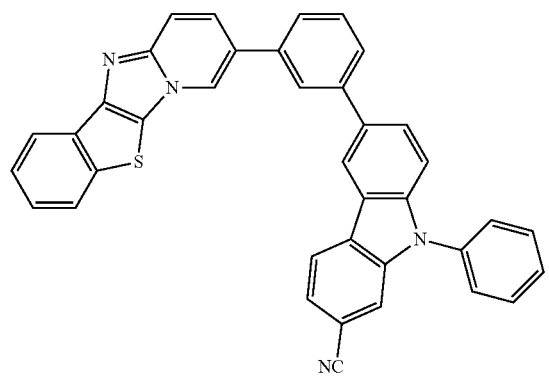
18
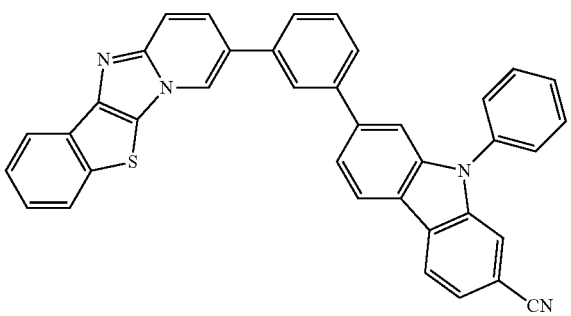
19
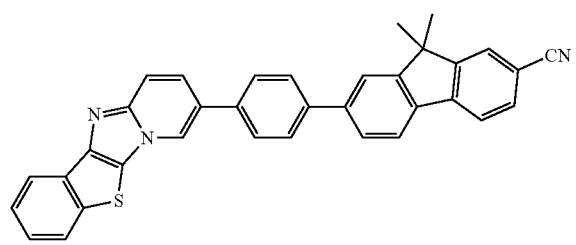
20
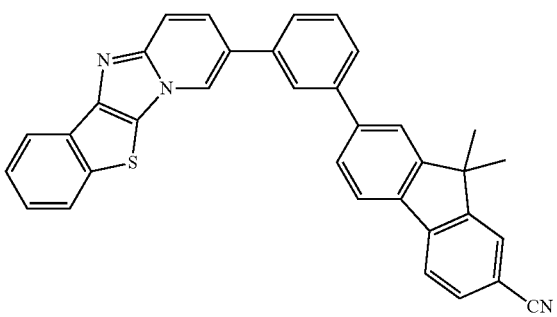
21
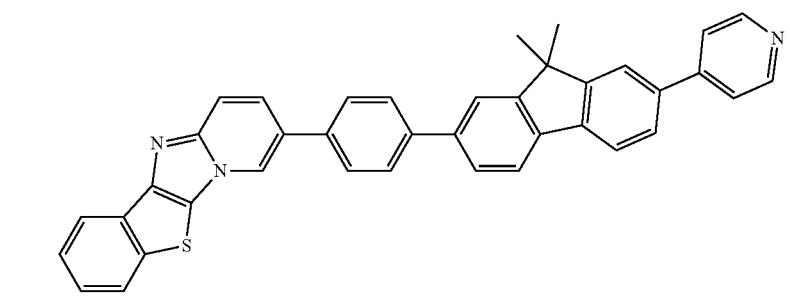

-continued
22
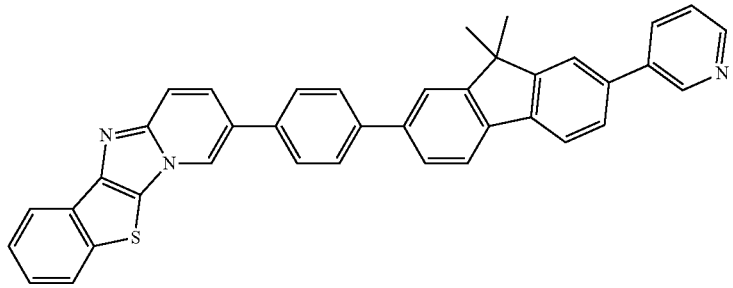
23
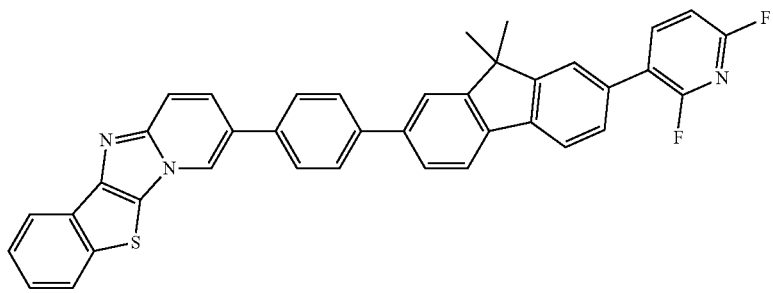
24
25
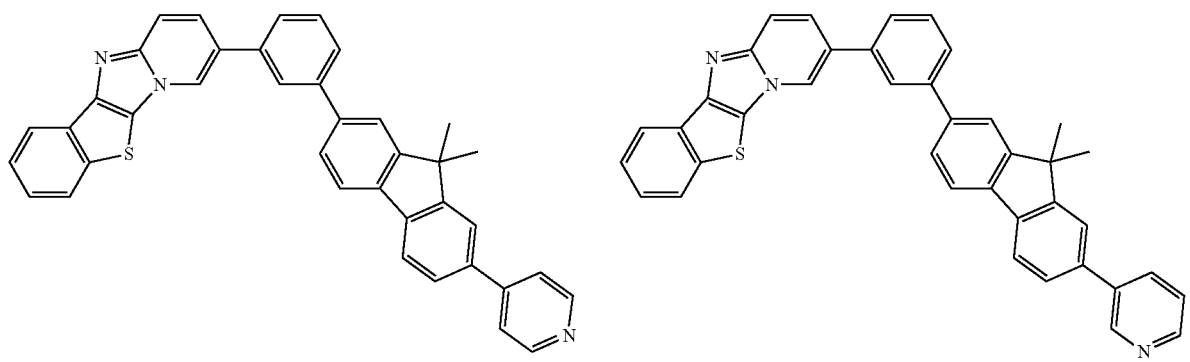
26
27
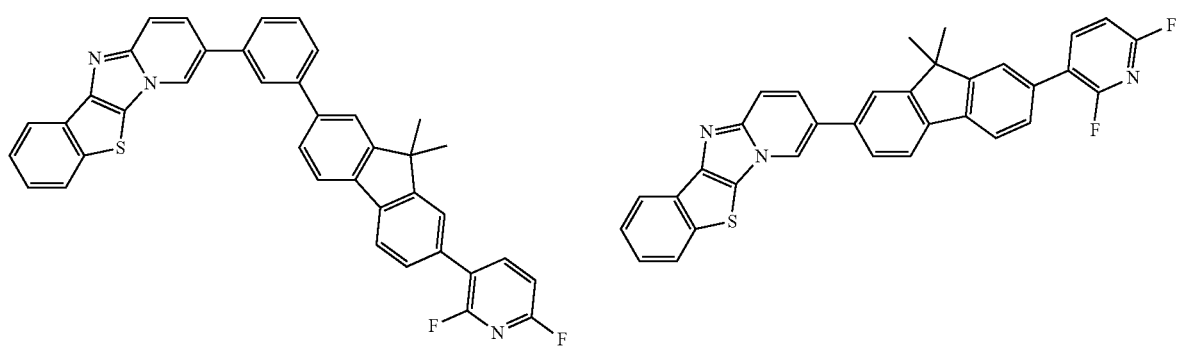
28
29
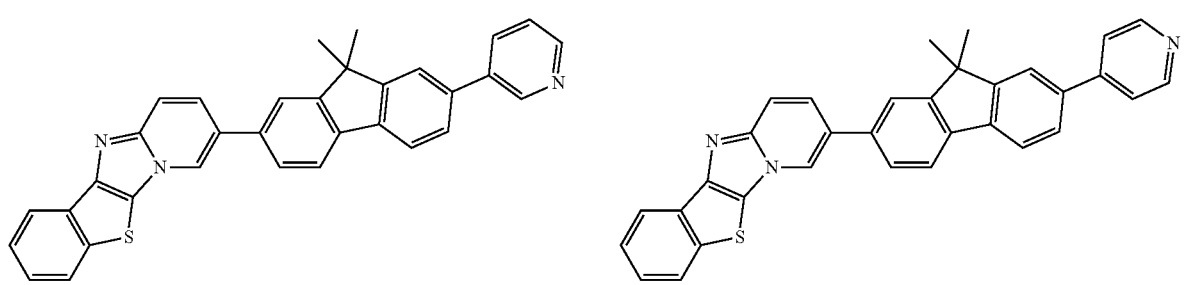

-continued
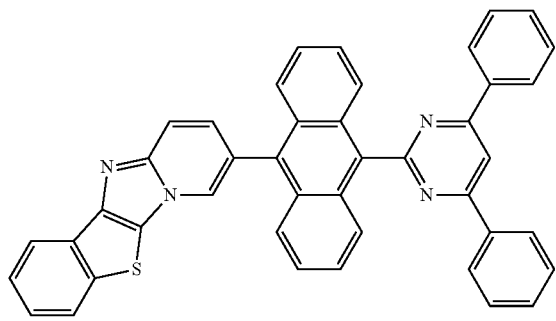
30
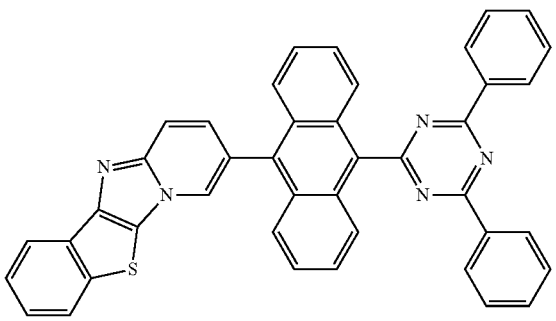
31
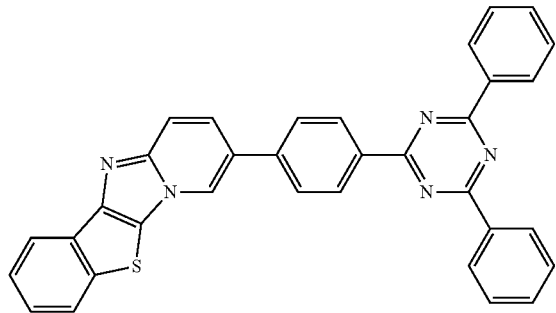
32
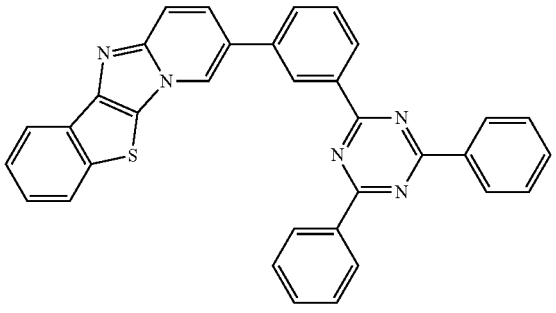
33
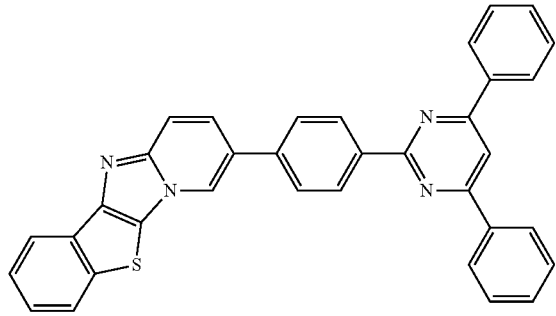
34
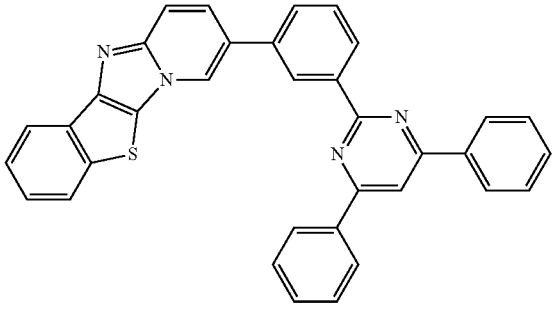
35
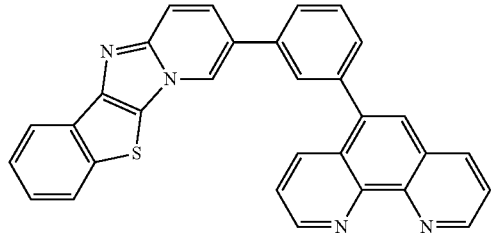
36
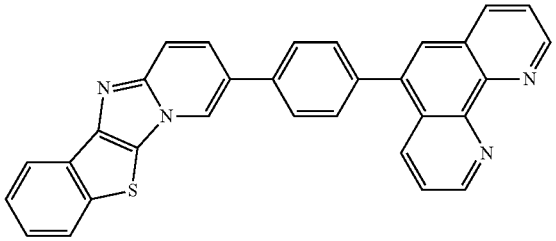
37
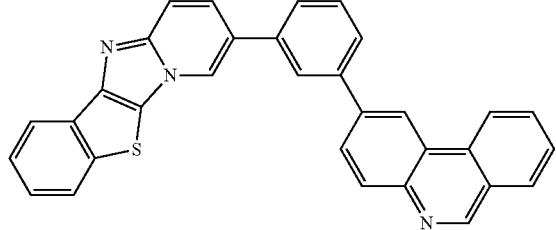
38
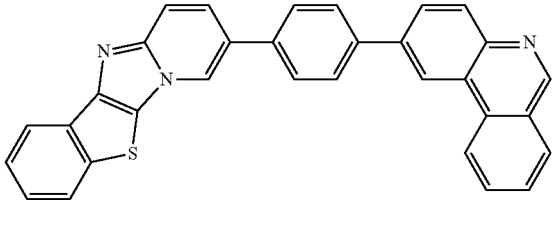
39

-continued
40
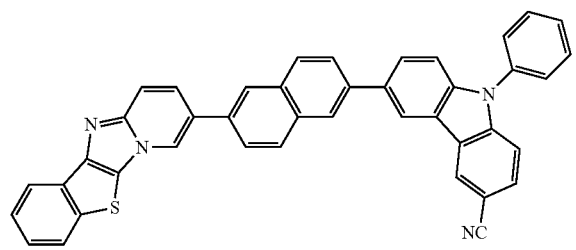
41
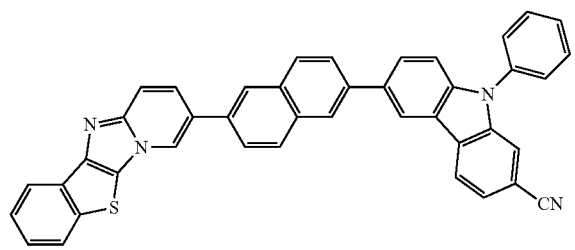
42
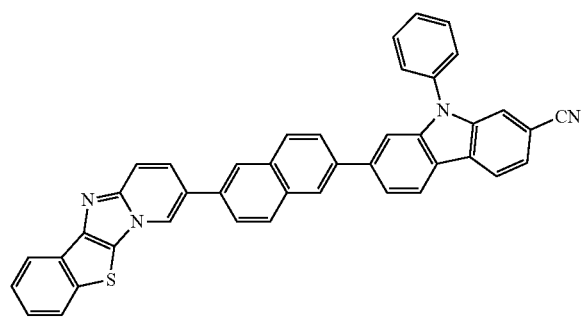
43
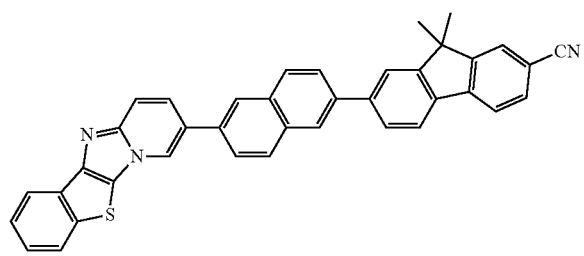
44
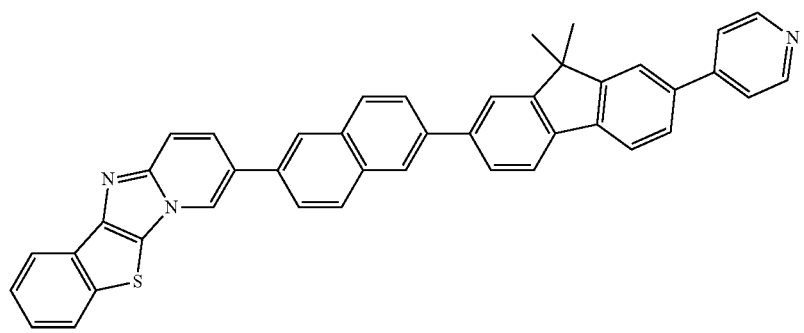
45
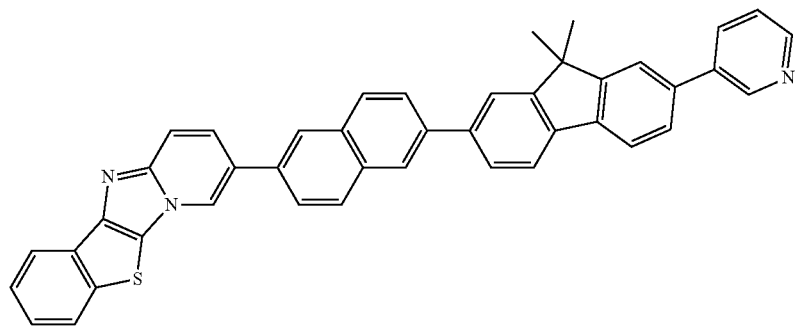
46
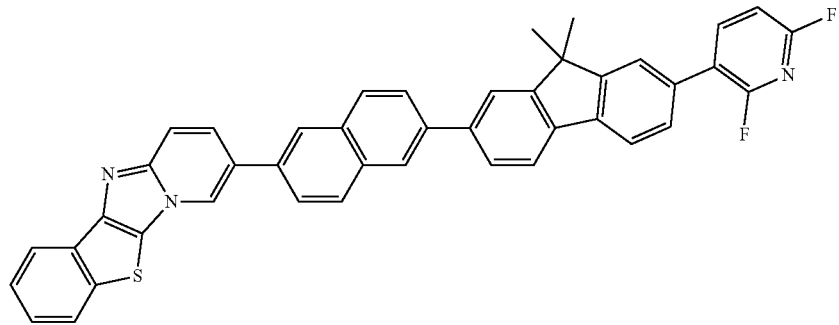

-continued
47
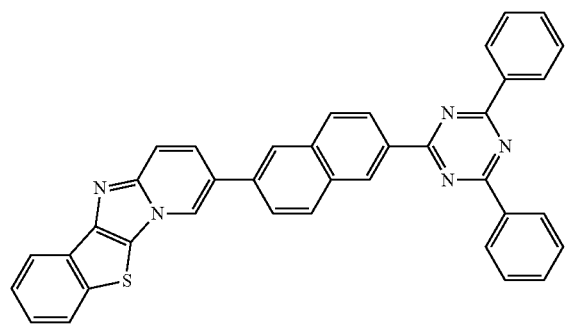
48
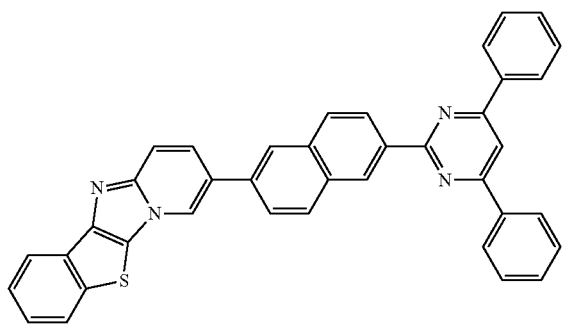
49
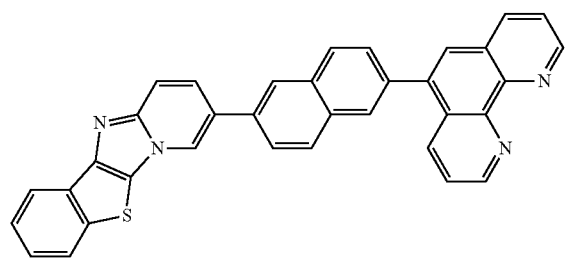
50
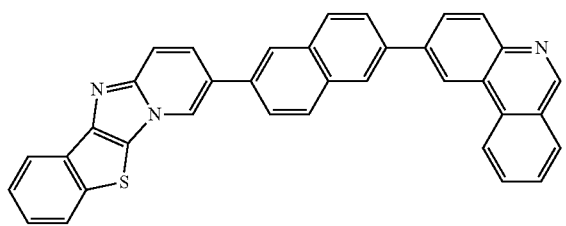
51
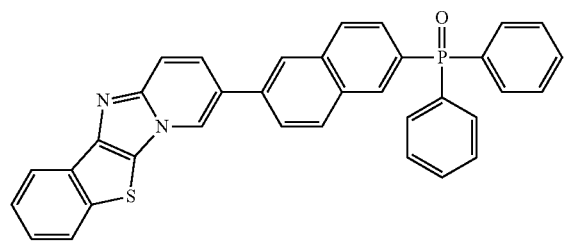
52
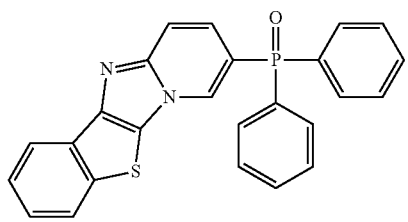
53
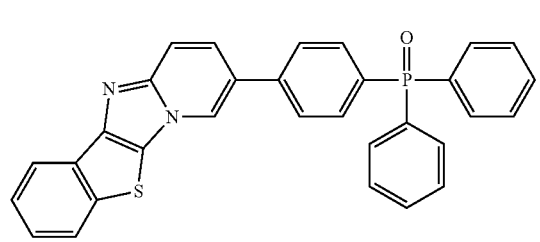
54
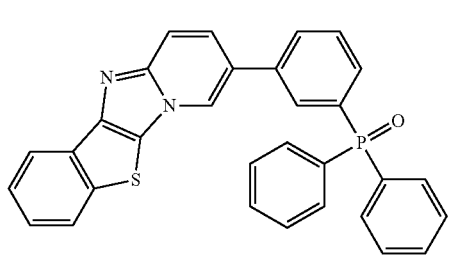
55
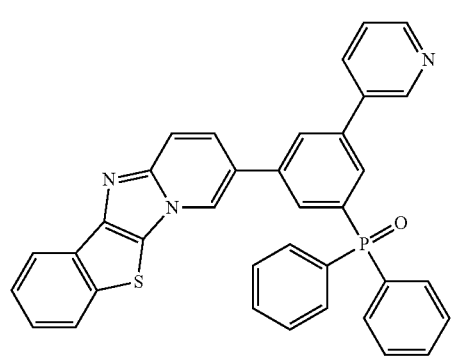
56
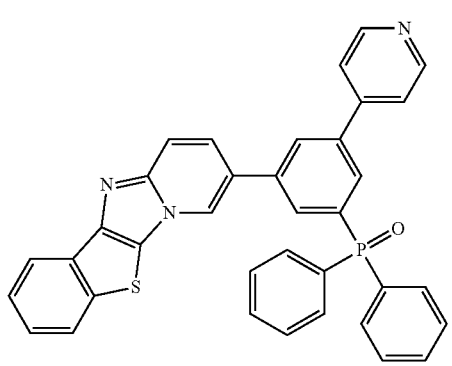

-continued
57
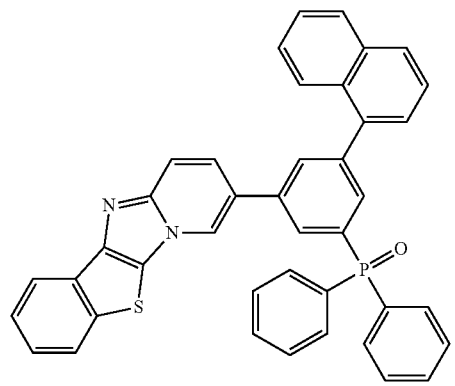
58
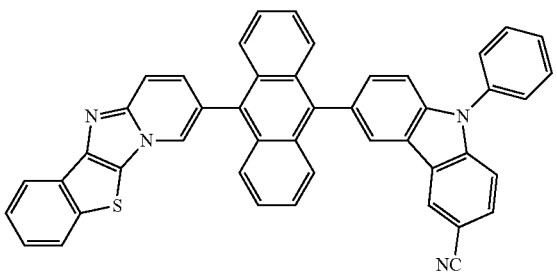
59
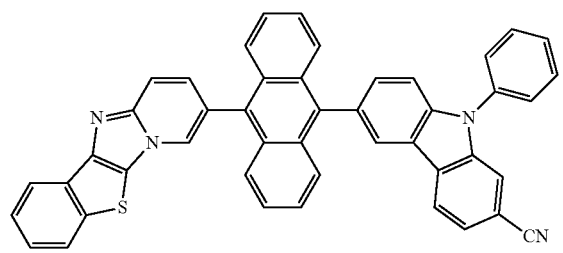
60
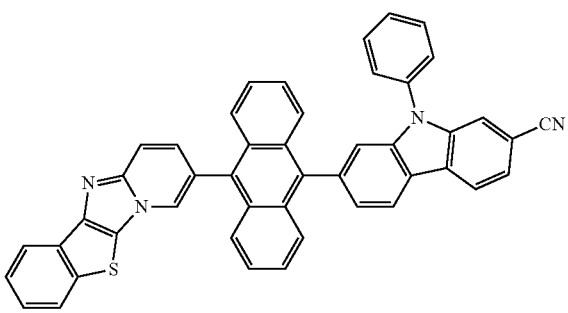
61
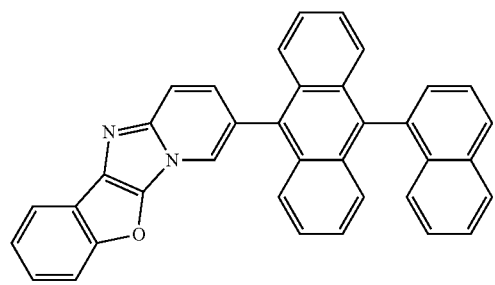
62
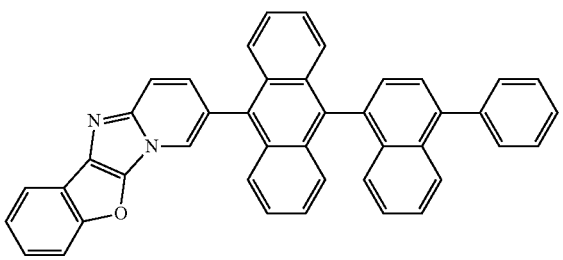
63
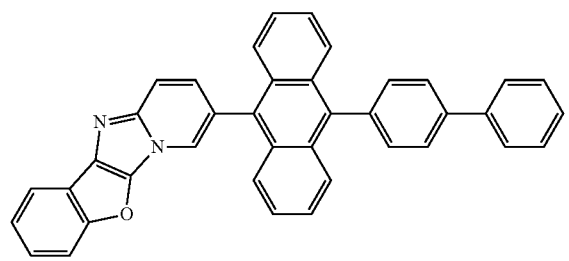
64
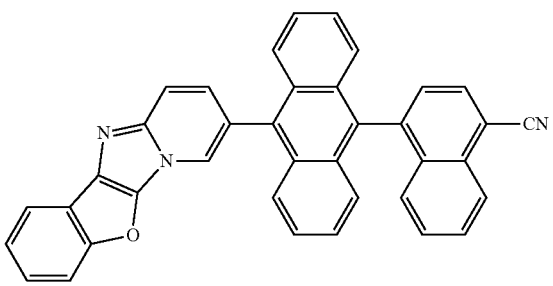
65
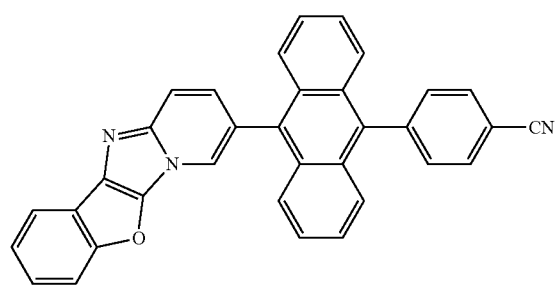
66
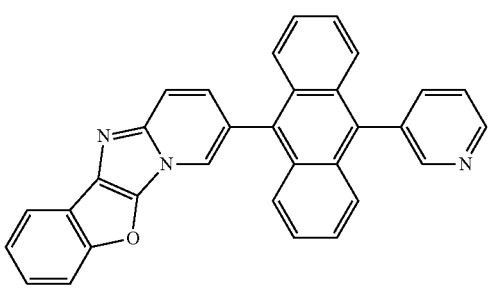

-continued
67
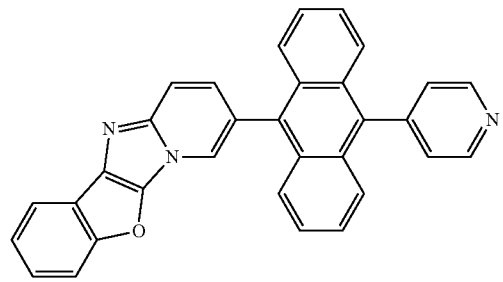
68
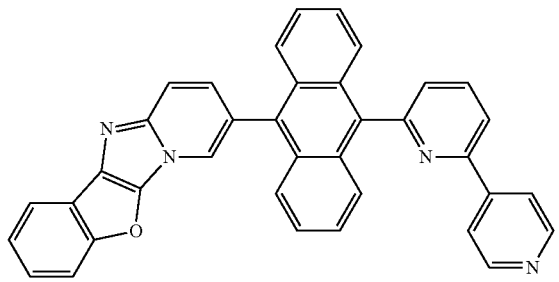
69
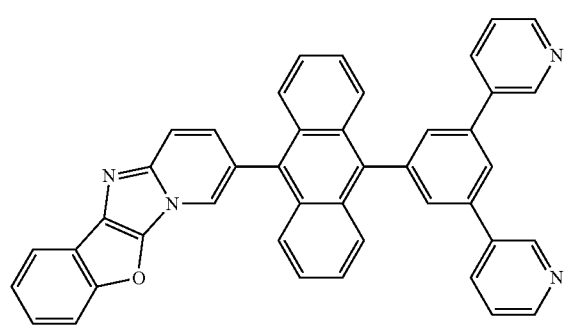
70
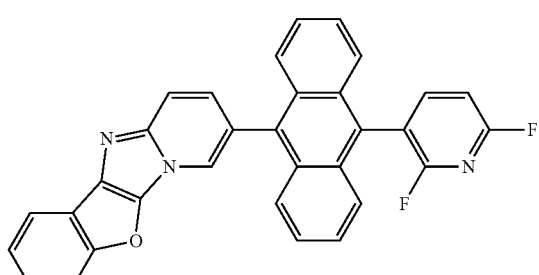
71
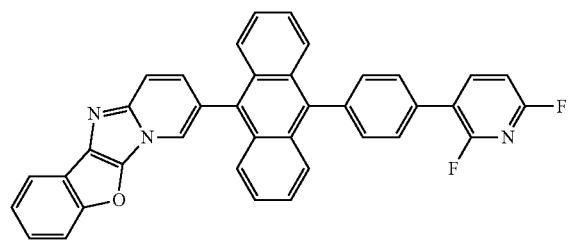
72
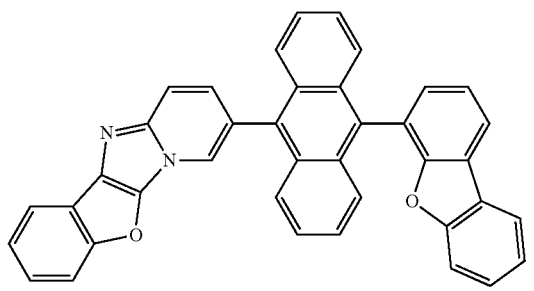
73
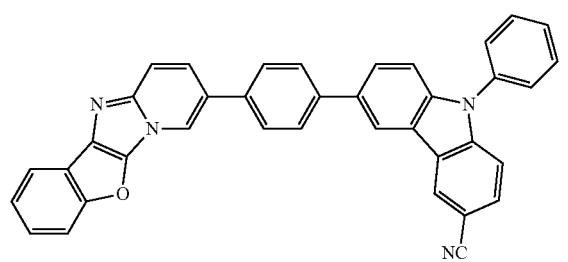
74
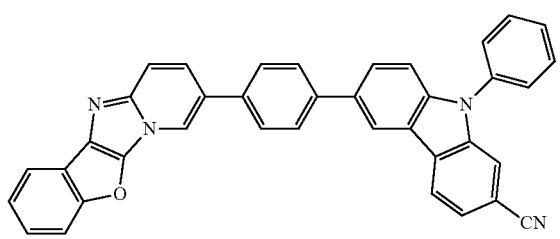
75
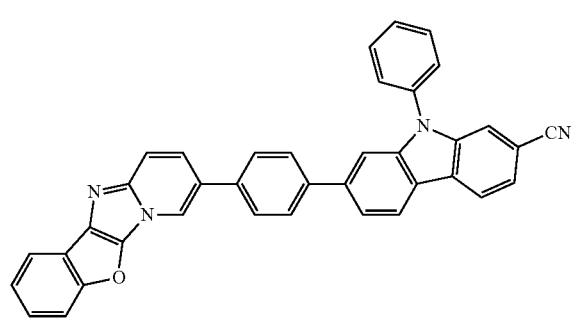
76
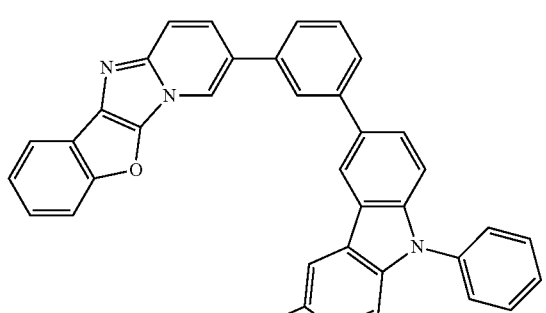

-continued
77
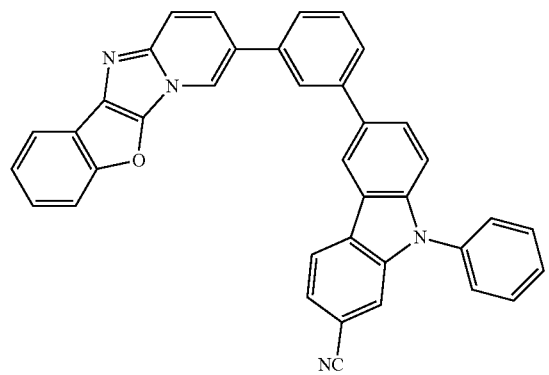
78
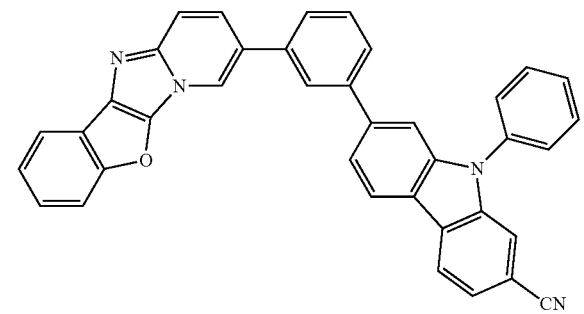
79
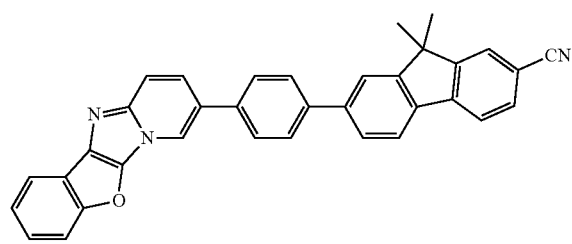
80
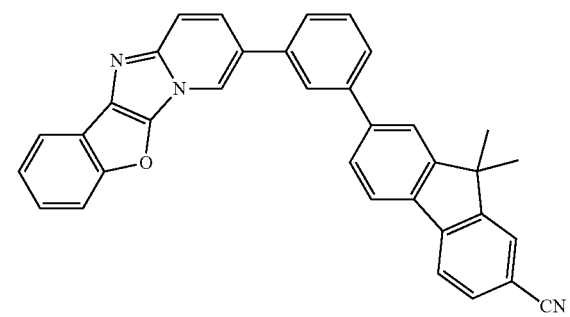
81
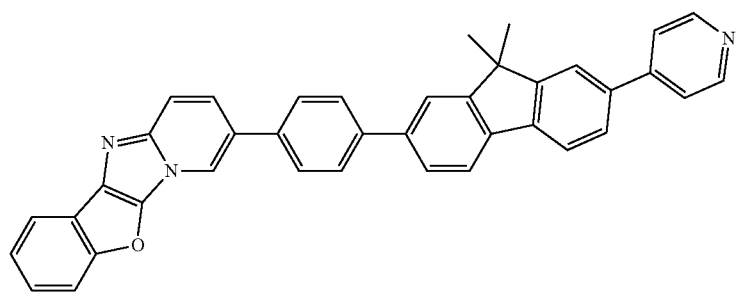
82
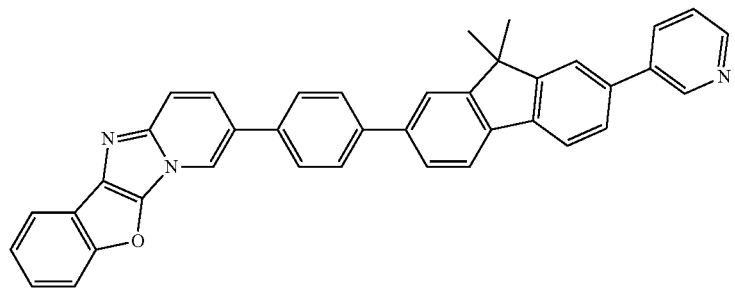

-continued
83
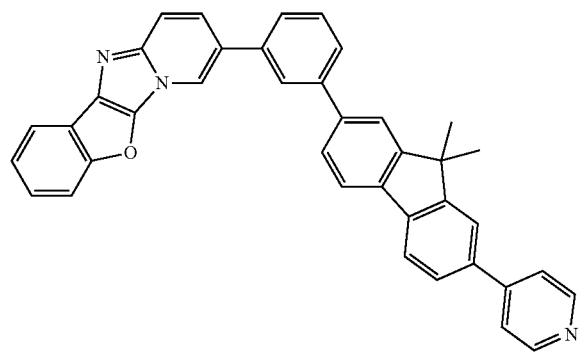
84
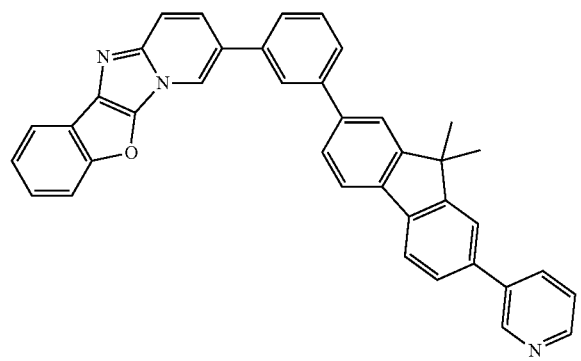
85
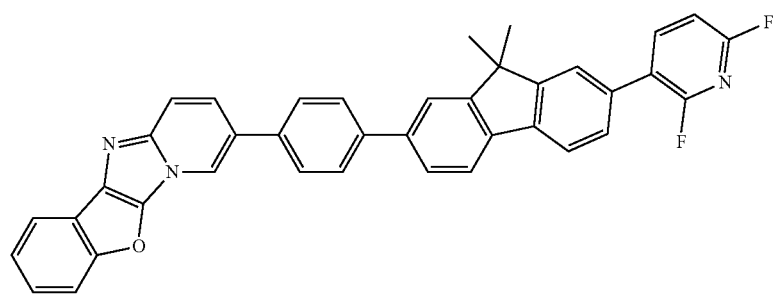
86
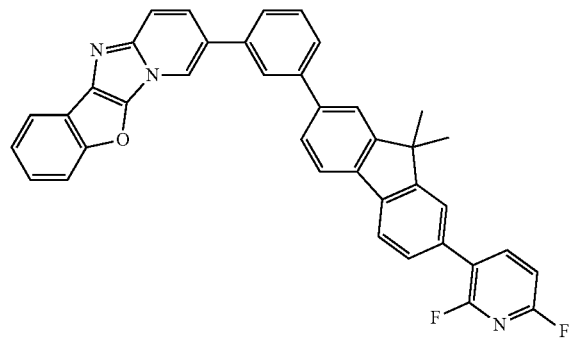
87
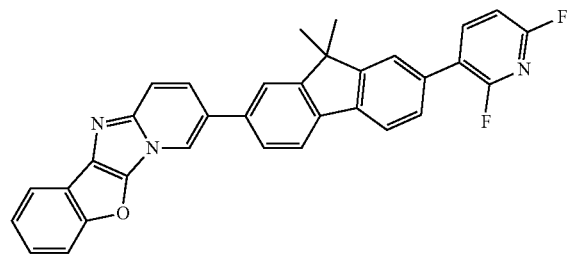
88
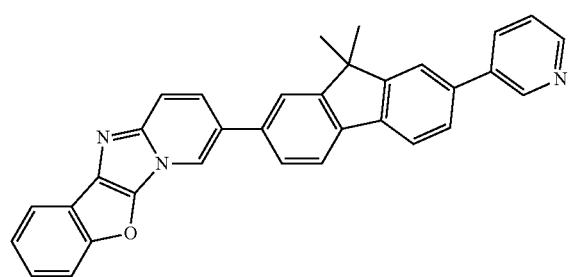
89
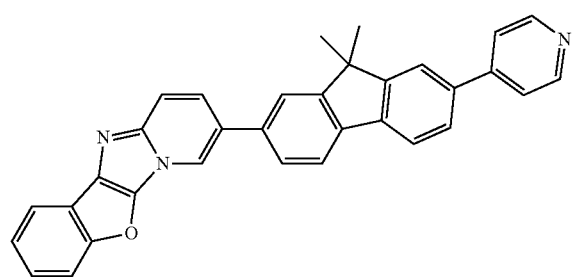

-continued
90
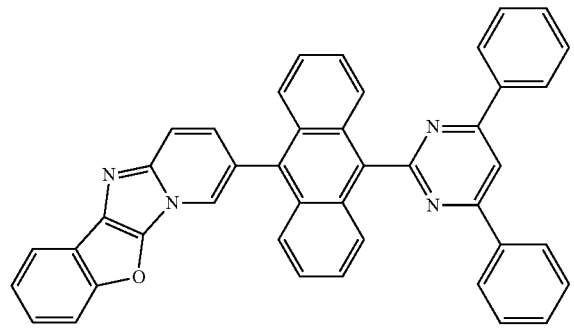
91
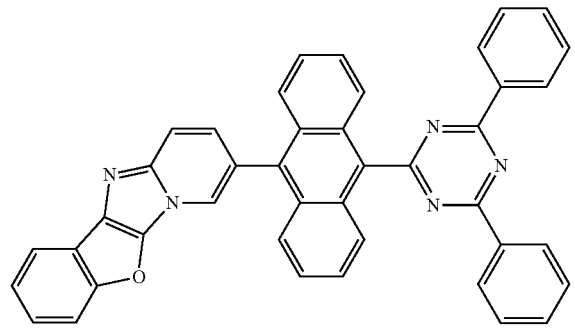
92
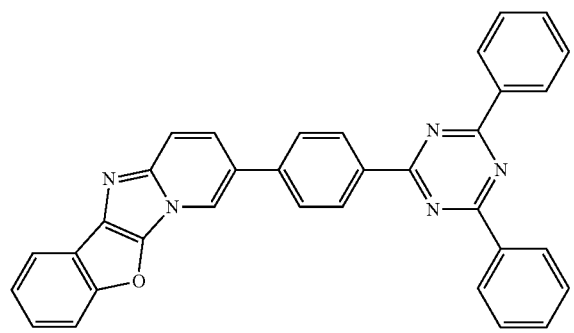
93
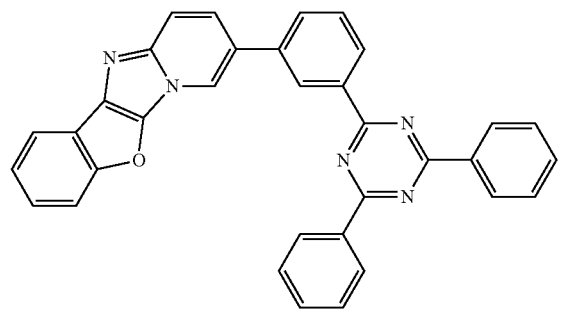
94
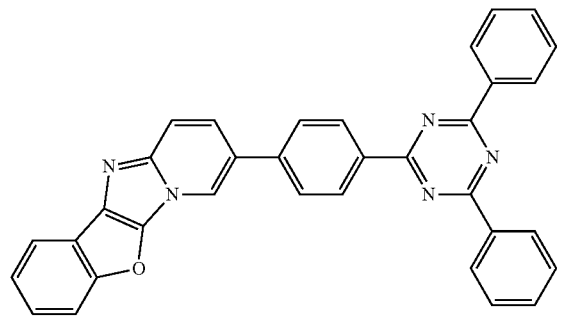
95
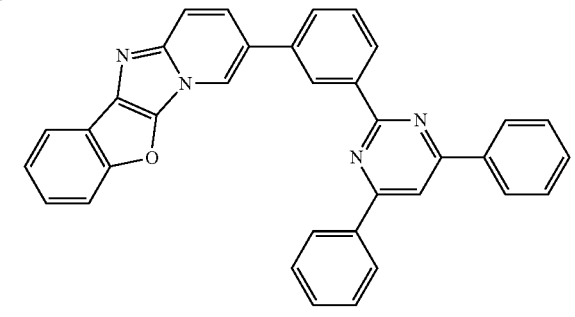
96
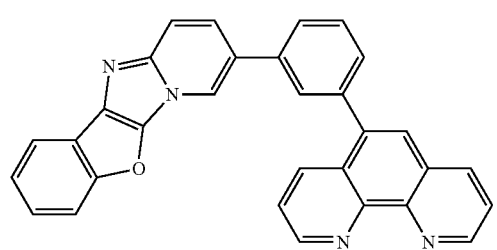
97
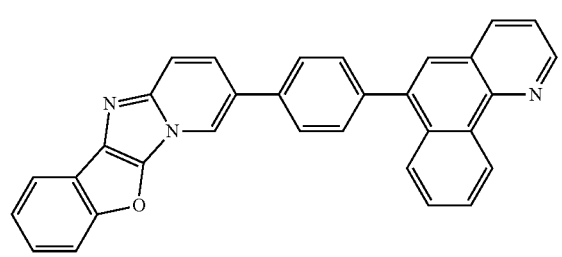
98
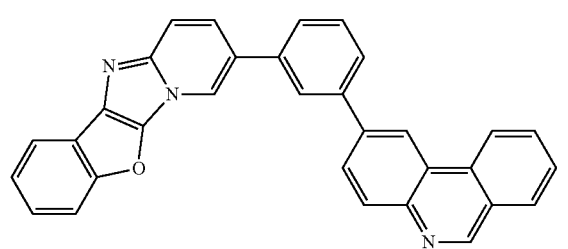
99
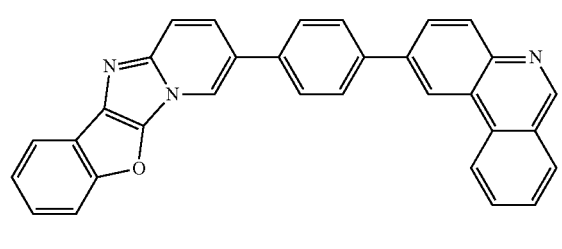

-continued
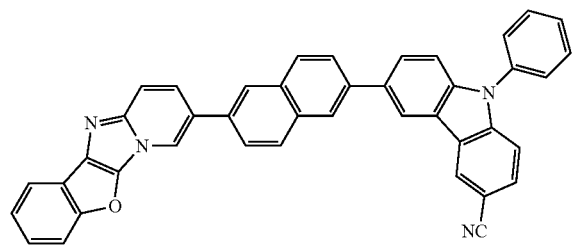
100
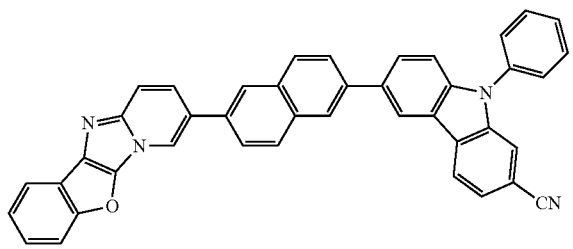
101
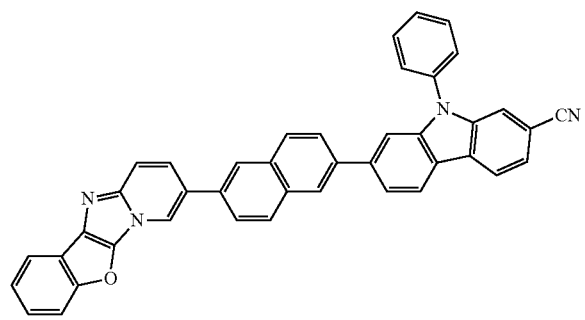
102
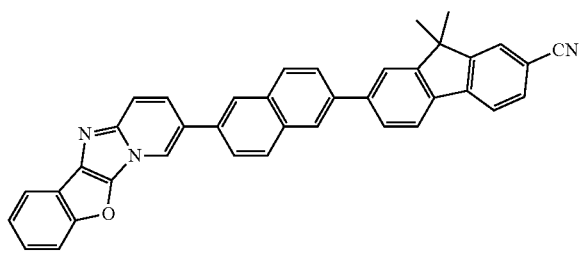
103
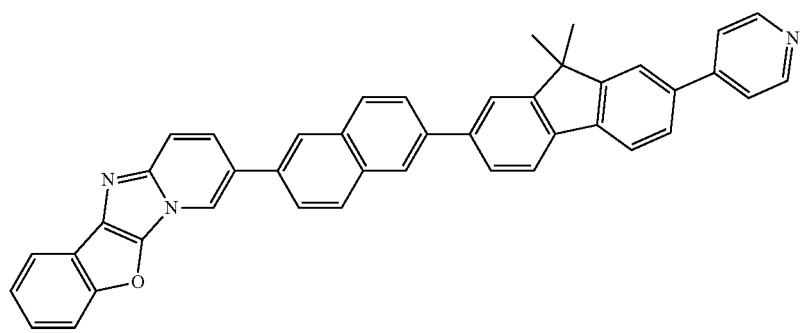
104
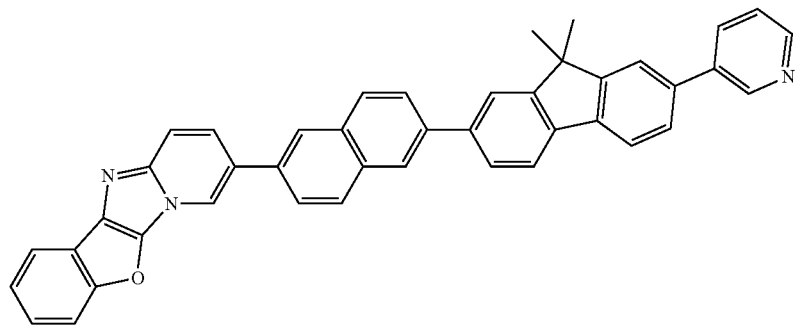
105
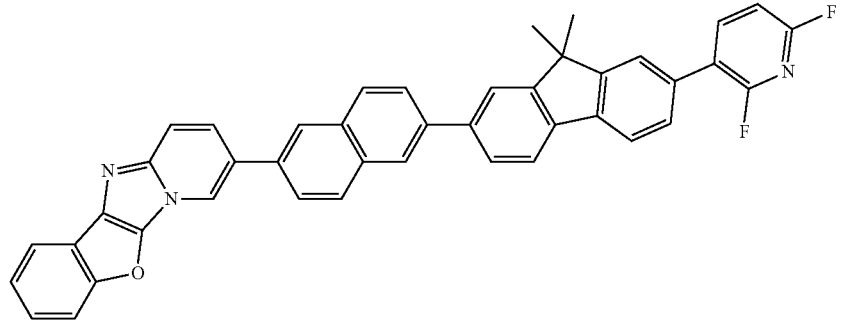
106

-continued
107
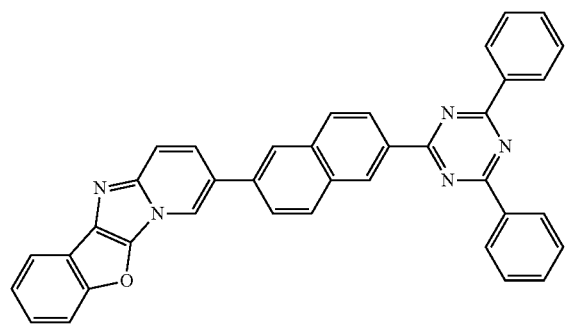
108
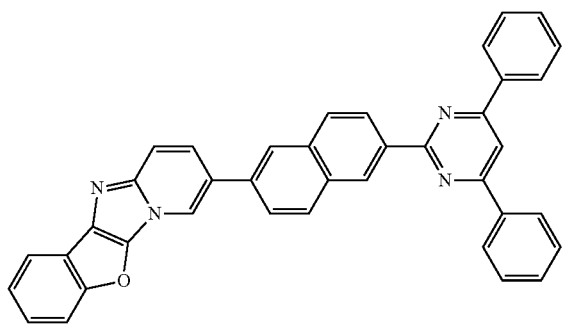
109
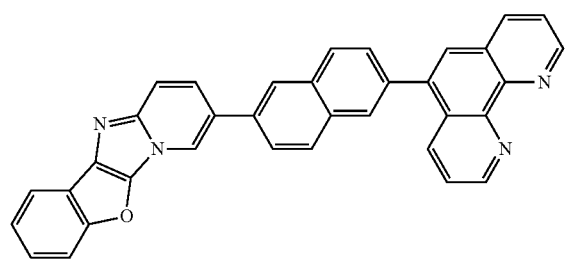
110
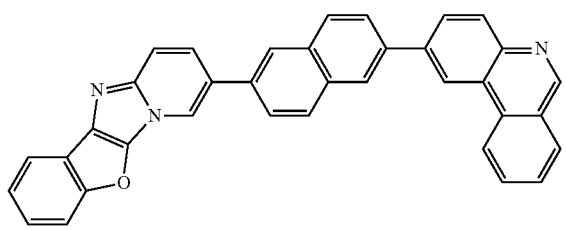
111
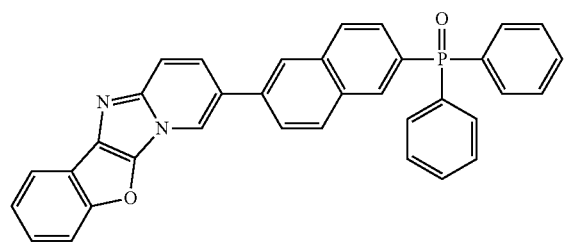
112
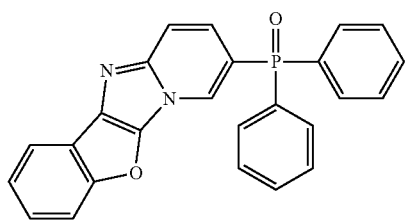
113
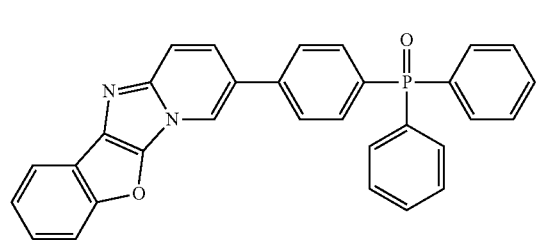
114
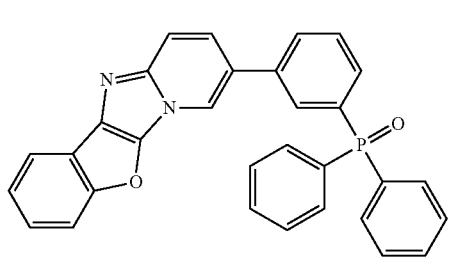
115
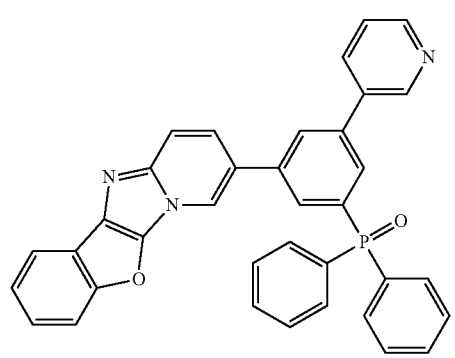
116
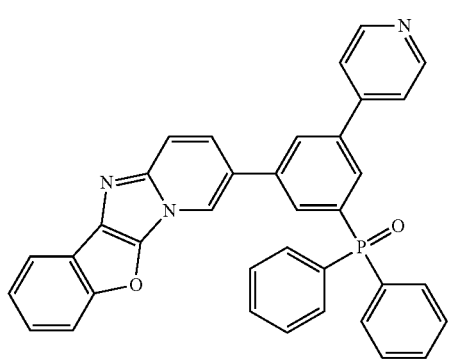

-continued
117
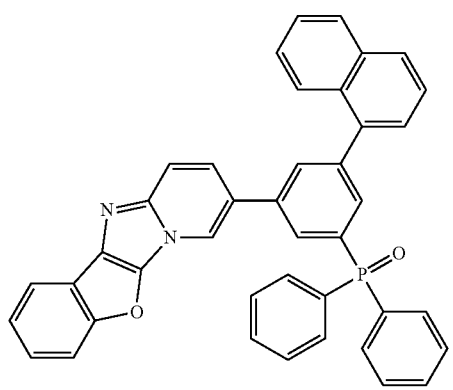
118
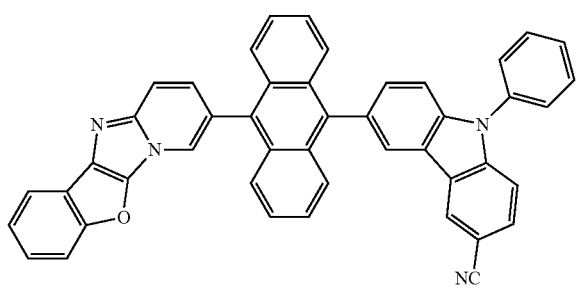
119
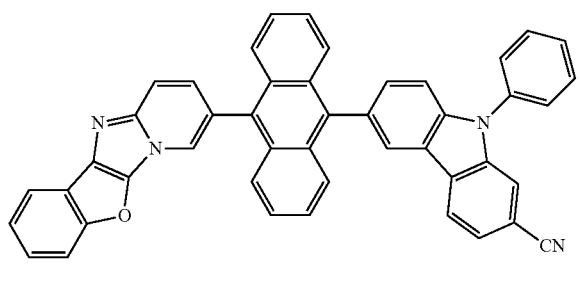
120
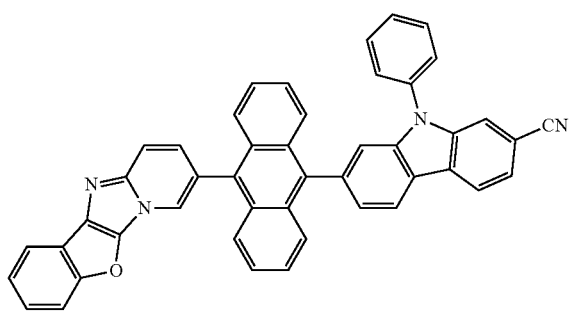
121
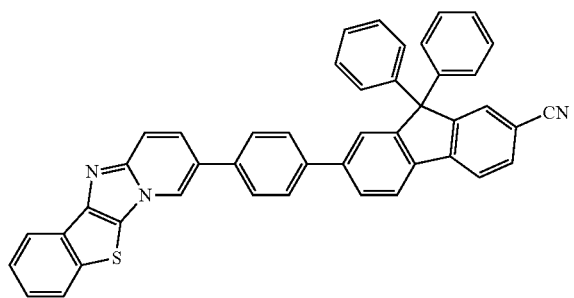
122
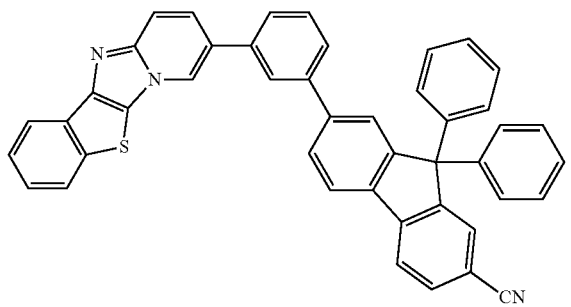
123
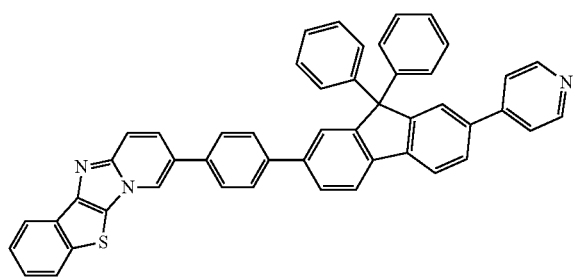
124
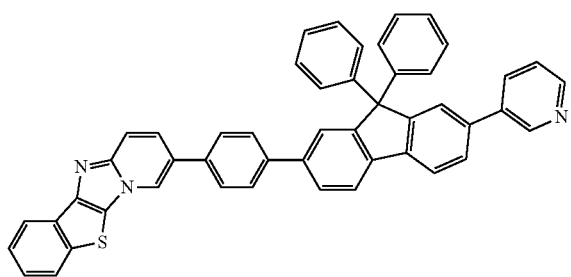

-continued
125
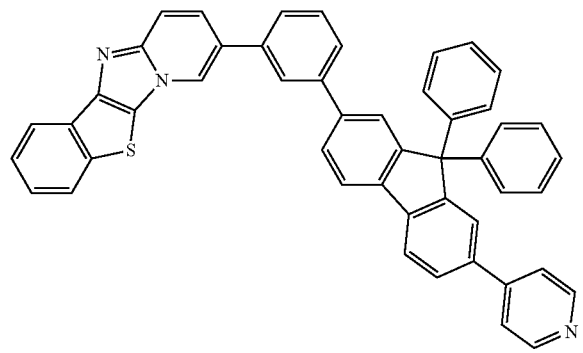
126
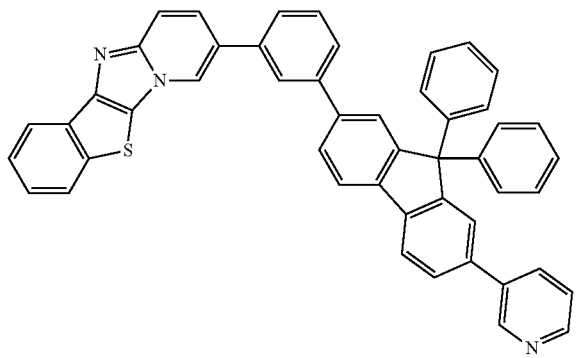
127
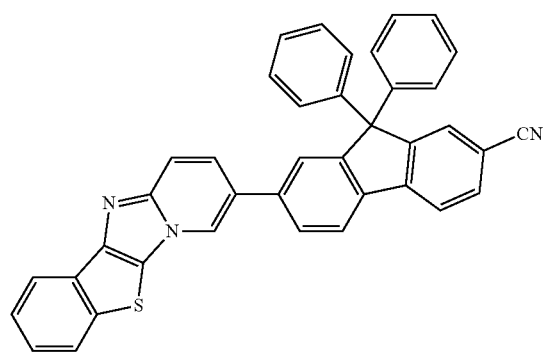
128
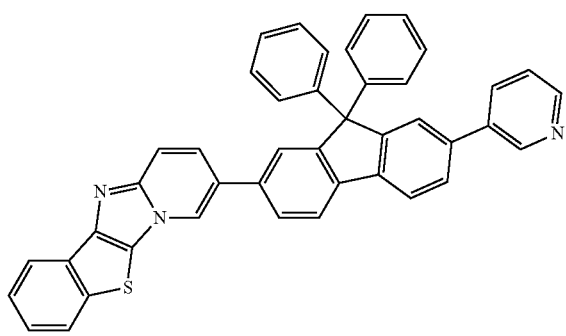
129
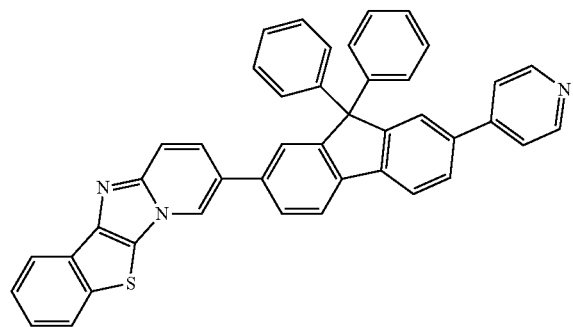
130
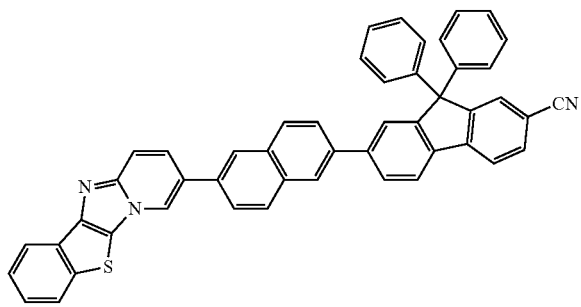
131
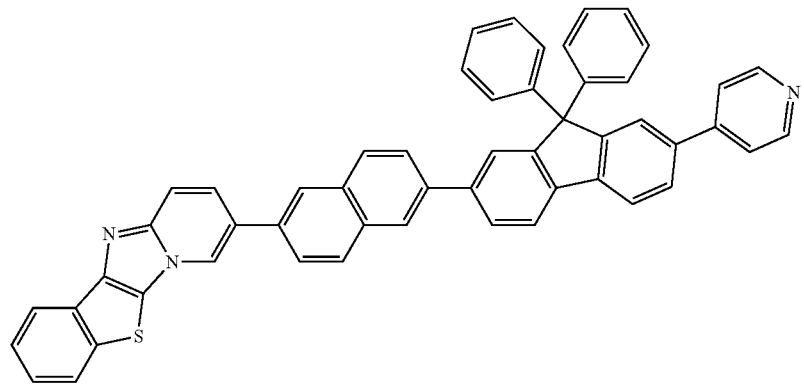

-continued
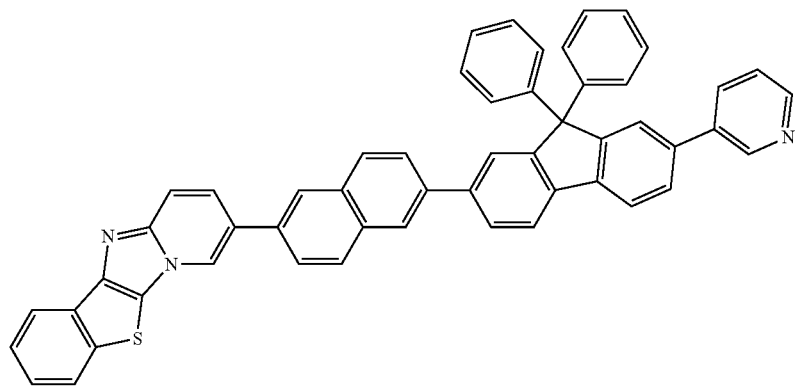
132
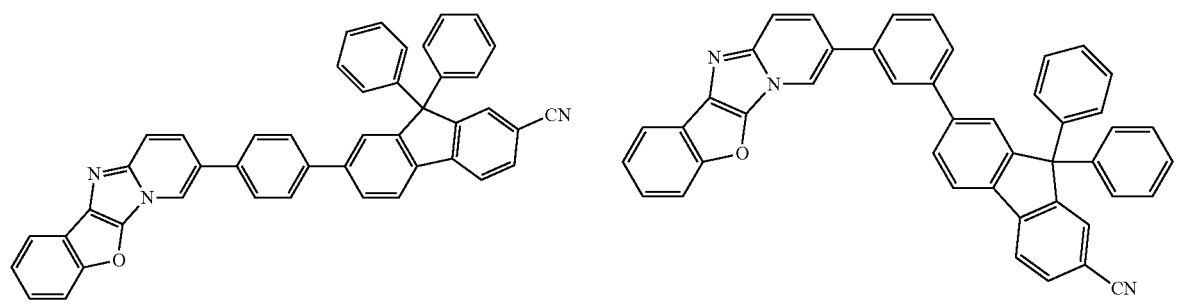
133 134
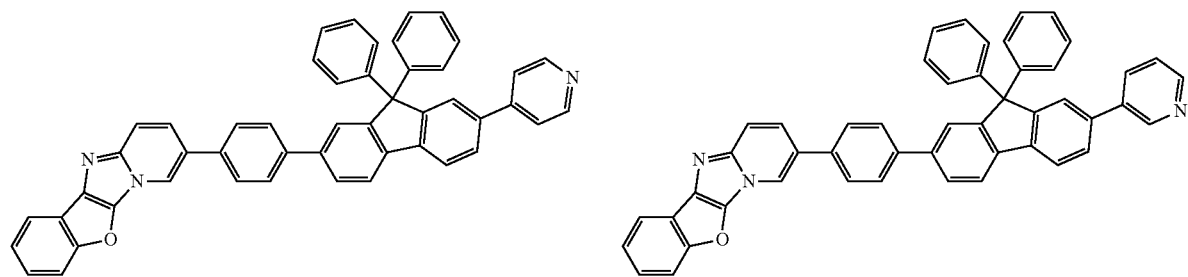
135 136
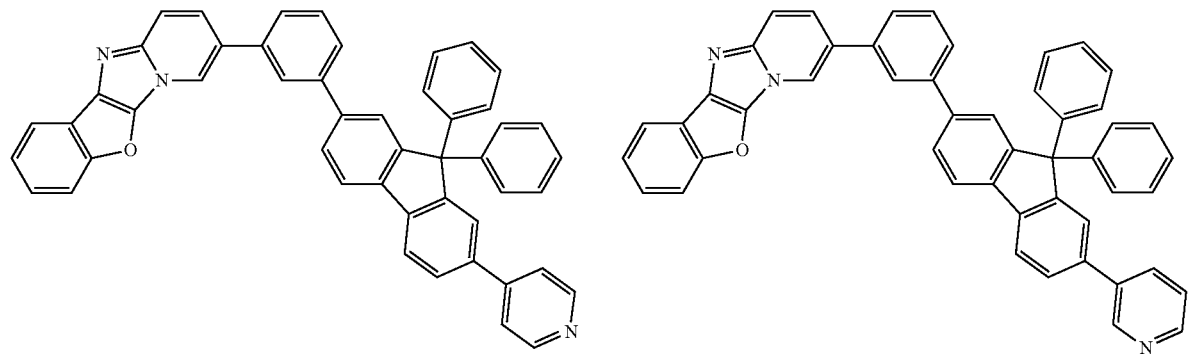
137 138

-continued
139
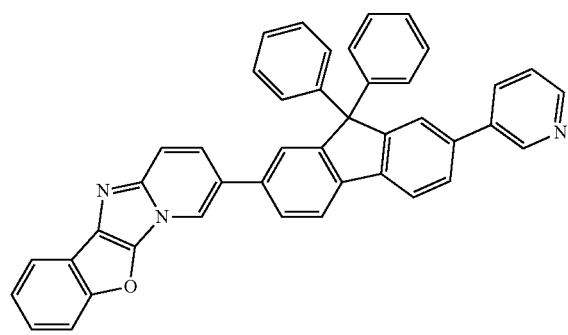
140
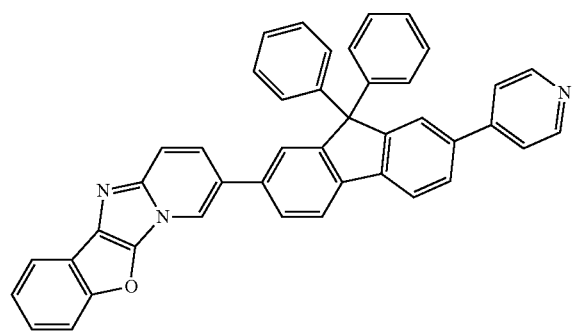
141
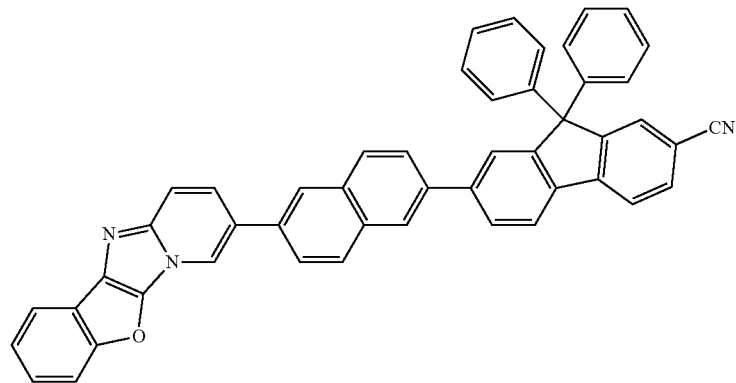
142
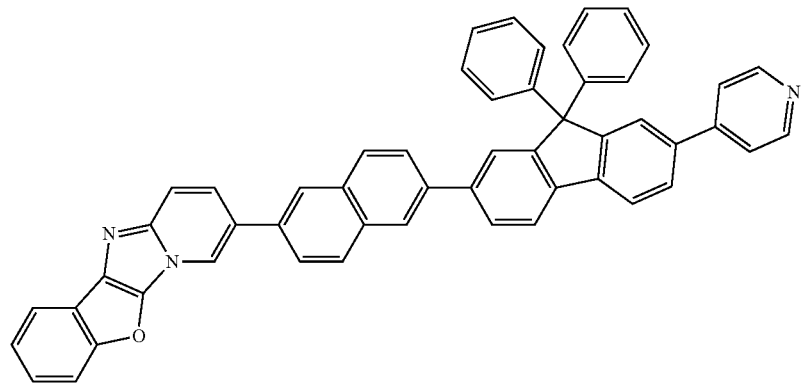
143
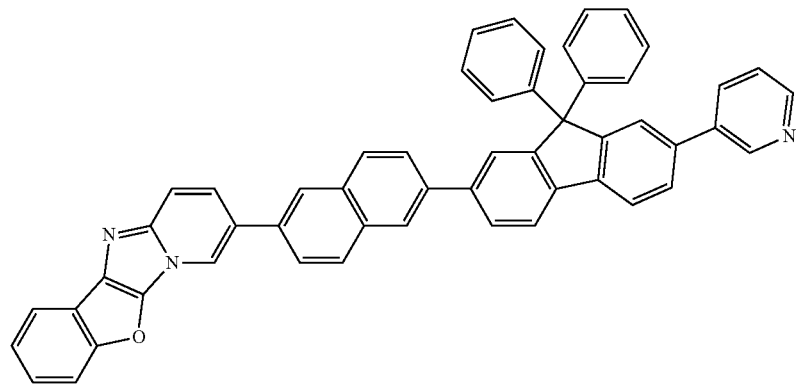

144
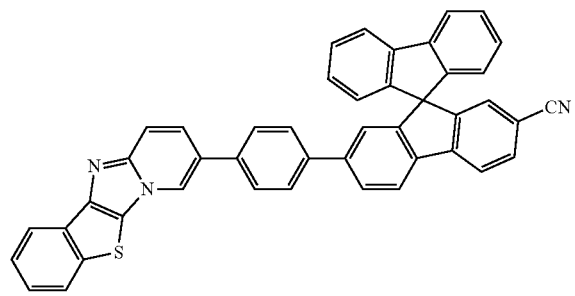
145
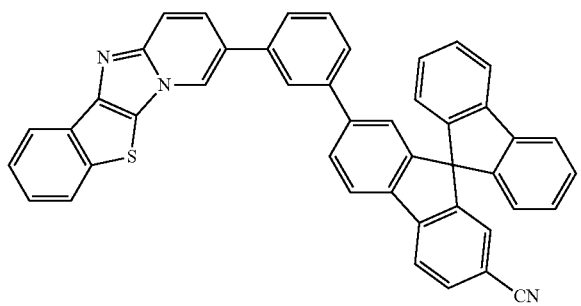
146
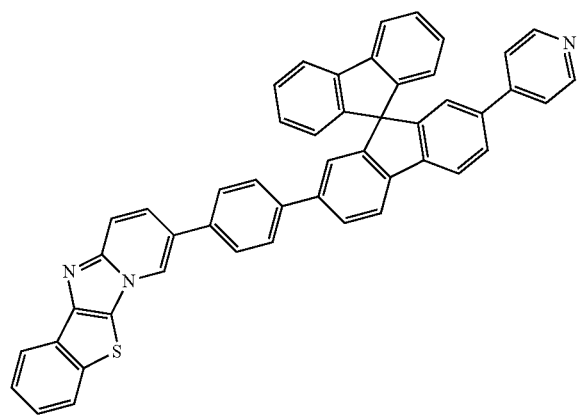
147
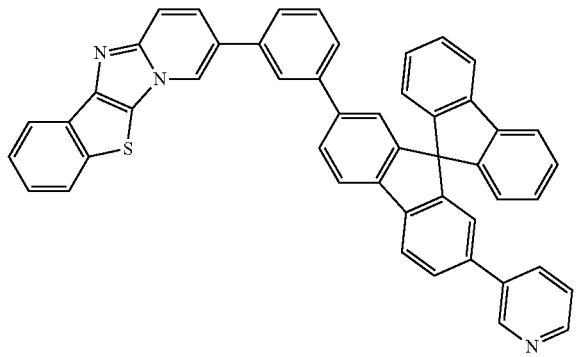
148
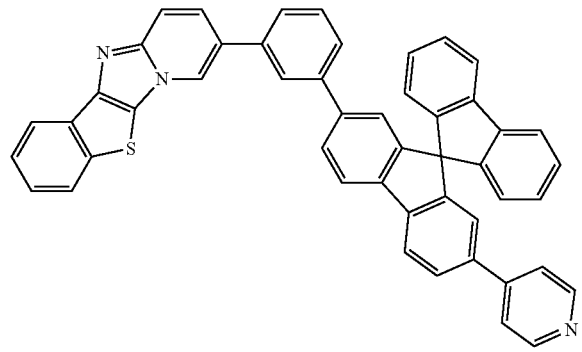
149
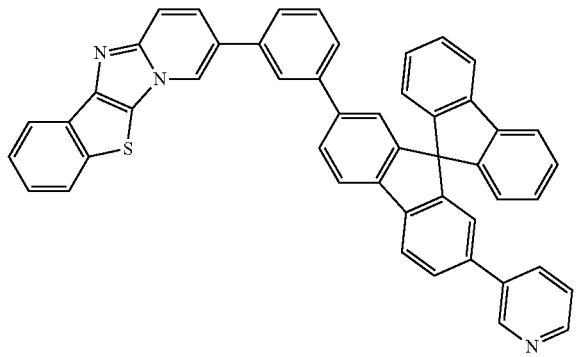
150
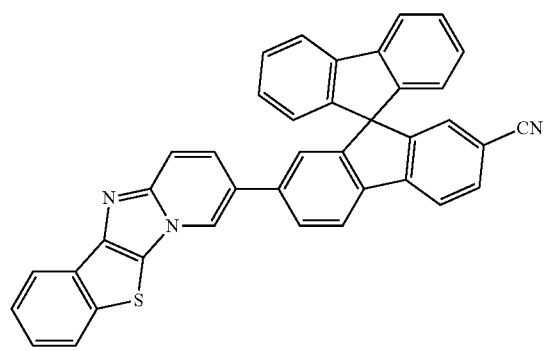
151
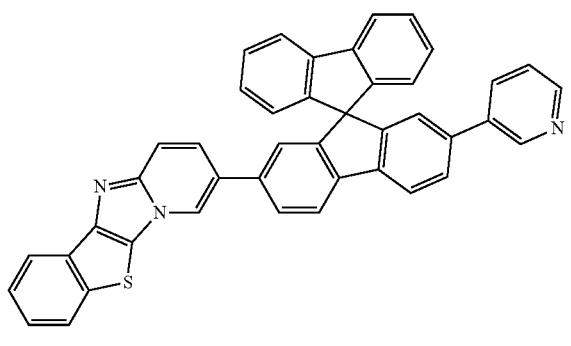

-continued
| 152 | 153 |
|---|---|
| 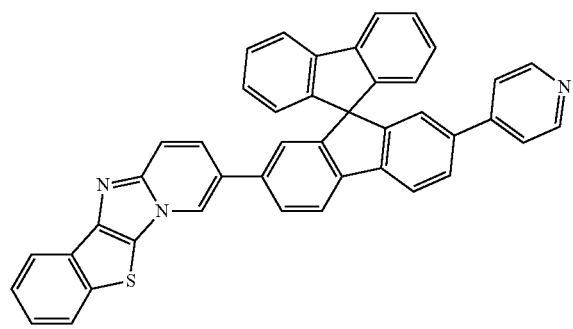 | 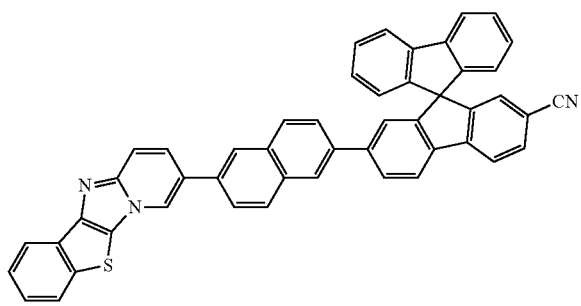 |
154
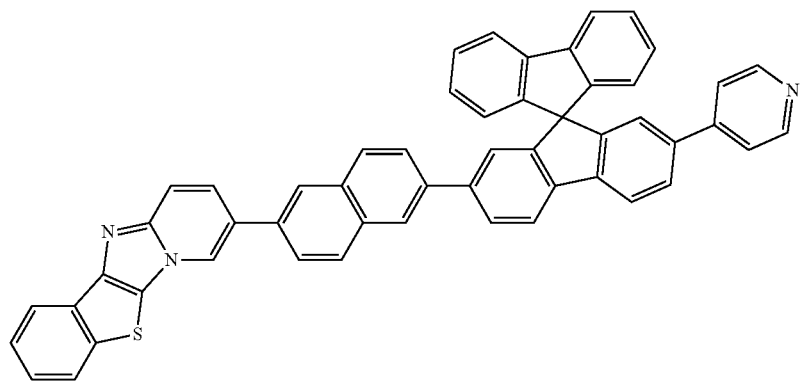
155
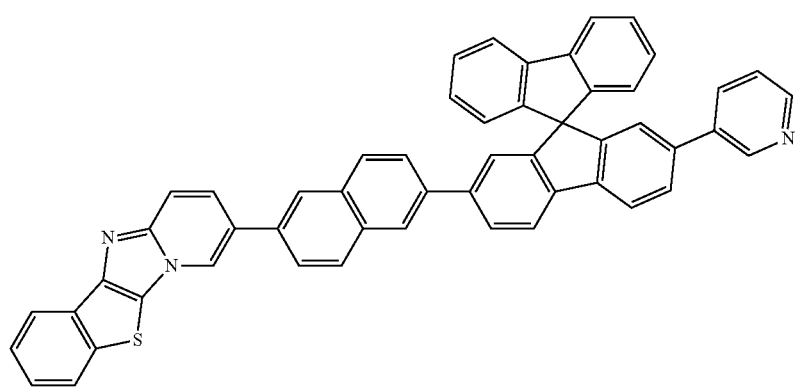
| 156 | 157 |
|---|---|
| 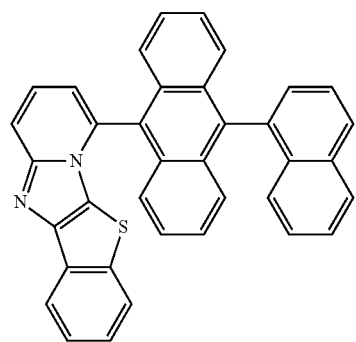 | 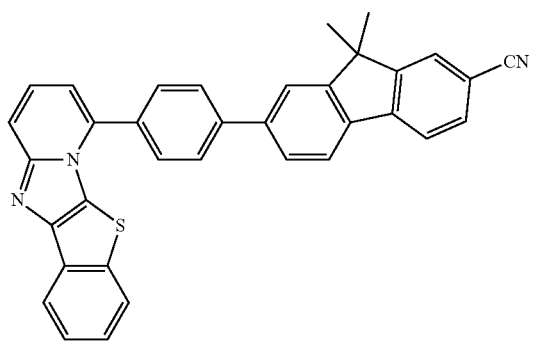 |

-continued
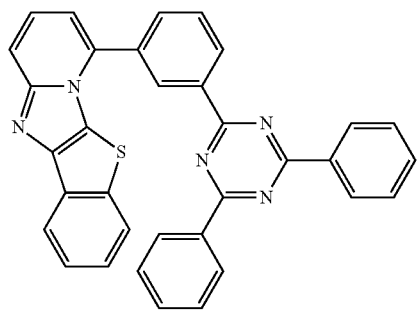
158
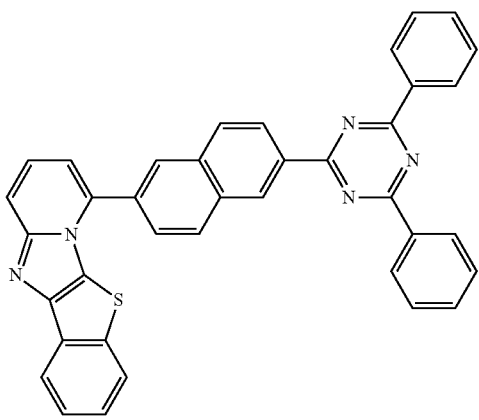
159
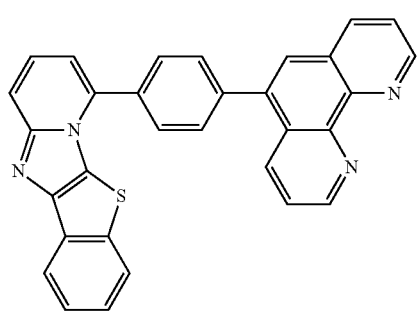
160
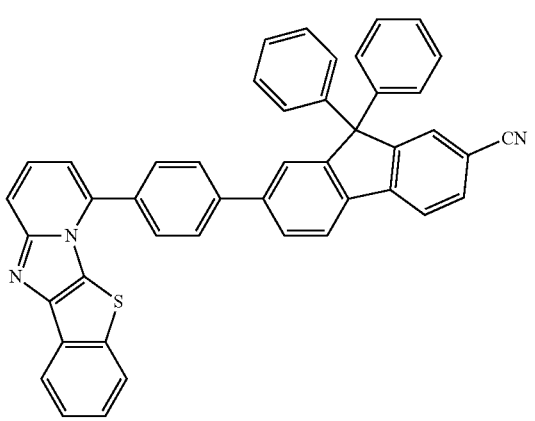
161
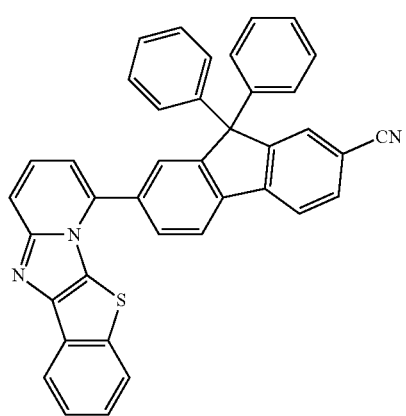
162
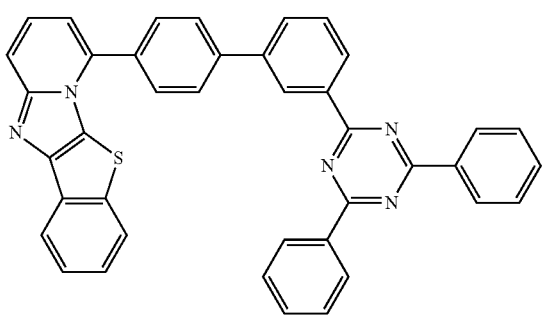
163

-continued
164
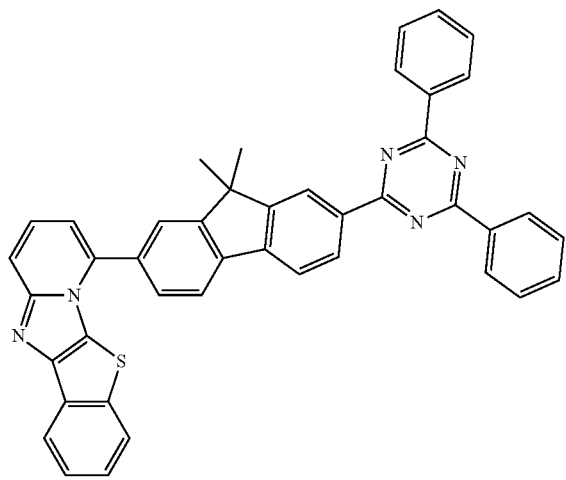
165
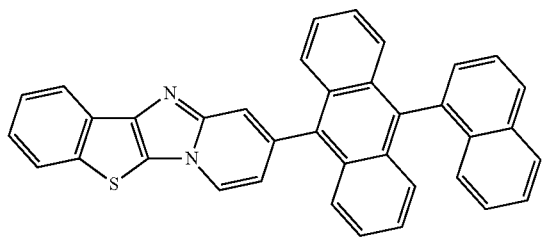
166
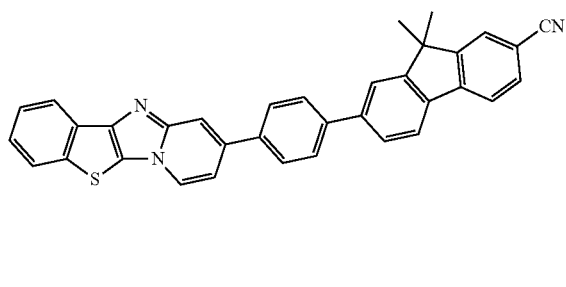
167
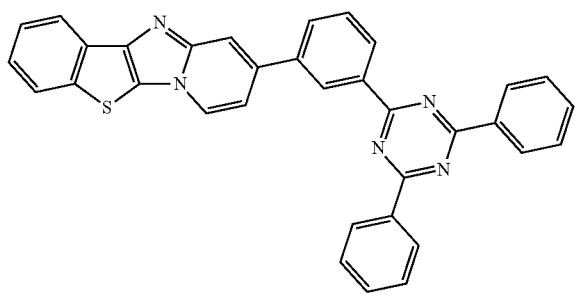
168
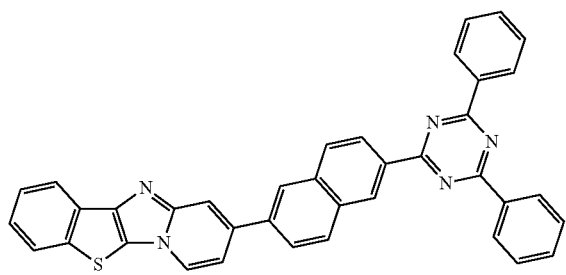
169
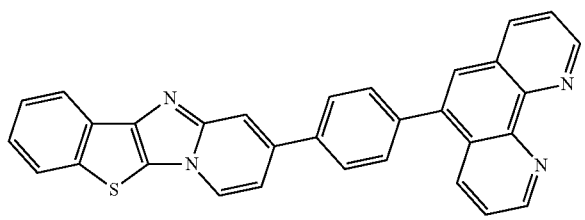
170
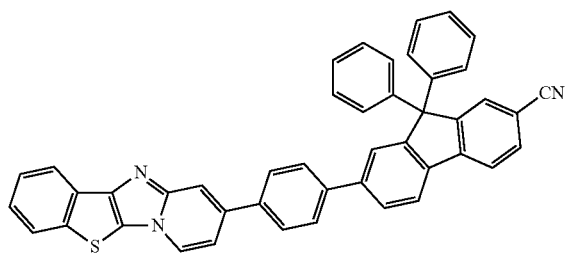
171
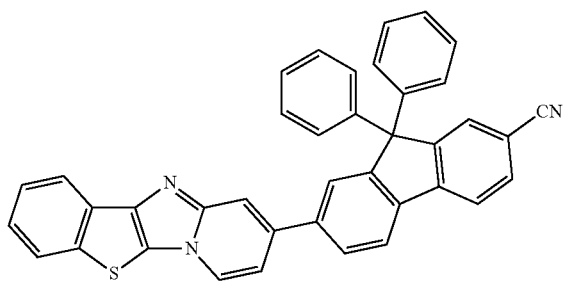

-continued
172
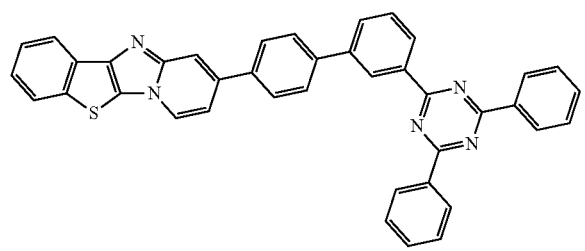
173
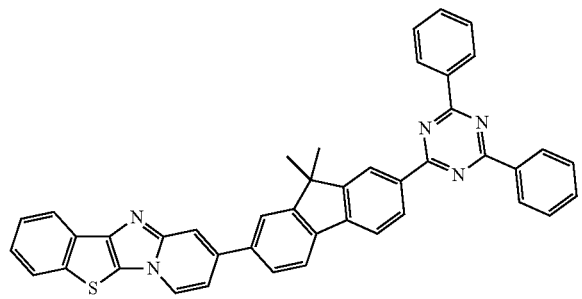
174
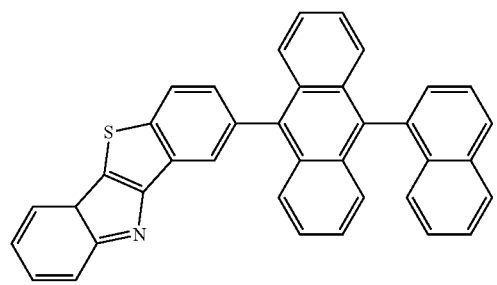
175
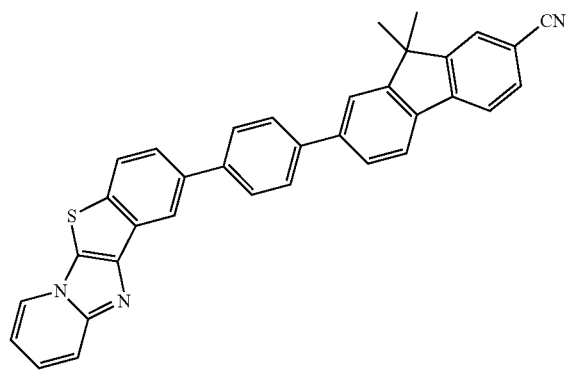
176
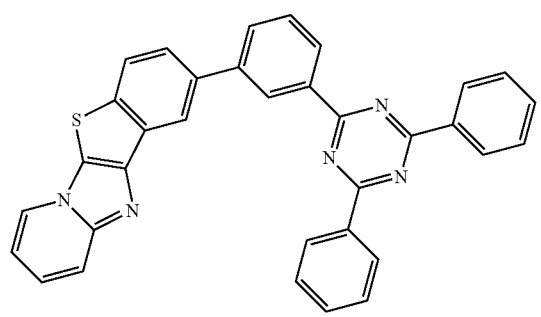
177
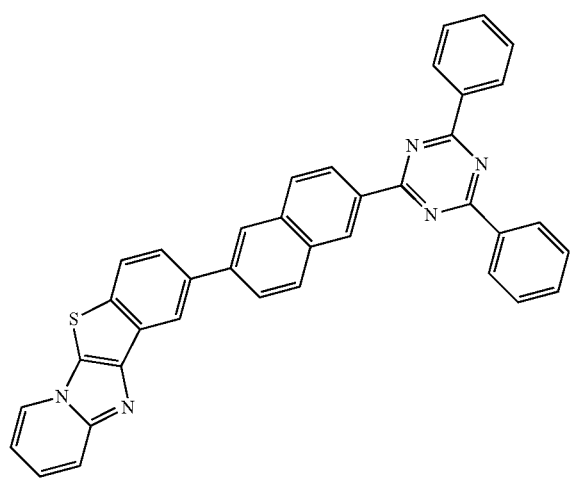

-continued
178
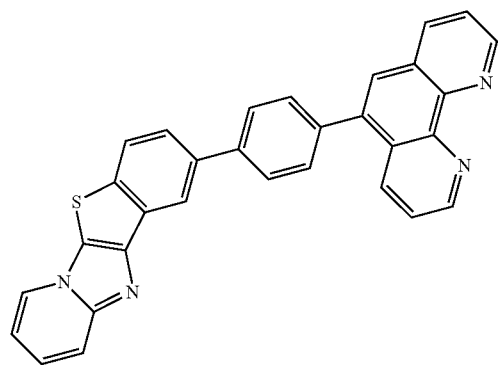
179
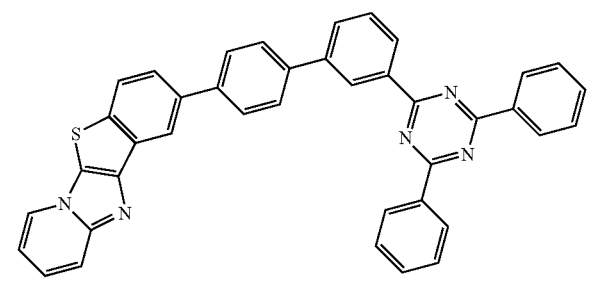
180
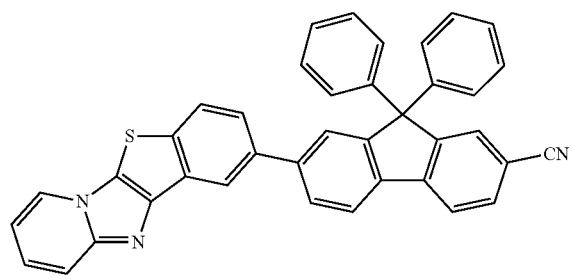
181
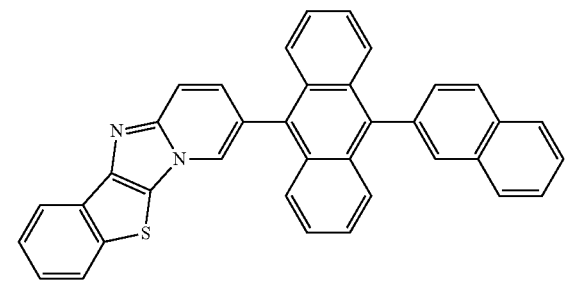
182
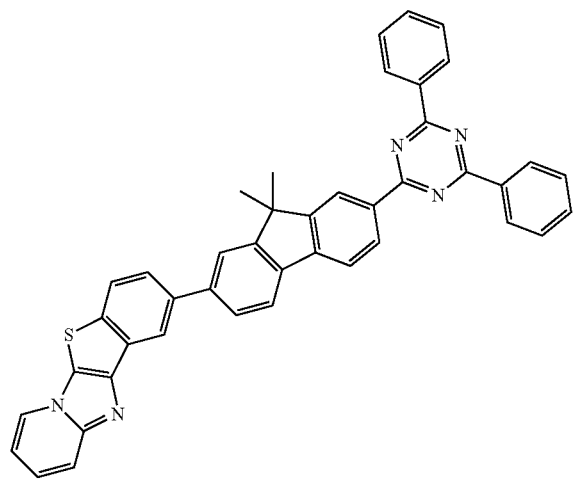
183
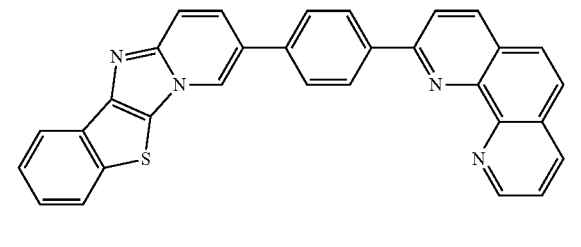
184
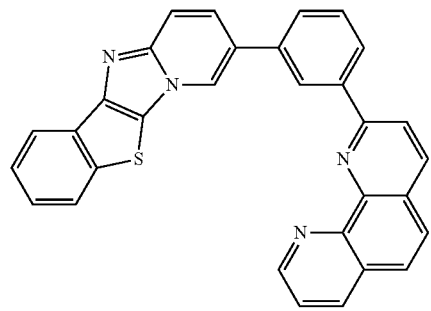
185
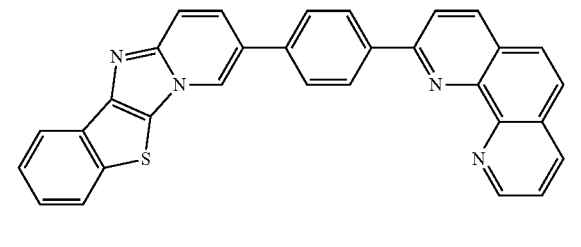

-continued
186
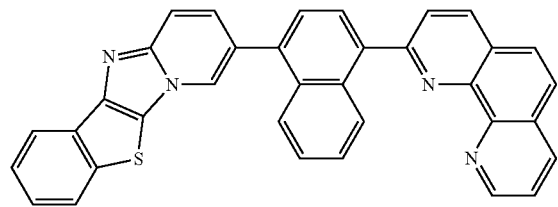
187
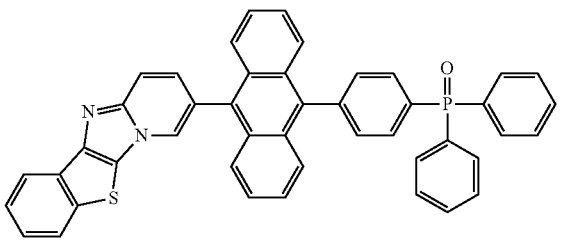
188
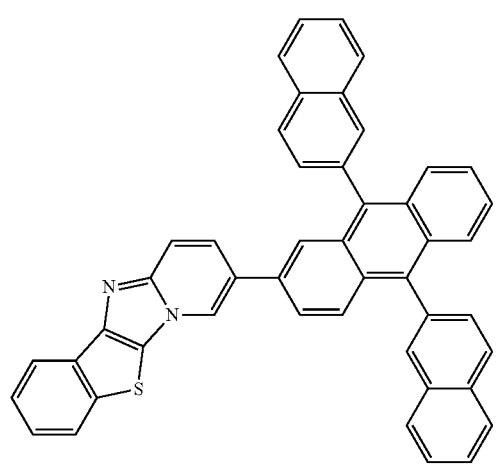
189
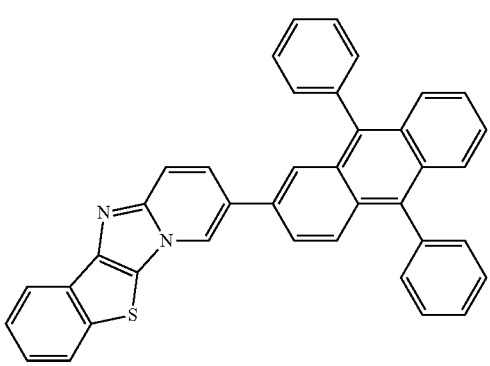
190
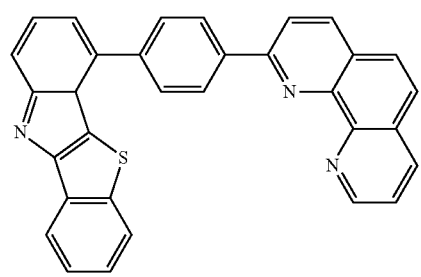
191
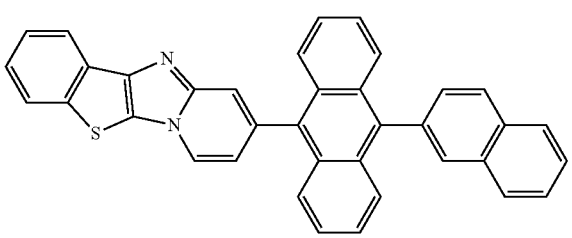
192
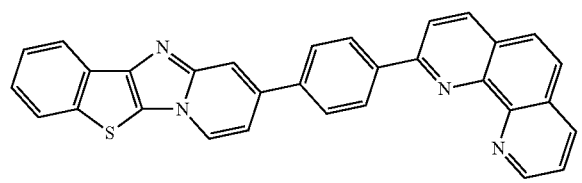
193
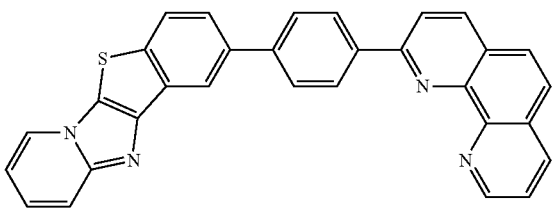

-continued
| 194 | 195 |
|---|---|
| 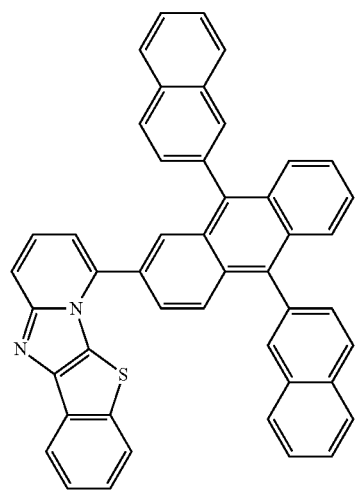 | 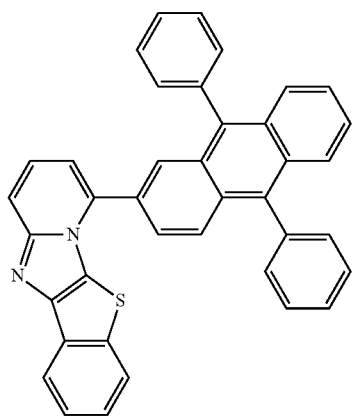 |
| 196 | 197 |
| 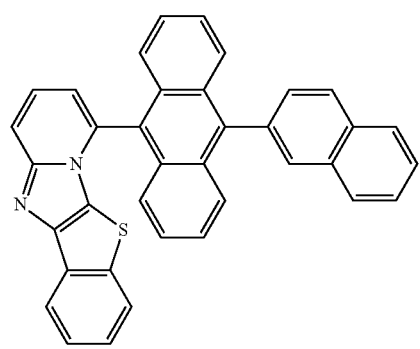 | 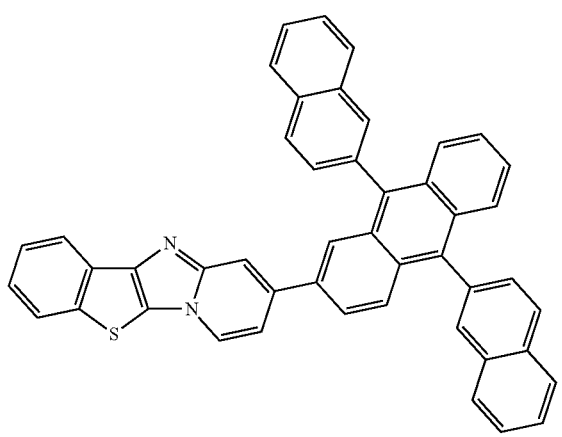 |
| 198 | 199 |
| 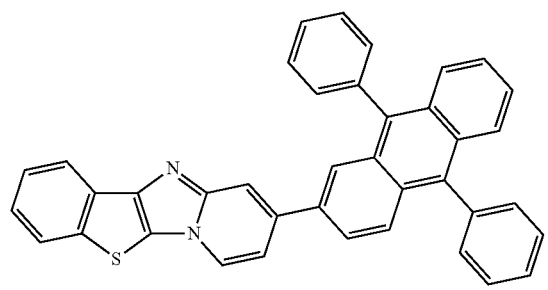 | 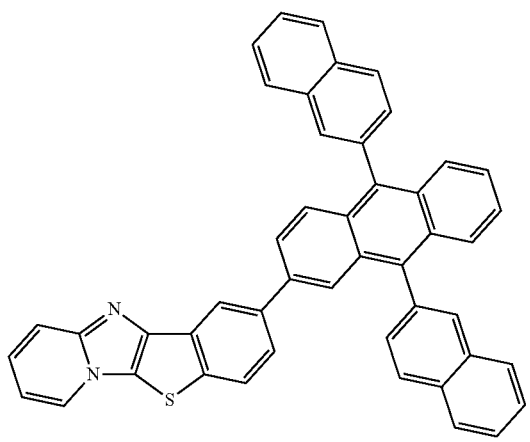 |

-continued
200
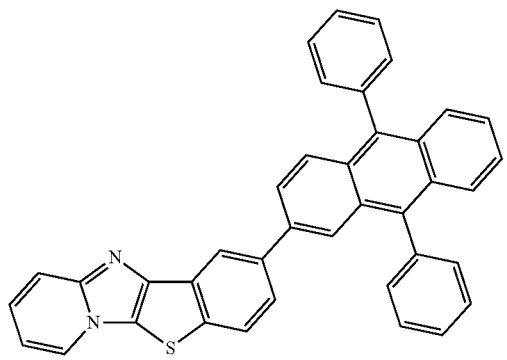
201
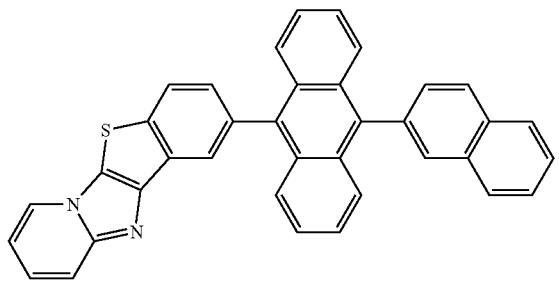
202
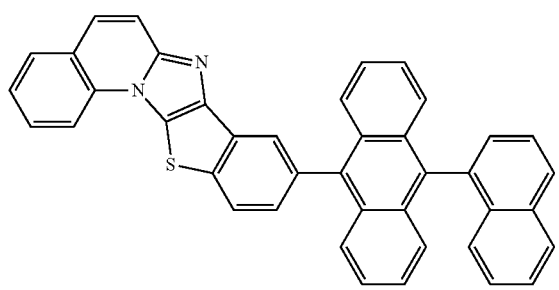
203
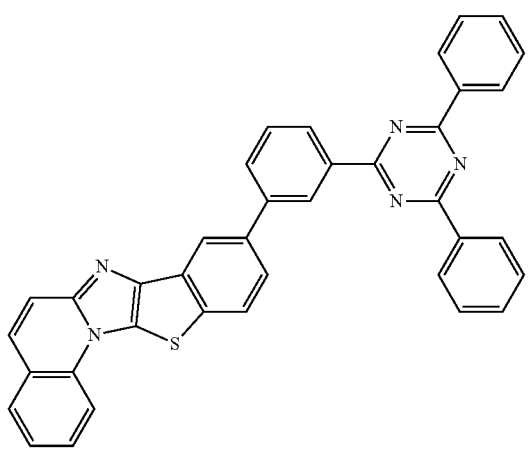
204
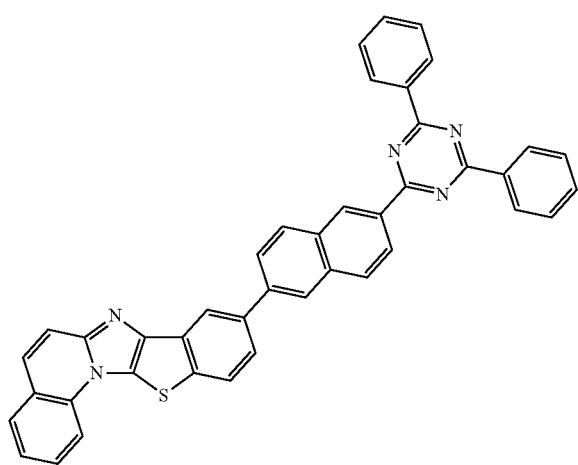
205
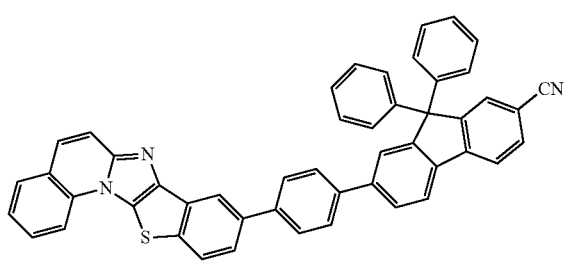

206

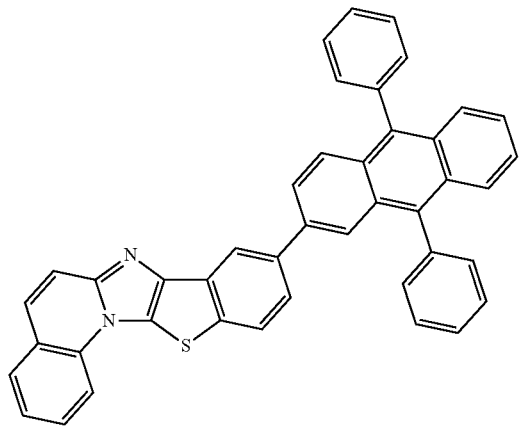

207

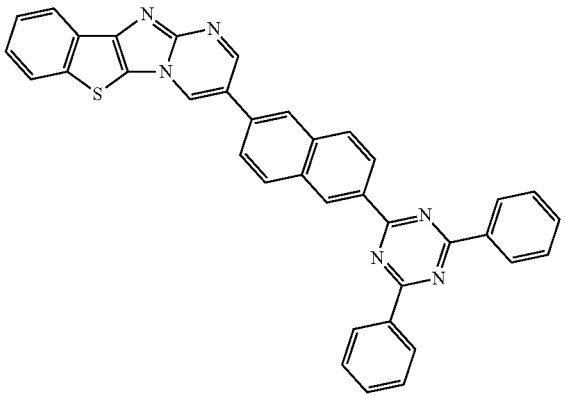

208

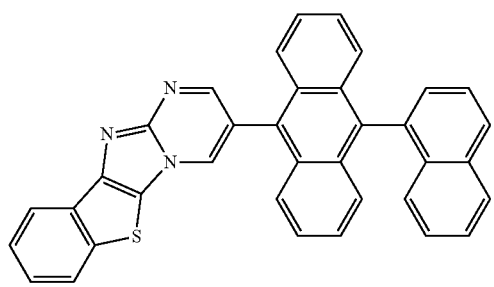

209

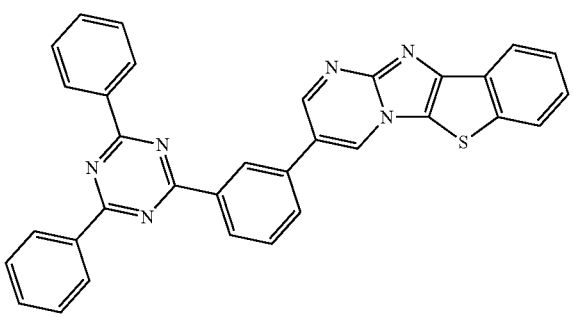

210

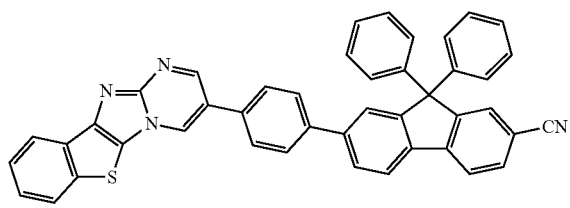

211

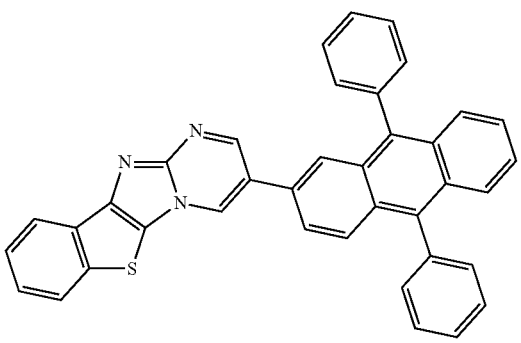

Since the condensed cyclic compound represented by Formula 1 includes a structure represented by

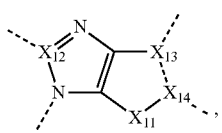

the condensed cyclic compound may be rigid. Thus, the condensed cyclic compound represented by Formula 1 may have enhanced physical, chemical, photochemical and/or electrochemical stability. Accordingly, an organic light-emitting device including the condensed cyclic compound represented by Formula 1 may exhibit long lifespan characteristics, enhanced storage stability, and/or enhanced reliability.

The condensed cyclic compound represented by Formula 1 includes at least two nitrogen atoms and one oxygen or sulfur atom in the structure represented by

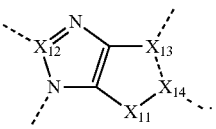

Due to the inclusion of the at least two nitrogen atoms, repulsion between hydrogen atoms included in a benzene ring may be reduced between neighboring molecules. Since a chalcogen atom such as O or S is included, an attraction between molecules may increase. Due to these two effects, molecules of the condensed cyclic compound may exhibit a dense packing tendency, resulting in an increase in charge mobility.

The condensed cyclic compound represented by Formula 1 has a structure in which two 5-membered rings are condensed with each other, like the structure represented by

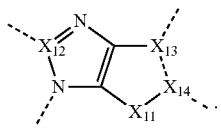

Accordingly, since hydrogen (for example, hydrogen of C—H) exists in the structure in which the two 5-membered rings are condensed with each other, steric hindrance caused by a neighboring hydrogen (for example, in the α-position) in a molecule may be excluded. Thus, condensed cyclic compound represented by Formula 1 has a planar structure and/or a rigid structure. Accordingly, an organic tight-emitting device including the condensed cyclic compound represented by Formula 1 may exhibit long lifespan characteristics, enhanced storage stability, and/or enhanced reliability.

The condensed cyclic compound of Formula 1 may be used between a pair of electrodes of an organic light-emitting device.

An exemplary embodiment of the present disclosure provides an organic light-emitting device that includes: a first electrode; a second electrode; and an organic layer between the first electrode and the second electrode, the organic layer including an emission layer, wherein the organic layer includes the condensed cyclic compound represented by Formula 1.

In an exemplary embodiment of the present disclosure, the first electrode may be an anode, the second electrode may be a cathode, the organic layer may further include an electron transport region between the second electrode and the emission layer, and the electron transport region may include the condensed cyclic compound, but the present disclosure is not limited thereto.

In an exemplary embodiment of the present disclosure, the electron transport region may further include an electron transport layer and an electron injection layer.

The electron transport layer may include the condensed cyclic compound, and the electron injection layer may include an alkali metal, an alkaline earth metal, a rare earth metal, an alkali metal compound, an alkaline earth metal compound, a rare earth metal compound, an alkali metal complex, an alkaline earth metal complex, a rare earth metal complex, or a combination thereof, but the present disclosure is not limited thereto.

The expression "(an organic layer) includes at least one condensed cyclic compound" used herein may include a case in which "(an organic layer) includes identical condensed cyclic compounds represented by Formula 1" and a case in which "(an organic layer) includes two or more different condensed cyclic compounds represented by Formula 1."

In an exemplary embodiment of the present disclosure, the organic layer may include, as the condensed cyclic compound, only Compound 1. In this regard, Compound 1 may exist in an emission layer of the organic light-emitting device. In an exemplary embodiment of the present disclosure, the organic layer may Include, as the condensed cyclic compound, Compound 1 and Compound 2. In this regard. Compound 1 and Compound 2 may exist in the same layer (for example, Compound 1 and Compound 2 may all exist in an electron transport layer), or different layers (for example, Compound 1 may exist in an electron transport layer and Compound 2 may exist in an emission layer).

The organic layer includes i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. At least one of the hole transport region and the emission layer may include at least one of the condensed cyclic compounds represented by Formula 1. In an exemplary embodiment of the present disclosure, the electron transport region of the organic light-emitting device may include at least one of the organometallic compounds represented by Formula 1.

The term "organic layer" used herein refers to a single layer and/or a plurality of layers disposed between the first electrode and the second electrode of the organic light-emitting device. A material included in the "organic layer" is not limited to an organic material.

[Description of FIG. 1]

FIG. 1 is a schematic view of an organic light-emitting device 10 according to an exemplary embodiment of the present disclosure. The organic light-emitting device 10 includes a first electrode 110, an organic layer 150, and a second electrode 190.

Hereinafter, the structure of the organic light-emitting device 10 according to an exemplary embodiment of the present disclosure and a method of manufacturing the organic light-emitting device 10 will be described in connection with FIG. 1.

[First Electrode 110]

In FIG. 1, a substrate may be additionally disposed under the first electrode 110 or above the second electrode 190. The substrate may be a glass substrate or a plastic substrate, each having excellent mechanical strength, thermal stability, transparency, surface smoothness, ease of handling, and water-resistance.

The first electrode 110 may be formed by depositing or sputtering a material for forming the first electrode 110 on the substrate. When the first electrode 110 is an anode, the material (or the first electrode 110 may be selected from materials with high work function to facilitate hole injection.

The first electrode 110 may be a reflective electrode, a semi-transmissive electrode, or a transmissive electrode. When the first electrode 110 is a transmissible electrode, a material for forming the first electrode 110 may be selected from indium tin oxide (ITO), indium zinc oxide (IZO), tin oxide ($SnO_2$), zinc oxide (ZnO), and any combinations thereof, but the present disclosure is not limited thereto. In an exemplary embodiment of the present disclosure, when the first electrode 110 is a semi-transmissible electrode or a resectable electrode, a material for forming the first electrode 110 may be selected from magnesium (Mg), silver (Ag), aluminum (Al), aluminum-lithium (Al—Li), calcium (Ca), magnesium-indium (Mg—In), magnesium-silver (Mg—Ag), and any combinations thereof, but the present disclosure is not limited thereto.

The first electrode 110 may have a single-layered structure, or a multi-layered structure including two or more layers. For example, the first electrode 110 may have a three-layered structure of ITO/Ag/ITO, but the present disclosure is not limited thereto.

[Organic Layer 150]

The organic layer 150 is disposed on the first electrode 110. The organic layer 150 may include an emission layer.

The organic layer 150 may further include a hole transport region disposed between the first electrode 110 and the emission layer, and an electron transport region disposed between the emission layer and the second electrode 190.

[Hole Transport Region in Organic Layer 150]

The hole transport region may have i) a single-layered structure including a single layer which includes a single material, ii) a single-layered structure including a single layer which includes a plurality of different materials, or iii) a multi-layered structure having a plurality of layers which include a plurality of different materials.

The hole transport region may include at least one layer selected from a hole injection layer (HIL), a hole transport layer (HTL), an emission auxiliary layer, and an electron blocking layer (EBL).

In an exemplary embodiment of the present disclosure, the hole transport region may have a single-layered structure including a single layer which includes a plurality of different materials, or a multi-layered structure having a hole injection layer/hole transport layer structure, a hole injection layer/hole transport layer/emission auxiliary layer structure, a hole injection layer/emission auxiliary layer structure, a hole transport layer/emission auxiliary layer structure, or a hole injection layer/hole transport layer/electron blocking layer structure, in which for each structure, constituting layers are sequentially stacked on and from the first electrode 110 in this stated order, but the present disclosure is not limited thereto.

The hole transport region may include at least one selected from 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), N,N'-di (naphthalene-1-yl)-N,N'-diphenylbenzidine (NPB, NPD), β-NPB, N,N'-bis(3-methylphenyl)-N,N'-diphenyl-[1,1'-biphenyl]4,4'-diamine (TPD), Spiro-TPD, Spiro-NPB, methylated-NPB, 4,4'-cyclohexylidenebis[N,N-bis(4-methylphenyl)benzenamine] (TAPC), 4,4'-bis[N,N'-(3-tolyl)amino]-3,3'-dimethylbiphenyl (HMTPD), 4,4',4''-tris(N-carbazolyl) triphenylamine (TCTA), polyaniline/ dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (Pani/PSS), a compound represented by Formula 201, and a compound represented by Formula 202:

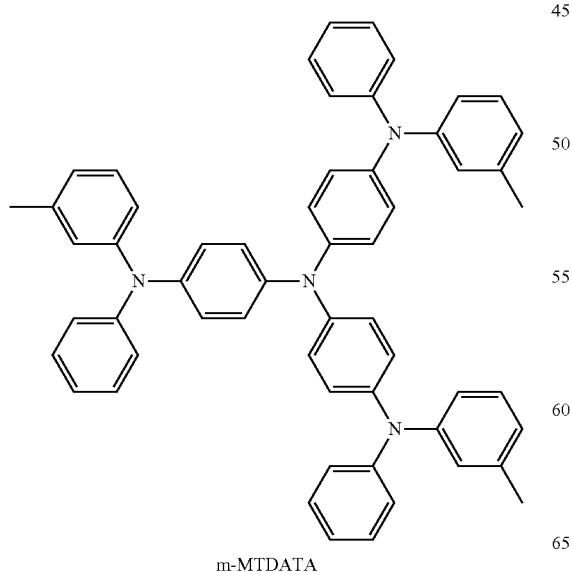

m-MTDATA

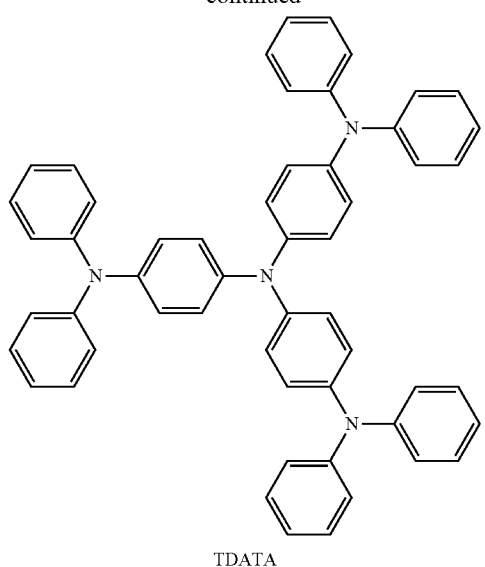

TDATA

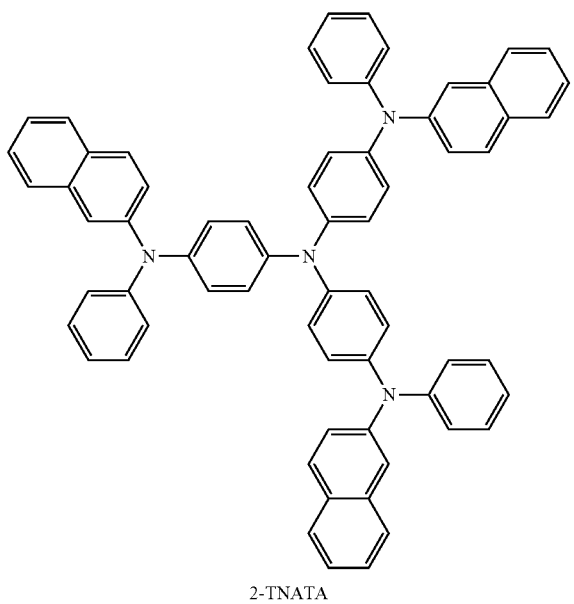

2-TNATA

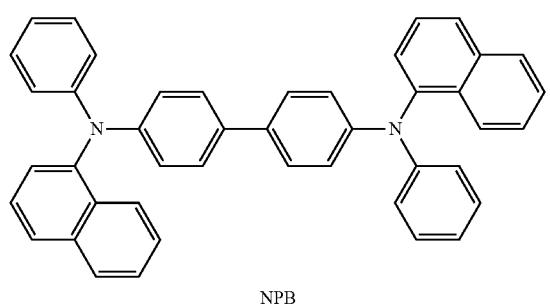

NPB

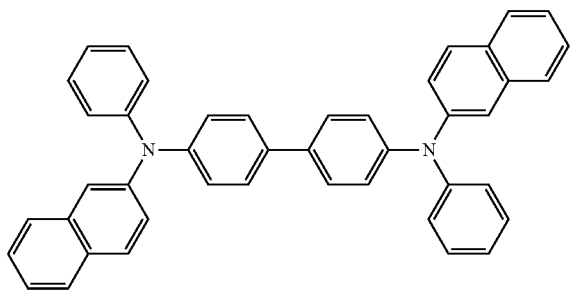
β-NPB

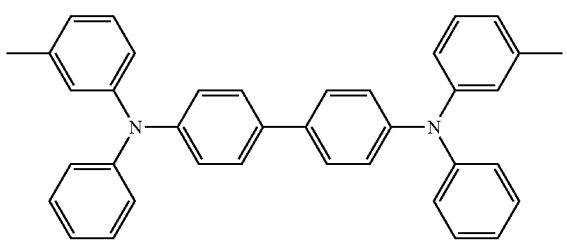
TPD

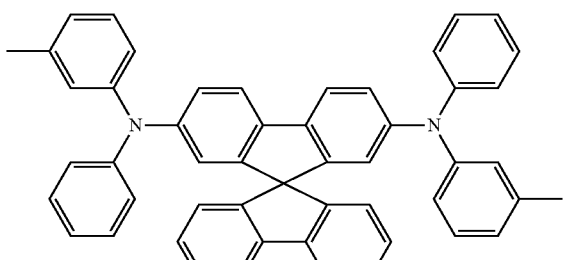
Spiro-TPD

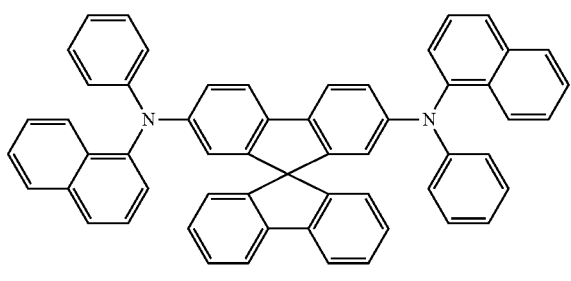
Spiro-NPB

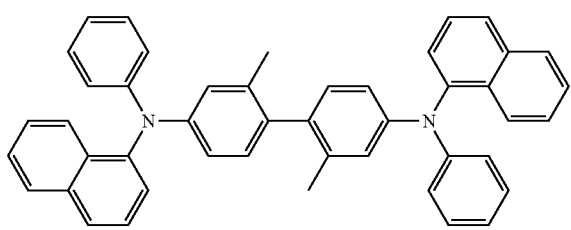
methylated NPB

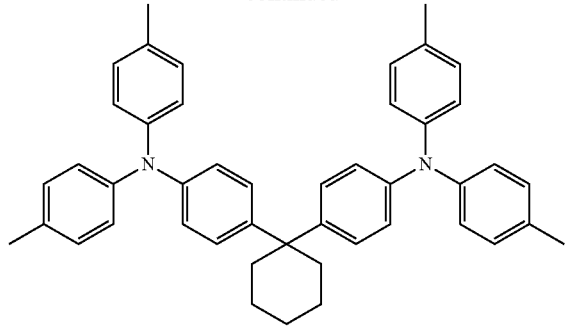
TAPC

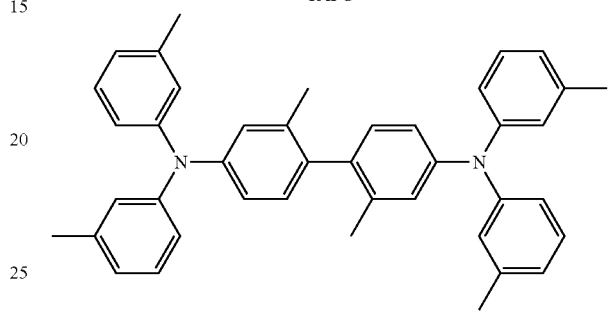
HMTPD

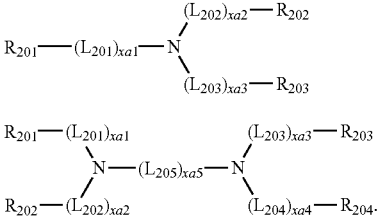

<Formula 201>

<Formula 202>

In Formulae 201 and 202, $L_{201}$ to $L_{204}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

$L_{205}$ may be selected from *—O—*', *—S—', *—N($Q_{201}$)-*', a substituted or unsubstituted $C_1$-$C_{20}$ alkylene group, a substituted or unsubstituted $C_2$-$C_{20}$ alkenylene group, a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xa1 to xa4 may each independently be an integer from 0 to 3, xa5 may be an integer from 1 to 10, $R_{201}$ to $R_{204}$ and $Q_{201}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In an exemplary embodiment of the present disclosure, in Formula 202, $R_{201}$ and $R_{202}$ may optionally be linked via a single bond, a dimethyl-methylene group, or a diphenyl-methylene group, and $R_{203}$ and $R_{204}$ may optionally be linked via a single bond, a dimethyl-methylene group, or a diphenyl-methylene group.

In an exemplary embodiment of the present disclosure, in Formulae 201 and 202.

$L_{201}$ to $L_{205}$ may each independently be selected from:

a phenylene group, a pentalenylene group, an indenylene group, a naphthylene group, an azulenylene group, a heptalenylene group, an indacenylene group, an acenaphthyene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group;

a phenylene group, a pentalenylene group, an indenylene group, a naphthylene group, an azulenylene group, a heptalenylene group, an indacenylene group, an acenaphthylene group, a fluorenylene group, a spiro-bifluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$); and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an exemplary embodiment of the present disclosure, xa1 to xa4 may each independently be 0, 1, or 2.

In an exemplary embodiment of the present disclosure, xa5 may be 1, 2, 3, or 4.

In an exemplary embodiment of the present disclosure, $R_{201}$ to $R_{204}$ and $Q_{201}$ may each independently be selected from a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group;

a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, —Si($Q_{31}$)($Q_{32}$)($Q_{33}$), and —N($Q_{31}$)($Q_{32}$); and $Q_{31}$ to $Q_{33}$ may be the same as described above.

In an exemplary embodiment of the present disclosure, at least one from $R_{201}$ to $R_{203}$ in Formula 201 may each independently be selected from:

a fluorenyl group, a spiro-bifluorenyl group, a carbazolyl group, a dibenzofuranyl group and a dibenzothiophenyl group; and a fluorenyl group, a spiro-bifluorenyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group, and a dibenzothiophenyl group, but the present disclosure is not limited thereto.

In an exemplary embodiment of the present disclosure, in Formula 202, i) $R_{201}$ and $R_{202}$ may be linked via a single bond, and/or ii) $R_{203}$ and $R_{204}$ may be linked via a single bond.

In an exemplary embodiment of the present disclosure, at least one from $R_{201}$ to $R_{204}$ in Formula 202 may be selected from:

a carbazolyl group; and a carbazolyl group, substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a naphthyl group, a fluorenyl group, a spiro-bifluorenyl group, a carbazolyl group, a dibenzofuranyl group and a dibenzothiophenyl group, but the present disclosure is not limited thereto.

The compound represented by Formula 201 may be represented by Formula 201A:

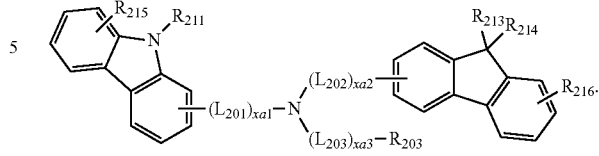

<Formula 201A>

In an exemplary embodiment of the present disclosure, the compound represented by Formula 201 may be represented by Formula 201A(1) below, but the present disclosure is not limited thereto:

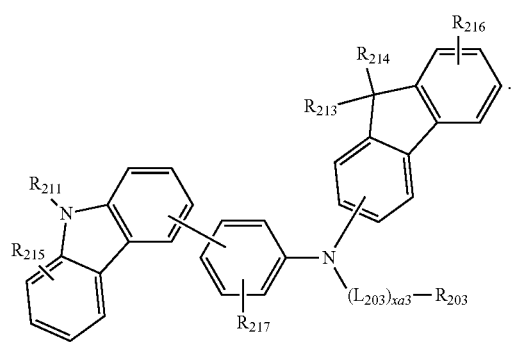

<Formula 201A(1)>

In an exemplary embodiment of the present disclosure, the compound represented by Formula 201 may be represented by Formula 201A-1 below, but the present disclosure is not limited thereto:

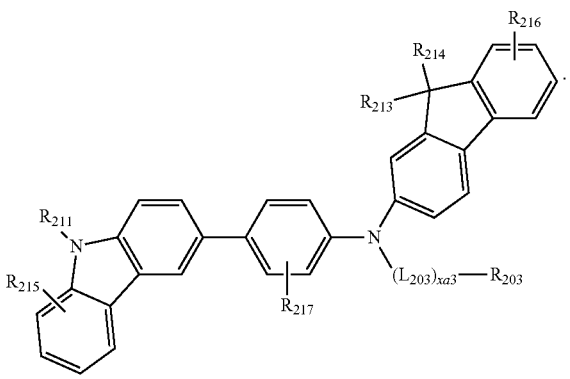

<Formula 201A-1>

In an exemplary embodiment of the present disclosure, the compound represented by Formula 202 may be represented by Formula 202A:

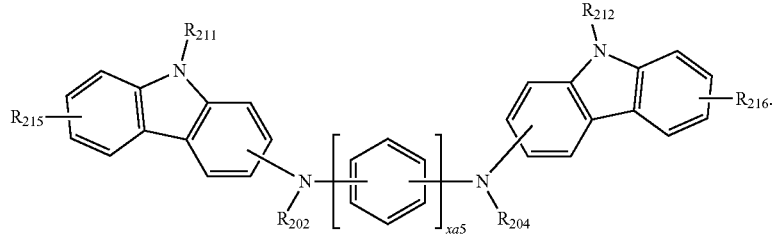

In an exemplary embodiment of the present disclosure, the compound represented by Formula 202 may be represented by Formula 202A-1:

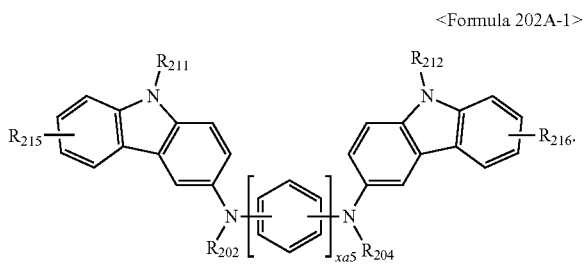

In Formulae 201A, 201A(1), 201A-1, 202A, and 202A-1, $L_{201}$ to $L_{203}$, xa1 to xa3, xa5 and $R_{202}$ to $R_{204}$ may be the same as described above, $R_{211}$ and $R_{212}$ may be the same as described in connection with $R_{203}$, and $R_{213}$ to $R_{217}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a phenyl group substituted with a $C_1$-$C_{10}$ alkyl group, a phenyl group substituted with —F, a pentalenyl group, an indenyl group, a naphthyl group, an azulenyl group, a heptalenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

The hole transport region may include at least one compound selected from Compounds HT1 to HT39, but the present disclosure is not limited thereto:

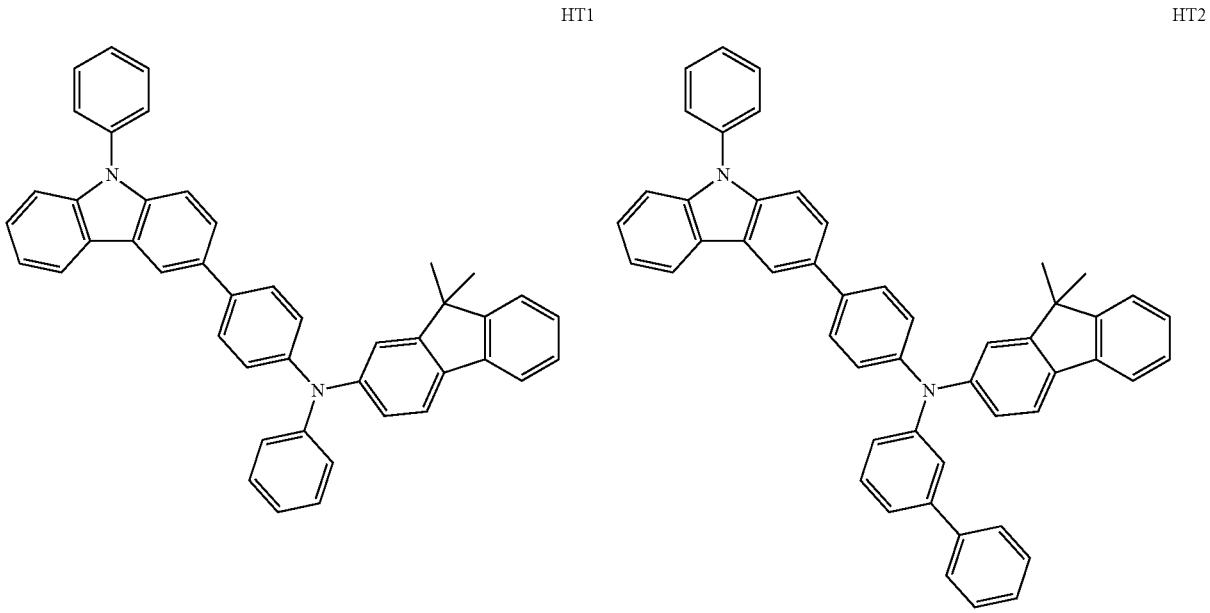

HT3
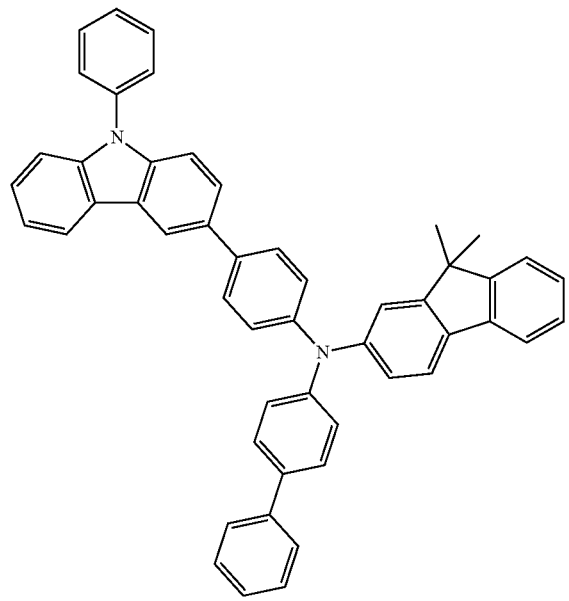
HT4
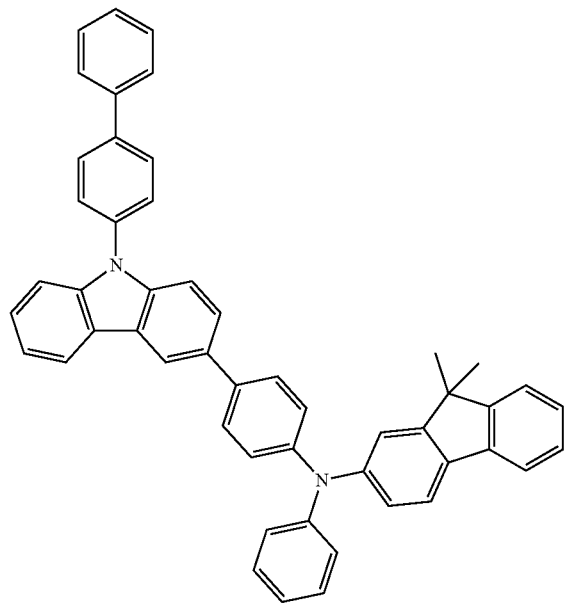
HT5
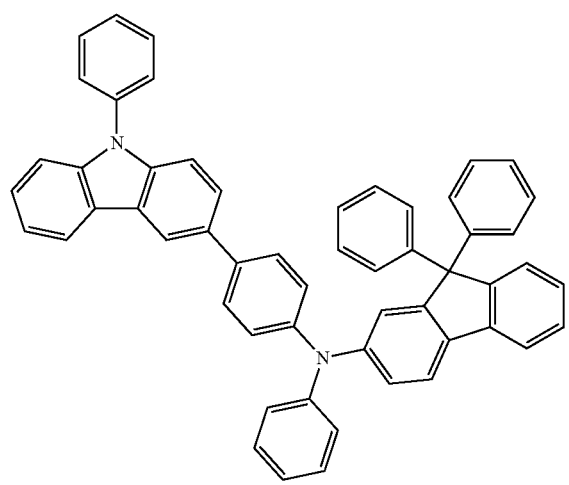
HT6
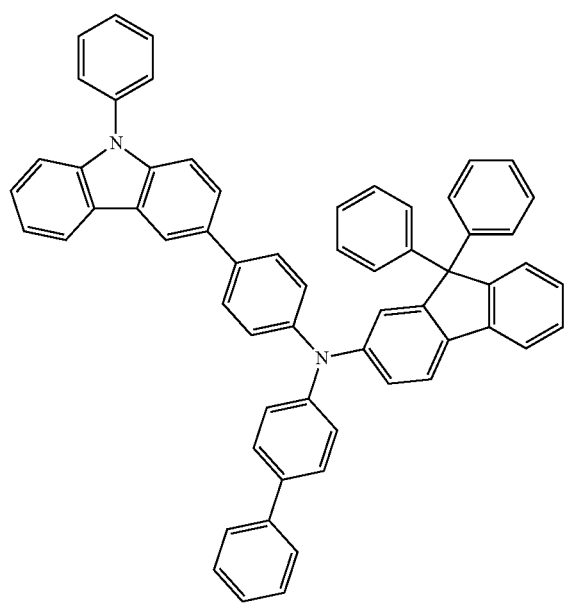

-continued
HT7
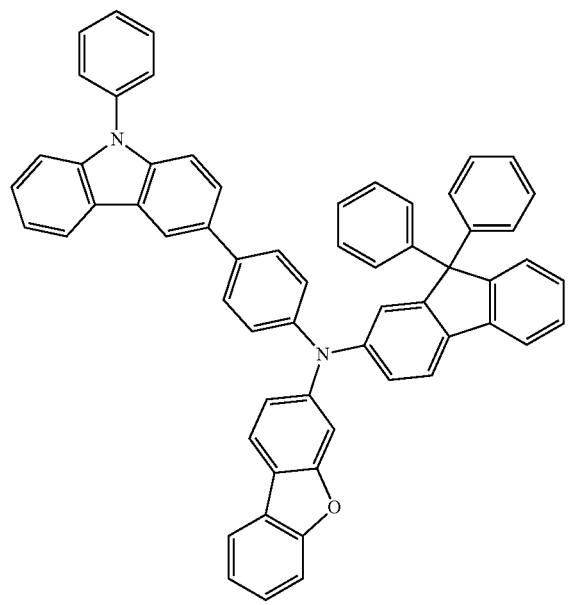
HT8
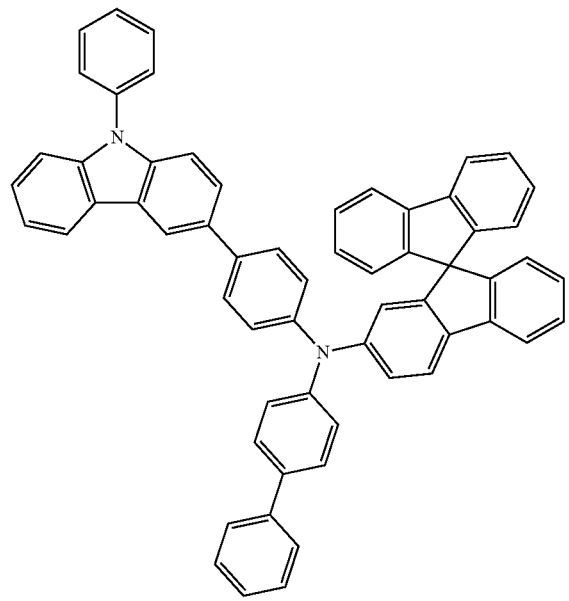
HT9
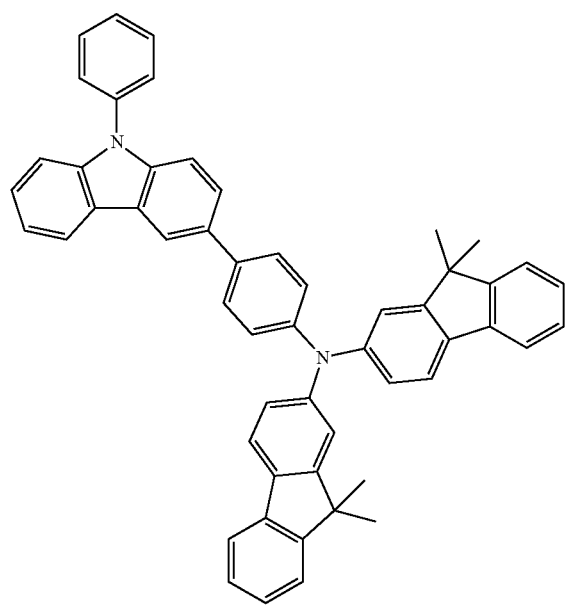
HT10
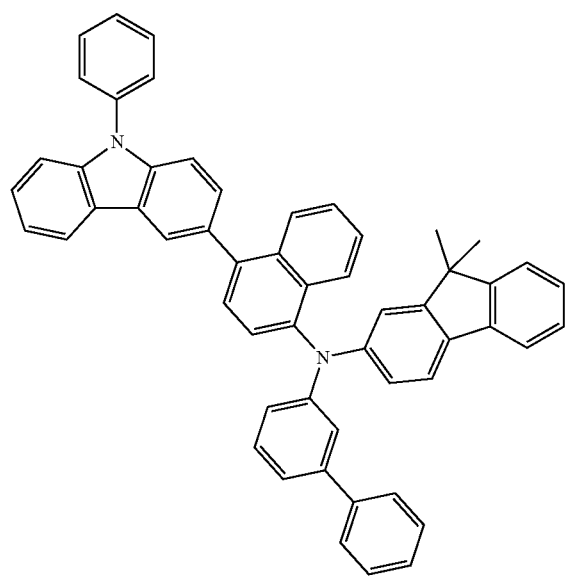

-continued
HT11
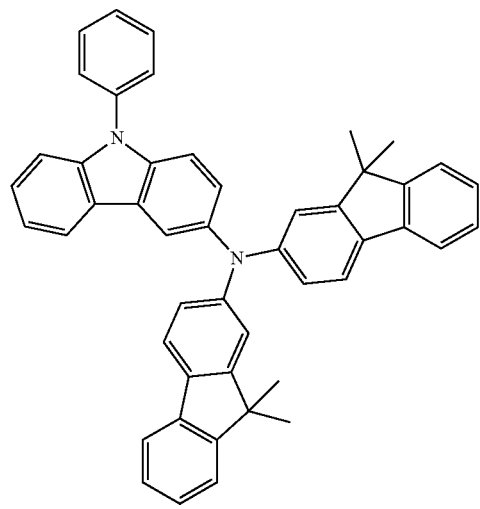
HT12
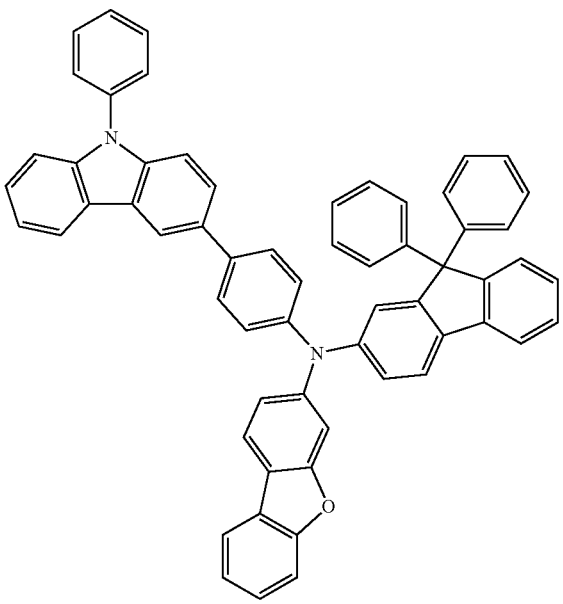
HT13
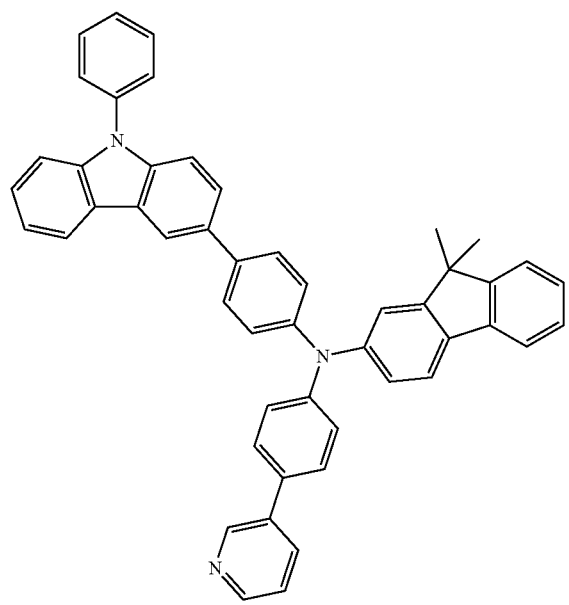
HT14
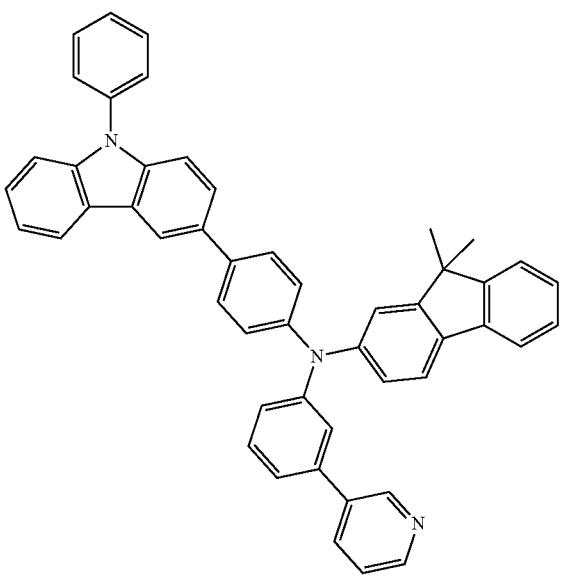

-continued
HT15
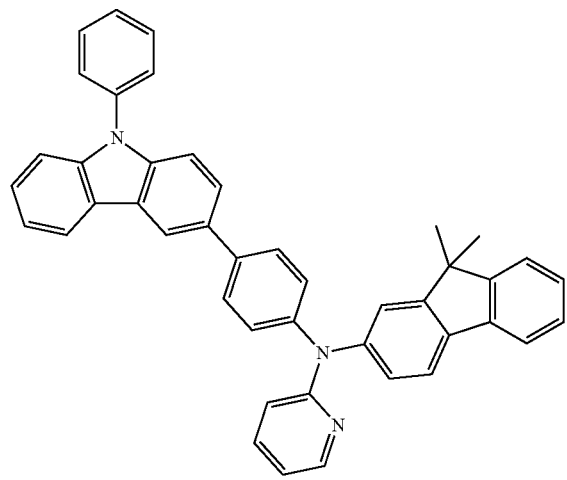
HT16
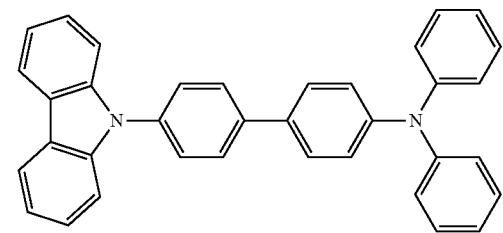
HT17
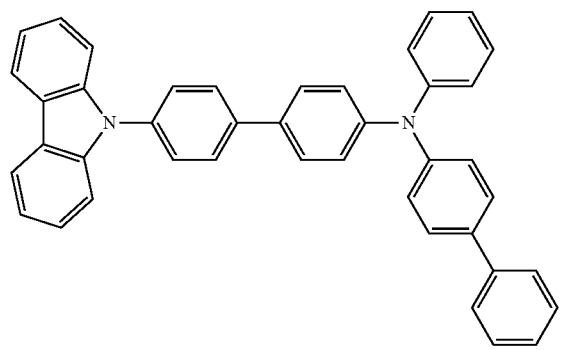
HT18
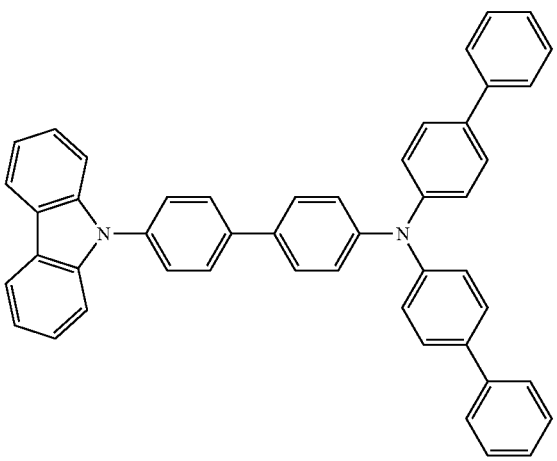
HT19
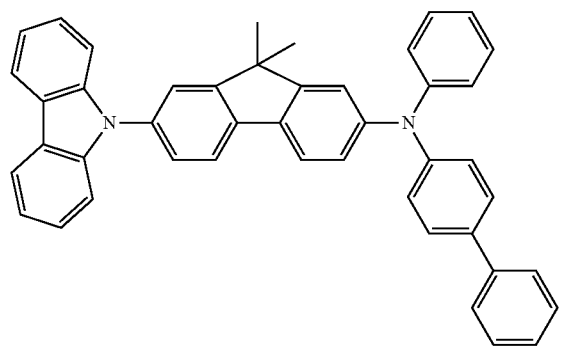
HT20
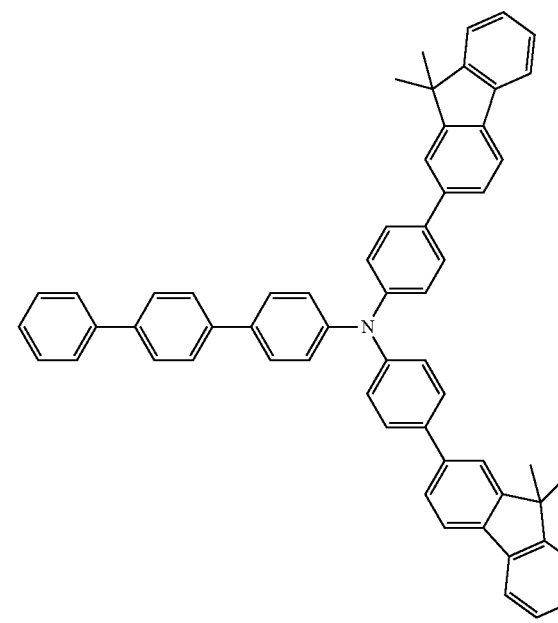

-continued
HT21
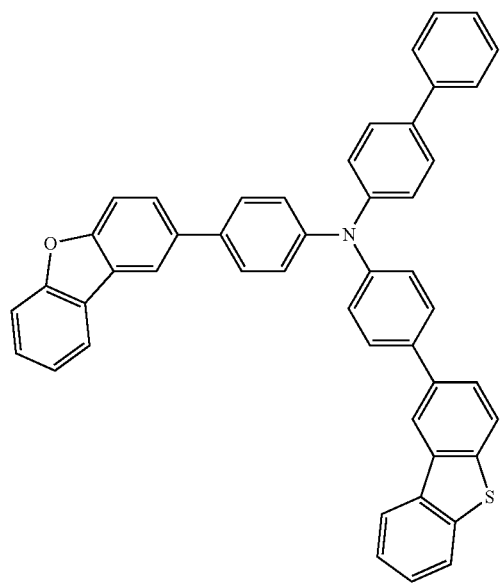
HT22
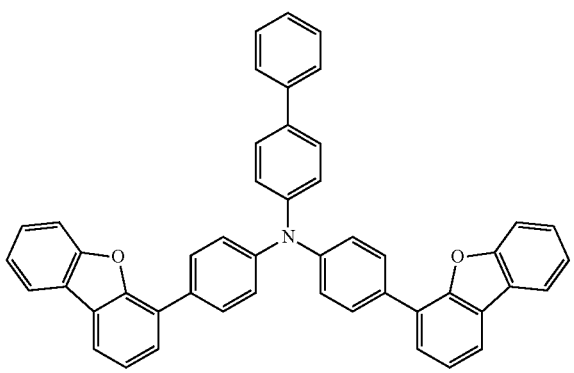
HT23
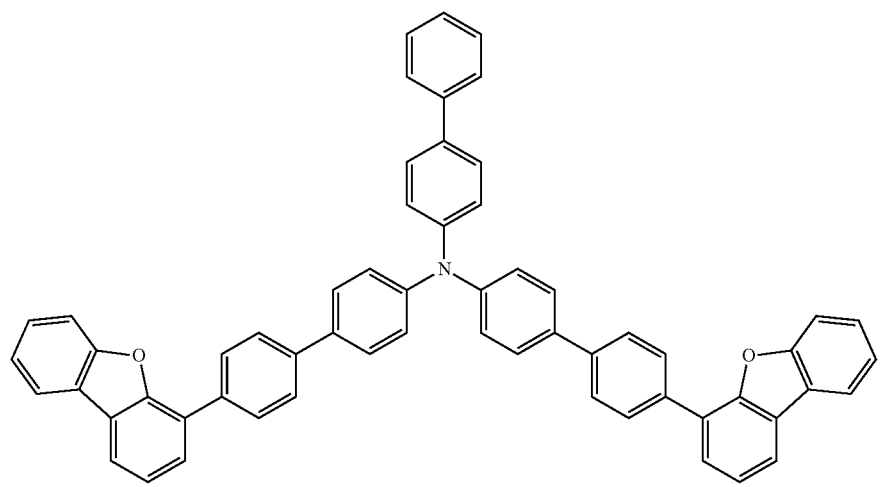
HT24
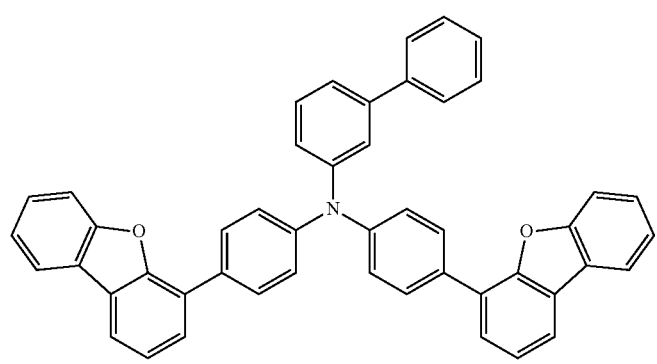

-continued
HT25
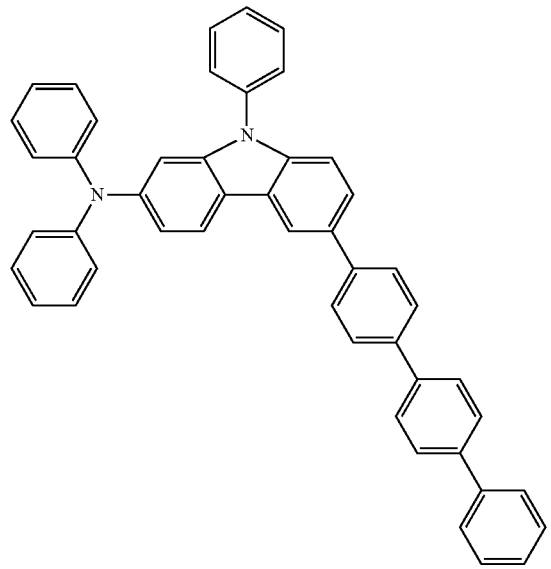
HT26
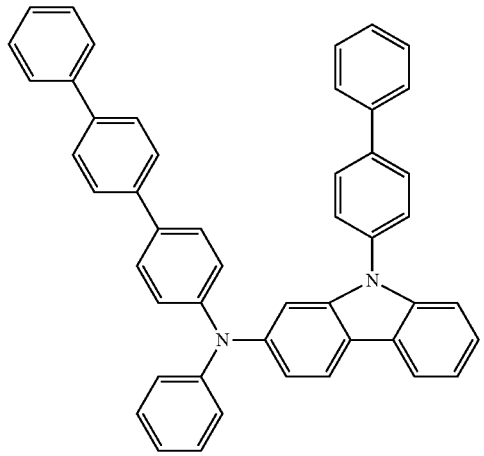
HT27
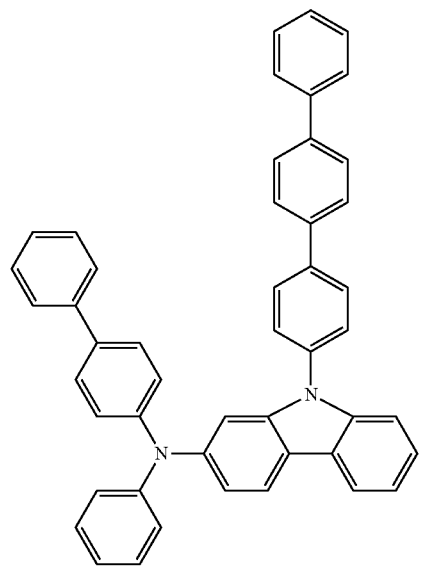
HT28
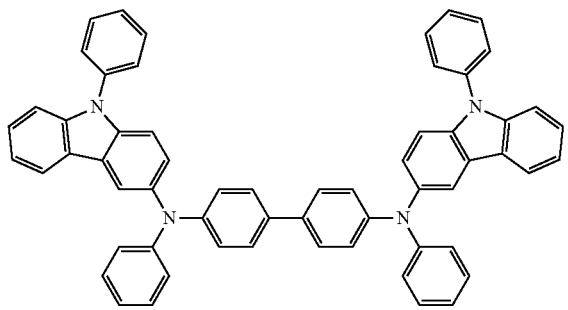
HT29
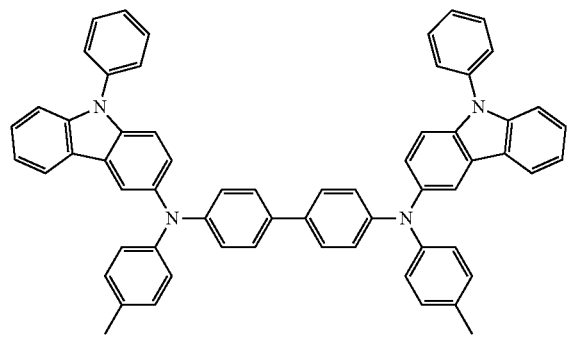
HT30
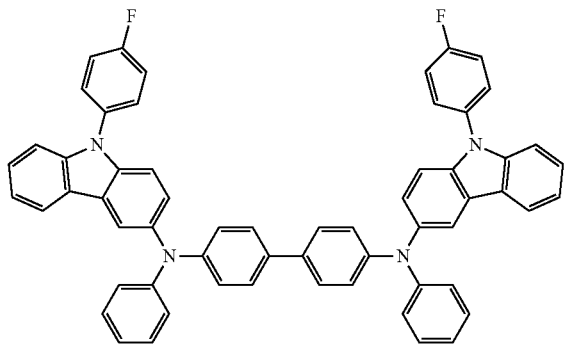

HT31
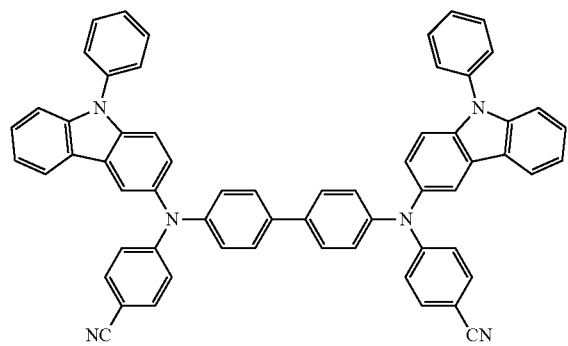
HT32
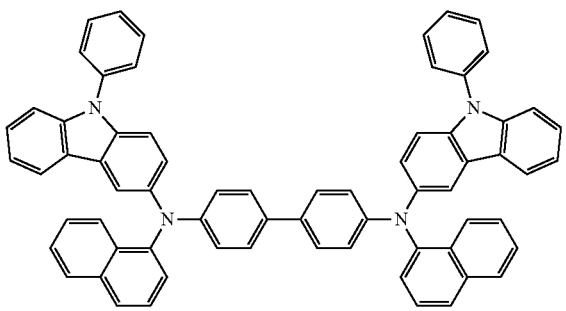
HT33
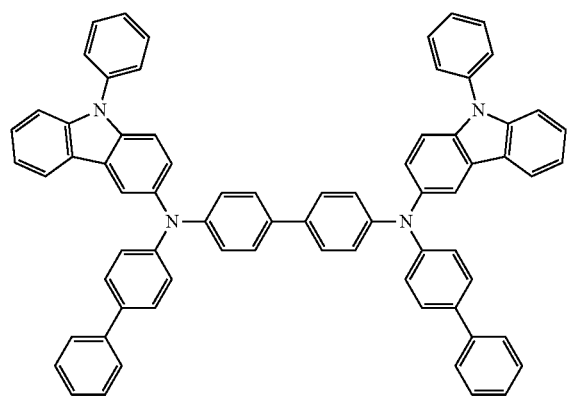
HT34
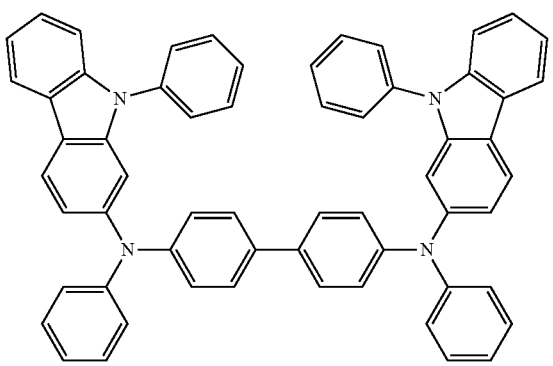
HT35
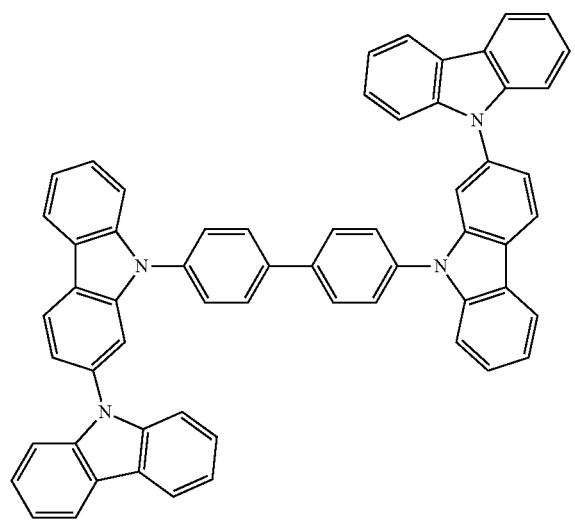
HT36
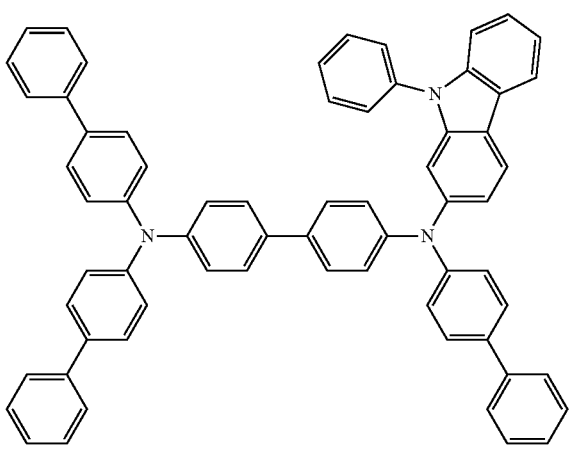

HT37

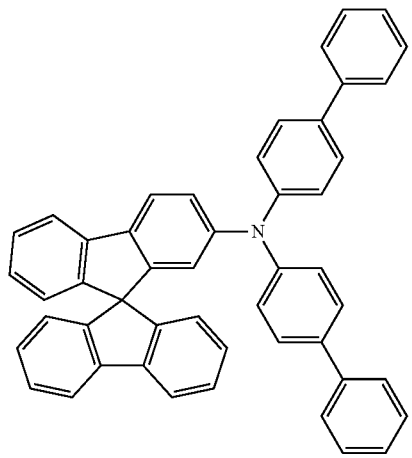

HT38

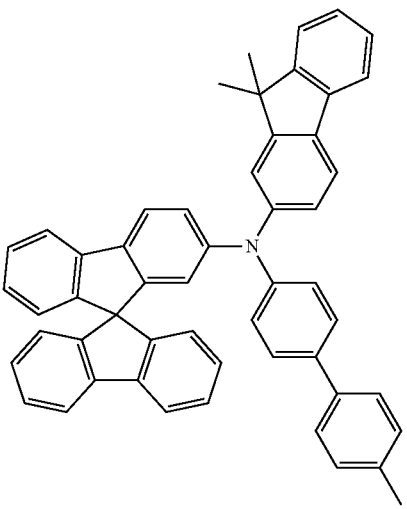

HT39

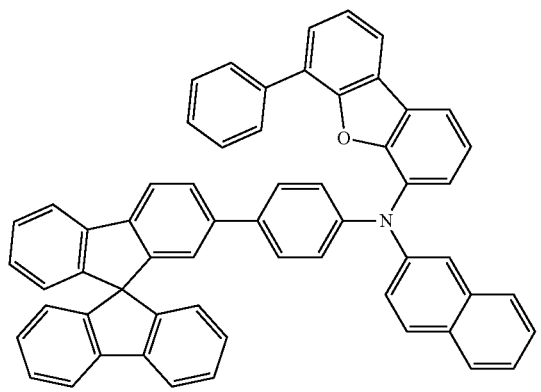

A thickness of the hole transport region may be in a range of about 100 Å to about 10,000 Å, for example, about 100 Å to about 1,000 Å. When the hole transport region includes at least one of a hole injection layer and a hole transport layer, a thickness of the hole injection layer may be in a range of about 100 Å to about 9,000 Å, for example, about 100 Å to about 1,000 Å, and a thickness of the hole transport layer may be in a range of about 50 Å to about 2,000 Å, for example about 100 Å to about 1,500 Å. When the thicknesses of the hole transport region, the hole injection layer and the hole transport layer are within these ranges, satisfactory hole transporting characteristics may be obtained without a substantial increase in driving voltage.

The emission auxiliary layer may increase light-emission efficiency by compensating for an optical resonance distance according to the wavelength of light emitted by an emission layer, and the electron blocking layer may block the flow of electrons from an electron transport region. The emission auxiliary layer and the electron blocking layer may include the materials as described above.

[P-Dopant]

The hole transport region may further include, in addition to these materials, a charge-generation material for the enhancement of conductive properties. The charge-generation material may be homogeneously or non-homogeneously dispersed in the hole transport region.

The charge-generation material may be, for example, a p-dopant.

In an exemplary embodiment of the present disclosure, a lowest unoccupied molecular orbital (LUMO) of the p-dopant may be −3.5 eV or less.

The p-dopant may include at least one selected from a quinone derivative, a metal oxide, and a cyano group-containing compound, but the present disclosure is not limited thereto.

In an exemplary embodiment of the present disclosure, the p-dopant may be selected from:

a quinone derivative, such as tetracyanoquinodimethane (TCNQ) and 2,3,5,6-tetrafluoro-7,7,8,8-tetracyanoquinodimethane (F4-TCNQ);

a metal oxide, such as tungsten oxide or molybdenum oxide;

1,4,5,8,9,11-hexaazatriphenylene-hexacarbonitrile (HAT-CN); and
a compound represented by Formula 221,
but the present disclosure is not limited thereto:

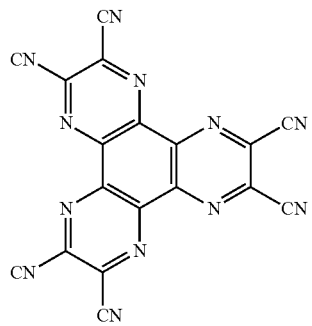
<HAT-CN>

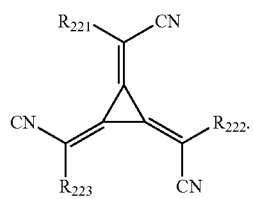
<F4-TCNQ>

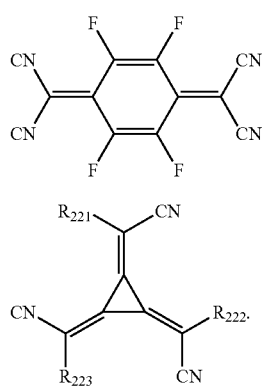
<Formula 221>

In Formula 221,
$R_{221}$ to $R_{223}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group, in which at least one from $R_{221}$ to $R_{223}$ may have at least one substituent selected from a cyano group, —F, —Cl, —Br, —I, a $C_1$-$C_{20}$ alkyl group substituted with —F, a $C_1$-$C_{20}$ alkyl group substituted with —Cl, a $C_1$-$C_{20}$ alkyl group substituted with —Br, and a $C_1$-$C_{20}$ alkyl group substituted with —I.

[Emission Layer in Organic Layer 150]

When the organic light-emitting device 10 is a full-color organic light-emitting device, the emission layer may be patterned into a red emission layer, a green emission layer, or a blue emission layer, according to a sub-pixel. In an exemplary embodiment of the present disclosure, the emission layer may have a stacked structure of two or more layers selected from a red emission layer, a green emission layer, and a blue emission layer, in which the two or more layers contact each other or are separated from each other. In an exemplary embodiment of the present disclosure, the emission layer may include two or more materials selected from a red-light emission material, a green-light emission material, and a blue-light emission material, in which the two or more materials are mixed with each other in a single layer to emit white light.

The emission layer may include a host and a dopant. The dopant may include at least one selected from a phosphorescent dopant and a fluorescent dopant.

An amount of the dopant in the emission layer may be, in general, in a range of about 0.01 parts to about 15 parts by weight based on 100 parts by weight of the host, but the present disclosure is not limited thereto.

A thickness of the emission layer may be in a range of about 100 Å to about 1,000 Å, for example, about 200 Å to about 600 Å. When the thickness of the emission layer is within this range, excellent light-emission characteristics may be obtained without a substantial increase in driving voltage.

[Host in Emission Layer]

In an exemplary embodiment of the present disclosure, the host may include a compound represented by Formula 301 below.

$$[Ar_{301}]_{xb11}-[(L_{301})_{xb1}-R_{301}]_{xb21}$$ <Formula 301>

In Formula 301,
$Ar_{301}$ may be a substituted or unsubstituted $C_5$-$C_{60}$ carbocyclic group or a substituted or unsubstituted $C_1$-$C_{60}$ heterocyclic group,
xb11 may be 1, 2, or 3,
$L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group,
xb1 may be an integer from 0 to 5,
$R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{301}$)($Q_{302}$)($Q_{303}$), —N($Q_{301}$)($Q_{302}$), —B($Q_{301}$)($Q_{302}$), —C(=O)($Q_{301}$), —S(=O)$_2$($Q_{301}$), and —P(=O)($Q_{301}$)($Q_{302}$),
xb21 may be an integer from 1 to 5, and
$Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group and a naphthyl group, but the present disclosure is not limited thereto.

In an exemplary embodiment of the present disclosure, $Ar_{301}$ in Formula 301 may be selected from:
a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group;

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but the present disclosure is not limited thereto.

When xb11 in Formula 301 is two or more, two or more Ar301(s) may be linked via a single bond.

In an exemplary embodiment of the present disclosure, the compound represented by Formula 301 may be represented by Formula 301-1 or 301-2:

group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), xb22 and xb23 may each independently be 0, 1, or 2.

$L_{301}$, xb1, $R_{301}$, and $Q_{31}$ to $Q_{33}$ may be the same as described above, $L_{302}$ to $L_{304}$ may be the same as described in connection with $L_{301}$, xb2 to xb4 may be the same as described in connection with xb1, and $R_{302}$ to $R_{304}$ may be the same as described in connection with $R_{301}$.

In an exemplary embodiment of the present disclosure, $L_{301}$ to $L_{304}$ in Formulae 301, 301-1, and 301-2 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofura-

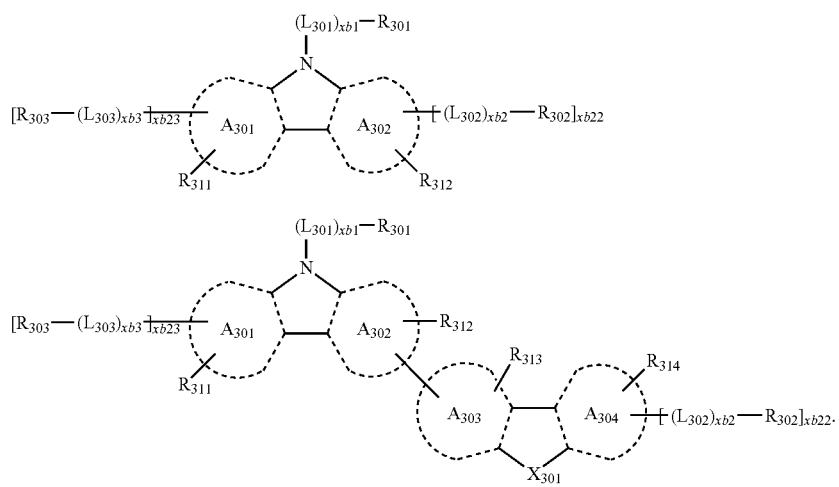

<Formula 301-1>

<Formula 301-2>

In Formulae 301-1 and 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-[($L_{304}$)$_{xb4}$-$R_{304}$], $R_{311}$ to $R_{314}$ may each independently be selected from hydrogen, deuterium, —F, —Cl, —Br, —I, a hydroxyl nylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group;

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may be the same as described above.

In an exemplary embodiment of the present disclosure, $R_{301}$ to $R_{304}$ in Formulae 301, 301-1, and 301-2 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazoryl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and $Q_{31}$ to $Q_{33}$ may be the same as described above.

In an exemplary embodiment of the present disclosure, the host may include an alkaline-earth metal complex. For example, the host may be selected from a Be complex (for example, Compound H55 as shown below), an Mg complex, and a Zn complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but the present disclosure is not limited thereto:

H1

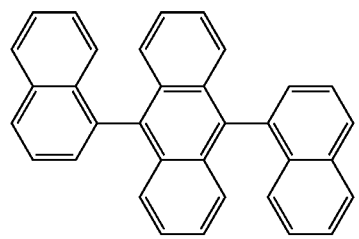

H2

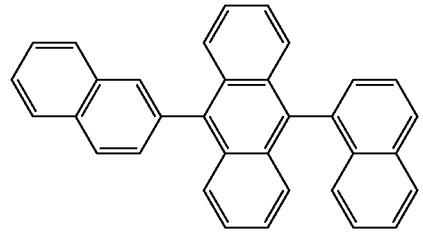

H3

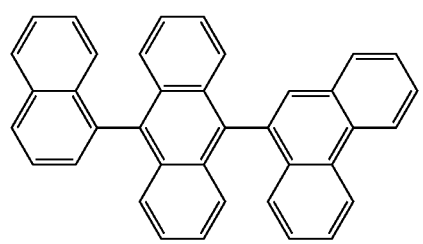

H4

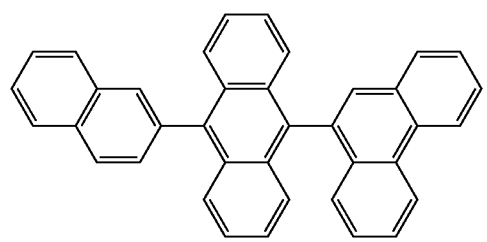

H5

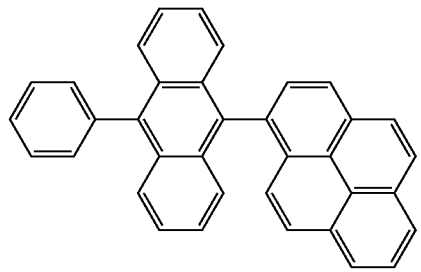

H6

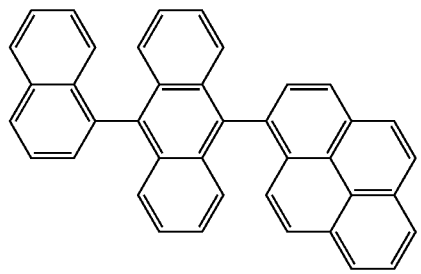

H7

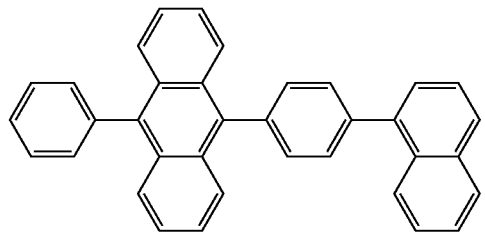

H8

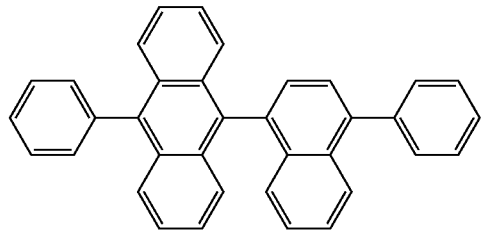

H9

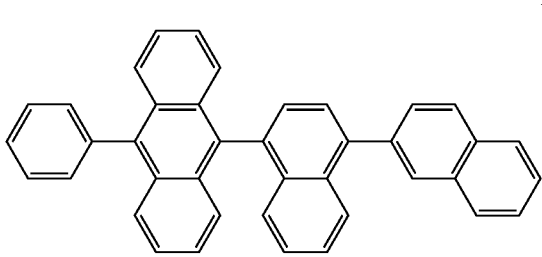

H10

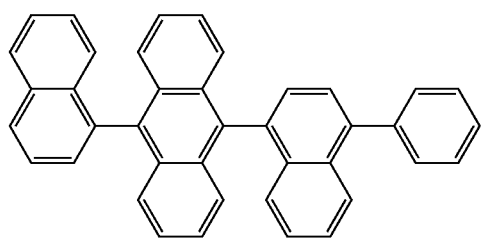

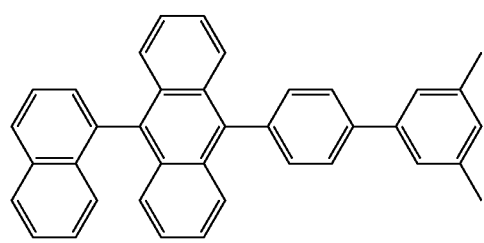
H11
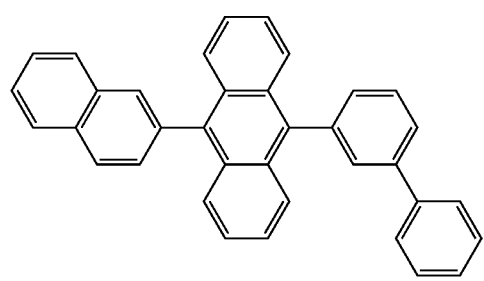
H12
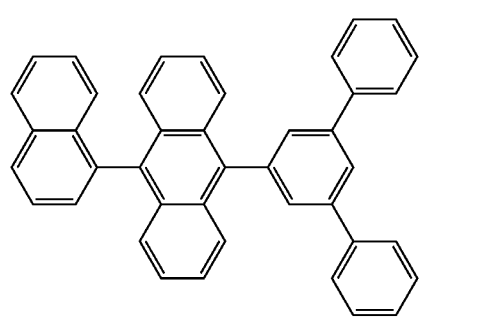
H13
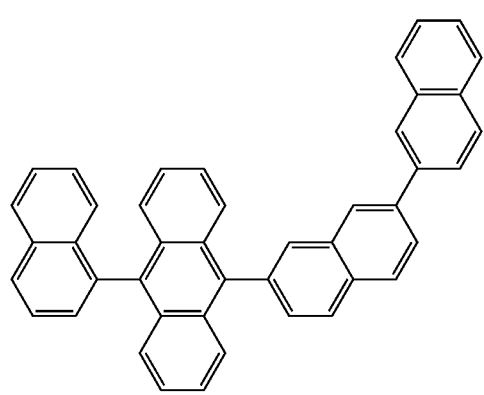
H14
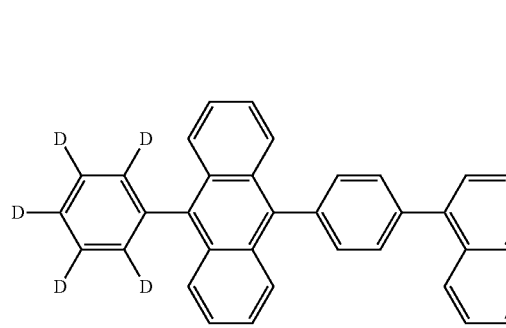
H15
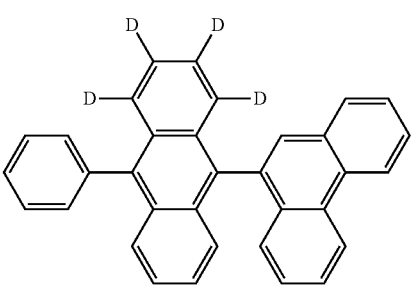
H16
H17
H18
H19
H20

H21
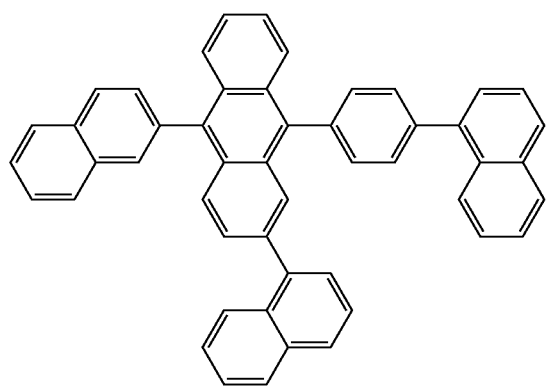
H22
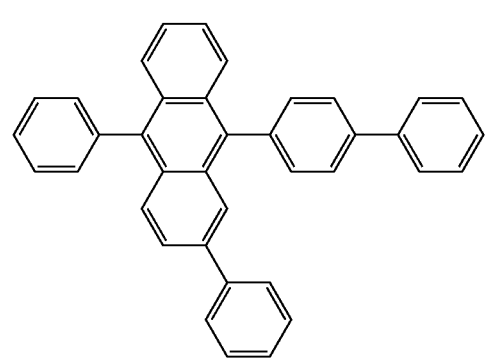
H23
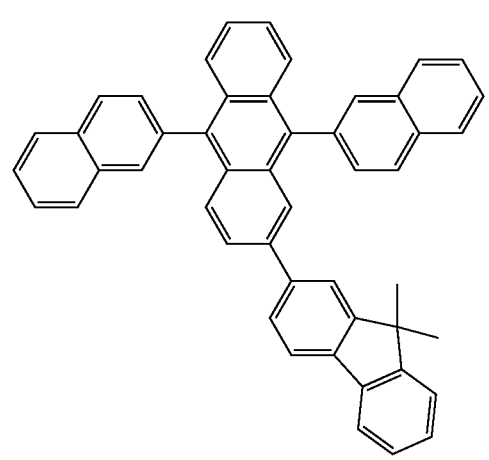
H24
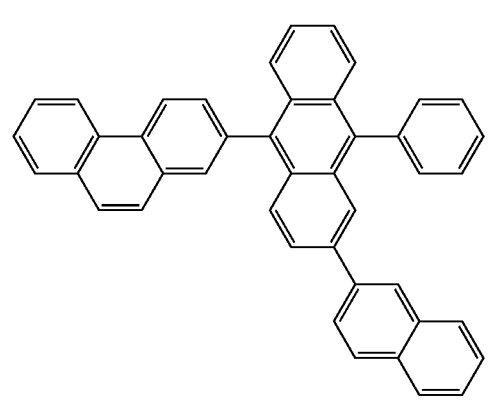
H25
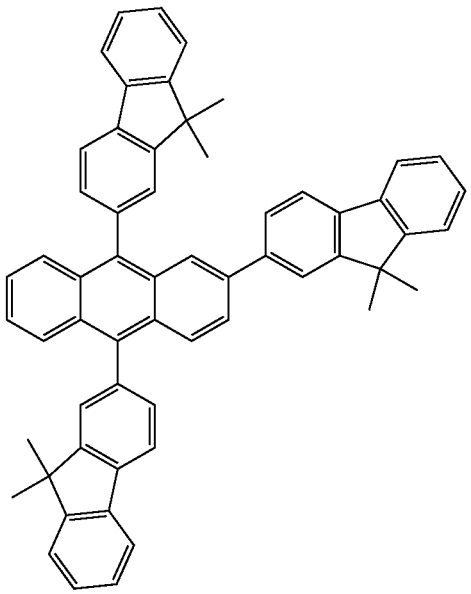
H26
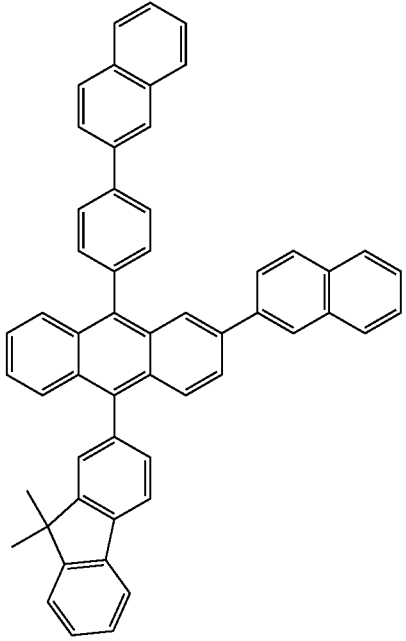

-continued
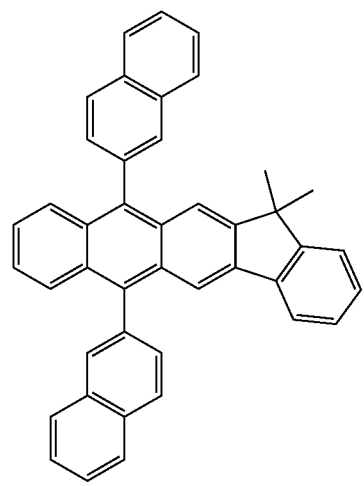
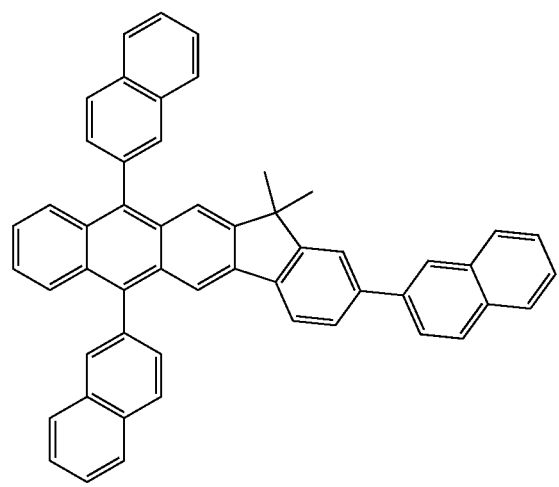
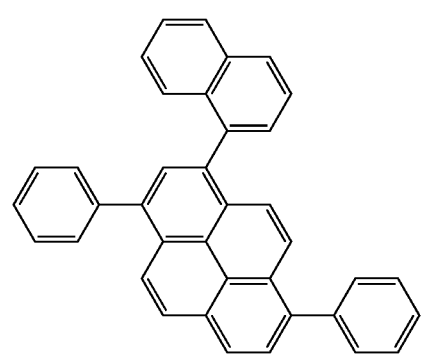
-continued
H27
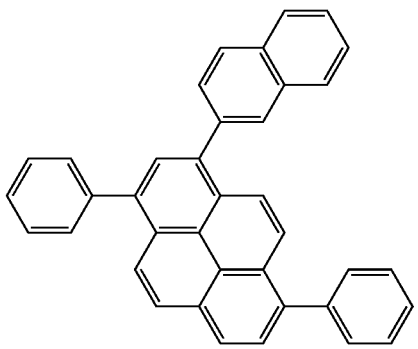
H28
H29
H30
H31
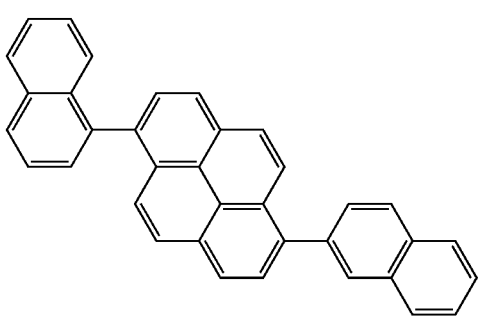
H32
H33
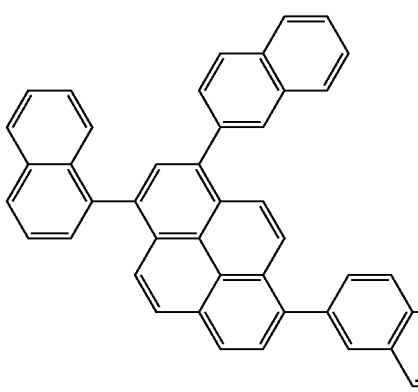
H34
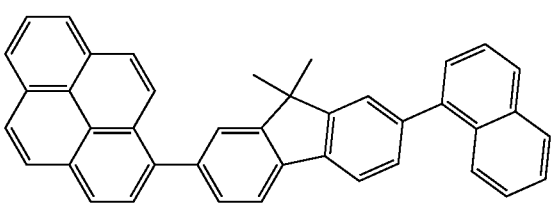
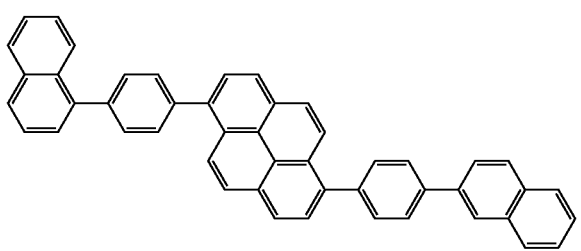

H35
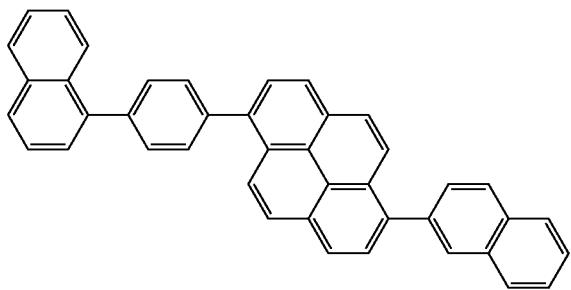
H36
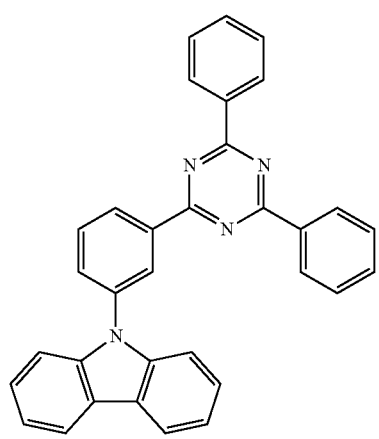
H37
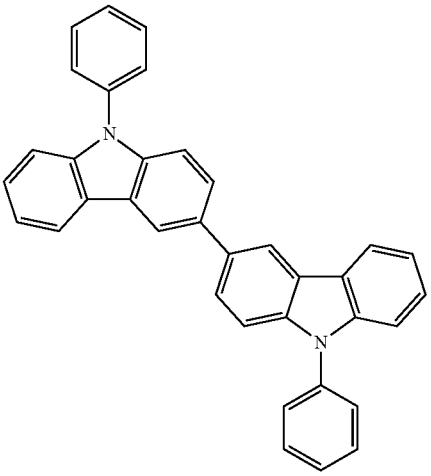
H38
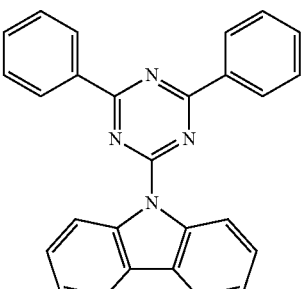
H39
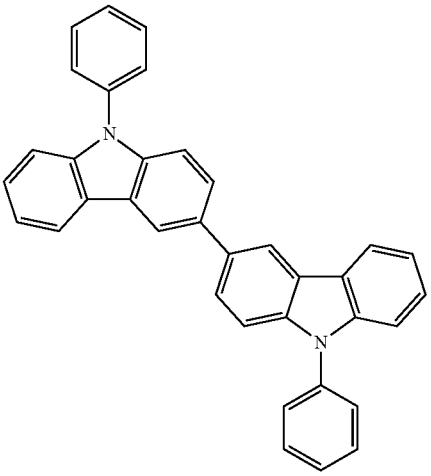
H40
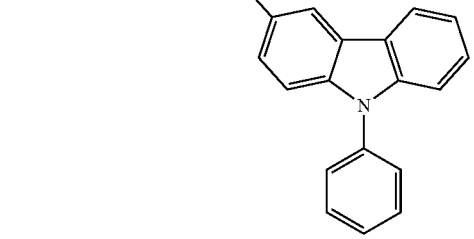
H41
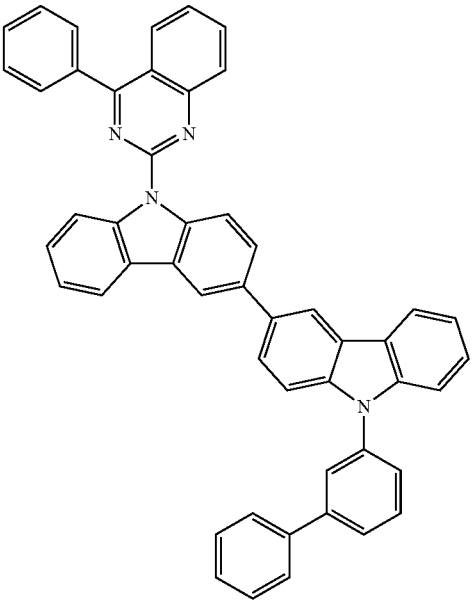

175
-continued
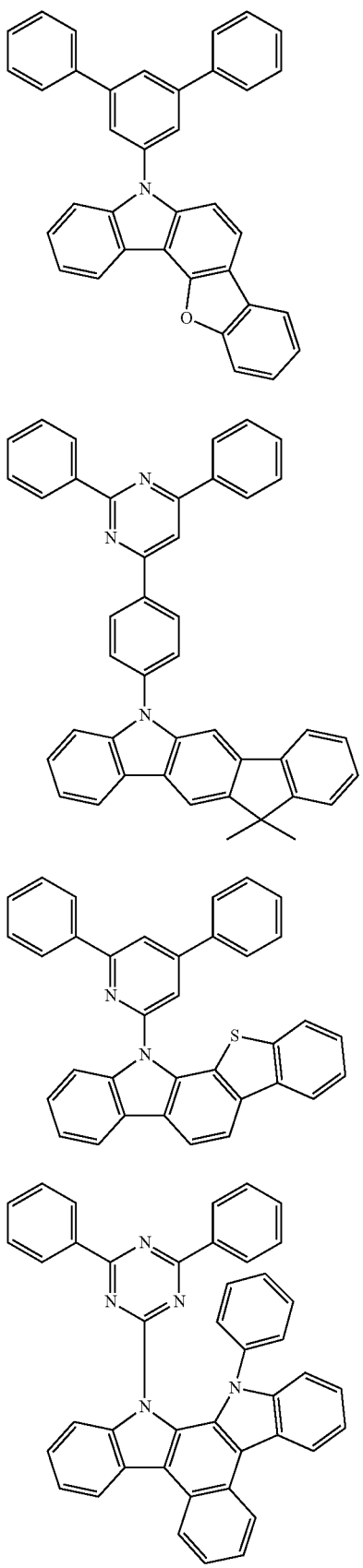
176
-continued
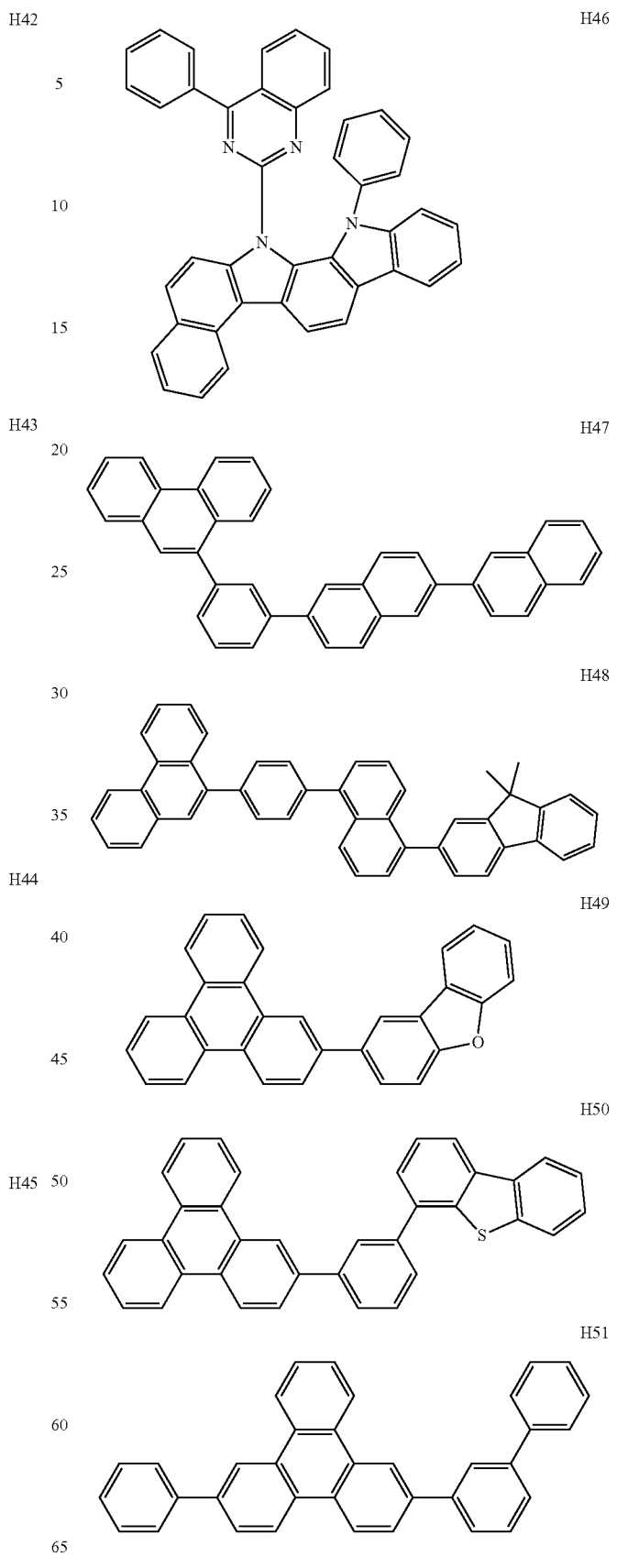

-continued

H52

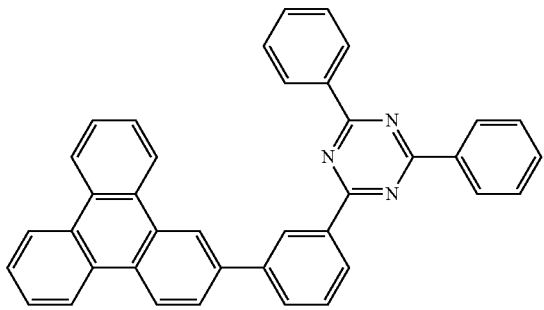

H53

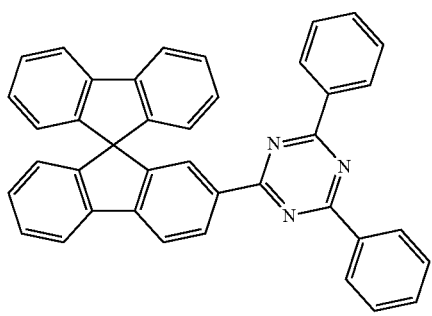

H54

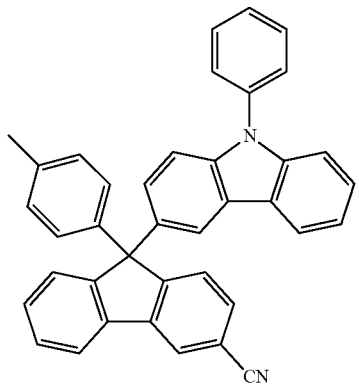

H55

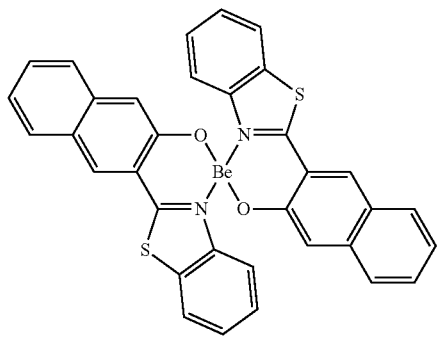

[Phosphorescent Dopant Included in Emission Layer in Organic Layer 150]

The phosphorescent dopant may include an organometallic complex represented by Formula 401 and a ligand represented by Formula 402 below:

$$M(L_{401})_{xc1}(L_{402})_{xc2}.$$ <Formula 401>

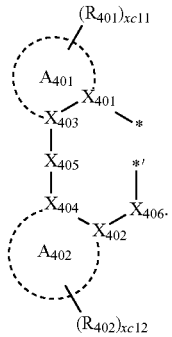

<Formula 402>

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from ligands represented by Formula 402, and xc1 may be 1, 2, or 3, wherein when xc1 is two or more, two or more $L_{401}$(s) may be identical to or different from each other.

$L_{402}$ may be an organic ligand, and xc2 may be an integer from 0 to 4, wherein when xc2 is two or more, two or more $L_{402}$(s) may be identical to or different from each other, $X_{401}$ to $X_{404}$ may each independently be nitrogen or carbon, $X_{401}$ and $X_{403}$ may be linked via a single bond or a double bond, and $X_{402}$ and $X_{404}$ may be linked via a single bond or a double bond, $A_{401}$ and $A_{402}$ may each independently be a $C_5$-$C_{60}$ carbocyclic group or a $C_1$-$C_{60}$ heterocyclic group, $X_{405}$ may be a single bond, *—O—*', *—S—*', *—C(=O)—*', *—N($Q_{411}$)-*', *—C($Q_{411}$)($Q_{412}$)-*', *—C($Q_{411}$)=C($Q_{412}$)-*', *—C($Q_{411}$)=*' or .=C($Q_{411}$)=*', $Q_{411}$ and $Q_{412}$ may be hydrogen, deuterium, $C_1$-$C_{20}$ alkyl group, a $C_1$-$C_{20}$ alkoxy group, a phenyl group, a biphenyl group, a terphenyl group, or a naphthyl group, $X_{406}$ may be a single bond, O, or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), $Q_{401}$ to $Q_{403}$ may each independently be selected from a $C_1$-$C_{10}$ alkyl group, a $C_1$-$C_{10}$ alkoxy group, a $C_6$-$C_{60}$ aryl group, and a $C_1$-$C_{20}$ heteroaryl group, xc11 and xc12 may each independently be an integer from 0 to 10, and

* and *' in Formula 402 each indicate a binding site to M in Formula 401.

In an exemplary embodiment of the present disclosure, $A_{401}$ and $A_{402}$ in Formula 402 may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In an exemplary embodiment of the present disclosure, in Formula 402, i) $X_{401}$ may be nitrogen, and $X_{402}$ may be carbon, or ii) $X_{401}$ and $X_{402}$ may each be nitrogen at the same time.

In an exemplary embodiment of the present disclosure, $R_{401}$ and $R_{402}$ in Formula 402 may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

—$Si(Q_{401})(Q_{402})(Q_{403})$, —$N(Q_{401})(Q_{402})$, —$B(Q_{401})(Q_{402})$, —$C(=O)(Q_{401})$, —$S(=O)_2(Q_{401})$, and —$P(=O)(Q_{401})(Q_{402})$, and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but the present disclosure is not limited thereto.

In an exemplary embodiment of the present disclosure, when xc1 in Formula 401 is two or more, two $A_{401}$(s) in two or more $L_{401}$(s) may be optionally linked to each other via $X_{407}$, which is a linking group, or two $A_{402}$(s) in two or more $L_{401}$(s) may be optionally linked to each other via $X_{408}$, which is a linking group (see Compounds PD1 to PD4 and PD7 as shown below). $X_{407}$ and $X_{408}$ may each independently be a single bond, *—O—*', *—S—*', *—C(=O)—*', *—N($Q_{413}$)-*', *'C($Q_{413}$)($Q_{414}$)-*', or *—C($Q_{413}$)=C($Q_{414}$)-*' (wherein $Q_{413}$ and $Q_{414}$ may each independently be hydrogen, deuterium, a $C_1$-$C_{20}$ alkyl group, a $C_1$-$C_{20}$ alkoxy group, a phenyl group, a biphenyl group, a terphenyl group, or a naphthyl group), but the present disclosure is not limited thereto.

$L_{402}$ in Formula 401 may be a monovalent, divalent, or trivalent organic ligand. For example, $L_{402}$ may be selected from halogen, diketone (for example, acetylacetonate), carboxylic acid (for example, picolinate), —C(=O), isonitrile, —CN, and phosphorus (for example, phosphine, or phosphite), but the present disclosure is not limited thereto.

In an exemplary embodiment of the present disclosure, the phosphorescent dopant may be selected from, for example, Compounds PD1 to PD25, but the present disclosure is not limited thereto:

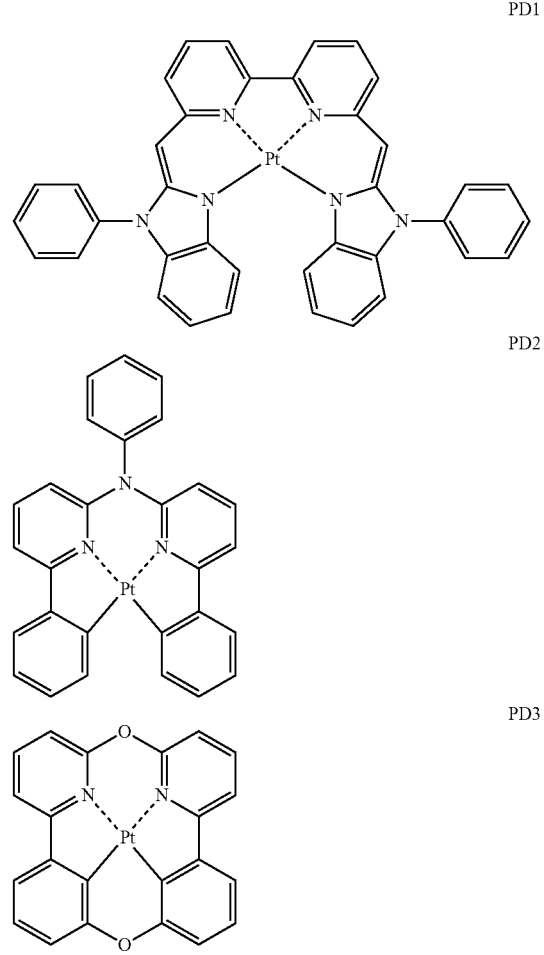

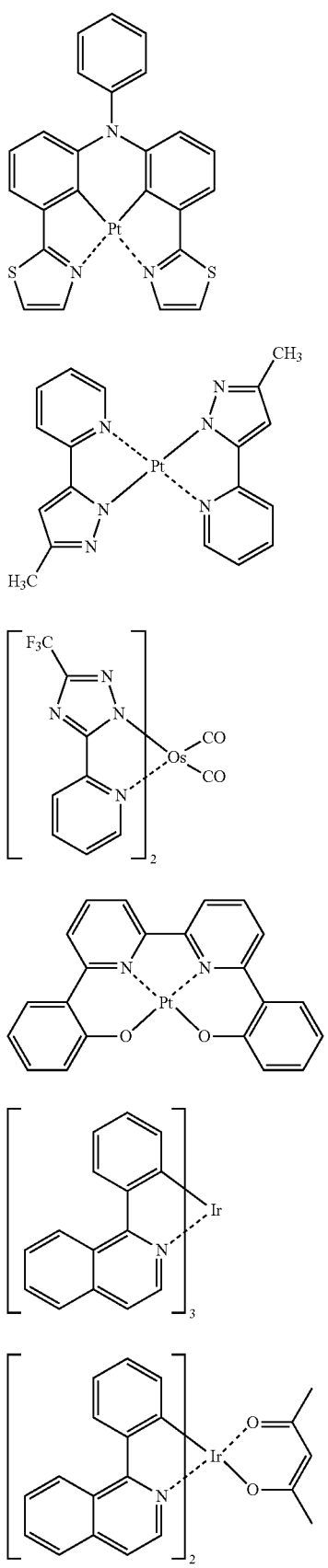

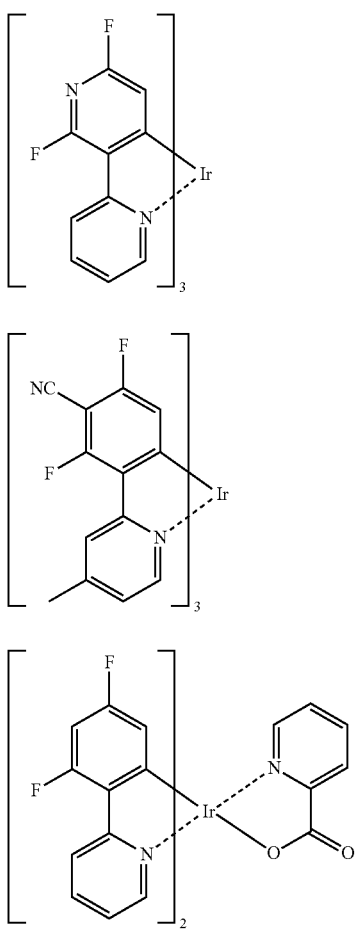
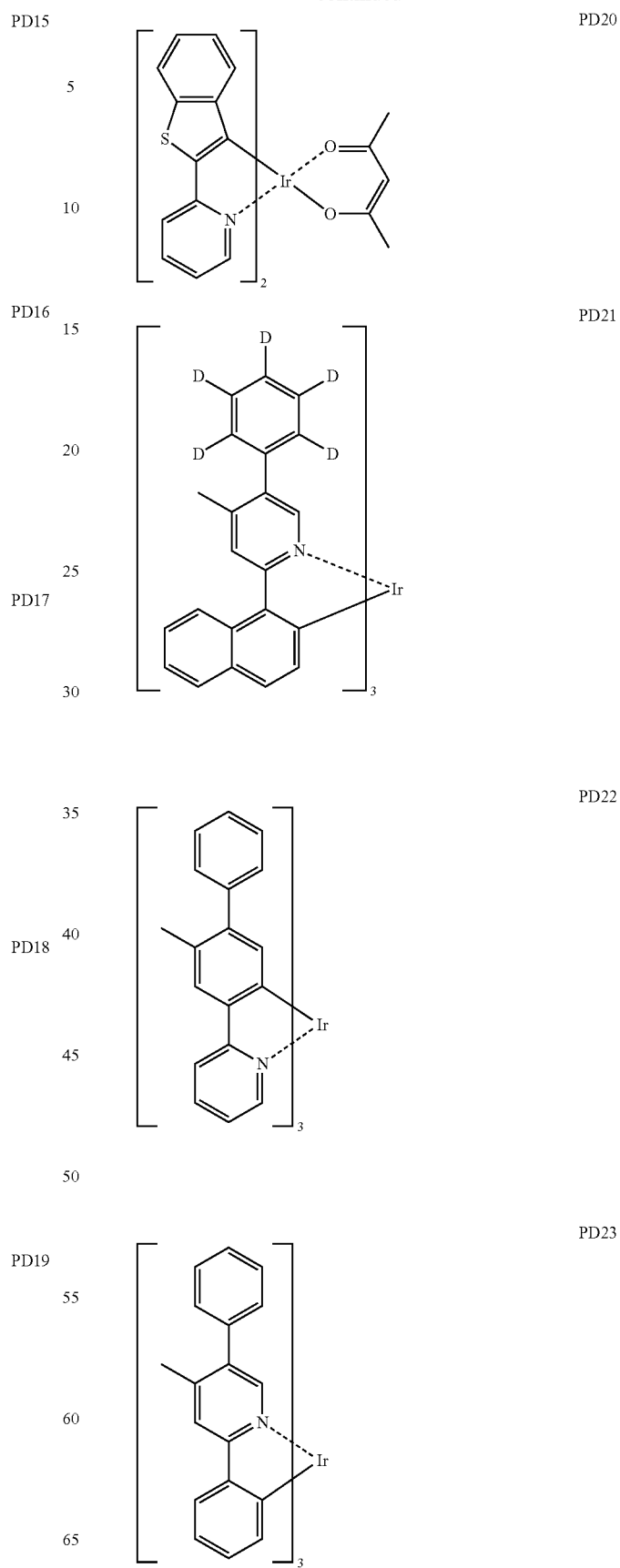

PD24

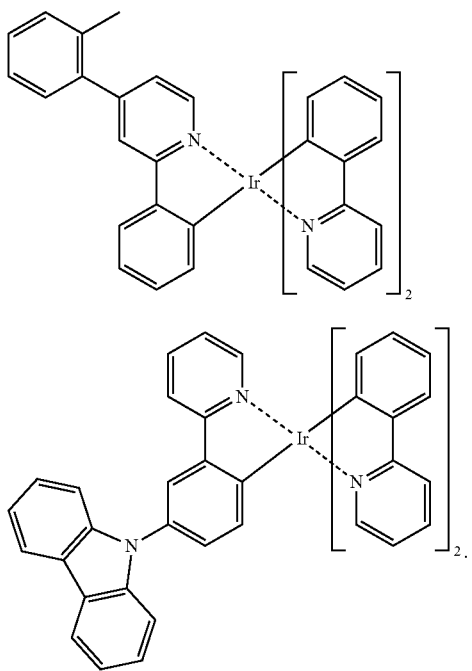

PD25

[Fluorescent Dopant in Emission Layer]

The fluorescent dopant may include an arylamine compound or a styrylamine compound.

The fluorescent dopant may include a compound represented by Formula 501 below.

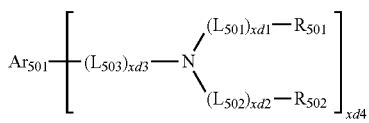

<Formula 501>

In Formula 501, $Ar_{501}$ may be a substituted or unsubstituted $C_5$-$C_{60}$ carbocyclic group or a substituted or unsubstituted $C_1$-$C_{60}$ heterocyclic group.

$L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer from 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer from 1 to 6.

In an exemplary embodiment of the present disclosure, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an exemplary embodiment of the present disclosure, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In an exemplary embodiment of the present disclosure, $R_{501}$ and $R_{502}$ in Formula 501 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$); and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

In an exemplary embodiment of the present disclosure, xd4 in Formula 501 may be 2, but the present disclosure is not limited thereto.

In an exemplary embodiment of the present disclosure, the fluorescent dopant may be selected from, for example, Compounds FD1 to FD22:

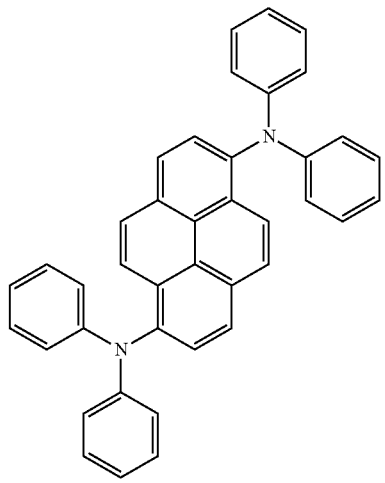

FD1

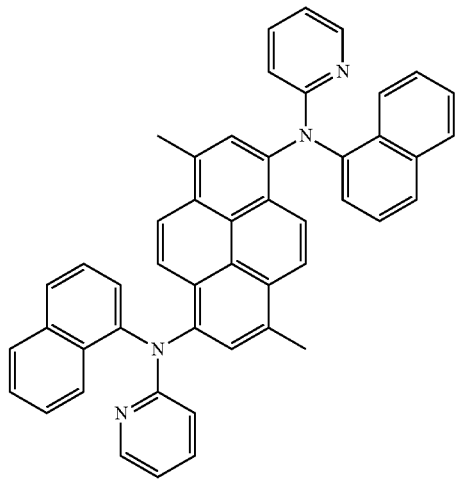

FD2

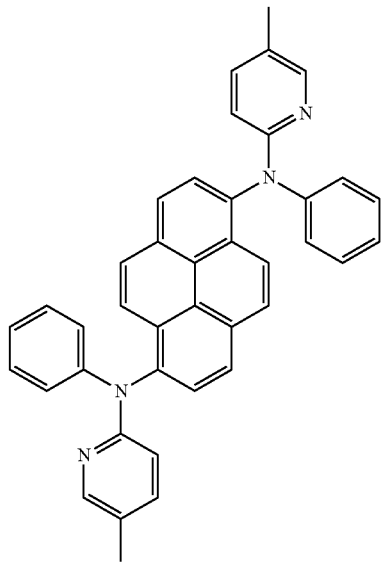

FD3

FD4
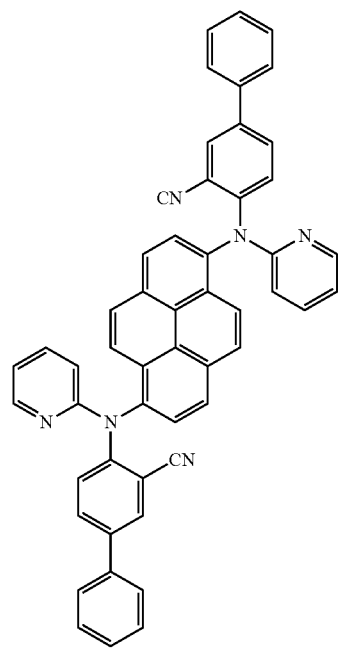
FD5
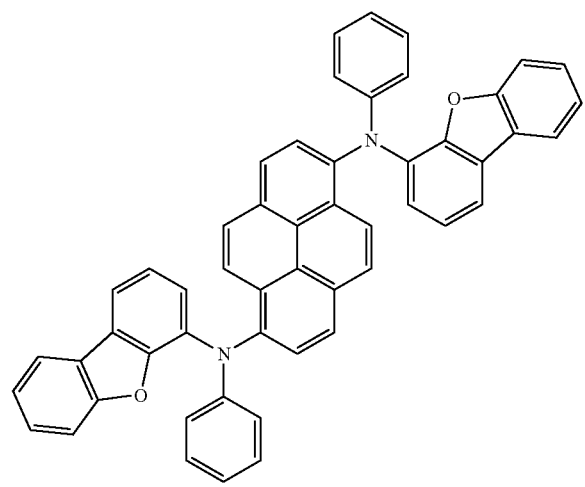
FD6
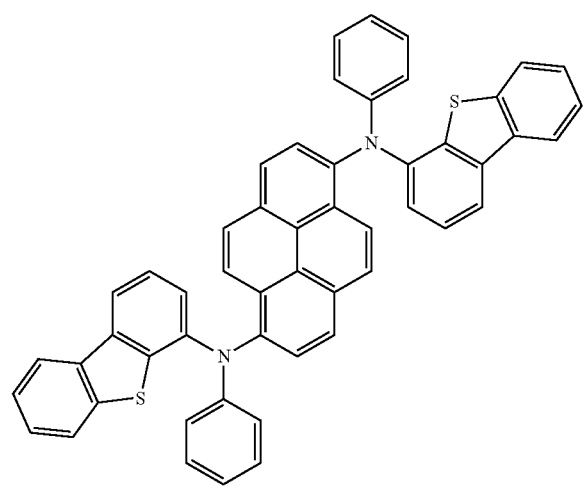
FD7
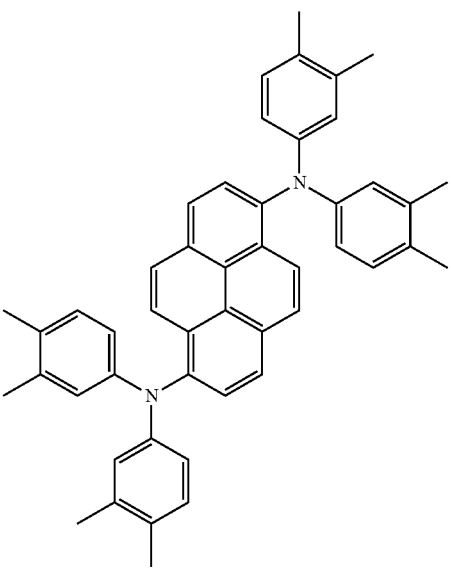
FD8
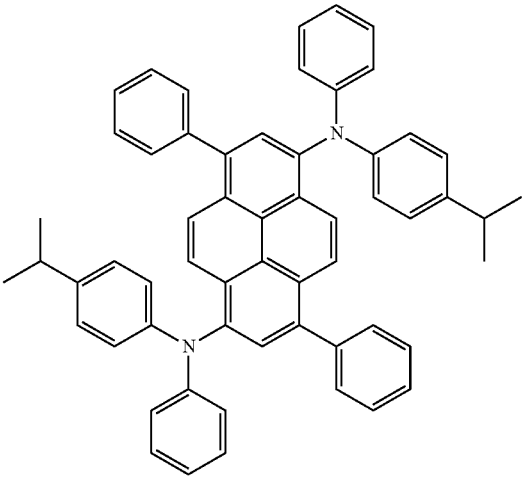
FD9
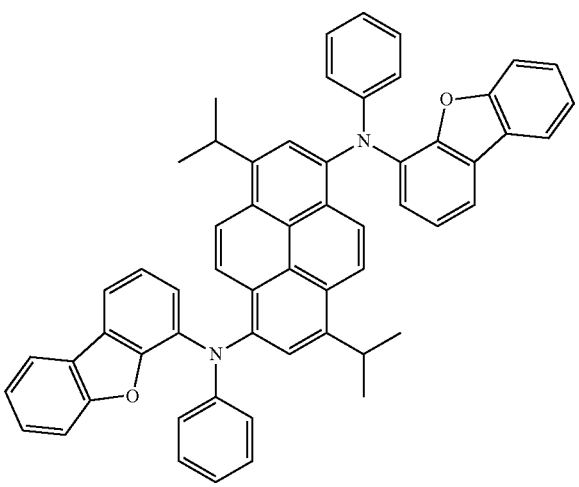

FD10
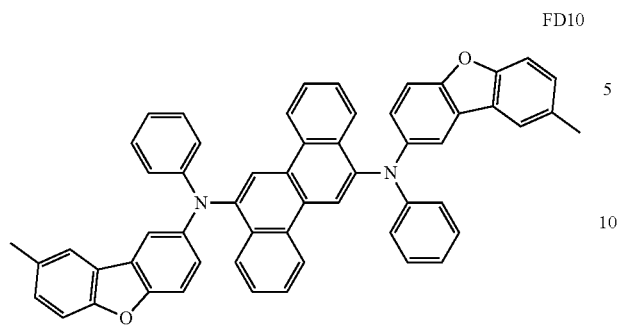
FD11
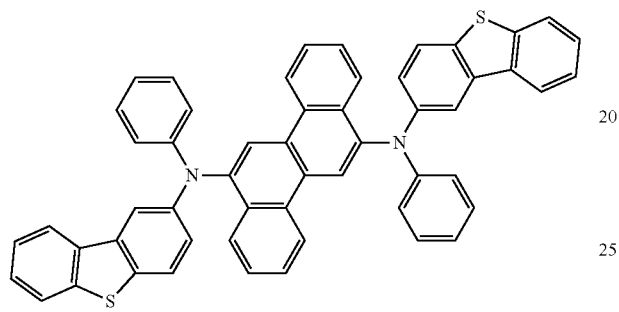
FD12
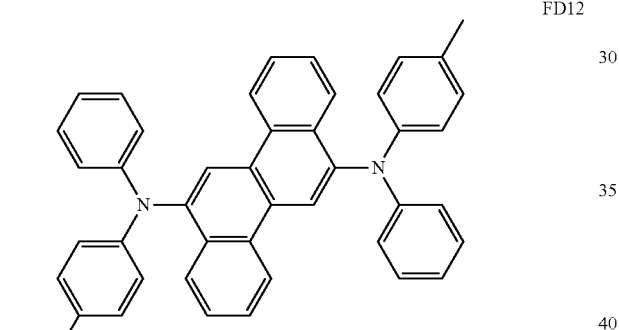
FD13
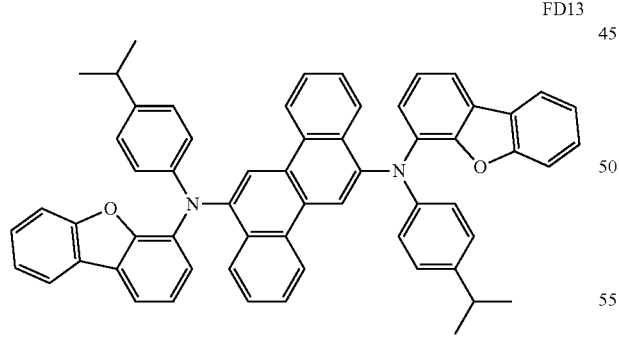
FD14
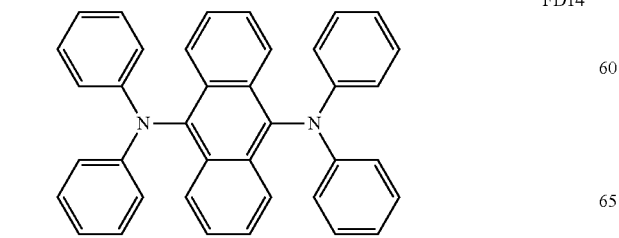
FD15
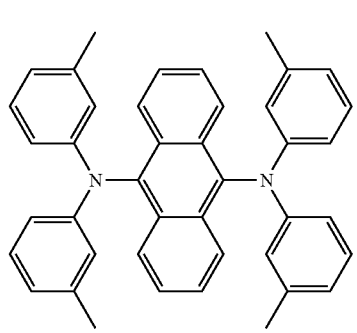
FD16
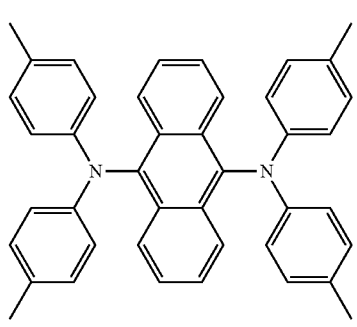
FD17
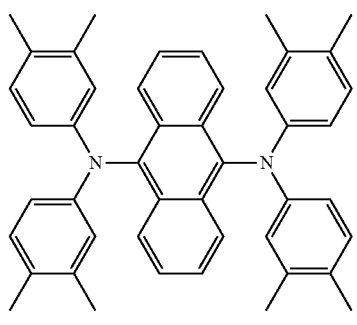
FD18
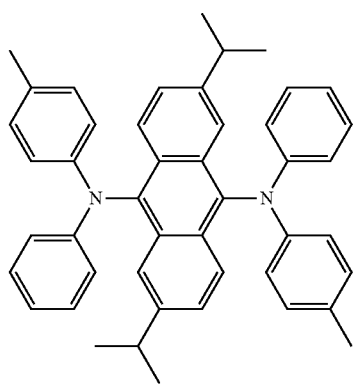

FD19
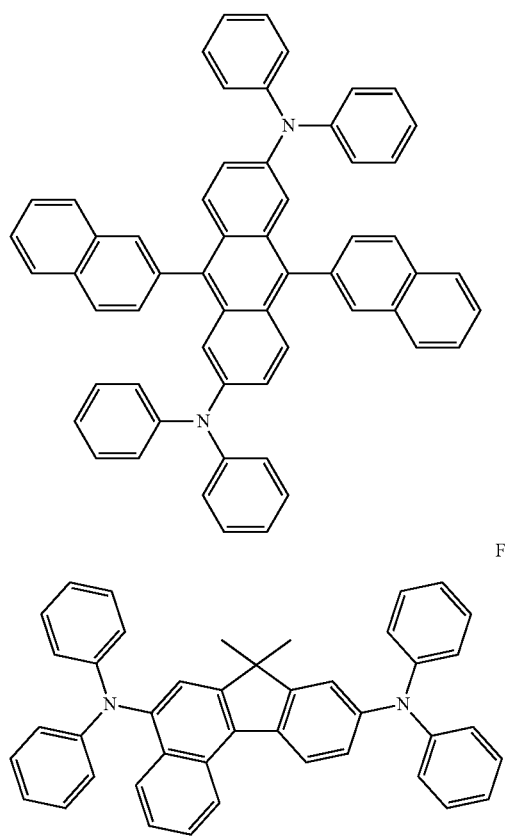
FD20
FD21
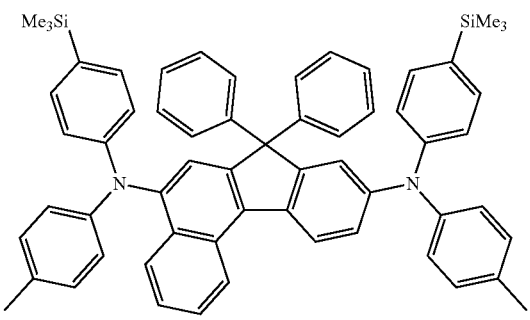
FD22
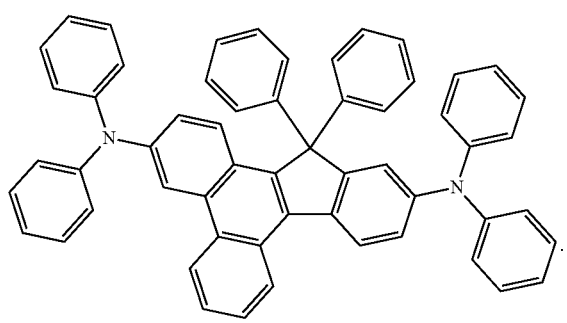
In an exemplary embodiment of the present disclosure, the fluorescent dopant may be selected from the following compounds, but the present disclosure is not limited thereto:
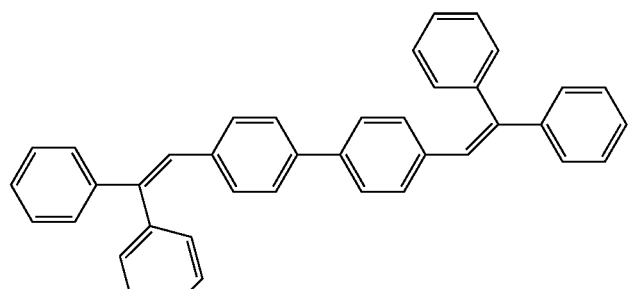
DPVBi
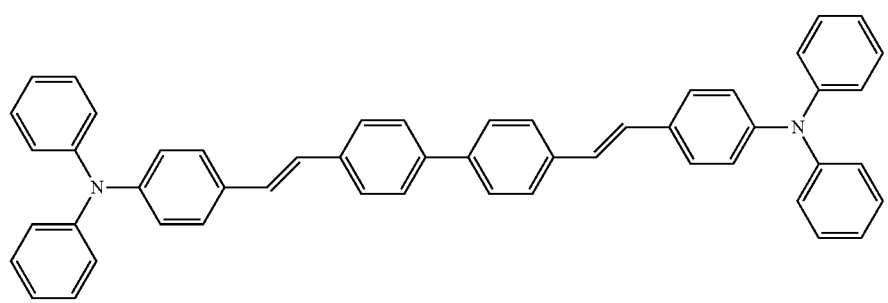
DPAVBi

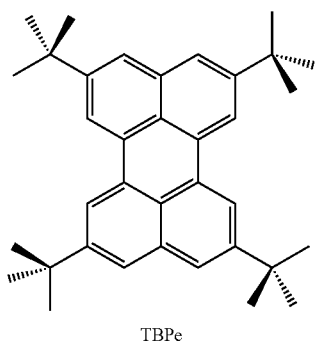

TBPe

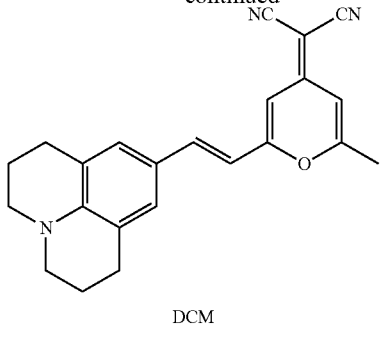

DCM

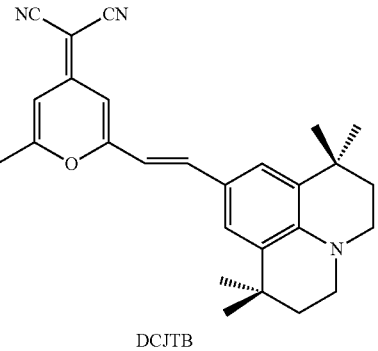

DCJTB

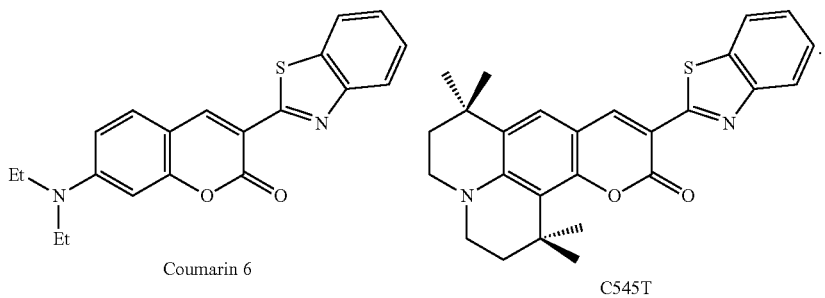

Coumarin 6

C545T

[Electron Transport Region in Organic Layer 150]

The electron transport region may have i) a single-layered structure including a single layer which includes a single material, ii) a single-layered structure including a single layer which includes a plurality of different materials, or iii) a multi-layered structure having a plurality of layers which include a plurality of different materials.

The electron transport region may include at least one selected from a buffer layer, a hole blocking layer, an electron control layer, an electron transport layer, and an electron injection layer, but the present disclosure is not limited thereto.

In an exemplary embodiment of the present disclosure, the electron transport region may have an electron transport layer/electron injection layer structure, a hole blocking layer/electron transport layer/electron injection layer structure, an electron control layer/electron transport layer/electron injection layer structure, or a buffer layer/electron transport layer/electron injection layer structure, in which, for each structure, constituting layers are sequentially stacked on and from an emission layer. However, the present disclosure is not limited thereto.

The electron transport region (for example, a buffer layer, a hole blocking layer, an electron control layer, and/or an electron transport layer in the electron transport region) may include, in addition to the condensed cyclic compound represented by Formula 1, a metal-free compound containing at least one π electron-depleted nitrogen-containing ring.

The "π electron-depleted nitrogen-containing ring" may indicate a $C_1$-$C_{60}$ heterocyclic group having at least one *—N=*' moiety as a ring-forming moiety.

In an exemplary embodiment of the present disclosure, the "π electron-depleted nitrogen-containing ring" may be i) a 5-membered to 7-membered heteromonocyclic group having at least one *—N=*' moiety, ii) a heteropolycyclic group in which two or more 5-membered to 7-membered heteromonocyclic groups each having at least one *—N=*' moiety are condensed with each other, or iii) a heteropolycyclic group in which at least one of 5-membered to 7-membered heteromonocyclic groups, each having at least one *—N=*' moiety, is condensed with at least one $C_5$-$C_{60}$ carbocyclic group.

Examples of the π electron-depleted nitrogen-containing ring may include an imidazole, a pyrazole, a thiazole, an isothiazole, an oxazole, an isoxazole, a pyridine, a pyrazine, a pyrimidine, a pyridazine, an indazole, a purine, a quinoline, an isoquinoline, a benzoquinoline, a phthalazine, a naphthyridine, a quinoxaline, a quinazoline, a cinnoline, a phenanthridine, an acridine, a phenanthroline, a phenazine, a benzimidazole, an isobenzothiazole, a benzoxazole, an isobenzoxazole, a triazole, a tetrazole, an oxadiazole, a triazine, thiadiazol, an imidazopyridine, an imidazopyrimidine, and an azacarbazole, but the present disclosure is not limited thereto.

In an exemplary embodiment of the present disclosure, the electron transport region may further include, in addition to the condensed cyclic compound represented by Formula 1, a compound represented by Formula 601.

$[Ar_{601}]_{xe11}$-$[(L_{601})_{xe1}$-$R_{601}]_{xe21}$.     <Formula 601>

In Formula 601, $Ar_{601}$ may be a substituted or unsubstituted $C_5$-$C_{60}$ carbocyclic group or a substituted or unsubstituted $C_1$-$C_{60}$ heterocyclic group, xe11 may be 1, 2, or 3, $L_{601}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xe1 may be an integer from 0 to 5, $R_{601}$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_{601})(Q_{602})(Q_{603})$, —$C(=O)(Q_{601})$, —$S(=O)_2(Q_{601})$, and —$P(=O)(Q_{601})(Q_{602})$, $Q_{601}$ to $Q_{603}$ may each independently be a $C_1$-$C_{10}$ alkyl group, a $C_1$-$C_{10}$ alkoxy group, a phenyl group, a biphenyl group, a terphenyl group, or a naphthyl group, and xe21 may be an integer from 1 to 5.

In an exemplary embodiment of the present disclosure, at least one of $Ar_{601}$(s) in the number of xe11 and/or at least one of $R_{601}$(s) in the number of xe21 may include the π electron-depleted nitrogen-containing ring.

In an exemplary embodiment of the present disclosure, ring $Ar_{601}$ in Formula 601 may be selected from:

a benzene group, a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group; and a benzene group, a naphthalene group, a fluorene group, a spiro-bifluorene group, a benzofluorene group, a di benzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, a dibenzothiophene group, a carbazole group, an imidazole group, a pyrazole group, a thiazole group, an isothiazole group, an oxazole group, an isoxazole group, a pyridine group, a pyrazine group, a pyrimidine group, a pyridazine group, an indazole group, a purine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, an iso-benzothiazole group, a benzoxazole group, an isobenzoxazole group, a triazole group, a tetrazole group, an oxadiazole group, a triazine group, a thiadiazol group, an imidazopyridine group, an imidazopyrimidine group, and an azacarbazole group, each substituted with at least one selected from deuterium, —F, —Cl, —Br, —I, a hydroxyl group, a cyano group, a nitro group, an amidino group, a hydrazino group,
a hydrazono group, a $C_1$-$C_{20}$ alkyl group, a $C_1$-$C_{20}$ alkoxy group, a phenyl group, a biphenyl group, a terphenyl group, a naphthyl group, —$Si(Q_{31})(Q_{32})(Q_{33})$, —$S(=O)_2(Q_{31})$, and —$P(=O)(Q_{31})(Q_{32})$; and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group.

When xe11 in Formula 601 is two or more, two or more Ar601(s) may be linked via a single bond.

In an exemplary embodiment of the present disclosure. $Ar_{601}$ in Formula 601 may be an anthracene group.

In an exemplary embodiment of the present disclosure, a compound represented by Formula 601 may be represented by Formula 601-1:

<Formula 601-1>

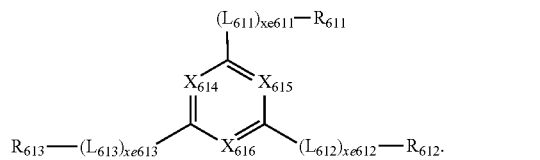

In Formula 601-1, $X_{614}$ may be N or $C(R_{614})$, $X_{615}$ may be N or $C(R_{615})$, $X_{616}$ may be N or $C(R_{616})$, and at least one selected from $X_{614}$ to $X_{616}$ may be N, $L_{611}$ to $L_{613}$ may each independently be the same as described in connection with $L_{601}$, xe611 to xe613 may each independently be the same as described in connection with xe1, $R_{611}$ to $R_{613}$ may each independently be the same as described in connection with $R_{601}$, and $R_{614}$ to $R_{616}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In an exemplary embodiment of the present disclosure, $L_{601}$ and $L_{611}$ to $L_{613}$ in Formulae 601 and 601-1 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a triazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridine group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, but the present disclosure is not limited thereto.

In an exemplary embodiment of the present disclosure, xe1 and xe611 to xe613 in Formulae 601 and 601-1 may each independently be 0, 1, or 2.

In an exemplary embodiment of the present disclosure, $R_{601}$ and $R_{611}$ to $R_{613}$ in Formulae 601 and 601-1 may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group;

—S(=O)$_2$(Q$_{601}$) and —P(=O)(Q$_{601}$)(Q$_{602}$); and Q$_{601}$ and Q$_{602}$ may be the same as described above.

The electron transport region may include, in addition to the condensed cyclic compound represented by Formula 1, at least one compound selected from, for example, Compounds ET1 to ET36, but the present disclosure is not limited thereto:

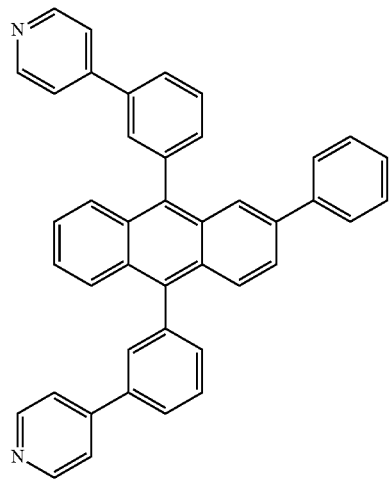
ET3

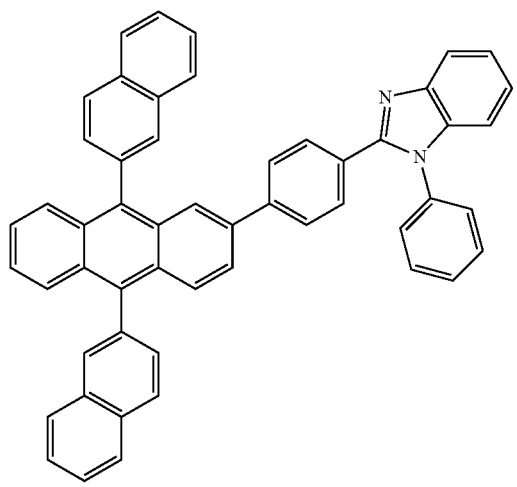
ET1

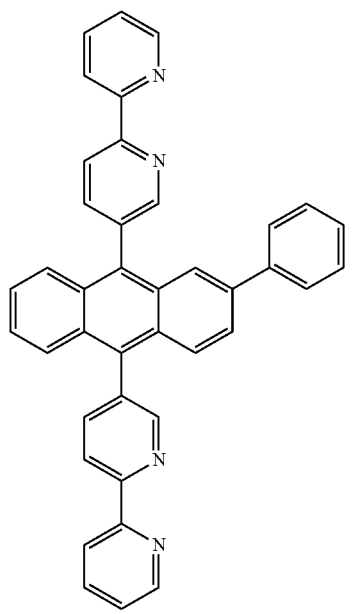
ET2

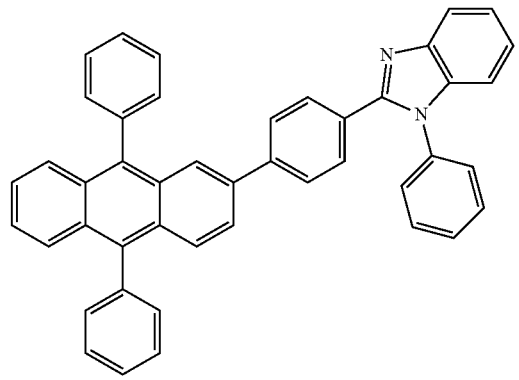
ET4

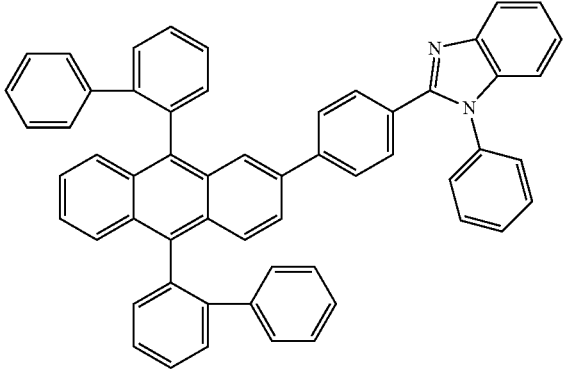
ET5

ET6
ET7
ET8
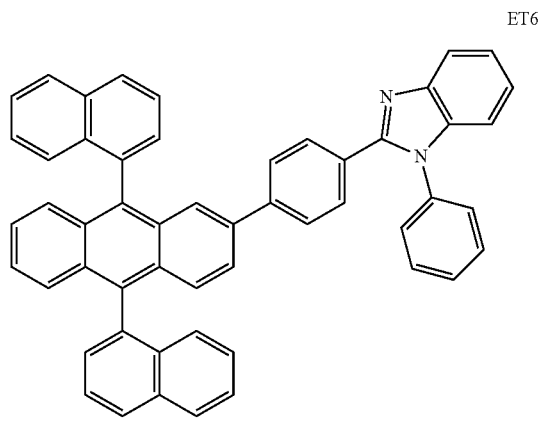
ET9
ET10
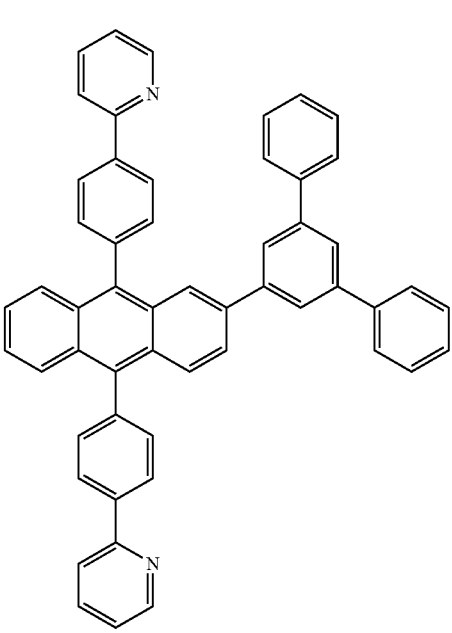

ET11
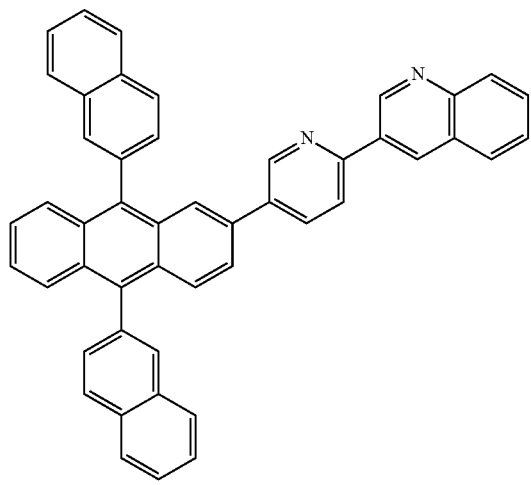
ET14
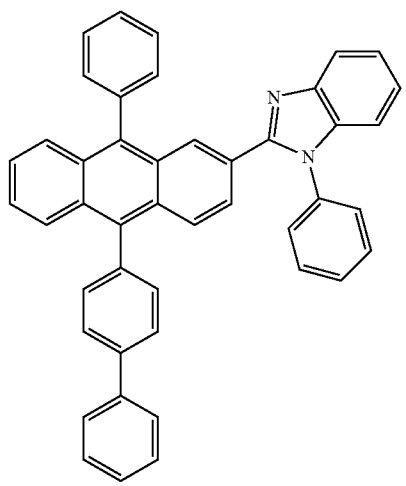
ET12
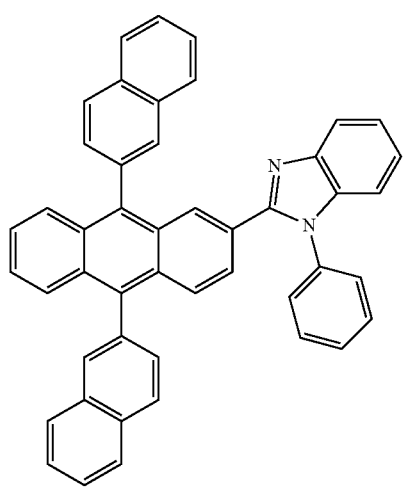
ET15
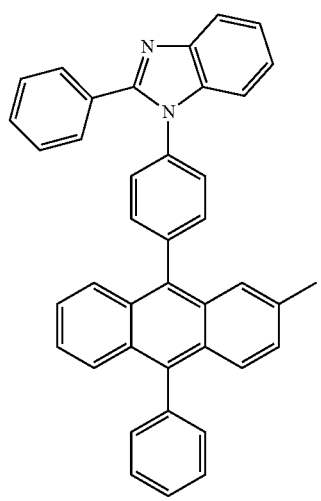
ET13
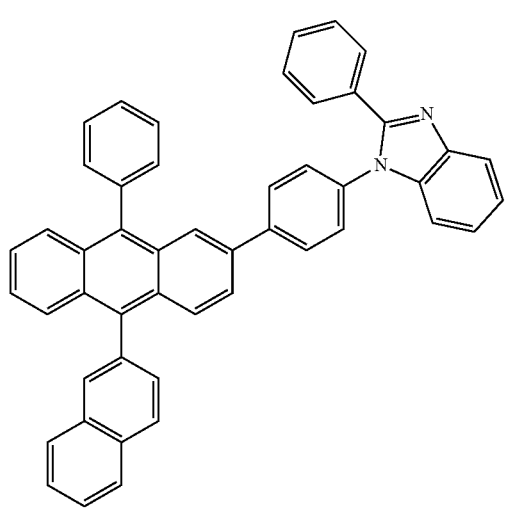
ET16
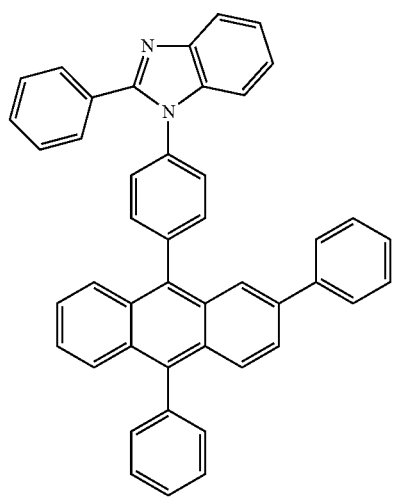

ET17
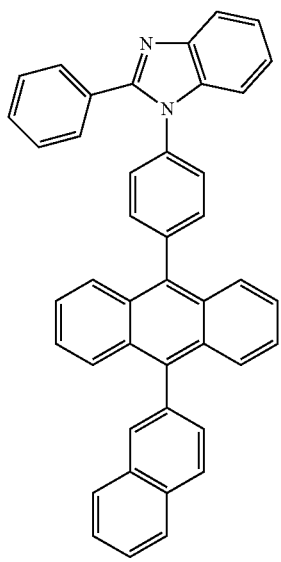
ET18
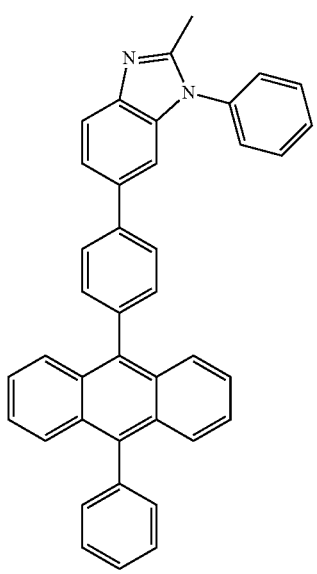
ET19
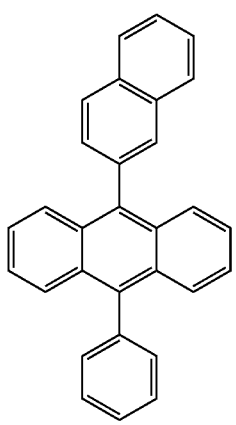
ET20
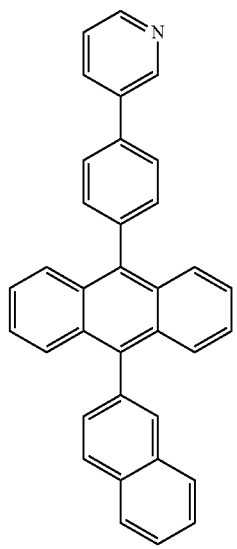
ET21
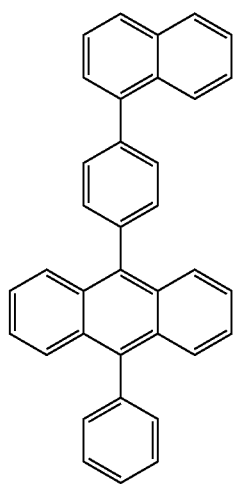
ET22
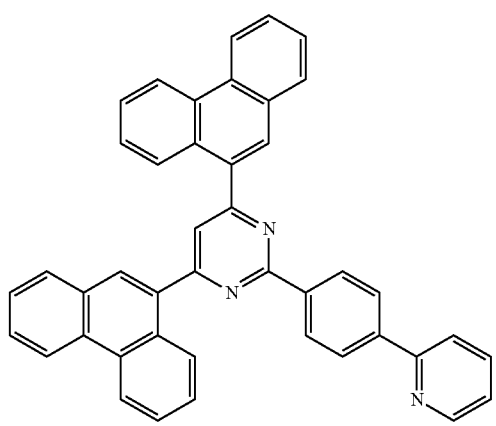

ET23
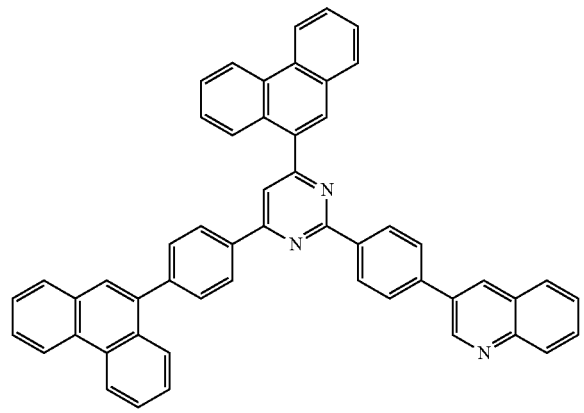
ET24
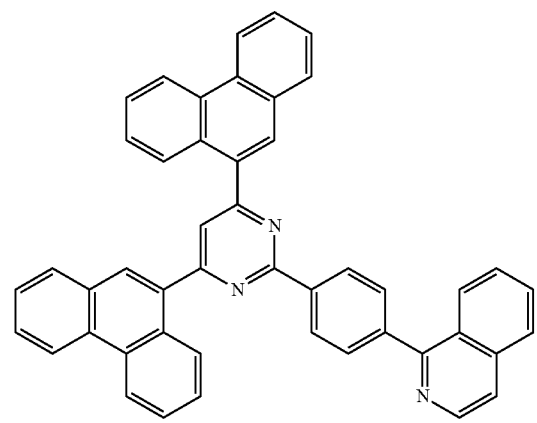
ET25
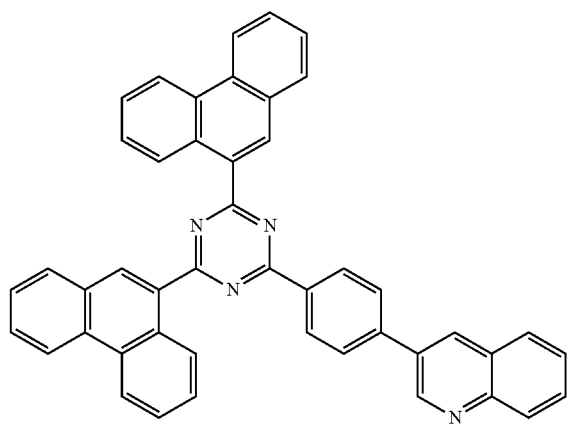
ET26
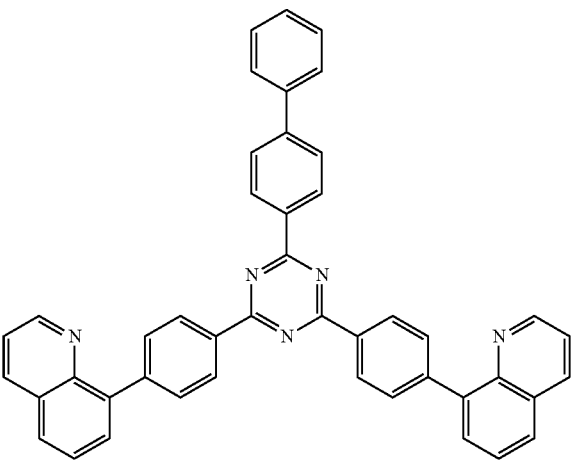
ET27
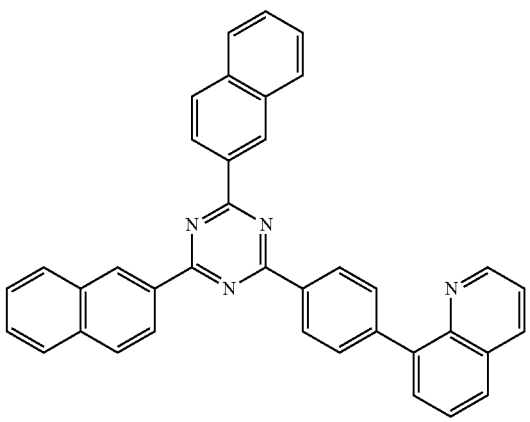
ET28
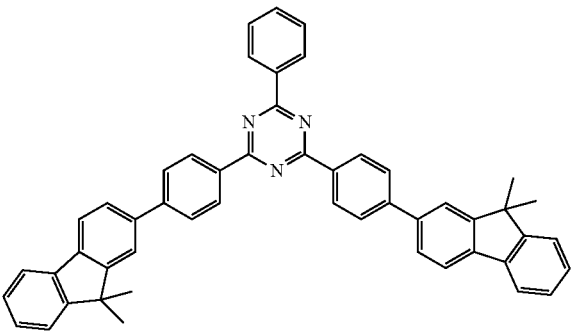

ET29 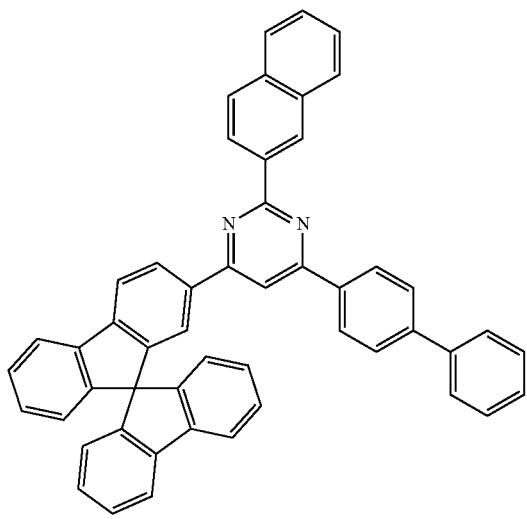
ET32 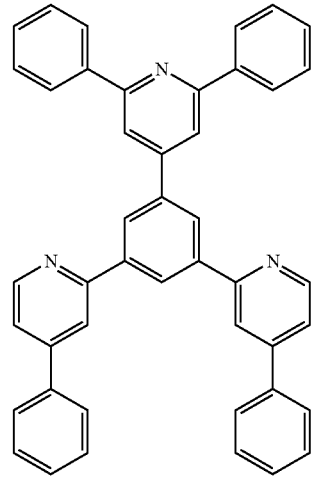
ET30 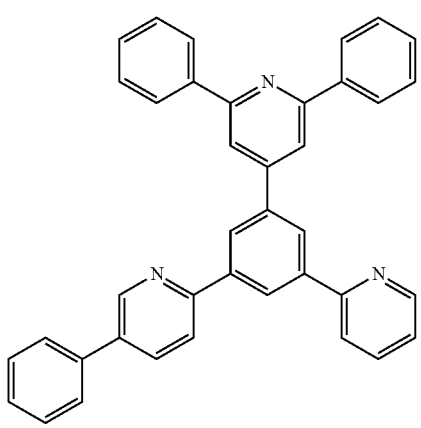
ET33 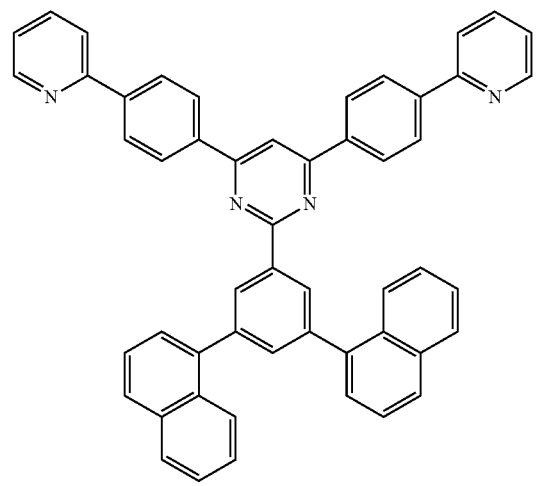
ET31
ET34 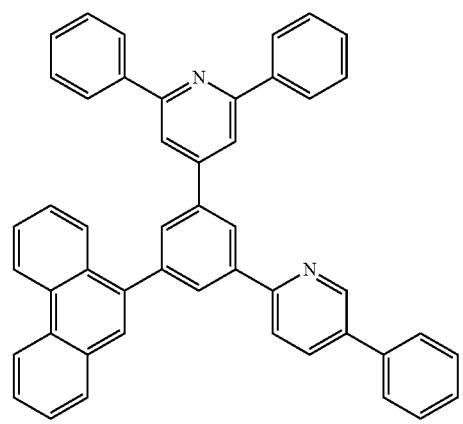

ET35

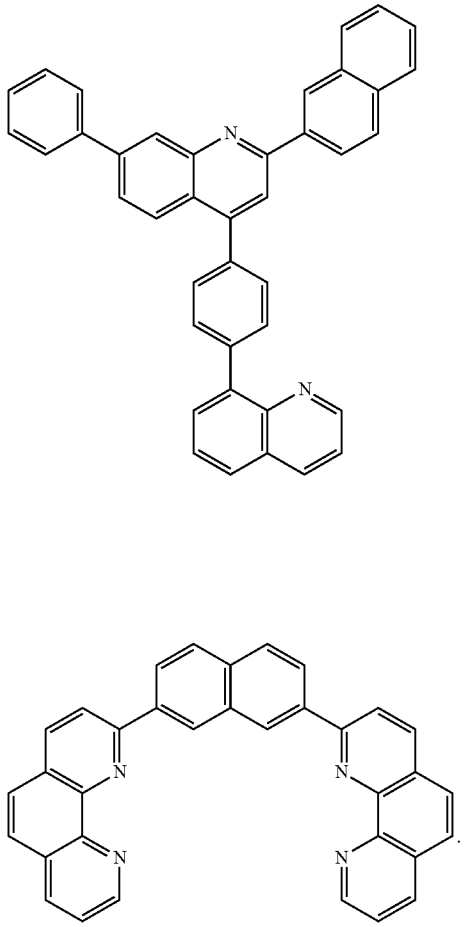

ET36

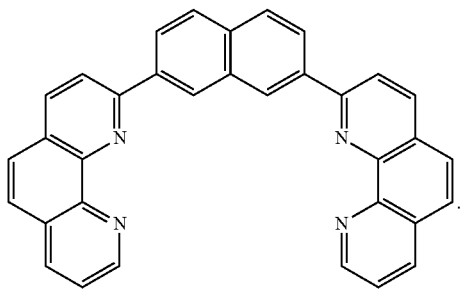

In an exemplary embodiment of the present disclosure, the electron transport region may include, in addition to the condensed cyclic compound represented by Formula 1, at least one compound selected from 2,9-dimethyl-4,7-diphenyl-1,10-phenanthroline (BCP), 4,7-diphenyl-1,10-phenanthroline (Bphen), tris(8-hydroxyquinolino)aluminum (Alq3), bis(2-methyl-8-quinolinolato-N1,O8)-(1,1'-biphenyl-4-olato)aluminum (BAlq), 3-(biphenyl-4-yl)-5-(4-tert-butylphenyl)-4-phenyl-4H-1,2,4-triazole (TAZ), and 4-(naphthalen-1-yl)-3,5-diphenyl-4H-1,2,4-triazole (NTAZ).

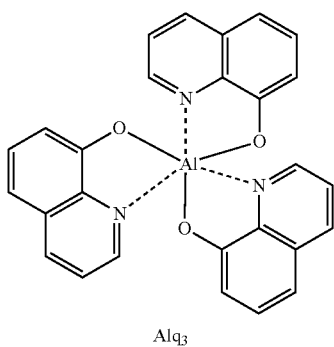

Alq3

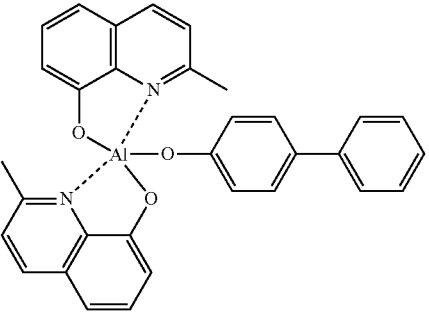

BAlq

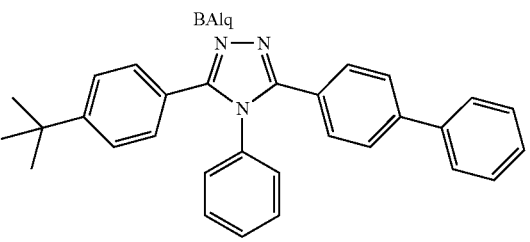

TAZ

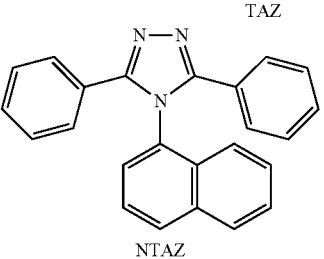

NTAZ

A thickness of the buffer layer, the hole blocking layer, or the electron control layer may be in a range of about 20 Å to about 1,000 Å, for example, about 30 Å to about 300 Å. When the thicknesses of the buffer layer, the hole blocking layer, and the electron control layer are within these ranges, the electron blocking layer may have excellent electron blocking characteristics or electron control characteristics without a substantial increase in driving voltage.

A thickness of the electron transport layer may be in a range of about 100 Å to about 1,000 Å, for example, about 150 Å to about 500 Å. When the thickness of the electron transport layer is within the range described above, the electron transport layer may have satisfactory electron transport characteristics without a substantial increase in driving voltage.

The electron transport region (for example, the electron transport layer in the electron transport region) may further include, in addition to the materials described above, a metal-containing material.

The metal-containing material may include at least one selected from an alkali metal complex and an alkaline earth-metal complex. The alkali metal complex may include a metal ion selected from an Li ion, a Na ion, a K ion, a Rb ion, and a Cs ion, and the alkaline earth-metal complex may include a metal ion selected from a Be ion, a Mg ion, a Ca ion, a Sr ion, and a Ba ion. A ligand coordinated with the metal ion of the alkali metal complex or the alkaline earth-metal complex may be selected from a hydroxy quinoline, a hydroxy isoquinoline, a hydroxy benzoquinoline, a hydroxy acridine, a hydroxy phenanthridine, a hydroxy phenylan oxazole, a hydroxy phenylthiazole, a hydroxy diphenylan oxadiazole, a hydroxy diphenylthiadiazol, a hydroxy phenylpyridine, a hydroxy phenylbenzimidazole, a hydroxy phenylbenzothiazole, a bipyridine, a phenanthroline, and a cyclopentadiene, but the present disclosure is not limited thereto.

In an exemplary embodiment of the present disclosure, the metal-containing material may include a Li complex. The Li complex may include, for example, Compound ET-D1 (lithium quinolate, LiQ) or ET-D2.

ET-D1

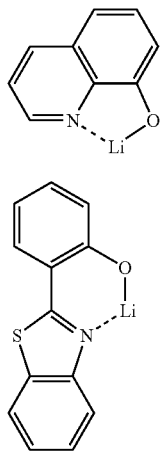

ET-D2

The electron transport region may include an electron injection layer that facilitates injection of electrons from the second electrode 190. The electron injection layer may directly contact the second electrode 190.

The electron injection layer may have i) a single-layered structure including a single layer which includes a single material, ii) a single-layered structure including a single layer which includes a plurality of different materials, or iii) a multi-layered structure having a plurality of layers which include a plurality of different materials.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof.

The alkali metal may be selected from, for example, Li, Na, K, Rb, and Cs. In an exemplary embodiment of the present disclosure, the alkali metal may be Li, Na, or Cs. In an exemplary embodiment of the present disclosure, the alkali metal may be Li or Cs, but the present disclosure is not limited thereto.

The alkaline earth metal may be selected from, for example, Mg, Ca, Sr, and Ba.

The rare earth metal may be selected from, for example, Sc, Y, Ce, Tb, Yb, and Gd.

The alkali metal compound, the alkaline earth-metal compound, and the rare earth metal compound may be selected from oxides and halides (for example, fluorides, chlorides, bromides, or iodides) of the alkali metal, the alkaline earth-metal and rare earth metal.

The alkali metal compound may be selected from alkali metal oxides, such as, for example, $Li_2O$, $Cs_2O$, and $K_2O$, and alkali metal halides, such as, for example, LiF, NaF, CsF, KF, LiI, NaI, CsI, KI, and RbI. In an exemplary embodiment of the present disclosure, the alkali metal compound may be selected from LiF, $Li_2O$, NaF, LiI, NaI, CsI, and KI, but the present disclosure is not limited thereto.

The alkaline earth-metal compound may be selected from alkaline earth-metal compounds, such as, for example, BaO, SrO, CaO, $Ba_xSr_{1-x}O$ (0<x<1), $Ba_xCa_{1-x}O$ (0<x<1). In an exemplary embodiment of the present disclosure, the alkaline earth-metal compound may be selected from, for example, BaO, SrO, and CaO, but the present disclosure is not limited thereto.

The rare earth metal compound may be selected from, for example, $YbF_3$, $ScF_3$, $ScO_3$, $Y_2O_3$, $Ce_2O_3$, $GdF_3$, and $TbF_3$. In an exemplary embodiment of the present disclosure, the rare earth metal compound may be selected from, for example, $YbF_3$, $ScF_3$, $TbF_3$, $YbI_3$, $ScI_3$, and $TbI_3$, but the present disclosure is not limited thereto.

The alkali metal complex, the alkaline earth-metal complex, and the rare earth metal complex may include an ion of alkali metal, alkaline earth-metal, and rare earth metal as described above, and a ligand coordinated with a metal ion of the alkali metal complex, the alkaline earth-metal complex, and the rare earth metal complex may each independently be selected from hydroxy quinoline, hydroxy isoquinoline, hydroxy benzoquinoline, hydroxy acridine, hydroxy phenanthridine, hydroxy phenylan oxazole, hydroxy phenylthiazole, hydroxy diphenylan oxadiazole, hydroxy diphenylthiadiazol, hydroxy phenylpyridine, hydroxy phenylbenzimidazole, hydroxy phenylbenzothiazole, bipyridine, phenanthroline, and cyclopentadiene, but the present disclosure is not limited thereto.

The electron injection layer may include an alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof, as described above. In an exemplary embodiment of the present disclosure, the electron injection layer may further include an organic material. When the electron injection layer further includes an organic material, alkali metal, an alkaline earth metal, a rare earth metal, an alkali metal compound, an alkaline earth-metal compound, a rare earth metal compound, an alkali metal complex, an alkaline earth-metal complex, a rare earth metal complex, or any combinations thereof may be homogeneously or non-homogeneously dispersed in a matrix including the organic material.

A thickness of the electron injection layer may be in a range of about 1 Å to about 100 Å, for example, about 3 Å to about 90 Å. When the thickness of the electron injection layer is within the range described above, the electron injection layer may have satisfactory electron injection characteristics without a substantial increase in driving voltage.

[Second Electrode 190]

The second electrode 190 may be disposed on the organic layer 150 having above described structure. The second electrode 190 may be a cathode which is an electron injection electrode, and in this regard, a material for forming the second electrode 190 may be selected from a metal, an alloy, an electrically conductive compound, and a combination thereof, which have a relatively low work function.

The second electrode 190 may include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but the present disclosure is not limited thereto. The second electrode 190 may be a transmissive electrode, a semi-transmissive electrode, or a reflective electrode.

The second electrode 190 may have a single-layered structure, or a multi-layered structure including two or more layers.

Figure 2:
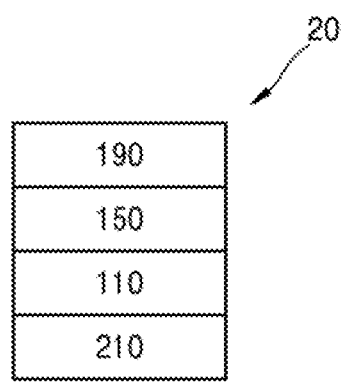
FIG. 2 is a schematic cross-sectional view of an organic light-emitting device according to an exemplary embodiment of the present disclosure.
Figure 3:
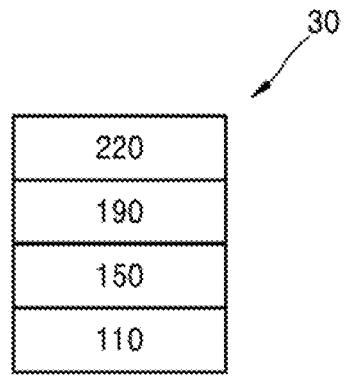
FIG. 3 is a schematic cross-sectional view of an organic light-emitting device according to an exemplary embodiment of the present disclosure.
Figure 4:
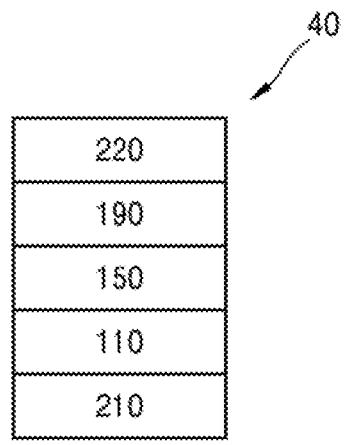
FIG. 4 is a schematic cross-sectional view of an organic light-emitting device according to an exemplary embodiment of the present disclosure.

[Description of FIGS. 2 to 4]

FIGS. 2-4 each represents a schematic cross-sectional view of an organic light-emitting device, in which: an organic light-emitting device 20 of FIG. 2 includes a first capping layer 210, a first electrode 110, an organic layer 150, and a second electrode 190, which are sequentially stacked in this stated order; an organic light-emitting device 30 of FIG. 3 includes a first electrode 110, an organic layer 150, a second electrode 190, and a second capping layer 220, which are sequentially stacked in this stated order; and an organic light-emitting device 40 of FIG. 4 includes a first capping layer 210, a first electrode 110, an organic layer 150, a second electrode 190, and a second capping layer 220, which are sequentially stacked in this stated order.

Regarding FIGS. 2 to 4, the first electrode 110, the organic layer 150, and the second electrode 190 may be understood by referring to the description presented in connection with FIG. 1.

In the organic layer 150 of each of the organic light-emitting devices 20 and 40, light generated in an emission layer may pass through the first electrode 110, which is a semi-transmissive electrode or a transmissive electrode, and the first capping layer 210 toward the outside, and in the organic layer 150 of each of the organic light-emitting devices 30 and 40, light generated in an emission layer may pass through the second electrode 190, which is a semi-transmissive electrode or a transmissive electrode, and the second capping layer 220 toward the outside.

The first capping layer 210 and the second capping layer 220 may increase external luminescent efficiency according to the principle of constructive interference.

The first capping layer 210 and the second capping layer 220 may each independently be an organic capping layer including an organic material, an inorganic capping layer including an inorganic material, or a composite capping layer including an organic material and an inorganic material.

The first capping layer 210 and the second capping layer 220 may each independently include at least one material selected from carbocyclic compounds, heterocyclic compounds, amine-based compounds, porphyrine derivatives, phthalocyanine derivatives, naphthalocyanine derivatives, alkali metal complexes, and alkaline earth-based complexes. The carbocyclic compound, the heterocyclic compound, and the amine-based compound may be optionally substituted with a substituent containing at least one element selected from O, N, S, Se, Si, F, Cl, Br, and I. In an exemplary embodiment of the present disclosure, the first capping layer 210 and the second capping layer 220 may each independently include an amine-based compound.

In an exemplary embodiment of the present disclosure, the first capping layer 210 and the second capping layer 220 may each independently include the compound represented by Formula 201 or the compound represented by Formula 202.

In an exemplary embodiment of the present disclosure, the first capping layer 210 and the second capping layer 220 may each independently include a compound selected from, for example, Compounds HT28 to HT33 and Compounds CP1 to CP5, but the present disclosure is not limited thereto.

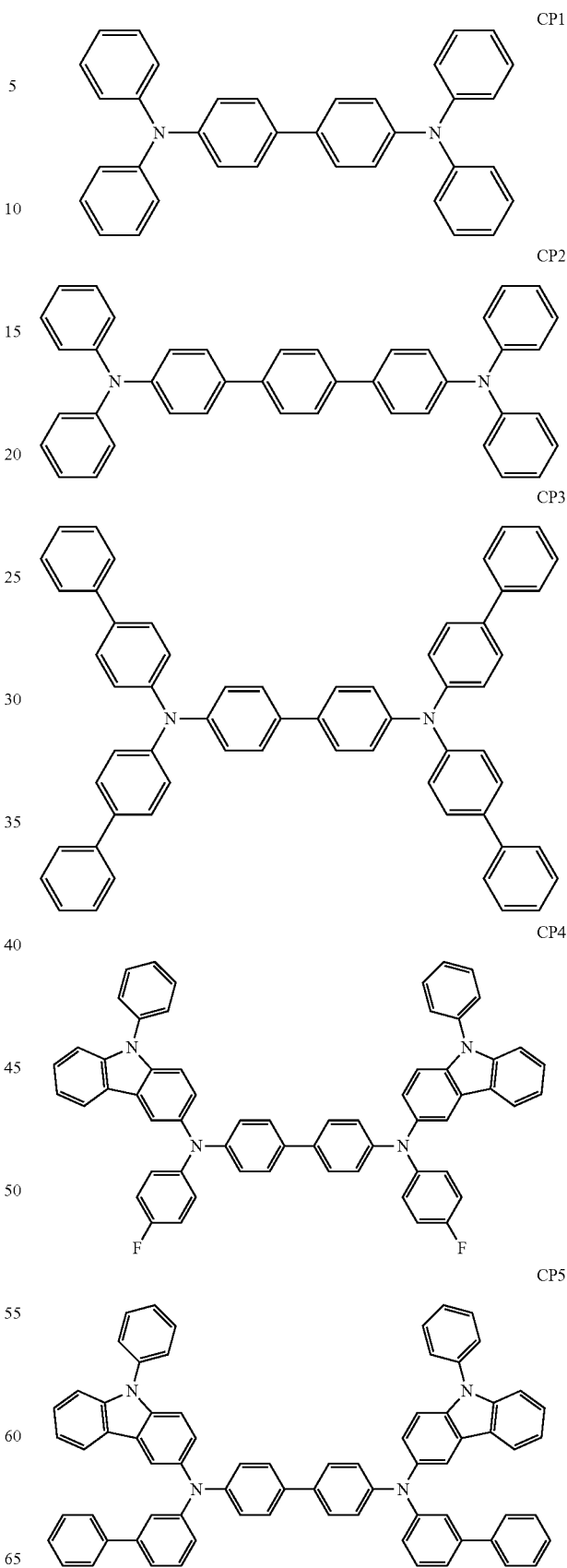

Hereinbefore, the organic light-emitting device according to an exemplary embodiment of the present disclosure has been described in connection with FIGS. 1-4. However, the present disclosure is not limited thereto.

Layers constituting the hole transport region, an emission layer, and layers constituting the electron transport region may be formed in a certain region by using one or more suitable methods selected from vacuum deposition, spin coating, casting, Langmuir-Blodgett (LB) deposition, ink-jet printing, laser-printing, and laser-induced thermal imaging.

When layers constituting the hole transport region, an emission layer, and layers constituting the electron transport region are formed by vacuum deposition, for example, the vacuum deposition may be performed at a deposition temperature of about 100° C. to about 500° C. at a vacuum degree of about $10^{-8}$ torr to about $10^{-8}$ torr, and at a deposition rate of about 0.01 Å/sec to about 100 Å/sec by taking into account the material to be included in a layer to be formed, and the structure of a layer to be formed.

When layers constituting the hole transport region, an emission layer, and layers constituting the electron transport region are formed by spin coating, the spin coating may be performed at a coating speed of about 2,000 rpm to about 5,000 rpm and at a heat treatment temperature of about 80° C. to 200° C. by taking into account the material to be included in a layer to be formed, and the structure of a layer to be formed.

[General Definition of Substituents]

The term "$C_1$-$C_{60}$ alkyl group" as used herein refers to a linear or branched saturated aliphatic hydrocarbon monovalent group having 1 to 60 carbon atoms, and examples thereof include a methyl group, an ethyl group, a propyl group, an isobutyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group and a propynyl group. The term "$C_2$-$C_{60}$ alkynylene group" as used herein refers to a divalent group having the same structure as the $C_2$-$C_{60}$ alkynyl group.

The term "$C_1$-$C_{60}$ alkoxy group" as used herein refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group" as used herein refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," used herein, refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and does not have aromaticity, and examples thereof include a cyclopentenyl group, a cyclohexenyl group, and a cycloheptenyl group. The term "$C_3$-$C_{10}$ cycloalkenylene group," used herein, refers to a divalent group having the same structure as the $C_3$-$C_{10}$ cycloalkenyl group.

The term "$C_2$-$C_{10}$ heterocycloalkenyl group" as used herein refers to a monovalent monocyclic group that has at least one heteroatom selected from N, O, Si, P, and S as a ring-forming atom, 2 to 10 carbon atoms, and at least one carbon-carbon double bond in its ring. Non-limiting examples of the $C_2$-$C_{10}$ heterocycloalkenyl group include a 2,3-dihydrofuranyl group and a 2,3-dihydrothiophenyl group. The term "$C_2$-$C_{10}$ heterocycloalkenylene group," used herein, refers to a divalent group having the same structure as the $C_2$-$C_{10}$ heterocycloalkenyl group.

The term "$C_6$-$C_{60}$ aryl group" as used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each includes two or more rings, the rings may be fused to each other.

The term "$C_1$-$C_{60}$ heteroaryl group" as used herein refers to a monovalent group having a heterocyclic aromatic system that contains at least one heteroatom selected from N, O, Si, P, and S as a ring-forming atom and 1 to 60 carbon atoms, and the term "$C_1$-$C_{60}$ heteroarylene group" as used herein refers to a divalent group having a heterocyclic aromatic system that contains at least one heteroatom selected from N, O, Si, P, and S as a ring-forming atom and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each includes two or more rings, the rings may be fused to each other.

The term "$C_6$-$C_{60}$ aryloxy group" used herein, indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

The term "$C_1$-$C_{60}$ heteroaryloxy group" as used herein refers to —$OA_{104}$ (where $A_{104}$ is the $C_1$-$C_{60}$ heteroaryl group), and the term "$C_1$-$C_{60}$ heteroarylthio group" as used herein refers to —$SA_{105}$ (where $A_{105}$ is the $C_1$-$C_{60}$ heteroaryl group).

The term "monovalent non-aromatic condensed polycyclic group" as used herein refers to a monovalent group (for example, having 8 to 60 carbon atoms) that has two or more rings condensed with each other, only carbon atoms as a ring-forming atom, and non-aromaticity in the entire molecular structure. A detailed example of the monovalent non-aromatic condensed polycyclic group is a fluorenyl group. The term "divalent non-aromatic condensed polycyclic group," used herein, refers to a divalent group having the same structure as the monovalent non-aromatic condensed polycyclic group.

The term "monovalent non-aromatic condensed heteropolycyclic group" as used herein refers to a monovalent group (for example, having 1 to 60 carbon atoms) that has two or more rings condensed to each other, has at least one heteroatom selected from N, O, Si, P, and S, other than carbon atoms, as a ring-forming atom, and has non-aromaticity in the entire molecular structure. An example of the monovalent non-aromatic condensed heteropolycyclic group is a carbazolyl group. The term "divalent non-aromatic condensed heteropolycyclic group," used herein, refers to a divalent group having the same structure as the monovalent non-aromatic condensed heteropolycyclic group.

The term "$C_5$-$C_{60}$ carbocyclic group" as used herein refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as a benzene group, a monovalent group, such as a phenyl group, or a divalent group, such as a phenylene group. In an exemplary embodiment of the present disclosure, depending on the number of substituents connected to the $C_5$-$C_{60}$ carbocyclic group, the $C_6$-$C_{60}$ carbocyclic group may be a bivalent group or a quadrivalent group.

The term "$C_1$-$C_{60}$ heterocyclic group" as used herein refers to a group having the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60). Heterocyclic group includes one or more heterocyclic rings.

At least one substituent of the substituted $C_5$-$C_{60}$ carbocyclic group, substituted $C_1$-$C_{60}$ heterocyclic group, substituted $C_3$-$C_{10}$ cycloalkylene group, substituted $C_1$-$C_{10}$ heterocycloalkylene group, substituted $C_3$-$C_{10}$ cycloalkenylene group, substituted $C_2$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_2$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted $C_1$-$C_{60}$ heteroaryloxy group, substituted $C_1$-$C_{60}$ heteroarylthio group, substituted monovalent non-aromatic condensed polycyclic group, and substituted monovalent non-aromatic condensed heteropolycyclic group may be selected from:

deuterium (-D), —F, —Cl, —Br, —I, a hydroxyl group, a cyano group, a nitro group, an amidino group, a hydrazino group, a hydrazono group, a $C_1$-$C_{60}$ alkyl group, a $C_1$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_1$-$C_{60}$ alkynyl group, and a $C_1$-$C_{60}$ alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{11}$)($Q_{12}$)($Q_{13}$), —N($Q_{11}$)($Q_{12}$), —B($Q_{11}$)($Q_{12}$), —C(=O)($Q_{11}$), —S(=O)$_2$($Q_{11}$), and —P(=O)($Q_{11}$)($Q_{12}$);

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, —Si($Q_{21}$)($Q_{22}$)($Q_{23}$), —N($Q_{21}$)($Q_{22}$), —B($Q_{21}$)($Q_{22}$), —C(=O)($Q_{21}$), —S(=O)$_2$($Q_{21}$) and —P(=O)($Q_{21}$)($Q_{22}$); —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$); and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a $C_1$-$C_{60}$ heteroaryloxy group, a $C_1$-$C_{60}$ heteroarylthio group, a monovalent non-aromatic condensed polycyclic group, a monovalent non-aromatic condensed heteropolycyclic group, a biphenyl group, and a terphenyl group.

The term "Ph" used herein refers to a phenyl group, the term "Me" used herein refers to a methyl group, the term "Et" used herein refers to an ethyl group, the term "ter-Bu" or "Bu$^t$" used herein refers to a tert-butyl, and the term "OMe" used herein refers to a methoxy group.

The term "biphenyl group" as used therein refers to "a phenyl group substituted with a phenyl group." In other words, the "biphenyl group" is one of a substituted phenyl group having a $C_6$-$C_{60}$ aryl group as a substituent.

The term "terphenyl group" as used herein refers to "a phenyl group substituted with a biphenyl group." In other words, the "terphenyl group" is one of a substituted phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

The condensed cyclic compound represented by Formula 1 may be synthesized by using a known organic synthesis method. A synthesis method of the condensed cyclic compound may be recognizable by one of ordinary skill in the art in view of the following exemplary embodiments.

Hereinafter, a compound according to an exemplary embodiment of the present disclosure and an organic light-emitting device according to an exemplary embodiment of the present disclosure will be described in detail with reference to Synthesis Examples and Examples. The wording "B was used instead of A" used in describing Synthesis Examples refers to that an identical molar equivalent of B was used in place of A.

SYNTHESIS EXAMPLES

Synthesis Example 1

Synthesis of Compound 1

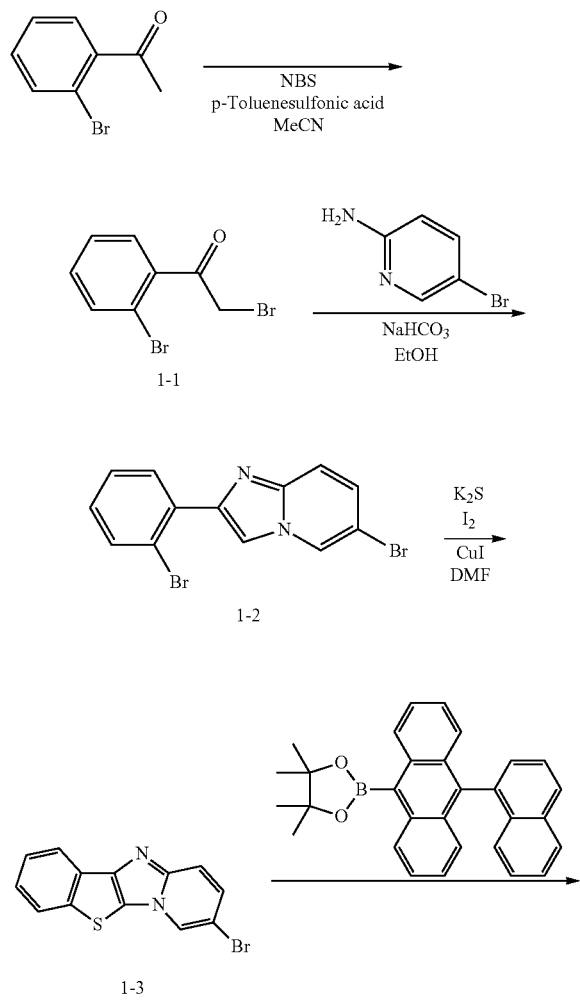

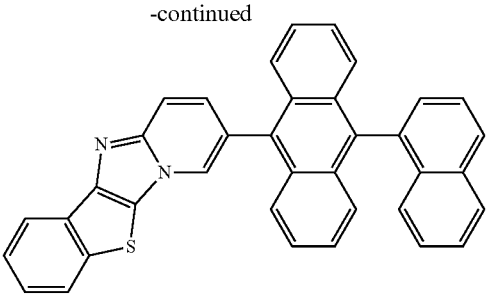

(1) Synthesis of Intermediate 1-1

2.0 g (10 mmol) of 2'-bromoacetophenone, 1.8 g (10 mmol) of N-bromosuccinimide, 1.9 g (10 mmol) of a p-toluene sulfonic acid, and 200 mL of acetonitrile were added to a reaction vessel, and the resultant mixture was stirred under reflux for 4 hours in a nitrogen atmosphere. After the reaction was completed, the reaction mixture was cooled to room temperature and distilled under reduced pressure. Then, an extraction process was performed thereon by using water and 100 mL of ethyl acetate. An organic layer collected therefrom was dried by using anhydrous magnesium sulfate and distilled under reduced pressure, thereby completing the preparation of 2.50 g (yield: 90%) of Intermediate 1-1. Intermediate 1-1 was used in a subsequent reaction without additional purification.

(2) Synthesis of Intermediate 1-2

2.78 g (10 mmol) of Intermediate 1-1, 1.24 g (15 mmol) of sodium hydrogen carbonate, 1.73 g (10 mmol) of 2-amino-5-bromopyridine, and 200 mL of ethanol were added to a reaction vessel, and the resultant mixture was stirred under reflux for 4 hours in a nitrogen atmosphere. After the reaction was completed, the reaction mixture was cooled to room temperature and distilled under reduced pressure. Then, an extraction process was performed thereon by using water and 100 mL of ethyl acetate. An organic layer collected therefrom was dried by using anhydrous magnesium sulfate and distilled under reduced pressure to obtain a crude product. The crude product was purified by column chromatography, thereby completing the preparation of 2.28 g (yield: 65%) of Intermediate 1-2.

(3) Synthesis of Intermediate 1-3

3.52 g (10 mmol) of Intermediate 1-2, 3.3 g (30 mmol) of potassium sulfide ($K_2S$), 2.53 g (10 mmol) of iodine ($I_2$), 0.38 g (2 mmol) of copper(I) iodide (CuI), and 150 mL of dimethylformamide (DMF) were added to a reaction vessel, and the resultant mixture was stirred at a temperature of 140° C. for 24 hours while supplying air into the reaction vessel (for supply of oxygen). After the reaction was completed, the reaction mixture was cooled to room temperature and filtered to obtain a filtrate. Then, an extraction process was performed on the filtrate by using water and 100 mL of ethyl acetate. An organic layer collected therefrom was dried by using anhydrous magnesium sulfate and distilled under reduced pressure to obtain a crude product. The crude product was purified by column chromatography, thereby completing the preparation of 1.8 g (yield: 60%) of Intermediate 1-3.

(4) Synthesis of Compound 1

3.03 g (10 mmol) of Intermediate 1-3, 4.3 g (10 mmol) of 4,4,5,5-tetramethyl-2-(10-(naphthalene-1-yl)anthracene-9-yl)-1,3,2-dioxaborolan, 0.58 g (0.5 mmol) of Tetrakis(triphenylphosphine)palladium(0) ($Pd(PPh_3)_4$), 4.15 g (30 mmol)

of potassium carbonate (K₂CO₃), 80 mL of distilled water, 160 mL of toluene, and 50 mL of ethanol were added to a reaction vessel, and the resultant mixture was stirred under reflux for 12 hours. After the reaction was completed, the reaction mixture was cooled to room temperature. Then, an extraction process was performed thereon by using 100 mL of dichloromethane. An organic layer collected therefrom was washed by using distilled water, dried by using anhydrous magnesium sulfate, and distilled under reduced pressure to obtain a crude product. The crude product was purified by column chromatography, thereby completing the preparation of 3.15 g (yield: 60%) of Compound 1.

Synthesis Example 2

Synthesis of Compound 33

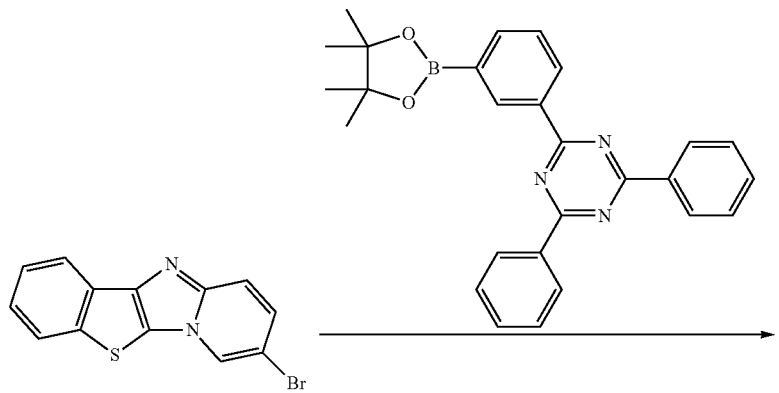

4.31 g (yield: 81%) of Compound 33 was synthesized in the same manner as in Synthesis of Compound 1, except that 2,4-diphenyl-6-(3-(4,4,5,5-tetramethyl-1,3,2-dioxaborolan-2-yl)phenyl)-1,3,5-triazine was used instead of 4,4,5,5-tetramethyl-2-(10-(naphthalene-1-yl)anthracene-9-yl)-1,3,2-dioxaborolan.

Synthesis Example 3

Synthesis of Compound 185

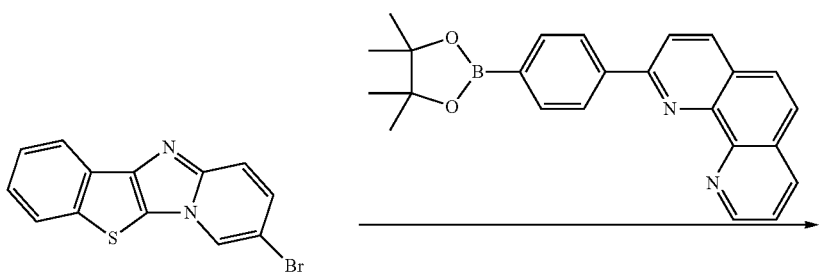

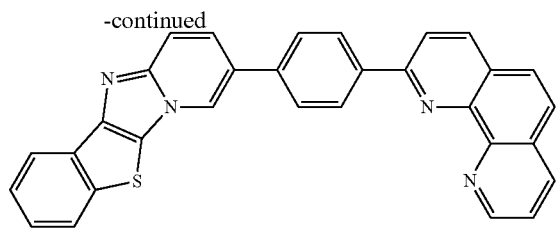

185

3.67 g (yield: 77%) of Compound 185 was synthesized in the same manner as in Synthesis of Compound 1, except that 2-(4-(4,4,5,5-tetramethyl-1,3,2-dioxaborolan-2-yl)phenyl)-1,10-phenanthroline was used instead of 4,4,5,5-tetramethyl-2-(10-(naphthalene-1-yl)anthracene-9-yl)-1,3,2-dioxaborolan.

Synthesis Example 4

Synthesis of Compound 187

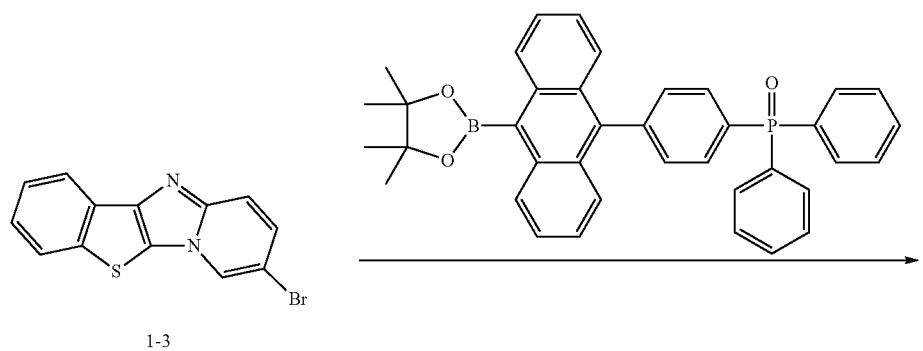

1-3

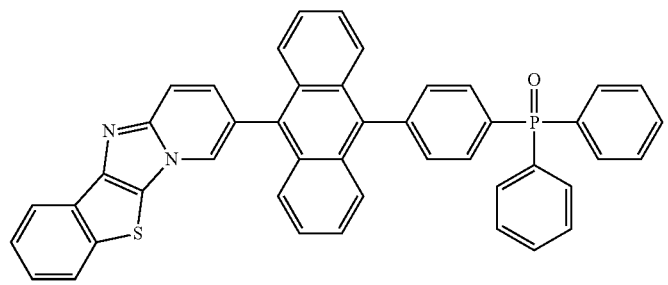

187

3.05 g (yield: 45%) of Compound 187 was synthesized in the same manner as in Synthesis of Compound 1, except that diphenyl(4-(10-(4,4,5,5-tetramethyl-1,3,2-dioxaborolan-2-yl)anthracene-9-yl)phenyl)phosphine oxide was used instead of 4,4,5,5-tetramethyl-2-(10-(naphthalene-1-yl)anthracene-9-yl)-1,3,2-dioxaborolan.

Synthesis Example 5

Synthesis of Compound 51

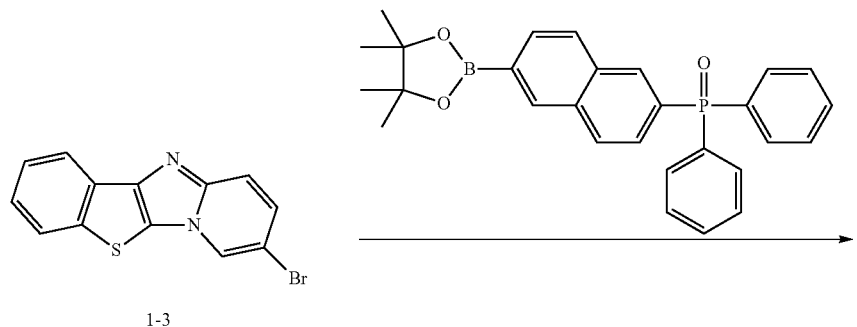

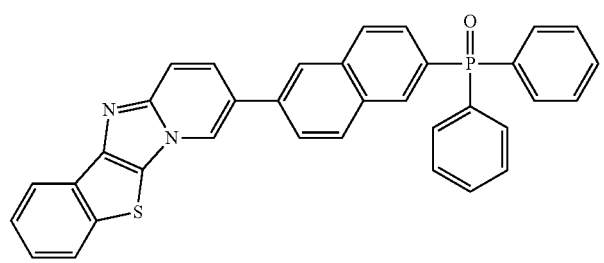

51

3.03 g (yield: 55%) of Compound 51 was synthesized in the same manner as in Synthesis of Compound 1, except that diphenyl(6-(4,4,5,5-tetramethyl-1,3,2-dioxaborolan-2-yl)naphthalene-2-yl)phosphine oxide was used instead of 4,4,5,5-tetramethyl-2-(10-(naphthalene-1-yl)anthracene-9-yl)-1,3,2-dioxaborolan.

Synthesis Example 6

Synthesis of Compound 189

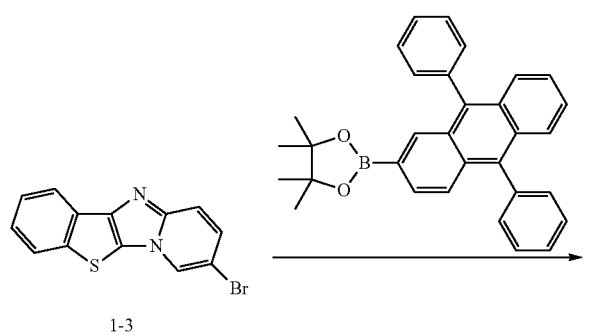

-continued

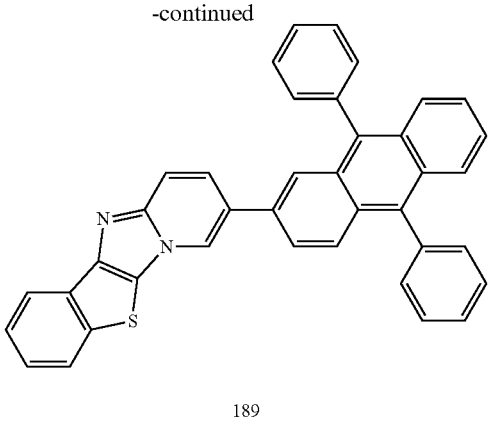

189

3.54 g (yield: 64%) of Compound 189 was synthesized in the same manner as in Synthesis of Compound 1, except that 2-(9,10-diphenylanthracene-2-yl)-4,4,5,5-tetramethyl-1,3,2-dioxaborolan was used instead of 4,4,5,5-tetramethyl-2-(10-(naphthalene-1-yl)anthracene-9-yl)-1,3,2-dioxaborolan.

Synthesis Example 7
Synthesis of Compound 127
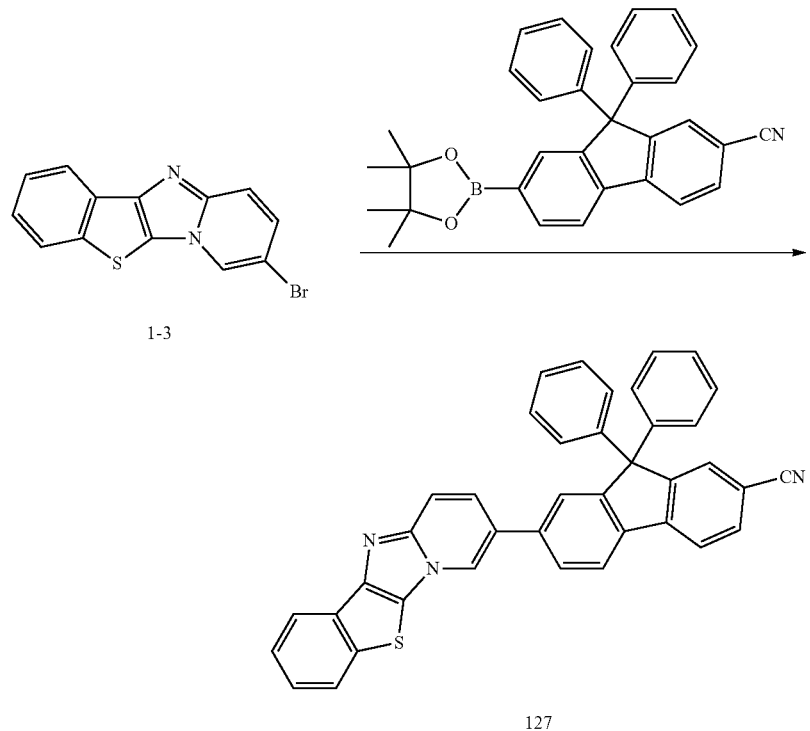
4.01 g (yield: 71%) of Compound 127 was synthesized in the same manner as in Synthesis of Compound 1, except that 9,9-diphenyl-7-(4,4,5,5-tetramethyl-1,3,2-dioxaborolan-2-yl)-9H-fluorene-2-carbonitrile was used instead of 4,4,5,5-tetramethyl-2-(10-(naphthalene-1-yl)anthracene-9-yl)-1,3,2-dioxaborolan.
Synthesis Example 8
Synthesis of Compound 158
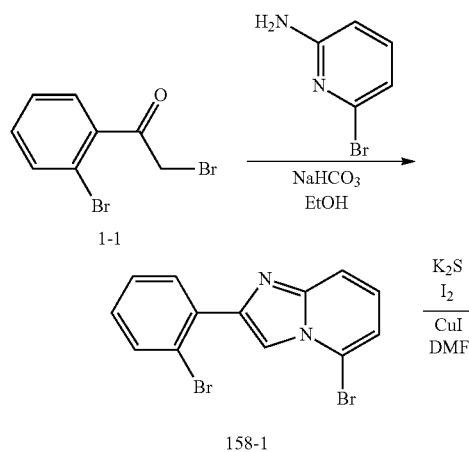
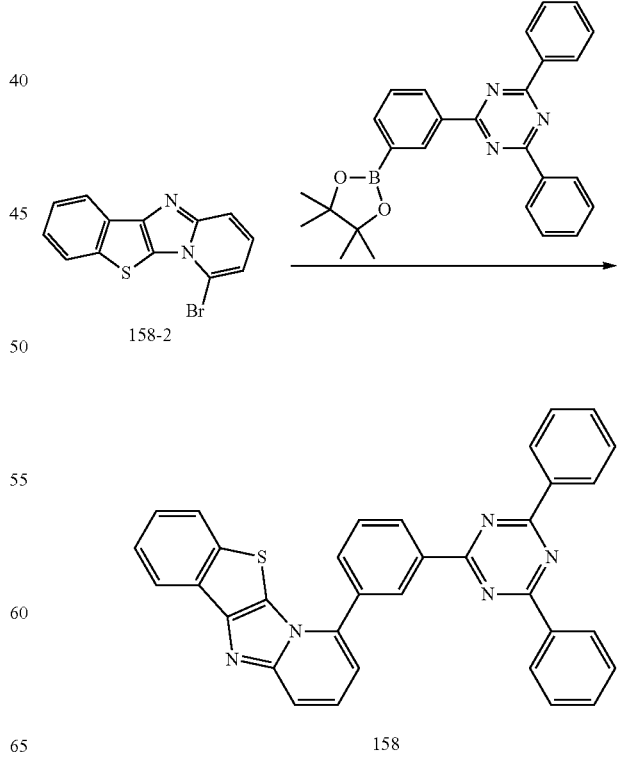

(1) Synthesis of Intermediate 158-1

2.13 g (yield: 61%) of Intermediate 158-1 was synthesized in the same manner as in Synthesis of Intermediate 1-2, except that 2-amino-6-bromopyridine was used instead of 2-amino-5-bromopyridine.

(2) Synthesis of Intermediate 158-2

1.52 g (yield: 55%) of Intermediate 158-2 was synthesized in the same manner as in Synthesis of Intermediate 1-3, except that Intermediate 158-1 was used instead of Intermediate 1-2.

(3) Synthesis of Compound 158

3.72 g (yield: 70%) of Compound 158 was synthesized in the same manner as in Synthesis of Compound 33, except that Intermediate 158-2 was used instead of Intermediate 1-3.

Synthesis Example 9

Synthesis of Compound 191

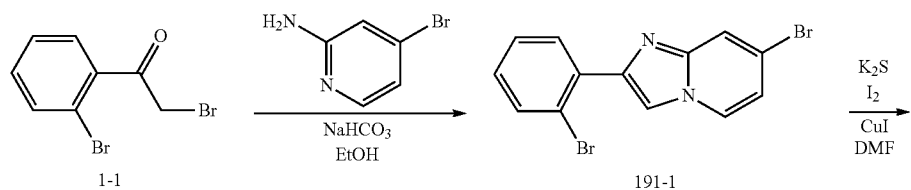

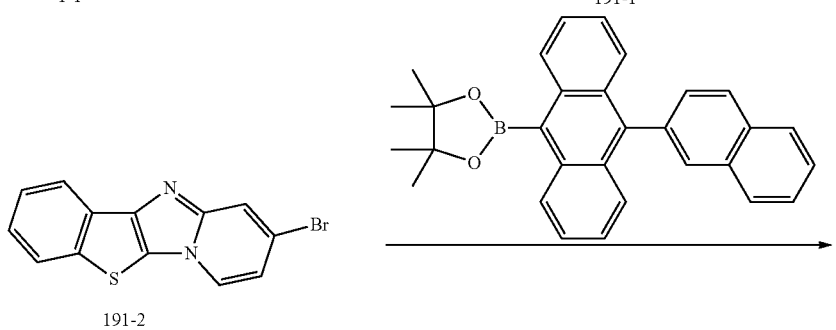

(1) Synthesis of Intermediate 191-1

1.94 g (yield: 55%) of Intermediate 191-1 was synthesized in the same manner as in Synthesis of Intermediate 1-2, except that 2-amino-4-bromopyridine was used instead of 2-amino-5-bromopyridine.

(2) Synthesis of Intermediate 191-2

1.52 g (yield: 55%) of Intermediate 191-2 was synthesized in the same manner as in Synthesis of Intermediate 1-3, except that Intermediate 191-1 was used instead of Intermediate 1-2.

(3) Synthesis of Compound 191

3.72 g (yield: 70%) of Compound 191 was synthesized in the same manner as in Synthesis of Compound 1, except that Intermediate 191-2 was used instead of Intermediate 1-3.

Synthesis Example 10

Synthesis of Compound 174

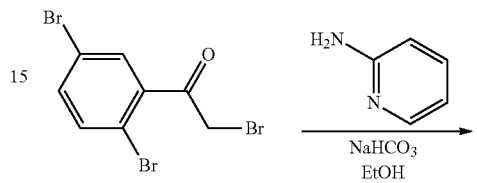

-continued

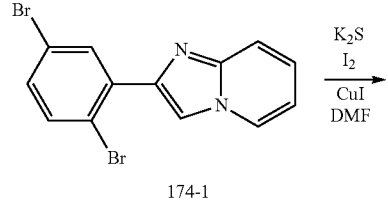

-continued

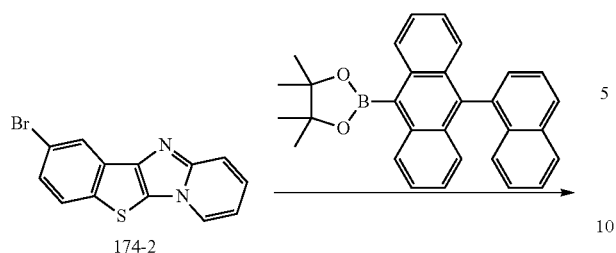

174-2

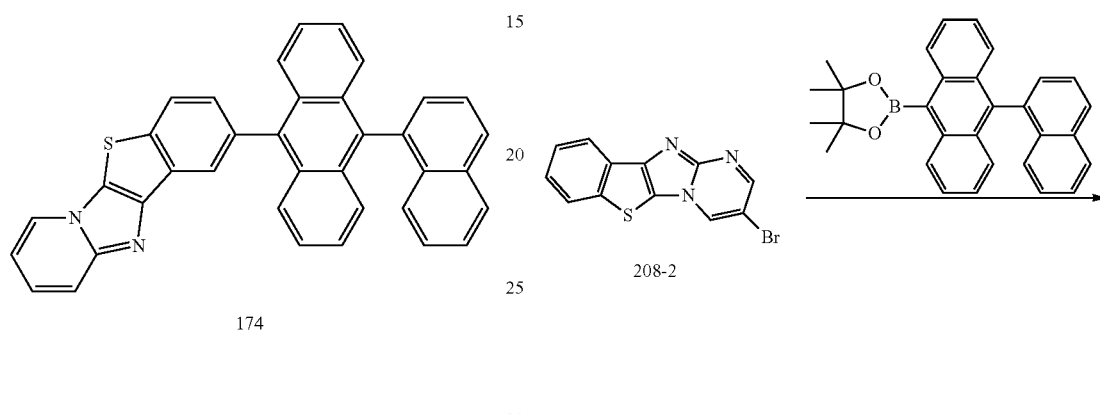

174

(1) Synthesis of Intermediate 174-1

1.48 g (yield: 42%) of Intermediate 174-1 was synthesized in the same manner as in Synthesis of Intermediate 1-2, except that 2-bromo-1-(2,5-dibromophenyl)ethane-1-one was used instead of Intermediate 1-1, and 2-aminopyridine was used instead of 2-amino-5-bromopyridine.

(2) Synthesis of Intermediate 174-2

1.82 g (yield: 60%) of Intermediate 174-2 was synthesized in the same manner as in Synthesis of Intermediate 1-3, except that Intermediate 174-1 was used instead of Intermediate 1-2.

(3) Synthesis of Compound 174

3.95 g (yield: 75%) of Compound 174 was synthesized in that same manner as in Synthesis of Compound 1, except mat Intermediate 174-2 was used instead of Intermediate 1-3.

Synthesis Example 11

Synthesis of Compound 208

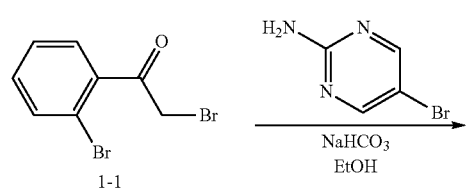

-continued

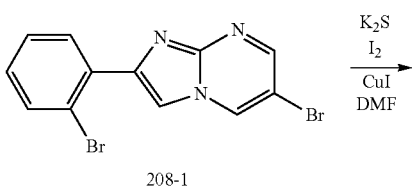

208-1

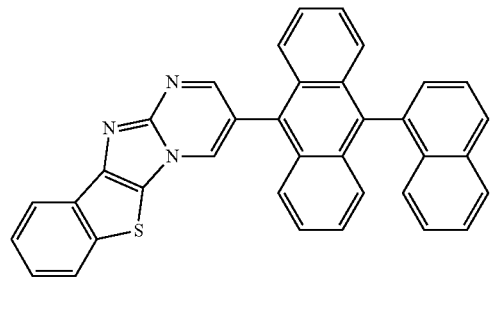

208-2

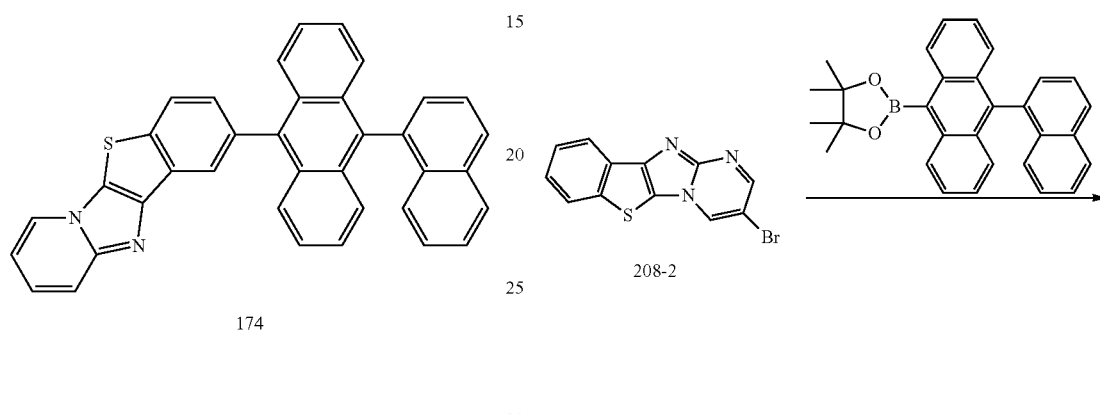

208

(1) Synthesis of Intermediate 208-1

2.12 g (yield: 60%) of Intermediate 208-1 was synthesized in the same manner as in Synthesis of Intermediate 1-2, except that 2-amino-5-bromopyrimidine was used instead of 2-amino-5-bromoa pyridine.

(2) Synthesis of Intermediate 208-2

1.86 g (yield: 61%) of Intermediate 208-2 was synthesized in the same manner as in Synthesis of Intermediate 1-3, except that Intermediate 208-1 was used instead of Intermediate 1-2.

(3) Synthesis of Compound 208

4.38 g (yield: 83%) of Compound 208 was synthesized in the same manner as in Synthesis of Compound 1, except that Intermediate 208-2 was used instead of Intermediate 1-3.

Synthesis Example 12

Synthesis of Compound 209

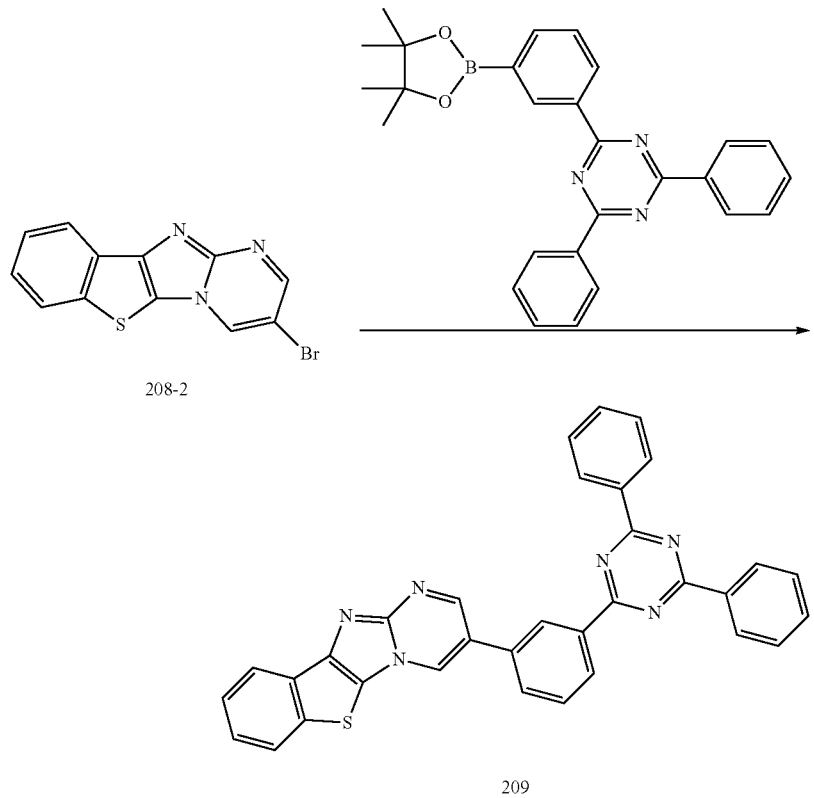

(1) Synthesis of Compound 209

4.53 g (yield: 85%) of Compound 209 was synthesized in the same manner as in Synthesis of Compound 1, except that Intermediate 208-2 was used instead of Intermediate 1-3.

Compounds 1, 33, 185, 187, 51, 189, 127, 158, 191, 174, 208, and 209 synthesized according to Synthesis Examples 1 to 12 were identified by $^1$H nuclear magnetic resonance (NMR) and fast atom bombardment mass spectroscopy (MS/FAB), and results thereof are shown in Table 1.

TABLE 1

| Compound | $^1$H NMR (CDCl$_3$, 400 MHz) | MS/FAB found | MS/FAB calcd. |
|---|---|---|---|
| 1 | 8.99-8.97(m, 1H), 8.14-8.06(m, 1H), 7.96-7.81(m, 7H), 7.80-7.76(m, 1H), 7.73-7.68(m, 2H), 7.60-7.50(m, 3H), 7.47-7.43(m, 1H), 7.42-7.37(m, 2H), 7.36-7.26(m, 3H), 6.98-6.94(m, 1H) | 526.64 | 526.66 |
| 33 | 8.88-8.85(m, 1H), 8.82-8.77(m, 4H), 8.75-7.72(m, 1H), 8.56-8.52(m, 1H), 8.13-8.06(m, 1H), 7.96-7.90(m, 1H), 7.80-7.77(m, 1H), 7.63-7.51(m, 7H), 7.45-7.31(m, 4H) | 531.64 | 531.64 |
| 185 | 9.21-9.17(m, 1H), 8.72-8.70(m, 1H), 8.32-8.30(m, 1H), 8.25-8.16(m, 4H), 8.13-8.07(m, 1H), 7.96-7.91(m, 1H), 7.82-7.70(m, 5H), 7.60-7.53(m, 3H), 7.37-7.35(m, 1H) | 478.58 | 478.57 |

TABLE 1-continued

| Compound | $^1$H NMR (CDCl$_3$, 400 MHz) | MS/FAB found | MS/FAB calcd. |
|---|---|---|---|
| 187 | 8.99-8.98(m, 1H), 8.13-8.07(m, 1H), 7.98-7.88(m, 8H), 7.80-7.77(m, 1H), 7.71-7.63(m, 6H), 7.60-7.48(m, 4H), 7.45-7.28(m, 8H) | 676.76 | 676.77 |
| 51 | 8.77-8.75(m, 1H), 8.40-8.38(m, 1H), 8.15-8.07(m, 2H), 7.96-7.86(m, 4H), 7.69-7.62(m, 6H), 7.60-7.47(m, 4H), 7.45-7.38(m, 4H), 7.37-7.32(m, 1H) | 550.61 | 550.62 |
| 189 | 8.93-8.92(m, 1H), 8.13-8.06(m, 2H), 8.01-7.90(m, 3H), 7.82-7.77(m, 5H), 7.71-7.69(m, 1H), 7.59-7.45(m, 7H), 7.42-7.28(m, 5H) | 552.88 | 552.69 |
| 127 | 8.97-8.95(m, 1H), 8.13-8.04(m, 2H), 7.96-7.91(m, 1H), 7.86-7.78(m, 2H), 7.59-7.53(m, 3H), 7.48-7.42(m, 2H), 7.34-7.27(m, 6H), 7.15-7.06(m, 6H) | 565.88 | 565.69 |
| 158 | 8.98-8.95(m, 1H), 8.80-8.77(m, 4H), 8.71-7.69(m, 1H), 8.15-8.08(m, 1H), 8.03-7.95(m, 2H), 7.77-7.73(m, 1H), 7.70-7.55(m, 8H), 7.43-7.38(m, 2H), 7.74-7.71(m, 1H) | 531.63 | 531.64 |
| 191 | 8.61-8.59(m, 1H), 8.23-8.16(m, 2H), 8.13-8.07(m, 1H), 8.05-8.04(m, 1H), 8.00-7.86(m, 7H), 7.69-7.63(m, 2H), 7.62-7.53(m, 4H), 7.37-7.30(m, 4H) | 528.65 | 526.66 |

TABLE 1-continued

| Compound | $^1$H NMR (CDCl$_3$, 400 MHz) | MS/FAB found | MS/FAB calcd. |
|---|---|---|---|
| 174 | 8.83-8.81(m, 1H), 8.19-8.16(m, 1H), 8.13-8.11(m, 1H), 7.98-7.96(m, 1H), 7.84-7.80(m, 3H), 7.72-7.66(m, 5H), 7.54-7.43(m, 2H), 7.41-7.27(m, 6H), 6.99-6.94(m, 2H) | 526.64 | 526.66 |
| 208 | 9.12-9.08(m, 2H), 8.22-8.16(m, 3H), 7.99-7.81(m, 4H), 7.72-7.63(m, 3H), 7.59-7.50(m, 4H), 7.46-7.44(m, 1H), 7.36-7.27(m, 3H), 6.98-6.94(m, 1H) | 527.63 | 527.64 |
| 209 | 9.14-9.12(m, 1H), 8.94-8.90(m, 2H), 8.81-7.78(m, 4H), 8.52-8.50(m, 1H), 8.19-8.17(m, 1H), 7.98-7.98(m, 1H), 7.71-7.53(m, 8H), 7.43-7.38(m, 2H) | 531.62 | 532.63 |

EXAMPLES

Example 1

An anode was prepared by cutting an ITO/Ag/ITO glass substrate, on which ITO/Ag/ITO were respectively deposited to a thickness of 70 Å/1,000 Å/70 Å, to a size of 50 mm×50 mm×0.5 mm, ultrasonically cleaning the ITO/Ag/ITO glass substrate by using isopropyl alcohol and pure water each for 5 minutes, and then, exposing the ITO/Ag/ITO glass substrate to UV irradiation and ozone for 30 minutes to clean the ITO/Ag/ITO glass substrate. The ITO/Ag/ITO glass substrate was then loaded into a vacuum deposition apparatus.

N-([1,1'-biphenyl]-4-yl)-9,9-dimethyl-N-(4-(9-phenyl-9H-carbazole-3-yl)phenyl-9H-fluorene-2-amine (Compound HT3) and F4-TCNQ were co-deposited on the ITO/Ag/ITO glass substrate at a weight ratio of 98:2 to form a hole injection layer having a thickness of 100 Å, Compound HT3 was vacuum-deposited on the hole transport layer to form a first hole transport layer having a thickness of 1,200 Å, and N,N-d([1,1'-biphenyl]-4-yl)-4'-(9H-carbazole-9-yl)-[1,1'-biphenyl]-4-amine (Compound HT18) was vacuum-deposited on the first hole transport layer to form a second hole transport layer having a thickness of 100 Å.

9,10-di-naphthalene-2-yl-anthracene (ADN) (blue fluorescent host) and N,N,N',N'-tetraphenyl-pyrene-1,6-diamine (FD1) (blue fluorescent dopant) were co-deposited on the second hole transport layer at a weight ratio of 98:2 to form an emission layer having a thickness of 300 Å.

Then, Compound 1 according to one or more embodiments and LiQ were co-deposited on the emission layer at a weight ratio of 5:5 to form an electron transport layer having a thickness of 300 Å, LiF was deposited on the electron transport layer to form an electron injection layer having a thickness of 10 Å, and Mg and Ag were vacuum-deposited on the electron injection layer at a weight ratio of 90:10 to form a cathode electrode having a thickness of 120 Å, thereby completing the manufacture of an organic light-emitting device.

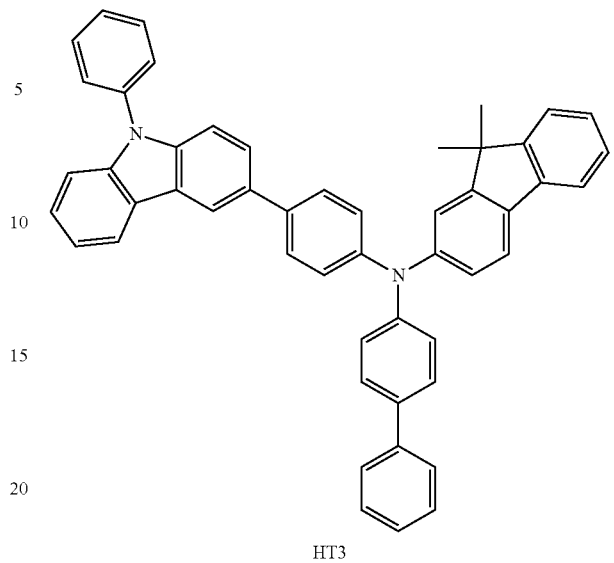

HT3

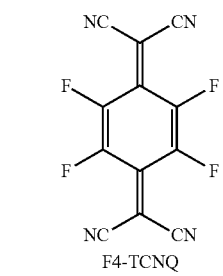

F4-TCNQ

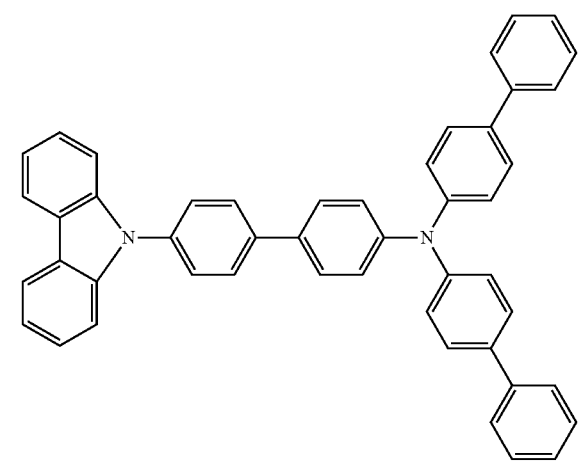

HT18

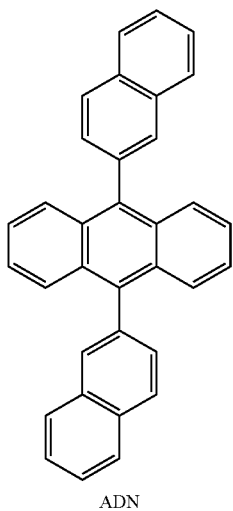

ADN

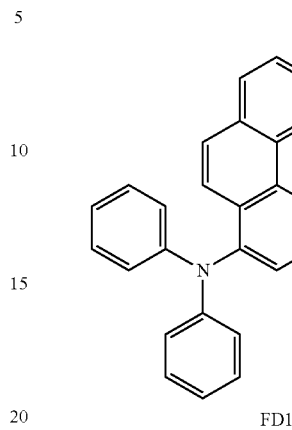

FD1

Examples 2 to 12 and Comparative Examples 1 to 3

Organic light-emitting devices of Examples 2 to 12 and Comparative Examples 1 to 3 were manufactured in the same manner as in Example 1, except that Compounds shown in Table 2 were each used instead of Compound 1 in forming an electron transport layer.

EVALUATION EXAMPLES

The driving voltage, luminance, efficiency, and lifespan of the organic light-emitting devices manufactured according to Examples 1 to 12 and Comparative Examples 1 to 3 were evaluated at a current density of 10 mA/cm² by using a Keithley SMU 236 and a luminance meter PR650, and results thereof are shown in Table 2. The lifespan indicates an amount of time mat lapsed when luminance was 97% of initial luminance (100%) after the organic light-emitting device was driven.

TABLE 2

|  | Electron transport layer Material | Driving voltage (V) | Current density (mA/cm$^2$) | Efficiency (cd/A) | Color coordinates CIE(x,y) | Lifespan (@ 10 mA/cm$^2$) |
|---|---|---|---|---|---|---|
| Example 1 | Compound 1 | 3.80 | 10 | 5.10 | 0.140, 0.051 | 135 |
| Example 2 | Compound 33 | 3.76 | 10 | 5.22 | 0.141, 0.052 | 142 |
| Example 3 | Compound 185 | 3.98 | 10 | 4.99 | 0.141, 0.050 | 115 |
| Example 4 | Compound 187 | 4.16 | 10 | 4.92 | 0.142, 0.051 | 240 |
| Example 5 | Compound 51 | 4.21 | 10 | 4.97 | 0.141, 0.052 | 221 |
| Example 6 | Compound 189 | 4.11 | 10 | 5.03 | 0.142, 0.050 | 107 |
| Example 7 | Compound 127 | 4.06 | 10 | 5.15 | 0.141, 0.052 | 128 |
| Example 8 | Compound 158 | 3.85 | 10 | 5.25 | 0.141, 0.052 | 142 |
| Example 9 | Compound 191 | 3.87 | 10 | 5.06 | 0.141, 0.052 | 121 |
| Example 10 | Compound 174 | 3.79 | 10 | 5.13 | 0.141, 0.052 | 131 |
| Example 11 | Compound 208 | 3.75 | 10 | 5.15 | 0.141, 0.052 | 140 |
| Example 12 | Compound 209 | 3.78 | 10 | 5.18 | 0.141, 0.052 | 128 |

TABLE 2-continued
|  | Electron transport layer Material | Driving voltage (V) | Current density (mA/cm²) | Efficiency (cd/A) | Color coordinates CIE(x,y) | Lifespan (@ 10 mA/cm²) |
|---|---|---|---|---|---|---|
| Comparative Example 1 | Compound A | 5.24 | 10 | 3.85 | 0.141, 0.051 | 35 |
| Comparative Example 2 | Compound B | 4.23 | 10 | 4.78 | 0.141, 0.050 | 101 |
| Comparative Example 3 | Compound C | 4.56 | 10 | 4.65 | 0.141, 0.051 | 70 |
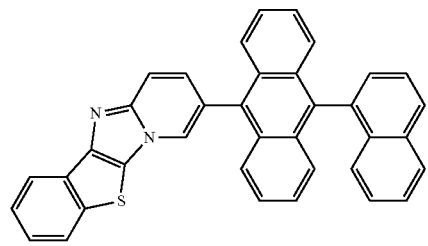
1
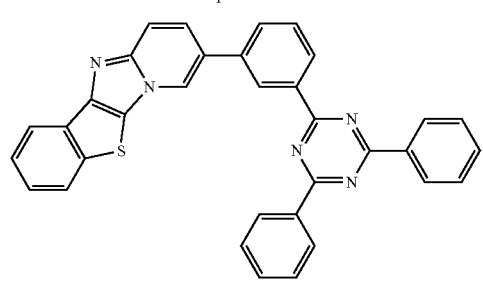
33
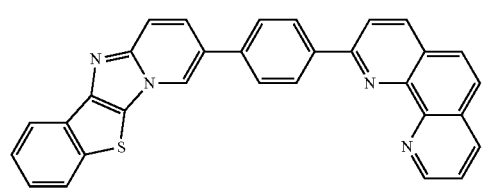
185
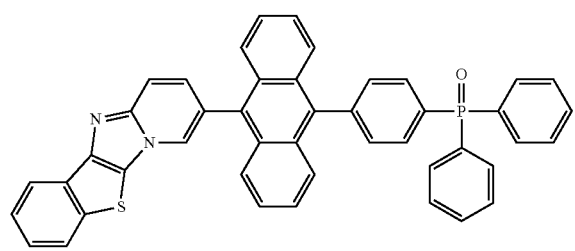
187
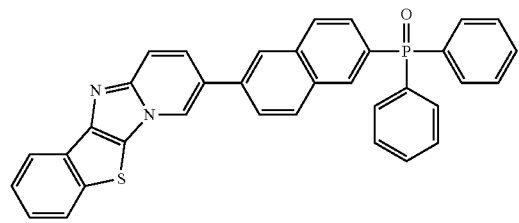
51

TABLE 2-continued
| Electron transport layer Material | Driving voltage (V) | Current density (mA/cm$^2$) | Efficiency (cd/A) | Color coordinates CIE(x,y) | Lifespan (@ 10 mA/cm$^2$) |
| --- | --- | --- | --- | --- | --- |
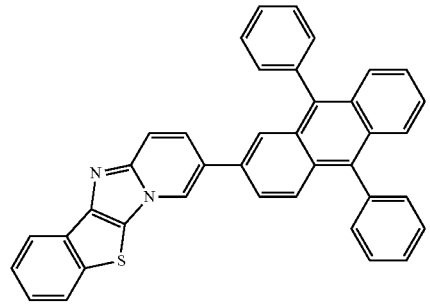
189
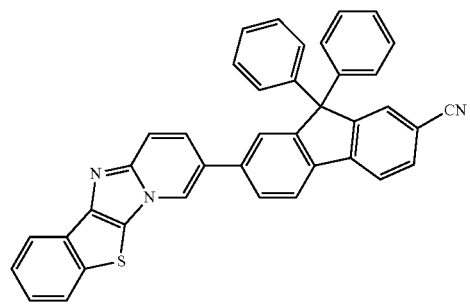
127
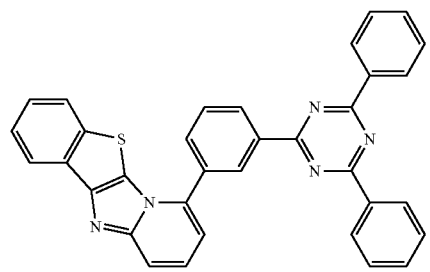
158
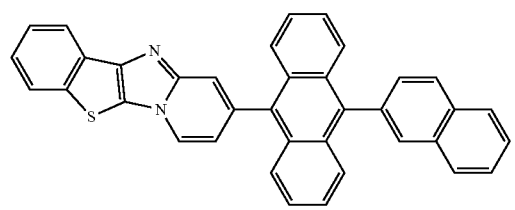
191
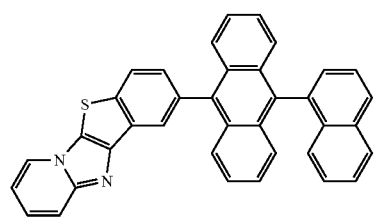
174

TABLE 2-continued
| Electron transport layer Material | Driving voltage (V) | Current density (mA/cm²) | Efficiency (cd/A) | Color coordinates CIE(x,y) | Lifespan (@ 10 mA/cm²) |
|---|---|---|---|---|---|
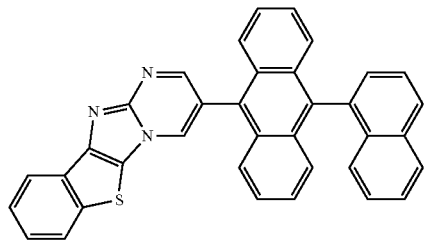
208
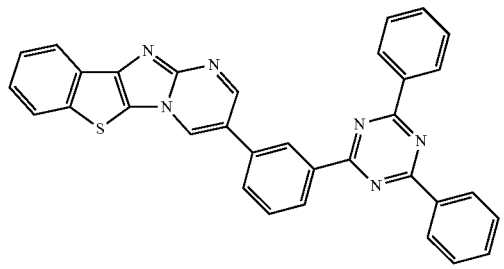
209
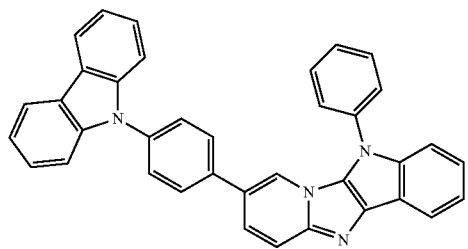
A
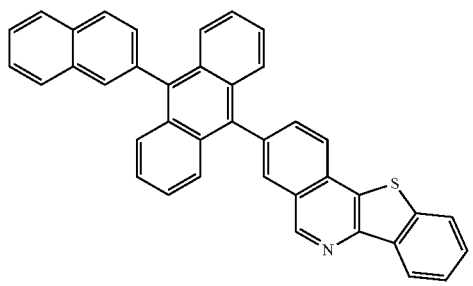
B TABLE 2-continued

| Electron transport layer Material | Driving voltage (V) | Current density (mA/cm$^2$) | Efficiency (c d/A) | Color coordinates CIE(x,y) | Lifespan (@ 10 mA/cm$^2$) |
|---|---|---|---|---|---|

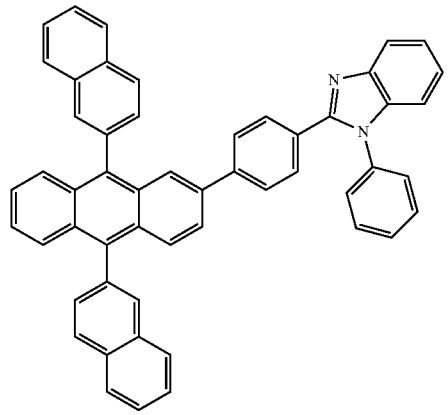

C

Referring to Table 2, it was confirmed that the organic light-emitting devices of Examples 1 to 12 had excellent driving voltage, efficiency, and lifespan, compared to those of the organic light-emitting devices of Comparative Examples 1 to 3.

An organic light-emitting device including the condensed cyclic compound may have a low driving voltage, high efficiency, high luminance, high color purity, and a long lifespan.

It should be understood that the specific exemplary embodiments of the present disclosure described herein should be considered in a descriptive sense only and not for purposes of limitation. Descriptions of features or aspects within each exemplary embodiment should typically be considered as available for other similar features or aspects in other exemplary embodiments.

While exemplary embodiments of the present disclosure have been described with reference to the figures, it will be understood by those of ordinary skill in the art that various changes in form and details may be made therein without departing from the spirit and scope as defined by the following claims.

What is claimed is:

1. A condensed cyclic compound represented by Formula 1:

<Formula 1>

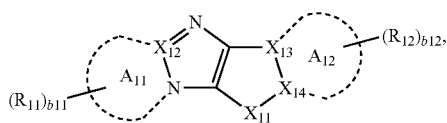

in Formula 1, $A_{11}$ is a $C_1$-$C_{60}$ heterocyclic group,
$A_{12}$ is a $C_5$-$C_{60}$ carbocyclic group or a $C_1$-$C_{60}$ heterocyclic group,
$X_{11}$ is O or S,
$X_{12}$ is C,
$X_{13}$ is selected from N, C, and C($R_{13}$),
$X_{14}$ is selected from N, C, and C($R_{14}$),
$X_{13}$ and $X_{14}$ are linked via a single bond or a double bond,
$R_{11}$ and $R_{12}$ are each independently selected from a group represented by *-($L_{11}$)$_{a11}$-($Ar_{11}$)$c_{11}$, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and at least one of $R_{11}$ and $R_{12}$ is a group represented by *-($L_{11}$)$_{a11}$-($Ar_{11}$)$c_{11}$, b11 and b12 are each independently selected from 1, 2, 3, 4, 5, 6, 7, 8, 9, and 10, $L_{11}$ is selected from —P(=O)($Q_1$)-, a substituted or unsubstituted $C_5$-$C_{60}$ carbocyclic group, and a substituted or unsubstituted $C_1$-$C_{60}$ heterocyclic group, a11 is selected from 1, 2, 3, and 4, $Ar_{11}$ is selected from —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O) ($Q_1$), —S(=O)$_2$($Q_1$), —P(=O)($Q_1$)($Q_2$), and —P(=S)($Q_1$)($Q_2$), c11 is selected from 1, 2, 3, 4, 5, and 6, $R_{13}$, $R_{14}$, and $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, and a substituted or unsubstituted monovalent non-aromatic condensed heteropolycyclic group, and

* indicates a binding site to a neighboring atom.

2. The condensed cyclic compound of claim 1, wherein $A_{11}$ is selected from a pyrrolidine group, a dihydropyrrole group, an isoindoline group, a piperidine group, a tetrahydropyridine group, a dihydropyridine group, a tetrahydroisoquinoline group, a dihydroisoquinoline group, an imidazole group, a pyrazole group, a thiazole group, an isothiazole group, an oxazole group, an isoxazole group, a pyridine group, a pyrazine group, a pyrimidine group, a quinoline group, an isoquinoline group, a benzoquinoline group, a quinoxaline group, a quinazoline group, a benzimidazole group, a benzothiazole group, a benzisothiazole group, a benzoxazole group, a benzisoxazole group, a triazine group, a tetrazine group, and an azacarbazole group.

3. The condensed cyclic compound of claim 1, wherein $A_{12}$ is selected from a pyrrolidine group, a dihydropyrrole group, an isoindoline group, a piperidine group, a tetrahydropyridine group, a dihydropyridine group, a tetrahydroisoquinoline group, a dihydroisoquinoline group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, an azacarbazole group, a benzimidazole group, a benzothiazole group, a benzisothiazole group, a benzoxazole group, a benzisoxazole group, a triazole group, a tetrazole group, a thiadiazol group, an oxadiazole group, a triazine group, a tetrazine group, a benzene group, a naphthalene group, a fluorene group, a spiro-bifluorene group, an indene group, a pyrrole group, a thiophene group, a furan group, a benzofuran group, a benzothiophene group, a dibenzofuran group, and a dibenzothiophene group.

4. The condensed cyclic compound of claim 1, wherein $R_{11}$ and $R_{12}$ are each independently selected from:

a group represented by *-($L_{11}$)$_{a11}$-($Ar_{11}$)$c_{11}$, hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphthobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, —Si($Q_3$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), wherein $Q_1$ to $Q_3$ and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

5. The condensed cyclic compound of claim 1, wherein $R_{11}$ and $R_{12}$ are each independently selected from:

a group represented by *-($L_{11}$)$_{a11}$-($Ar_{11}$)$c_{11}$, hydrogen, deuterium, —F, —Cl, —Br, —I, a cyano group, and a $C_1$-$C_{20}$ alkyl group;

a $C_1$-$C_{20}$ alkyl group, substituted with at least one selected from deuterium, —F, —Cl, —Br, —I, and a cyano group;

groups represented by Formulae 5-1 to 5-138; and

—Si(Q)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$):

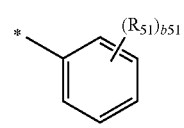

5-1

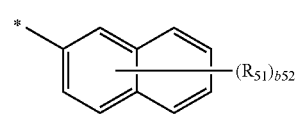

5-2

-continued
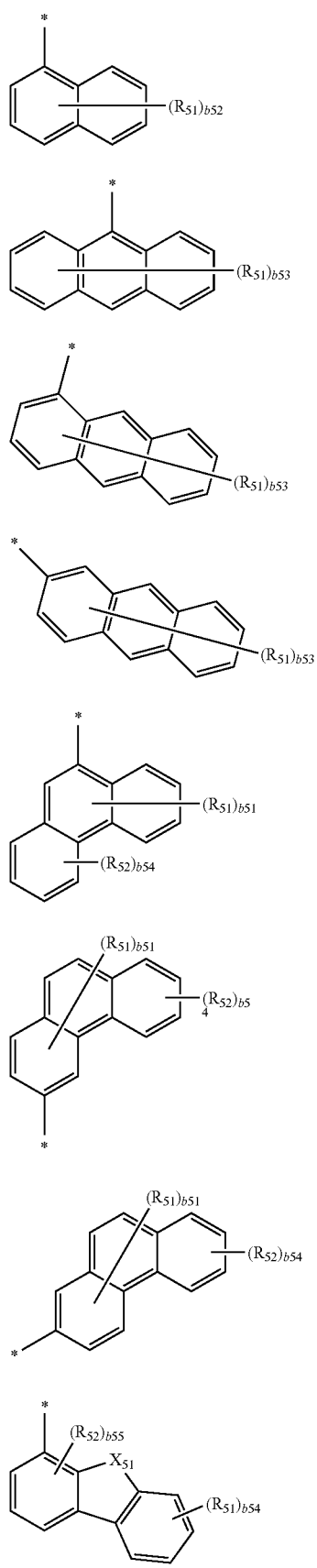
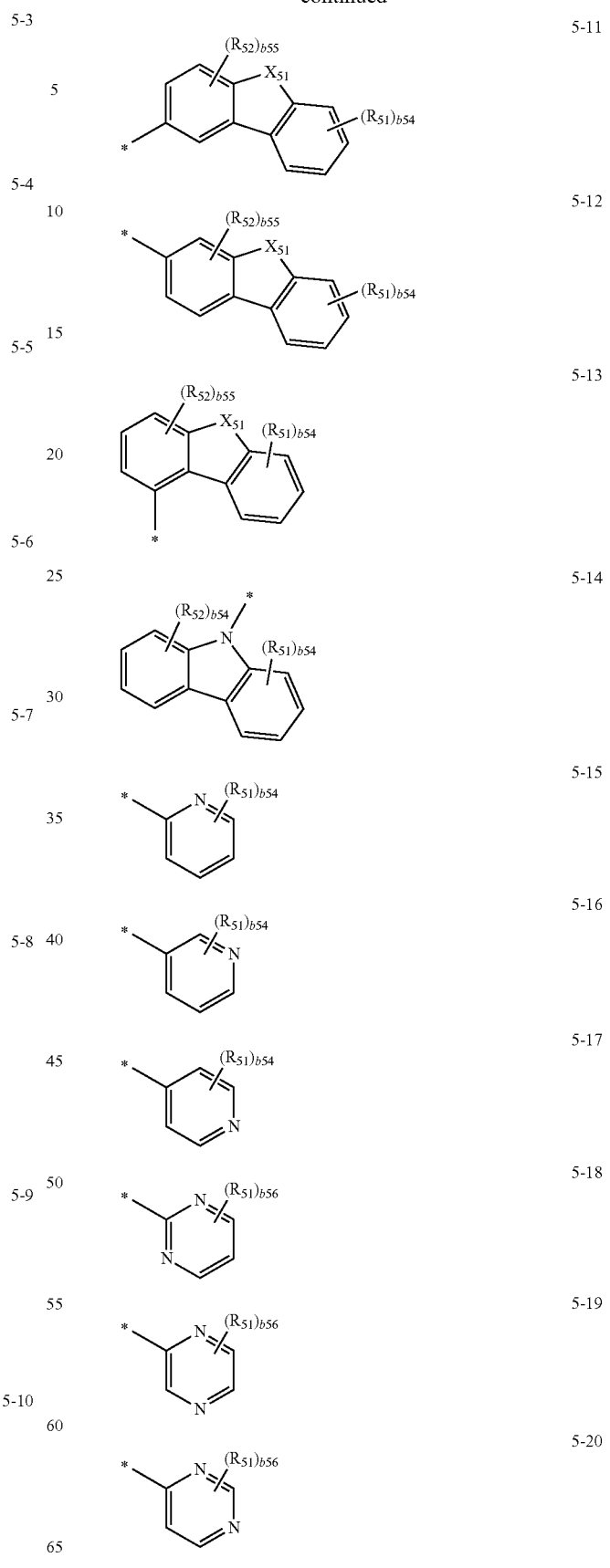

5-21 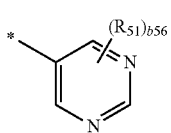
5-22 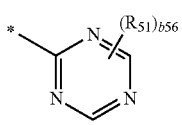
5-23 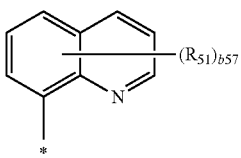
5-24 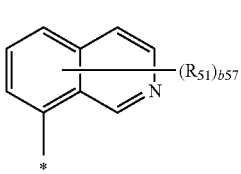
5-25 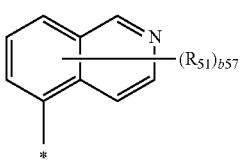
5-26 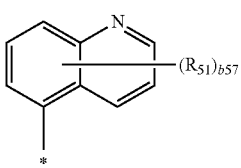
5-27 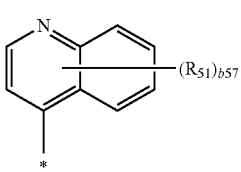
5-28 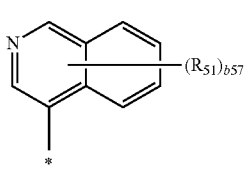
5-29 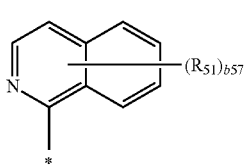
5-30 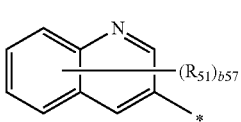
5-31 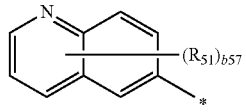
5-32 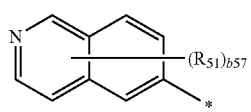
5-33 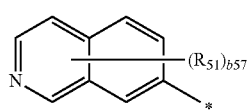
5-34 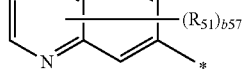
5-35 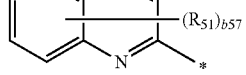
5-36 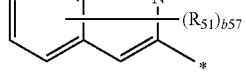
5-37 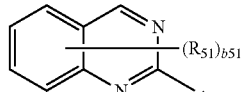
5-38 
5-39 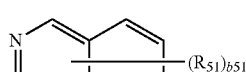
5-40 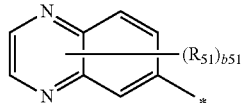
5-41
5-42

| | |
|---|---|
| 5-43 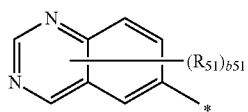 | 5-54 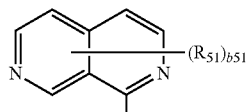 |
| 5-44 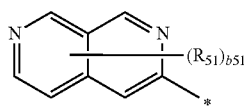 | 5-55 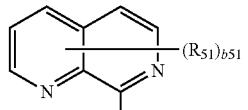 |
| 5-45 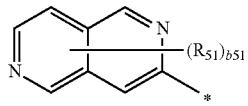 | 5-56 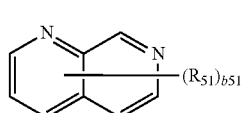 |
| 5-46 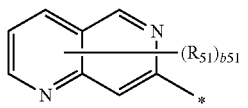 | 5-57 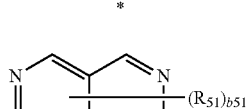 |
| 5-47 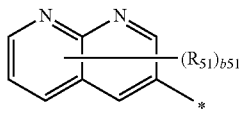 | 5-58 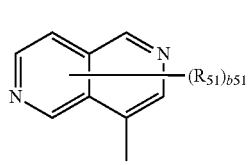 |
| 5-48 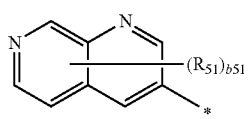 | 5-59 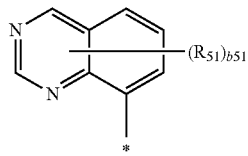 |
| 5-49 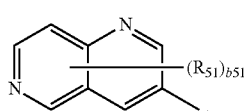 | 5-60 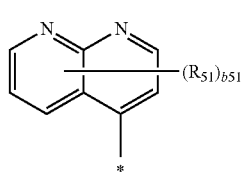 |
| 5-50 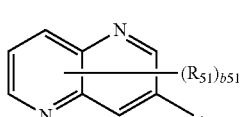 | 5-61 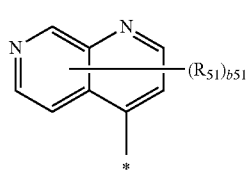 |
| 5-51 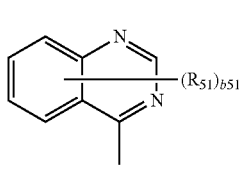 | 5-62 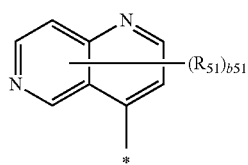 |
| 5-52 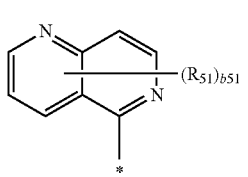 | |
| 5-53 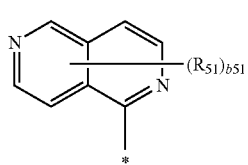 | |

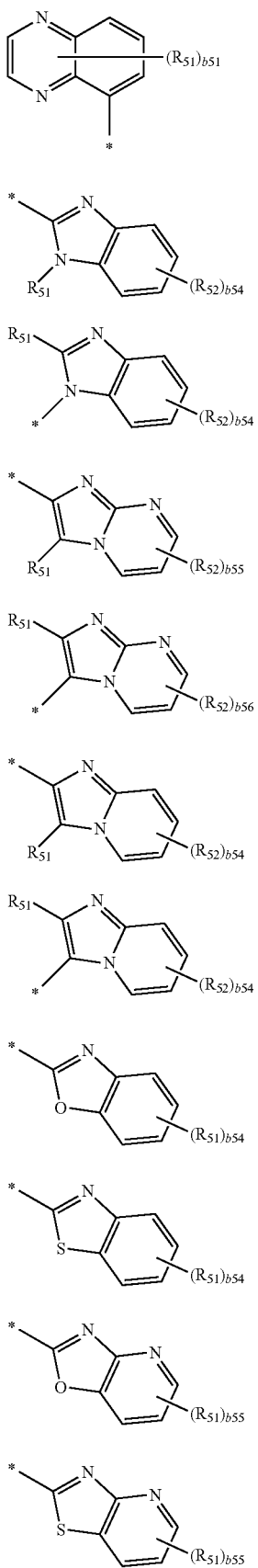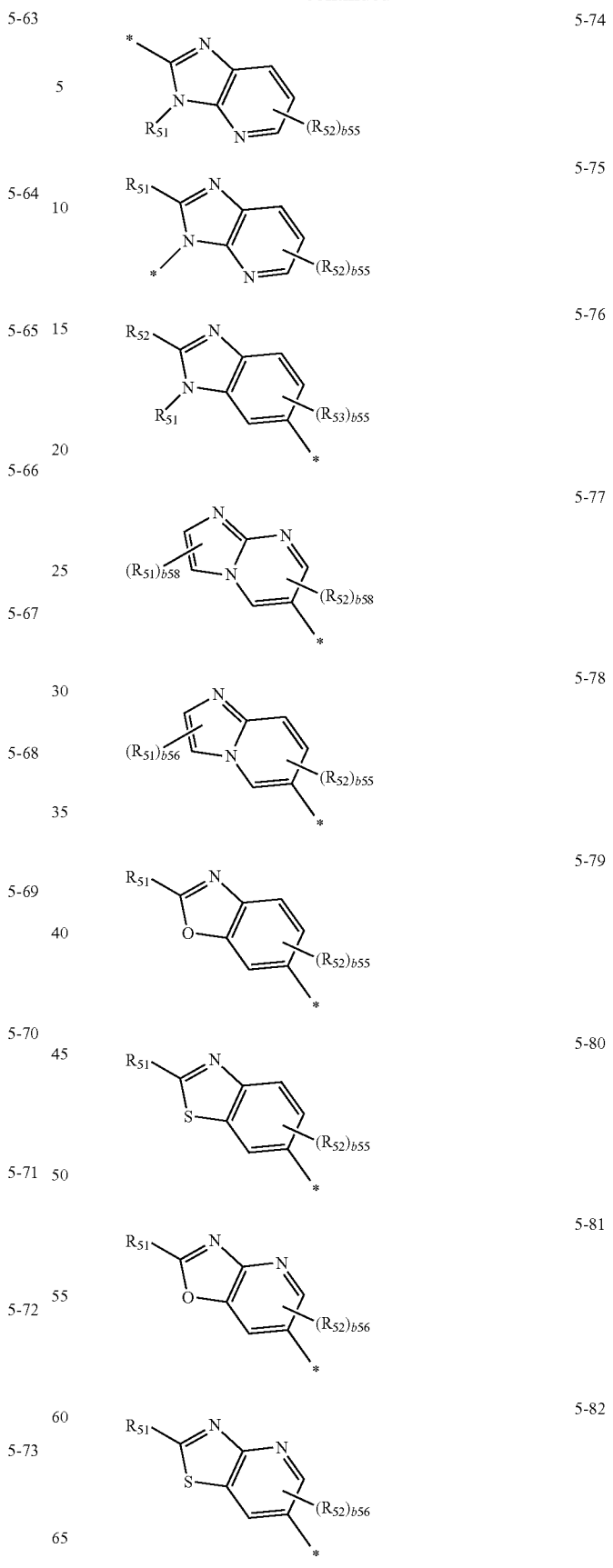

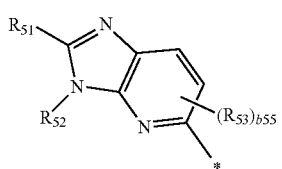 5-83
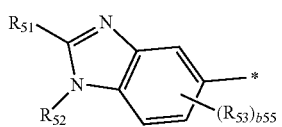 5-84
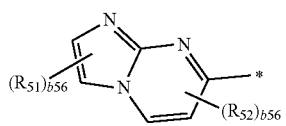 5-85
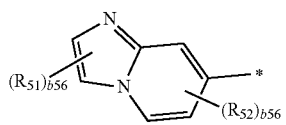 5-86
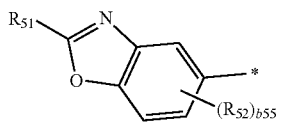 5-87
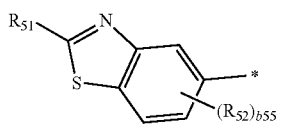 5-88
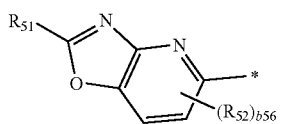 5-89
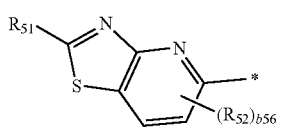 5-90
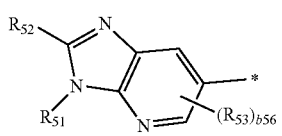 5-91
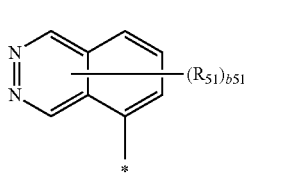 5-92
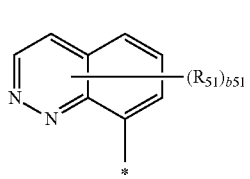 5-93
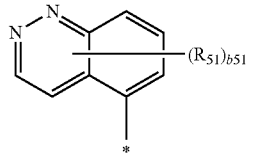 5-94
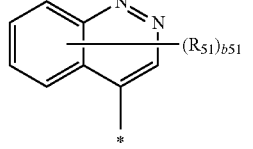 5-95
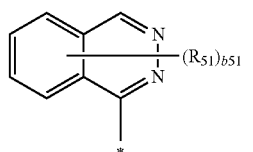 5-96
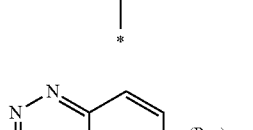 5-97
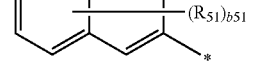 5-98
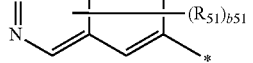 5-99
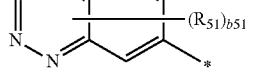 5-100
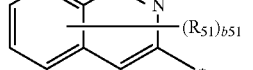 5-101
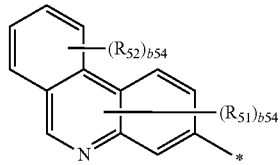 5-102
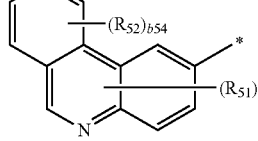 5-103
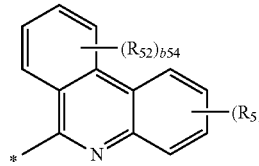

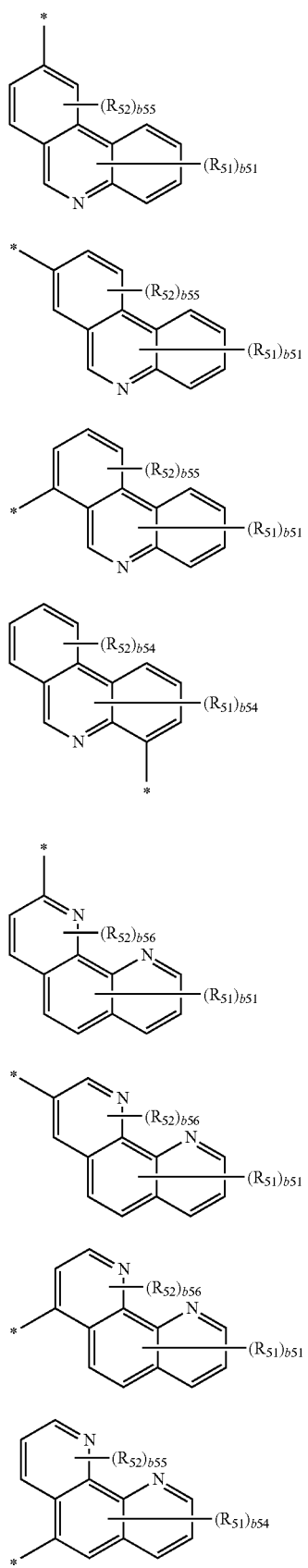
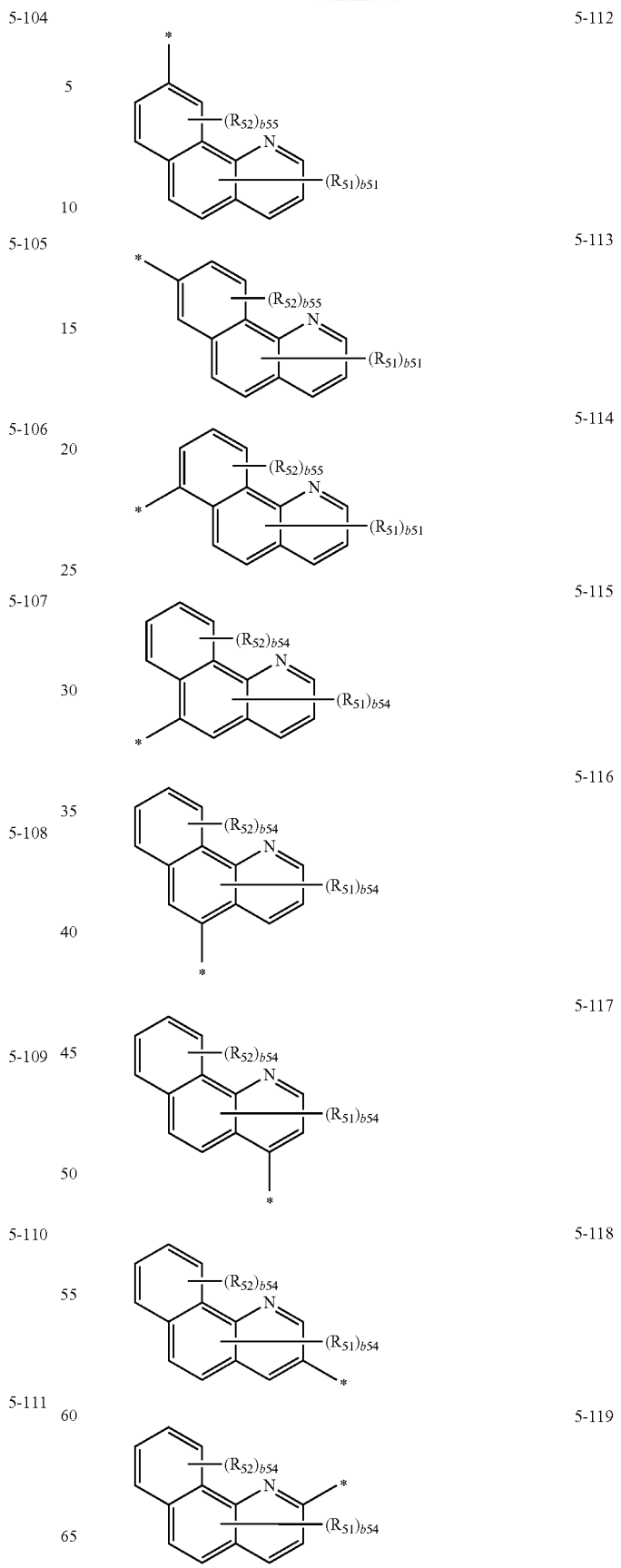

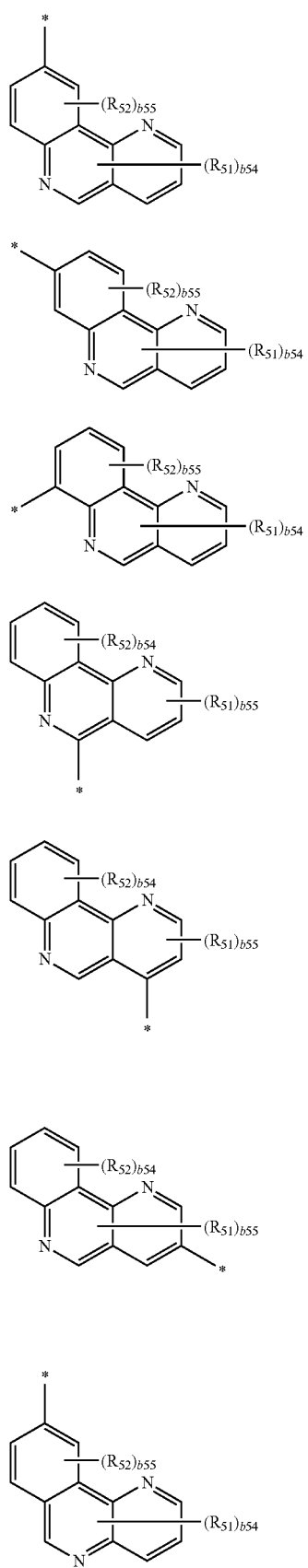
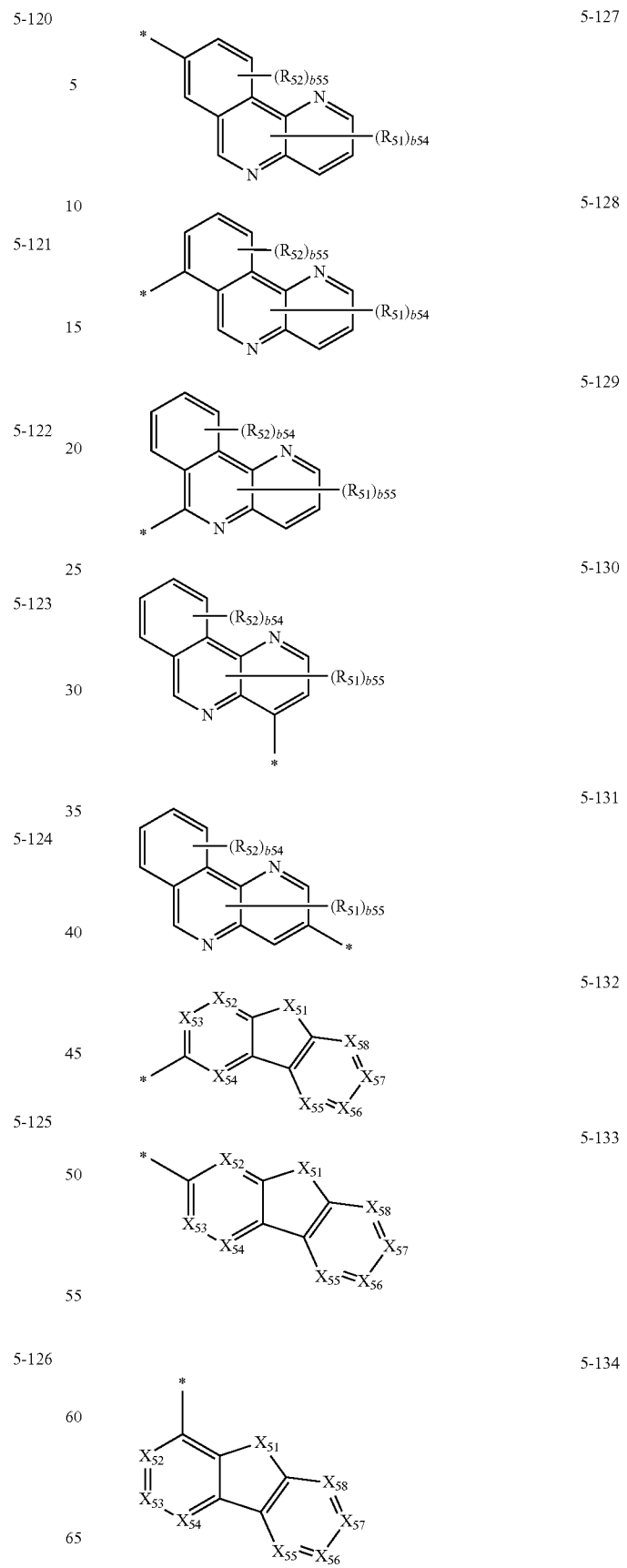

-continued

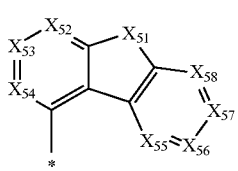
5-135

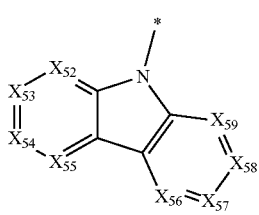
5-136

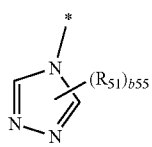
5-137

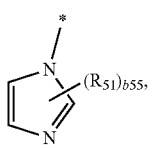
5-138 in Formulae 5-1 to 5-138, $X_{51}$ is selected from O, S, $N(R_{51})$, and $C(R_{51})(R_{60})$, $X_{52}$ is N or $C(R_{52})$, $X_{53}$ is N or $C(R_{53})$, $X_{54}$ is N or $C(R_{54})$, $X_{55}$ is N or $C(R_{55})$, $X_{56}$ is N or $C(R_{56})$, $X_{57}$ is N or $C(R_{57})$, $X_{58}$ is N or $C(R_{58})$, and $X_{59}$ is N or $C(R_{59})$, $R_{51}$ to $R_{60}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$), $Q_1$ to $Q_3$ and $Q_{31}$ to $Q_{33}$ are each independently selected from a $C_1$-$C_{60}$ alkyl group, a phenyl group, a biphenyl group, and a terphenyl group, b51 is selected from 1, 2, 3, 4, and 5,
b52 is selected from 1, 2, 3, 4, 5, 6, and 7,
b53 is selected from 1, 2, 3, 4, 5, 6, 7, 8, and 9,
b54 is selected from 1, 2, 3, and 4,
b55 is selected from 1, 2, and 3,
b56 is 1 or 2,
b57 is selected from 1, 2, 3, 4, 5, and 6, and
* indicates a binding site to a neighboring atom.

6. The condensed cyclic compound of claim 1, wherein $L_{11}$ is selected from:

a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a pentacene group, a rubicene group, a coronene group, an ovalene group, a pyrrole group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, a dibenzosilole group, a pyridine group, an imidazole group, a pyrazole group, a thiazole group, an isothiazole group, an oxazole group, an isoxazole group, a thiadiazol group, an oxadiazole group, a pyrazine group, a pyrimidine group, a pyridazine group, a triazine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzothiazole group, a benzisothiazole group, a benzoxazole group, a benzisoxazole group, a triazole group, a tetrazole group, an imidazopyridinyl group, an imidazopyrimidinyl group, and an azacarbazole group; and a benzene group, a pentalene group, an indene group, a naphthalene group, an azulene group, a heptalene group, an indacene group, an acenaphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, a hexacene group, a pentacene group, a rubicene group, a coronene group, an ovalene group, a pyrrole group, a thiophene group, a furan group, a silole group, a carbazole group, an indole group, an isoindole group, a benzofuran group, a benzothiophene group, a benzosilole group, a dibenzofuran group, a dibenzothiophene group, a benzocarbazole group, a dibenzocarbazole group, a dibenzosilole group, a pyridine group, an imidazole group, a pyrazole group, a thiazole group, an isothiazole group, an oxazole group, an isoxazole group, a thiadiazol group, an oxadiazole group, a pyrazine group, a pyrimidine group, a pyridazine group, a triazine group, a quinoline group, an isoquinoline group, a benzoquinoline group, a phthalazine group, a naphthyridine group, a quinoxaline group, a quinazoline group, a cinnoline group, a phenanthridine group, an acridine group, a phenanthroline group, a phenazine group, a benzimidazole group, a benzothiazole group, a benzisothiazole group, a benzoxazole group, a benzisoxazole group, a triazole group, a tetrazole group, an imidazopyridinyl group, an imidazopyrimidinyl group, and an azacarbazole group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a pyrrolyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, a benzothiazolyl group, a benzisothiazolyl group, a benzoxazolyl group, a benzisoxazolyl group, a triazolyl group, a tetrazolyl group, an imidazopyridinyl group, an imidazopyrimidinyl group, an azacarbazolyl group, —Si$(Q_{31})(Q_{32})(Q_{33})$, —N$(Q_{31})(Q_{32})$, —B$(Q_{31})(Q_{32})$, —C($=$O)$(Q_{31})$, —S($=$O)$(Q_{31})$, —S($=$O)$_2(Q_{31})$, —P($=$O)$(Q_{31})(Q_{32})$, and —P($=$S)$(Q_{31})(Q_{32})$, wherein $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_6$(alkenyl group, a $C_2$-$C_{60}$ alkynyl group, a $C_1$-$C_{60}$, alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

7. The condensed cyclic compound of claim 1, wherein $L_{11}$ is selected from groups represented by Formulae 3-1 to 3-41:

3-1
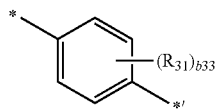

3-2
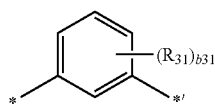

3-3
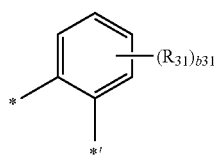

3-4
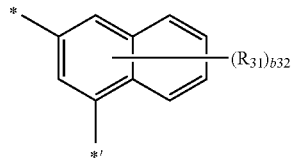

3-5
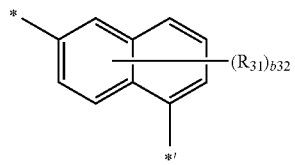

3-6
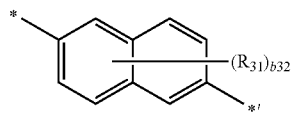

3-7
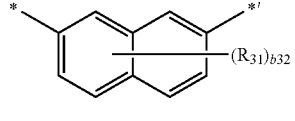

3-8
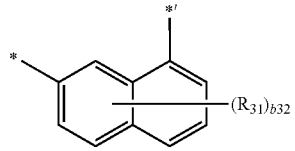

3-9
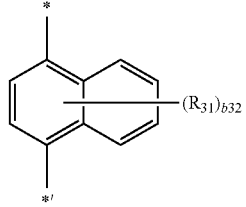

3-10
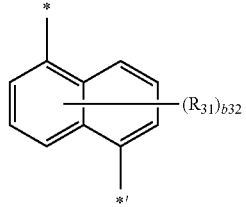

3-11
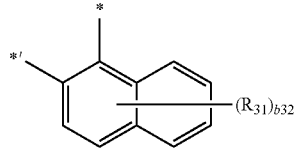

3-12
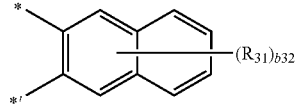

-continued
3-13
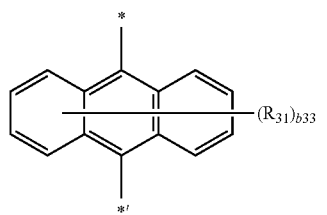
3-14
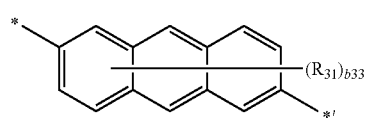
3-15
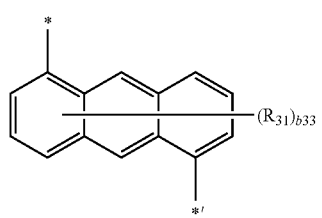
3-16
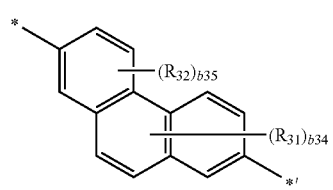
3-17
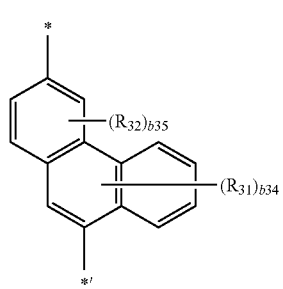
3-18
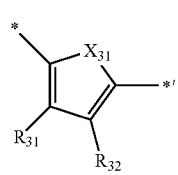
3-19
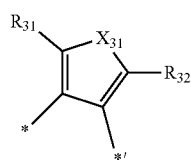
-continued
3-20
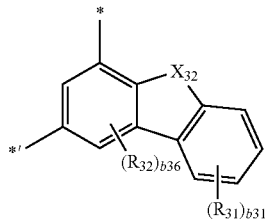
3-21
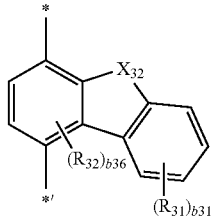
3-22
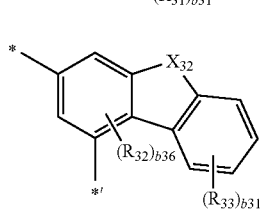
3-23
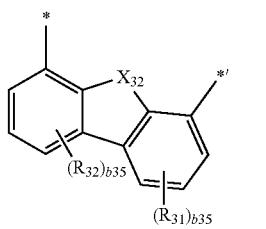
3-24
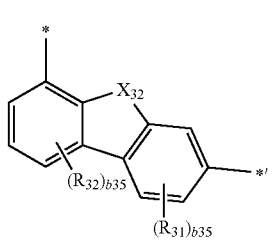
3-25
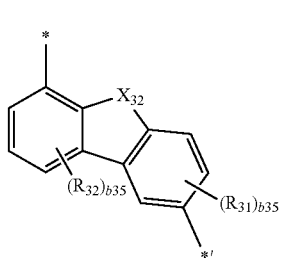
3-26
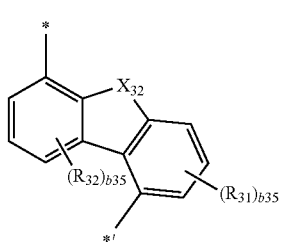

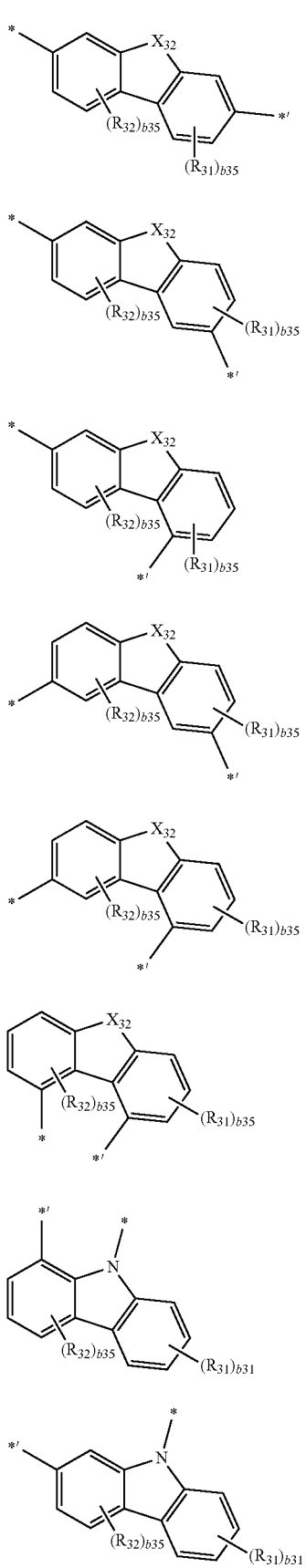
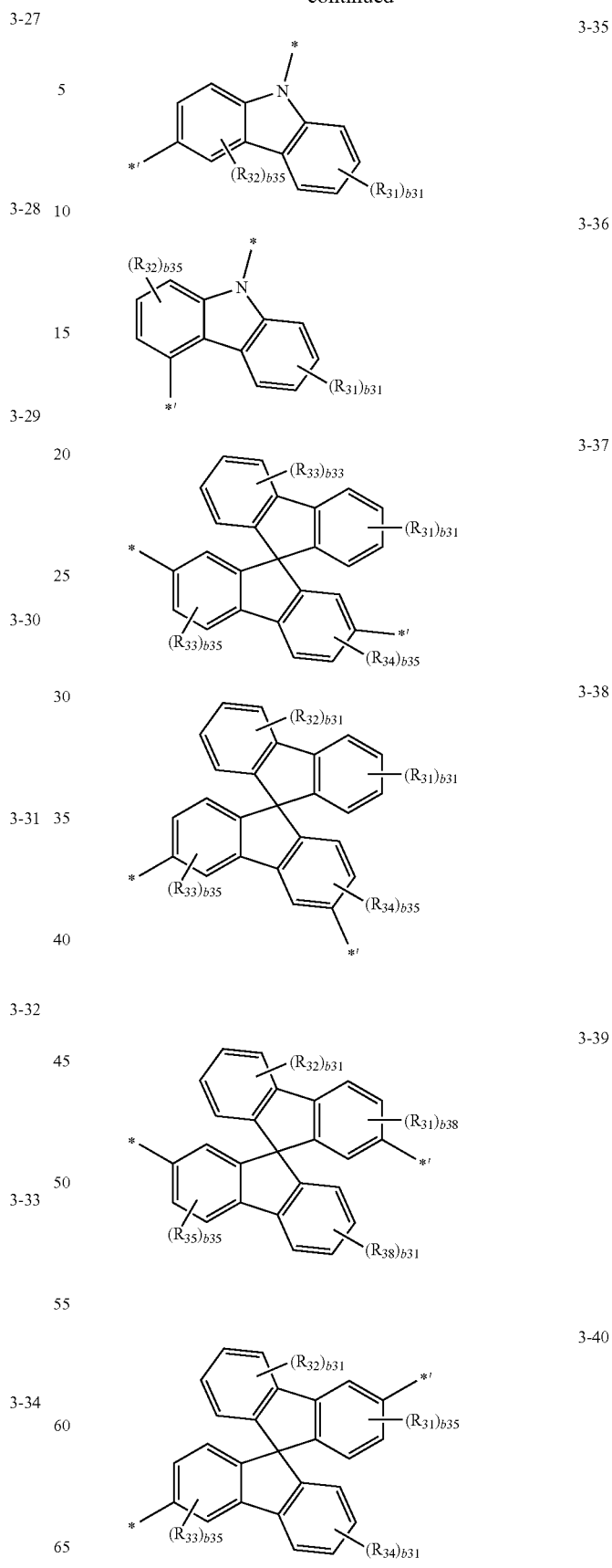

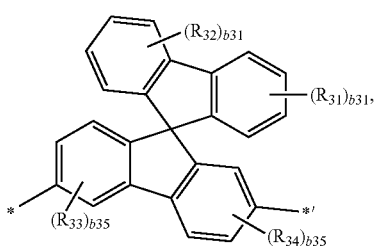

3-41 in Formulae 3-1 to 3-41, $X_{31}$ is O or S, $X_{32}$ is selected from O, S, $N(R_{33})$, and $C(R_{33})(R_{34})$, $R_3$ to $R_{34}$ are each independently selected from hydrogen, deuterium, —F, —C, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, —$Si(Q_{31})(Q_{32})(Q_{33})$, —$N(Q_{31})(Q_{32})$, and —$B(Q_{31})(Q_{32})$, $Q_{31}$ to $Q_{33}$ are each independently selected from a $C_1$-$C_{60}$ alkyl group, a phenyl group, a biphenyl group, and a terphenyl group, b31 is selected from 1, 2, 3, and 4, b32 is selected from 1, 2, 3, 4, 5, and 6, b33 is selected from 1, 2, 3, 4, 5, 6, 7, and 8, b34 is selected from 1, 2, 3, 4, and 5, b35 is selected from 1, 2, and 3, b36 is 1 or 2, and

* and *' each indicate a binding site to a neighboring atom.

8. The condensed cyclic compound of claim 1, wherein a11 is selected from 1, and 2.

9. The condensed cyclic compound of claim 1, wherein $Ar_{11}$ is selected from:

—F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, and a biphenyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group;

a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, and an indolocarbazolyl group, each substituted with at least one selected from deuterium, —F, —Cl, —Br, —I, a cyano group, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a biphenyl group, a terphenyl group, a pentalenyl group, an indenyl group, a naphthyl group, an azulenyl group, an indacenyl group, an acenaphthyl group, a fluorenyl group, a spiro-bifluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a perylenyl group, a pentacenyl group, a pyrrolyl group, a thiophenyl group, a furanyl group, a silolyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an indolyl group, an isoindolyl group, an indazolyl group, a purinyl group, a quinolinyl group, an isoquinolinyl group, a benzoquinolinyl group, an isoquinolinyl group, a phthalazinyl group, a naphthyridinyl group, a quinoxalinyl group, a benzoquinoxalinyl group, a quinazolinyl group, a benzoquinazolinyl group, a cinnolinyl group, a phenanthridinyl group, an acridinyl group, a phenanthrolinyl group, a phenazinyl group, a benzimidazolyl group, a benzofuranyl group, a benzothiophenyl group, a benzosilolyl group, a benzothiazolyl group, a benzoisothiazolyl group, a benzoxazolyl group, a benzoisoxazolyl group, a triazolyl group, a tetrazolyl group, a thiadiazolyl group, an oxadiazolyl group, a triazinyl group, a carbazolyl group, a dibenzofuranyl group, a dibenzothiophenyl group, a dibenzosilolyl group, a benzocarbazolyl group, a naphthobenzofuranyl group, a naphthobenzothiophenyl group, a naphtobenzosilolyl group, a dibenzocarbazolyl group, a dinaphthofuranyl group, a dinaphthothiophenyl group, a dinaphthosilolyl group, an imidazopyridinyl group, an imidazopyrimidinyl group, an oxazolopyridinyl group, a thiazolopyridinyl group, a benzonaphthyridinyl group, an azafluorenyl group, an azaspiro-bifluorenyl group, an azacarbazolyl group, an azadibenzofuranyl group, an azadibenzothiophenyl group, an azadibenzosilolyl group, an indenopyrrolyl group, an indolopyrrolyl group, an indenocarbazolyl group, an indolocarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)($Q_{31}$), —S(=O)$_2$($Q_{31}$), —P(=O)($Q_{31}$)($Q_{32}$), and —P(=S)($Q_{31}$)($Q_{32}$); and —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), wherein $Q_1$ to $Q_3$ and $Q_{31}$ to $Q_{33}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

10. The condensed cyclic compound of claim 1, wherein $Ar_{11}$ is selected from:

—F, —Cl, —Br, —I, a cyano group, and a $C_1$-$C_{20}$ alkyl group;

a $C_1$-$C_{20}$ alkyl group, substituted with at least one selected from deuterium, —F, —Cl, —Br, —I, and a cyano group;

groups represented by Formulae 5-1 to 5-138; and

—Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$):

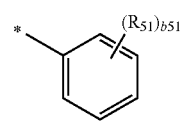

5-1

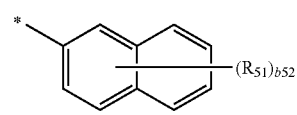

5-2

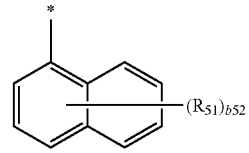

5-3

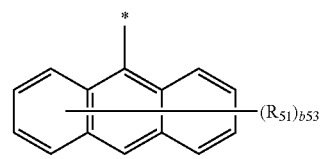

5-4

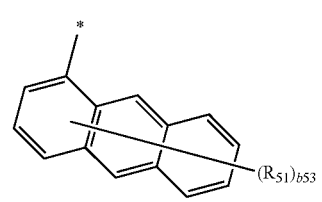

5-5

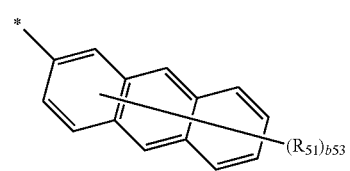

5-6

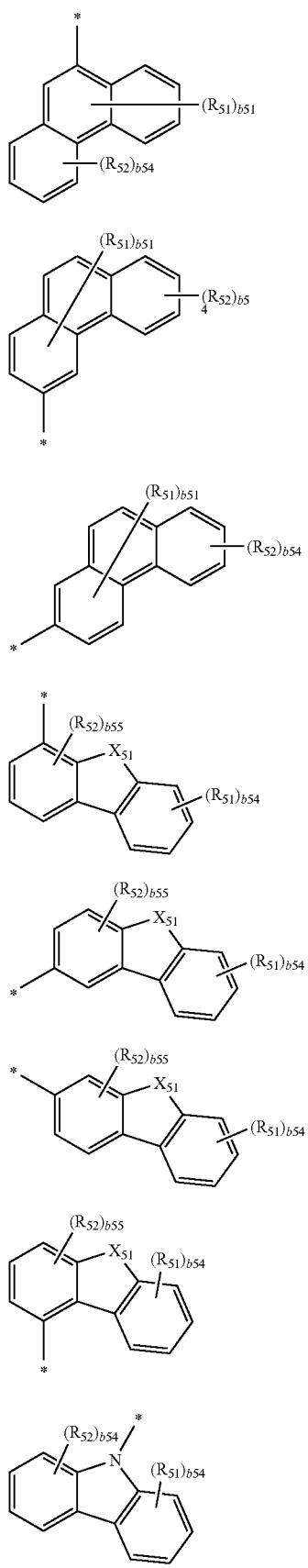
5-7
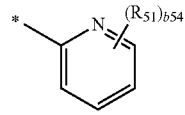
5-15
5-8
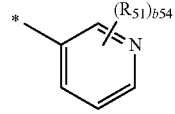
5-16
5-9
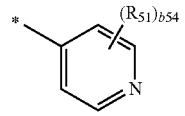
5-17
5-10
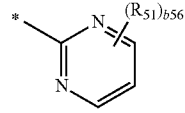
5-18
5-11
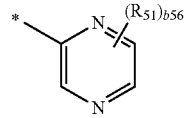
5-19
5-12
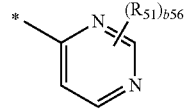
5-20
5-13
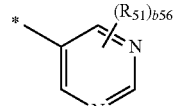
5-21
5-14
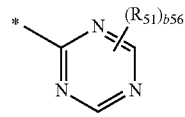
5-22
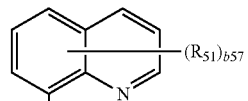
5-23
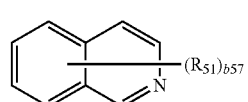
5-24
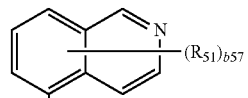
5-25

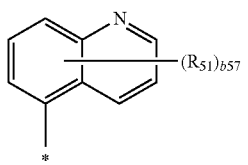
5-26
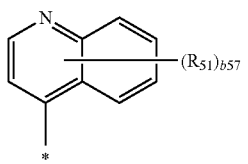
5-27
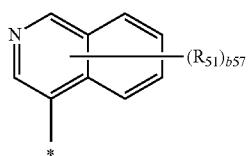
5-28
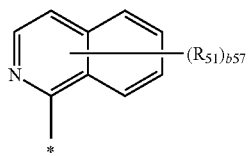
5-29
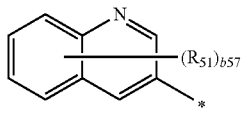
5-30
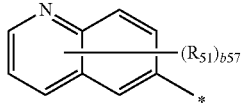
5-31
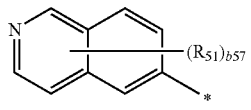
5-32
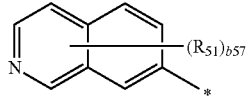
5-33
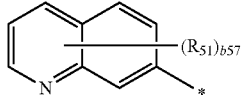
5-34
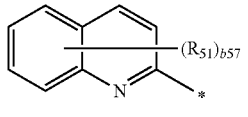
5-35
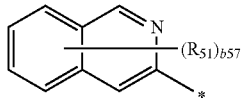
5-36
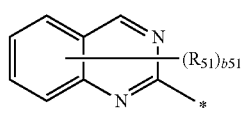
5-37
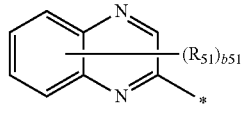
5-38
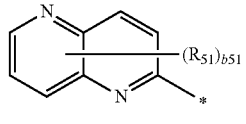
5-39
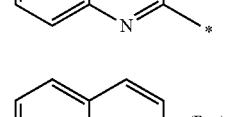
5-40
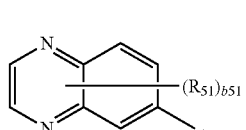
5-41
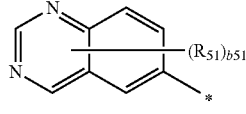
5-42
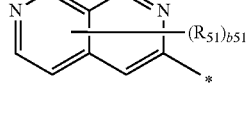
5-43
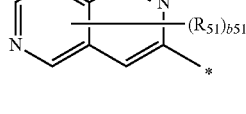
5-44
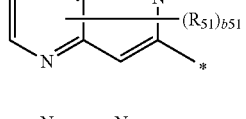
5-45
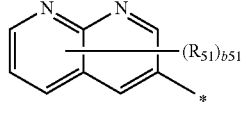
5-46
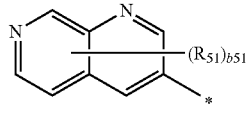
5-47
5-48

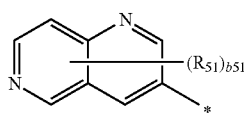 5-49
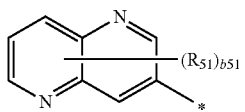 5-50
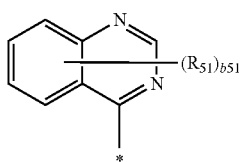 5-51
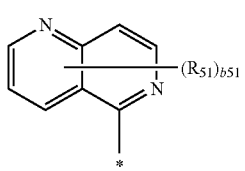 5-52
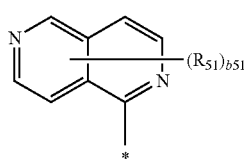 5-53
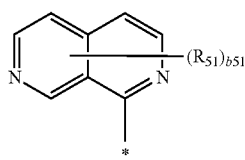 5-54
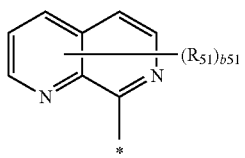 5-55
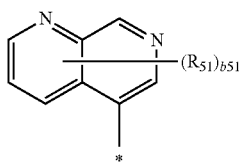 5-56
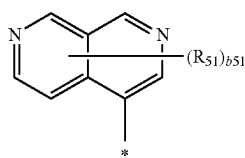 5-57
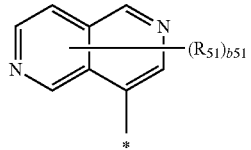 5-58
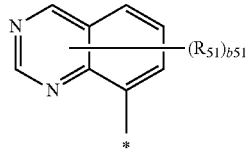 5-59
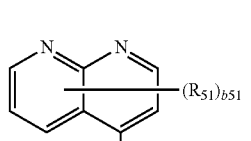 5-60
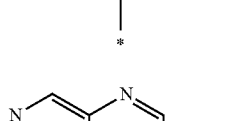 5-61
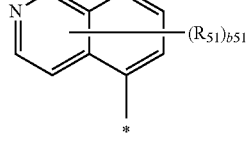 5-62
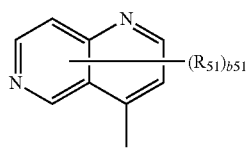 5-63
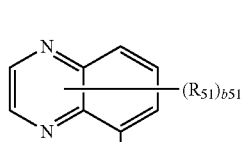 5-64
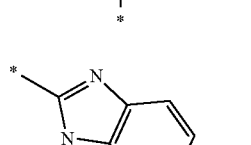 5-65
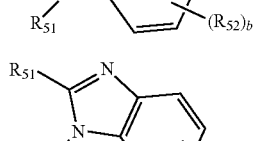 5-66
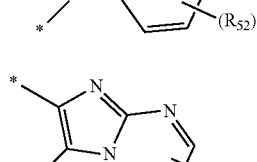 5-67

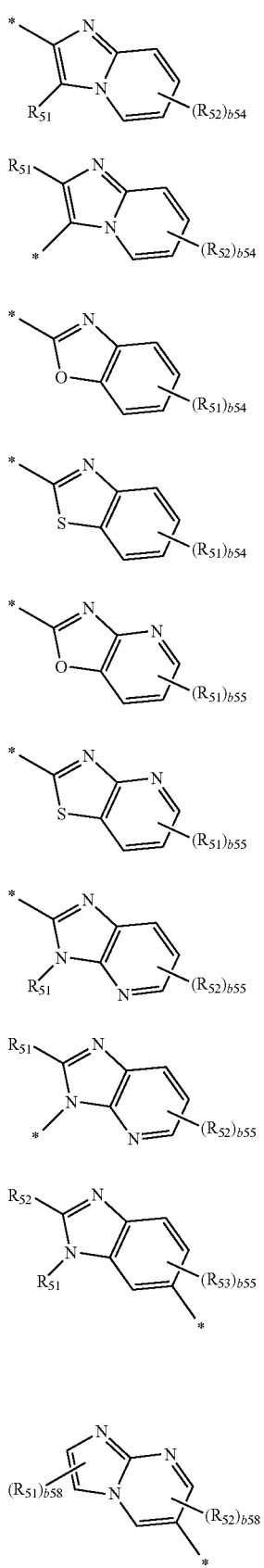
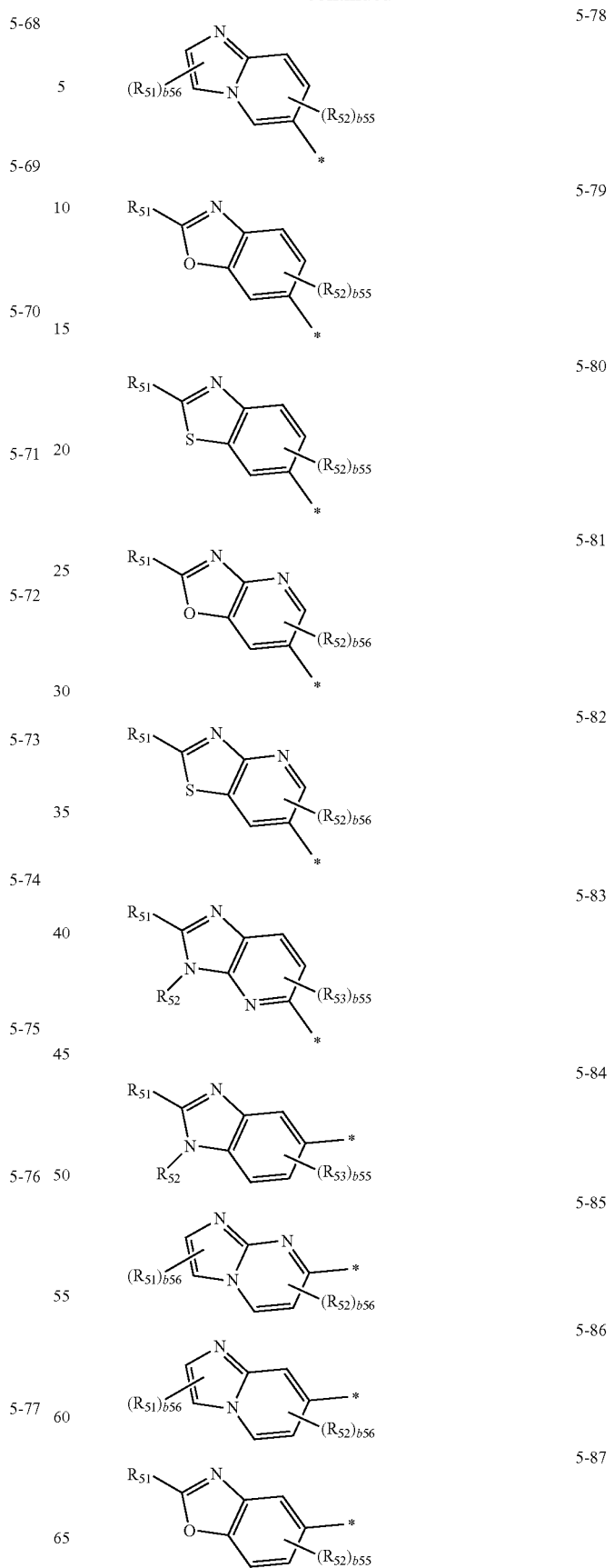

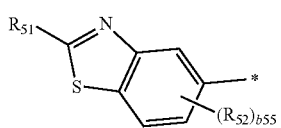
5-88
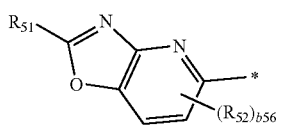
5-89
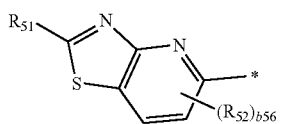
5-90
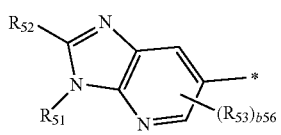
5-91
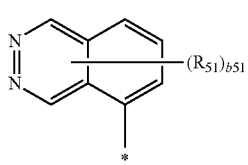
5-92
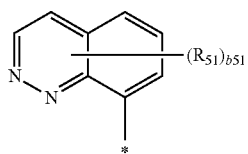
5-93
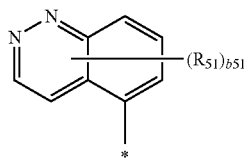
5-94
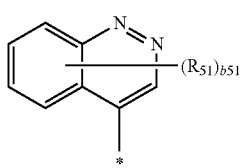
5-95
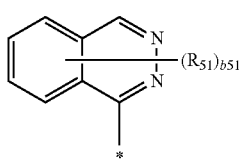
5-96
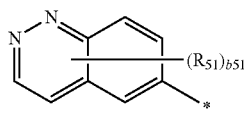
5-97
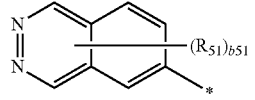
5-98
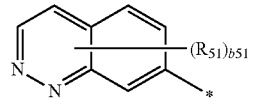
5-99
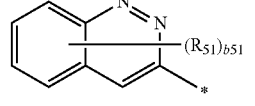
5-100
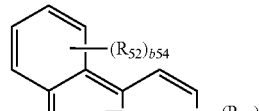
5-101
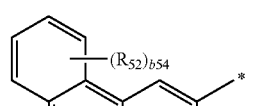
5-102
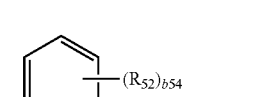
5-103
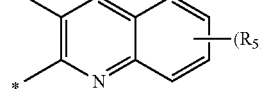
5-104
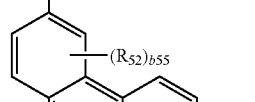
5-105
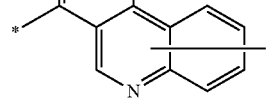
5-106

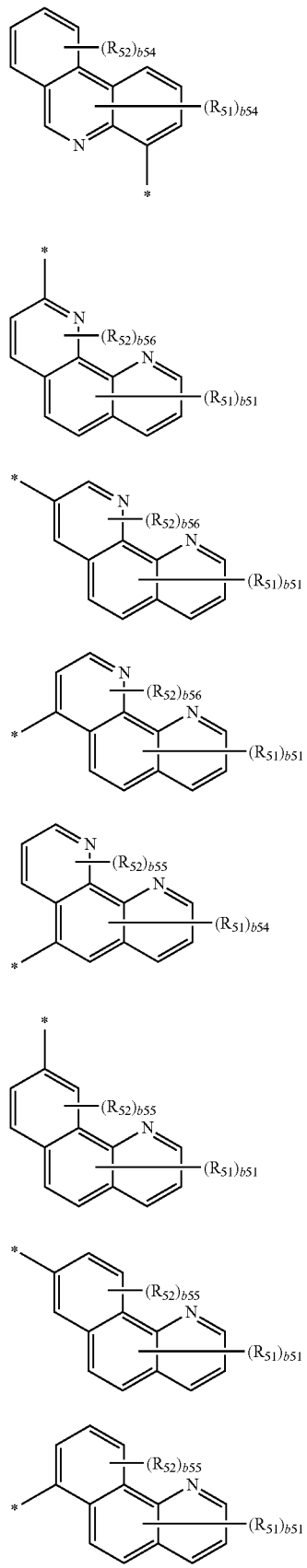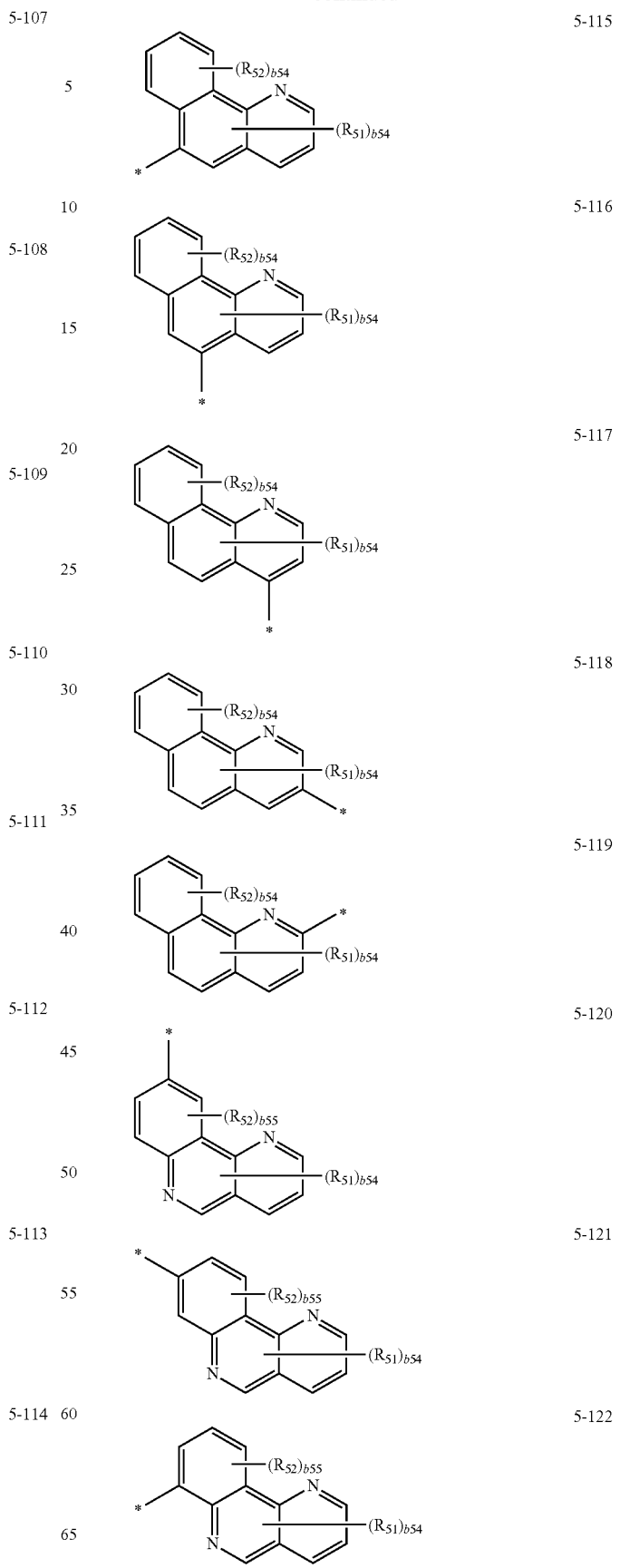

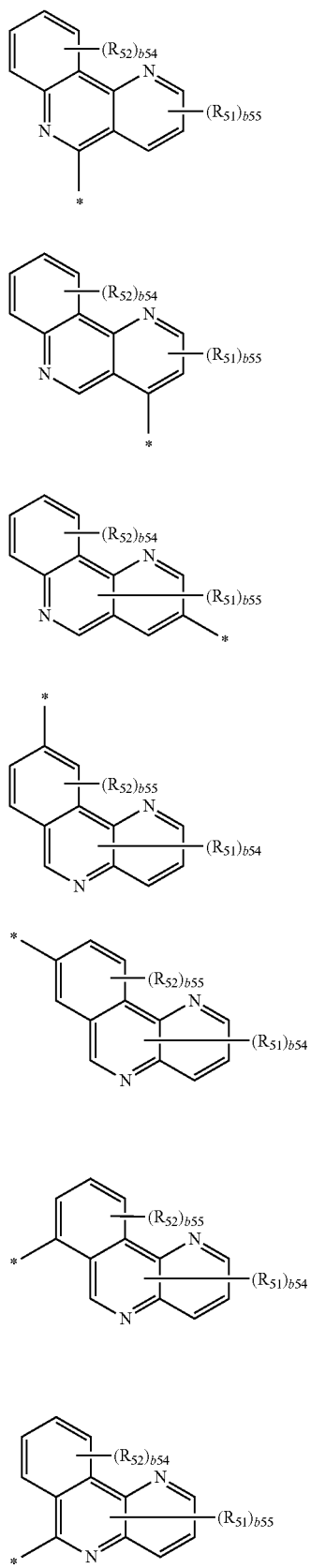
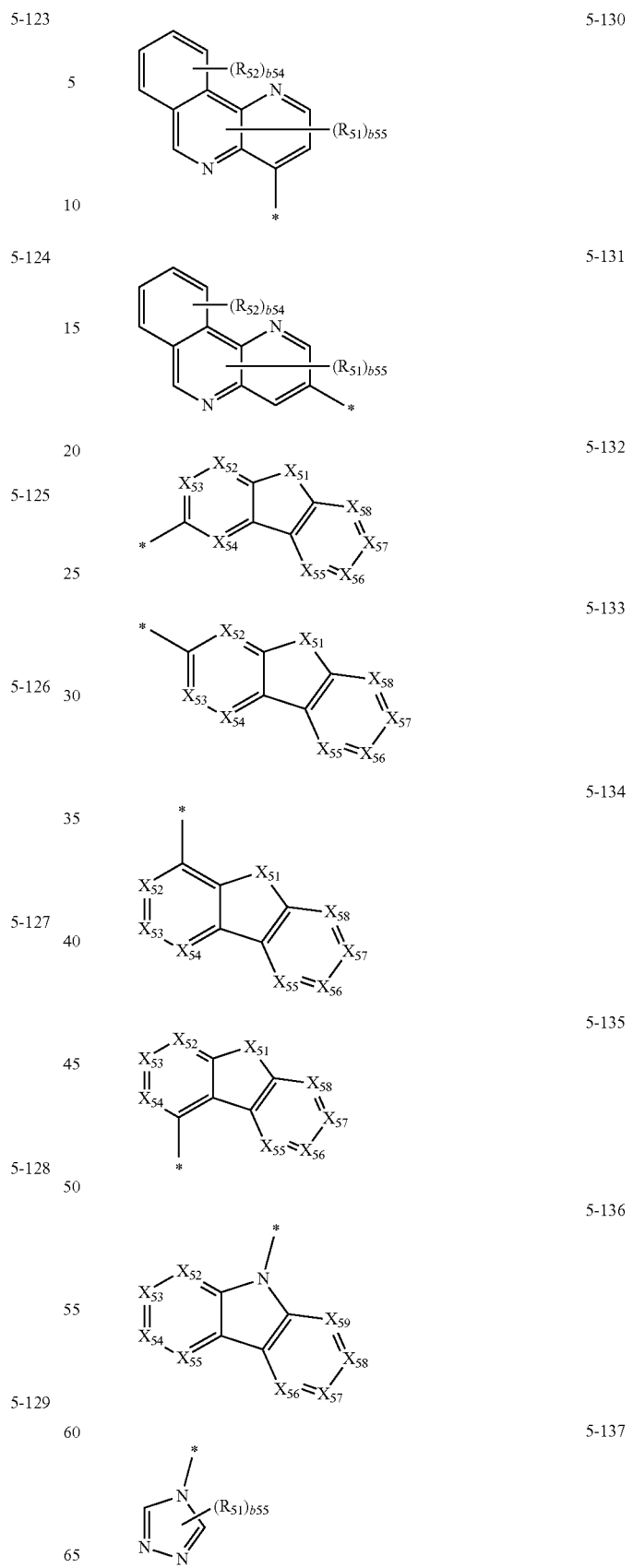

5-138

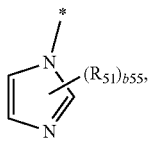

in Formulae 5-1 to 5-138, $X_{51}$ is selected from O, S, $N(R_{51})$, and $C(R_{51})(R_{60})$, $X_{52}$ is N or $C(R_{52})$, $X_{53}$ is N or $C(R_{53})$, $X_{54}$ is N or $C(R_{54})$, $X_{55}$ is N or $C(R_{55})$, $X_{56}$ is N or $C(R_{56})$, $X_{57}$ is N or $C(R_{57})$, $X_{58}$ is N or $C(R_{58})$, and $X_{59}$ is N or $C(R_{59})$ $R_{51}$ to $R_{60}$ are each independently selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a thiophenyl group, a furanyl group, a silolyl group, a carbazolyl group, an indolyl group, an isoindolyl group, a benzofuranyl group, a benzothiophenyl group, a benzosilolyl group, a dibenzofuranyl group, a dibenzothiophenyl group, a benzocarbazolyl group, a dibenzocarbazolyl group, a dibenzosilolyl group, $-Si(Q_{31})(Q_{32})(Q_{33})$, $-N(Q_{31})(Q_{32})$, $-B(Q_{31})(Q_{32})$, $-C(=O)(Q_{31})$, $-S(=O)(Q_{31})$, $-S(=O)_2(Q_{31})$, $-P(=O)(Q_{31})(Q_{32})$, and $-P(=S)(Q_{31})(Q_{32})$, $Q_1$ to $Q_3$ and $Q_{31}$ to $Q_{33}$ are each independently selected from a $C_1$-$C_{60}$ alkyl group, a phenyl group, a biphenyl group, and a terphenyl group, b51 is selected from 1, 2, 3, 4, and 5,
b52 is selected from 1, 2, 3, 4, 5, 6, and 7,
b53 is 1, 2, 3, 4, 5, 6, 7, 8, and 9,
b54 is selected from 1, 2, 3, and 4,
b55 is selected from 1, 2, and 3,
b56 is 1 or 2,
b57 is selected from 1, 2, 3, 4, 5, and 6, and
* indicates a binding site to a neighboring atom.

11. The condensed cyclic compound of claim 1, wherein $Ar_{11}$ is selected from:

—F, —Cl, —Br, —I, a cyano group, a methyl group, an ethyl group, an n-propyl group, an iso-propyl group, an n-butyl group, an iso-butyl group, a sec-butyl group, and a tert-butyl group;

a methyl group, an ethyl group, an n-propyl group, an iso-propyl group, an n-butyl group, an iso-butyl group, a sec-butyl group, and a tert-butyl group, each substituted with at least one selected from deuterium, —F, —Cl, —Br, —I, and a cyano group;

groups represented by Formulae 6-1 to 6-257; and

—S(=O)(Ph), —S(=O)$_2$(Ph), —P(=O)(Ph)$_2$, and —P(=S)(Ph)$_2$:

6-1

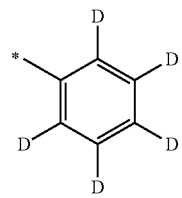

6-2

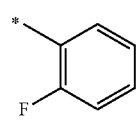

6-3

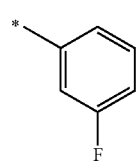

6-4

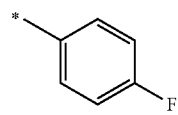

6-5

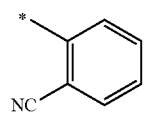

6-6

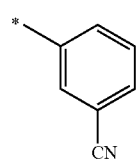

6-7

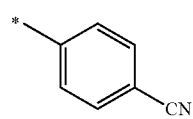

6-8

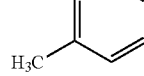

6-9

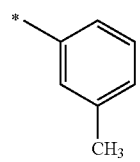

6-10

6-11

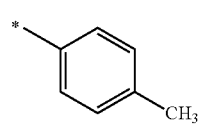

6-12

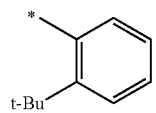

-continued
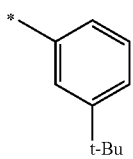
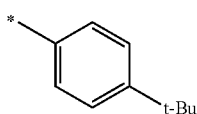
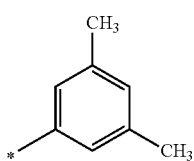
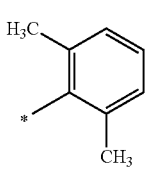
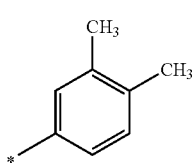
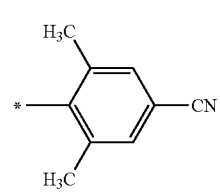
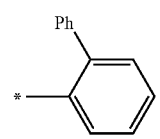
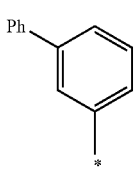
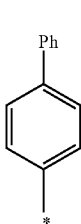
-continued
6-13
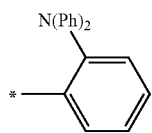
6-14
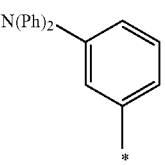
6-15
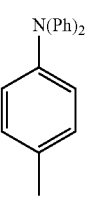
6-16
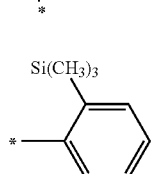
6-17
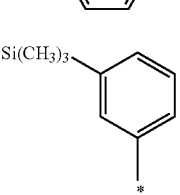
6-18
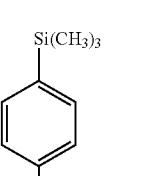
6-19
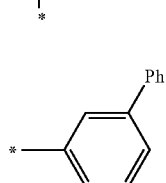
6-20
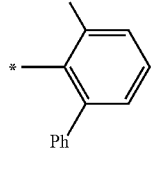
6-21
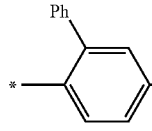
6-22
6-23
6-24
6-25
6-26
6-27
6-28
6-29
6-30

| | |
|---|---|
| 6-31 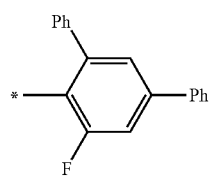 | 6-39 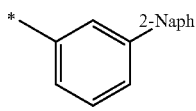 |
| 6-32 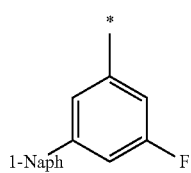 | 6-40 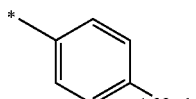 |
| 6-33 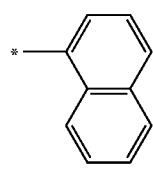 | 6-41 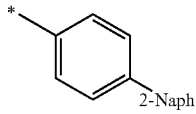 |
| 6-34 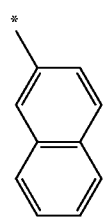 | 6-42 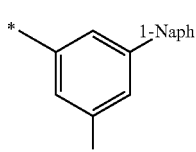 |
| 6-35 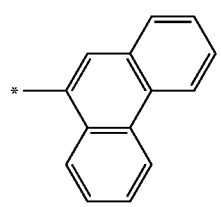 | 6-43 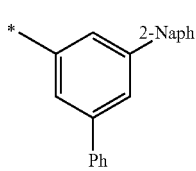 |
| 6-36 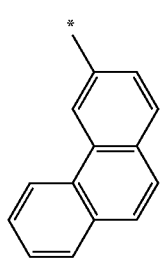 | 6-44 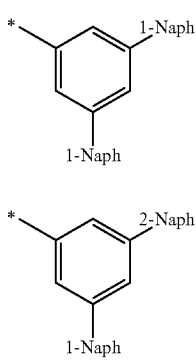 |
| 6-37 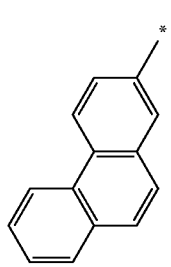 | 6-45 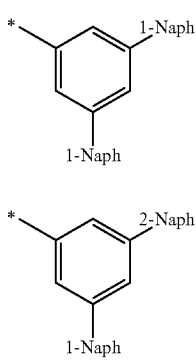 |
| 6-38 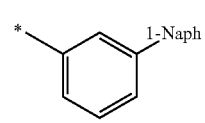 | 6-46 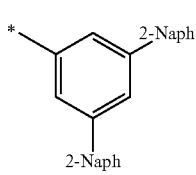 |
| | 6-47 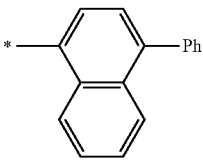 |
| | 6-48 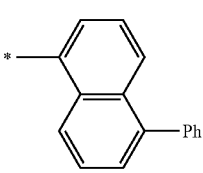 |

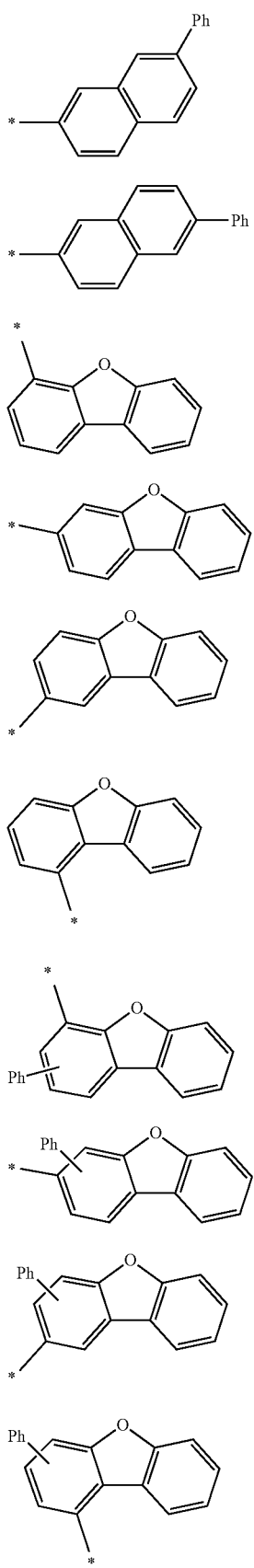
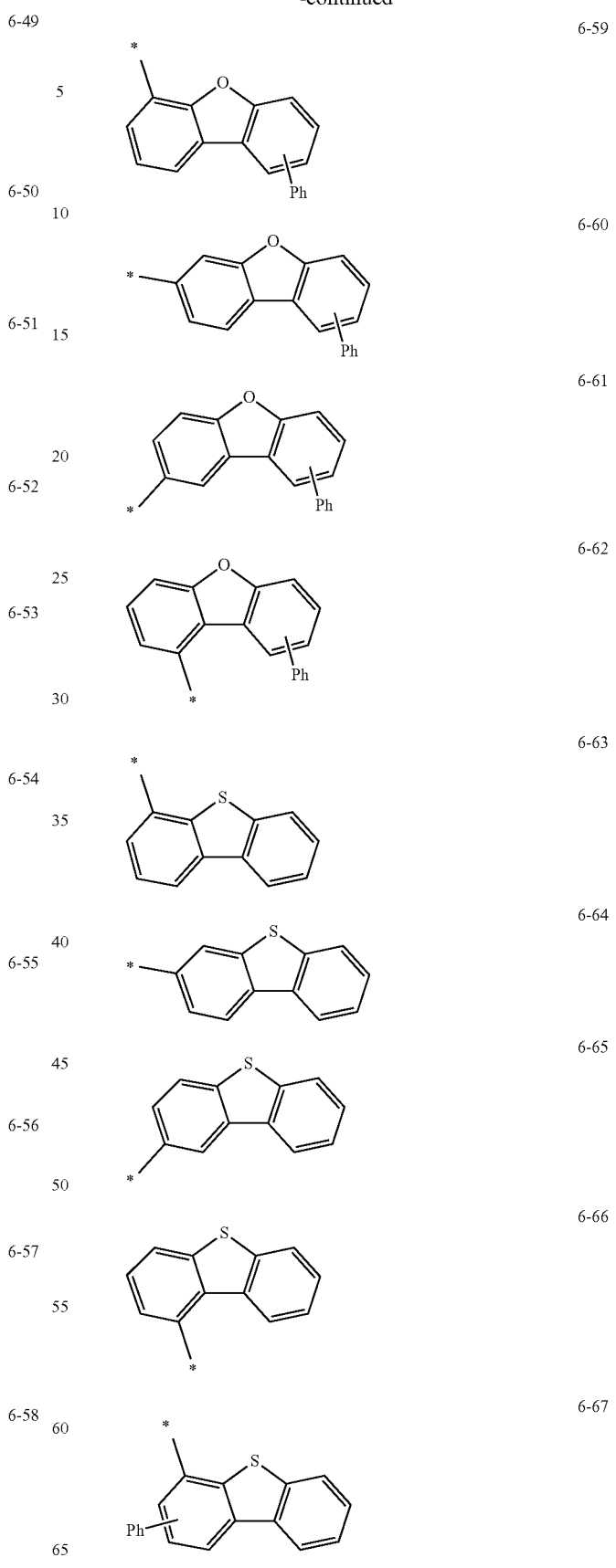

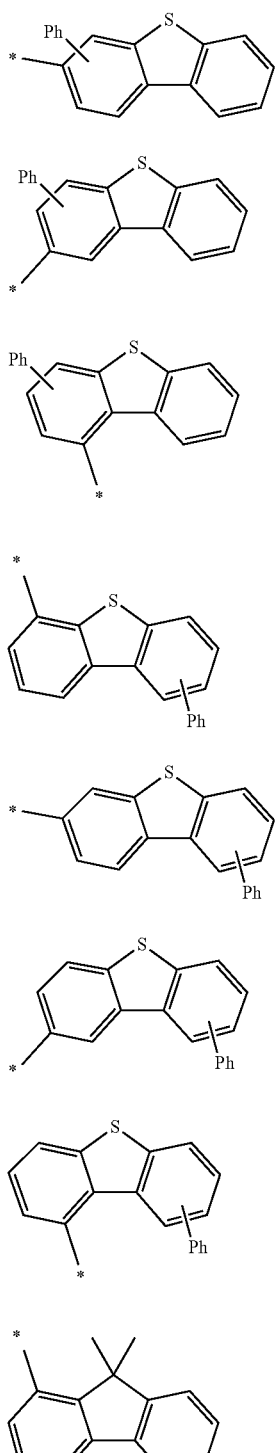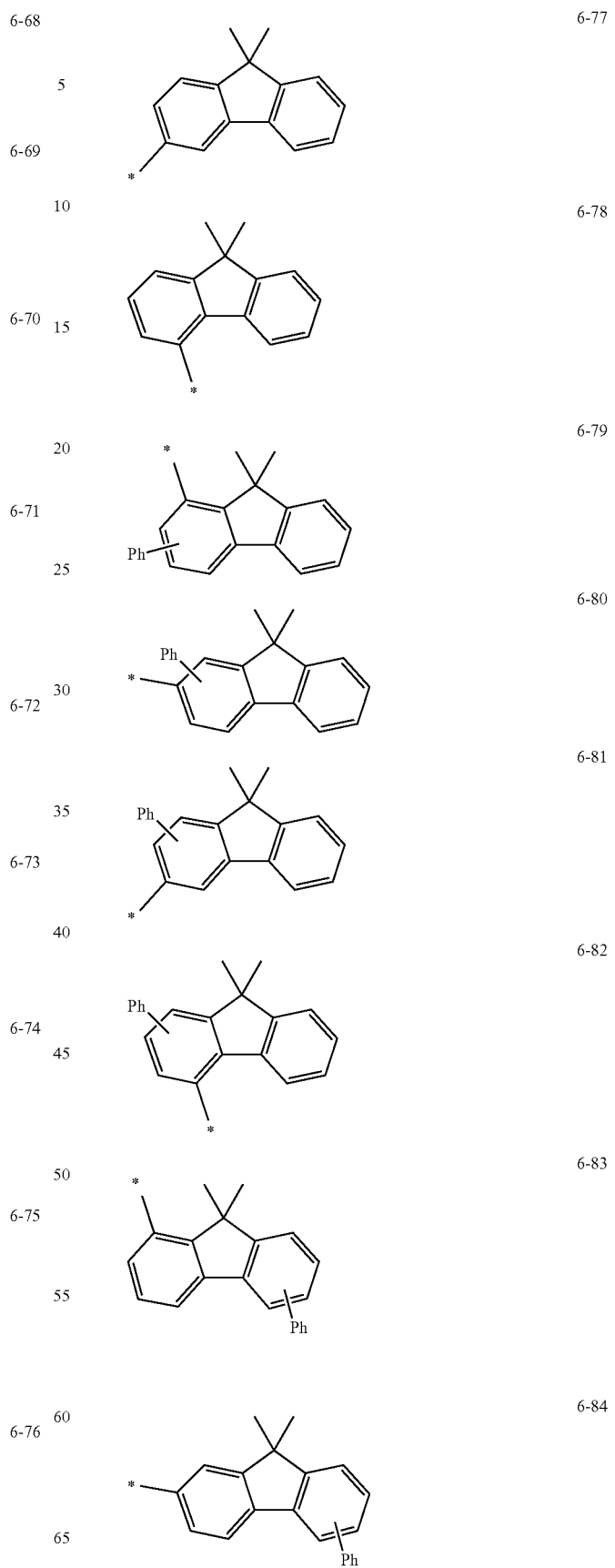

6-85 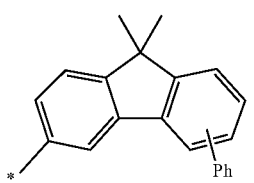
6-86 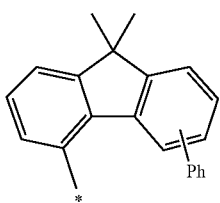
6-87 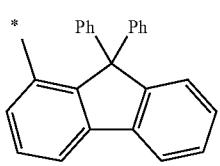
6-88 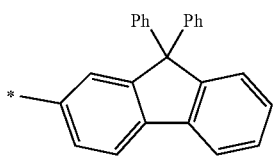
6-89 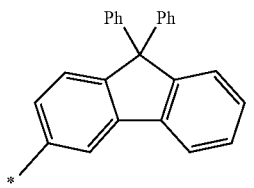
6-90 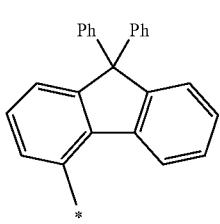
6-91 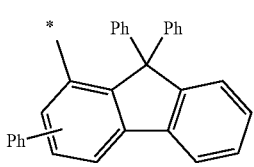
6-92 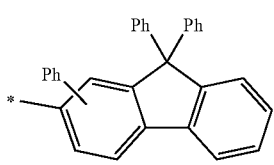
6-93 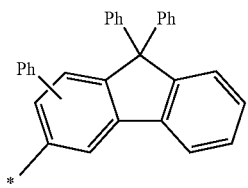
6-94 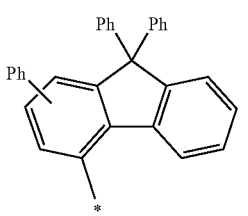
6-95 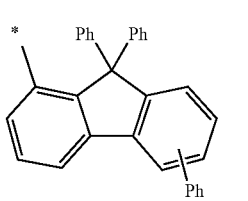
6-96 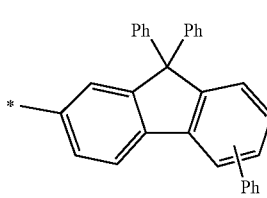
6-97 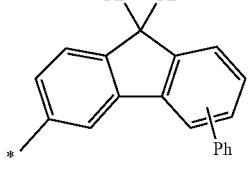
6-98 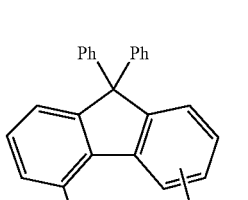
6-99 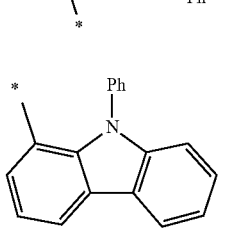
6-100 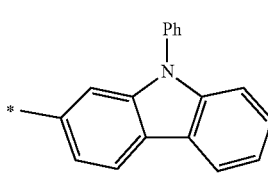

-continued
6-101 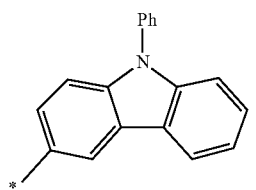
6-102 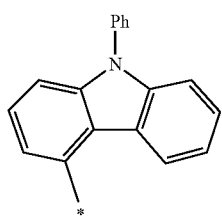
6-103 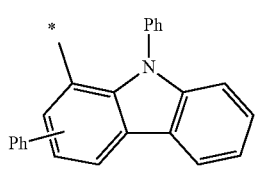
6-104 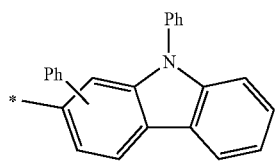
6-105 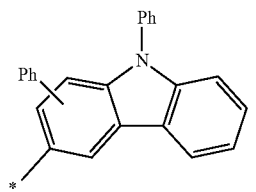
6-106 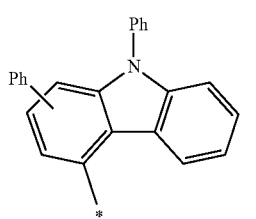
6-107 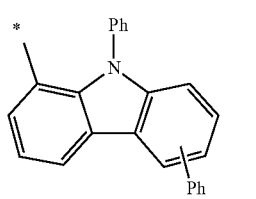
6-108 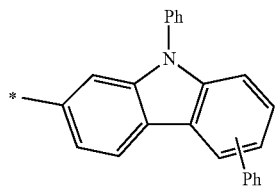
-continued
6-109 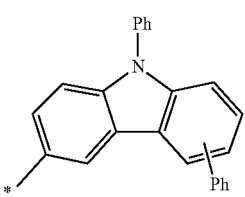
6-110 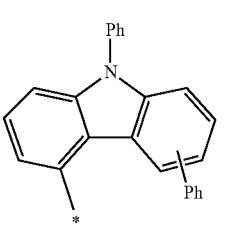
6-111 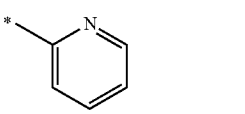
6-112 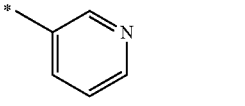
6-113 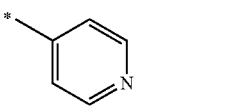
6-114 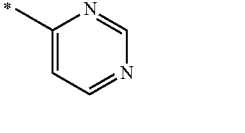
6-115 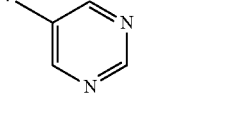
6-116 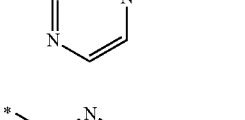
6-117 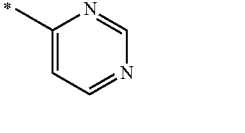
6-118 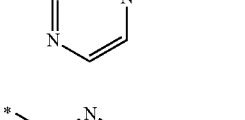
6-119 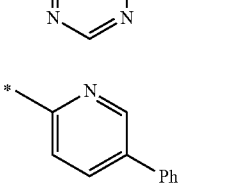

| | |
|---|---|
| 6-120 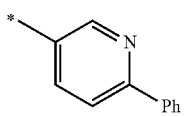 | 6-133 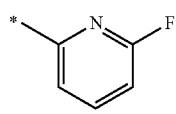 |
| 6-121 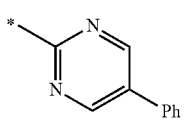 | 6-134 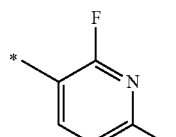 |
| 6-122 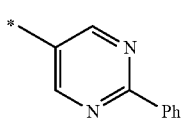 | 6-135 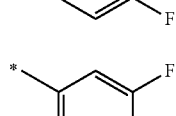 |
| 6-123 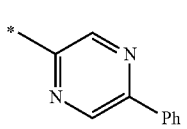 | 6-136 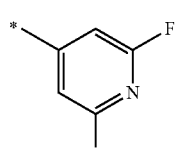 |
| 6-124 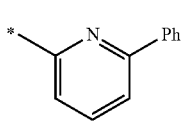 | 6-137 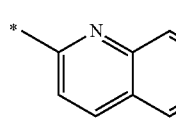 |
| 6-125 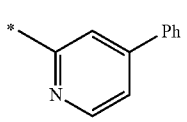 | 6-138 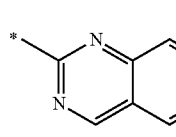 |
| 6-126 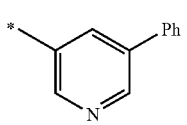 | 6-139 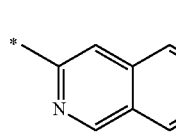 |
| 6-127 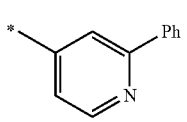 | 6-140 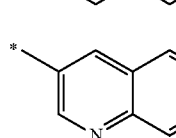 |
| 6-128 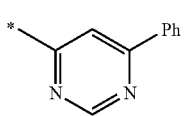 | 6-141 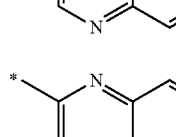 |
| 6-129 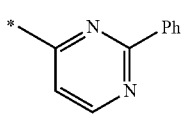 | 6-142 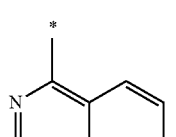 |
| 6-130 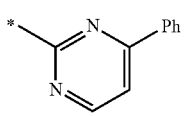 | 6-143 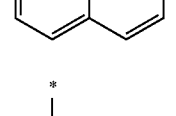 |
| 6-131 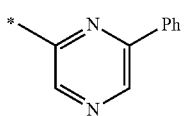 | 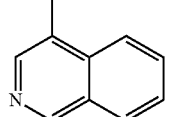 |
| 6-132 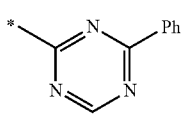 | 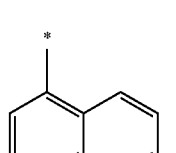 |

6-144
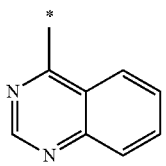
6-145
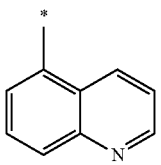
6-146
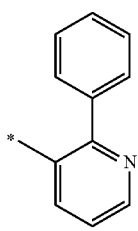
6-147
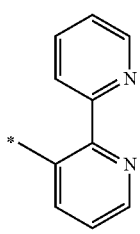
6-148
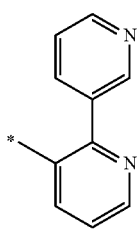
6-149
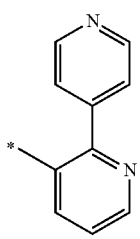
6-150
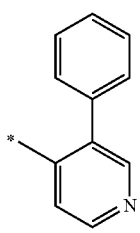
6-151
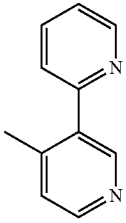
6-152
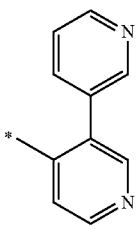
6-153
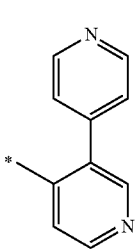
6-154
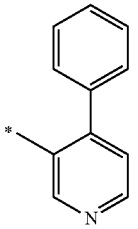
6-155
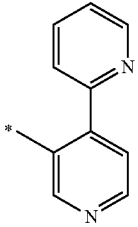
6-156
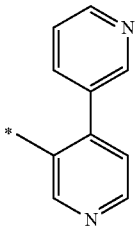

| | |
|---|---|
| 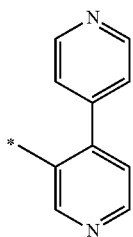 6-157 | 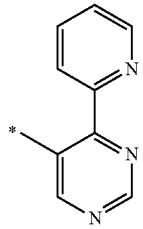 6-163 |
| 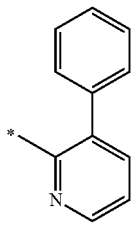 6-158 | 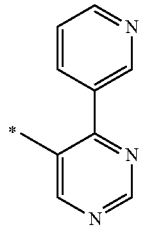 6-164 |
| 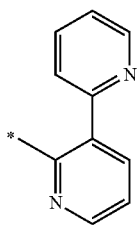 6-159 | 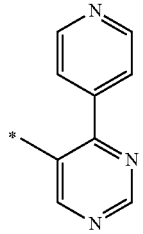 6-165 |
| 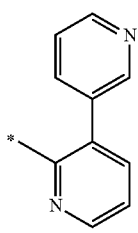 6-160 | 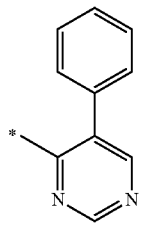 6-166 |
| 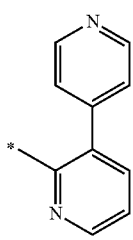 6-161 | 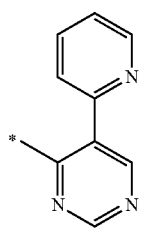 6-167 |
| 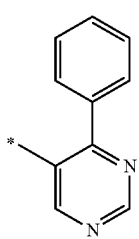 6-162 | 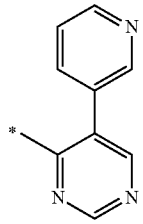 6-168 |

315
-continued
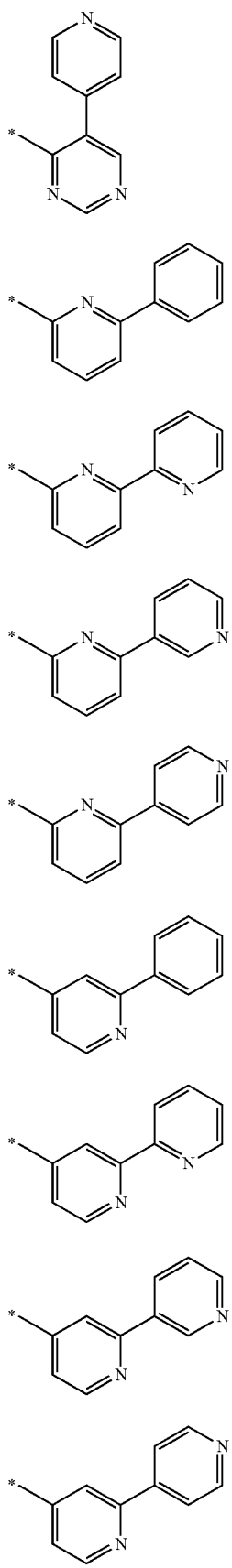
316
-continued
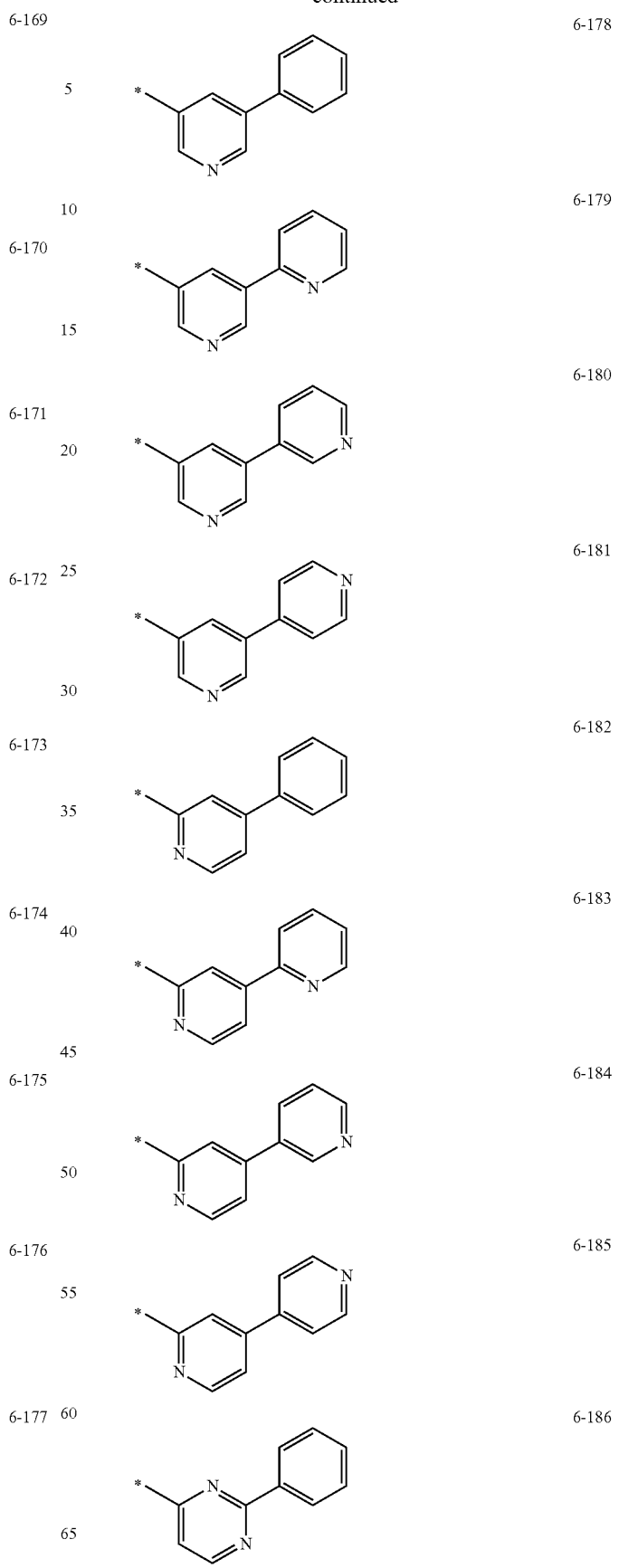

6-187 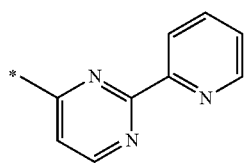
6-188 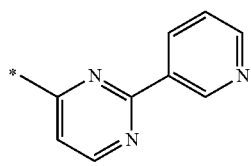
6-189 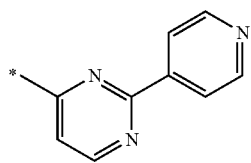
6-190 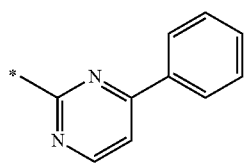
6-191 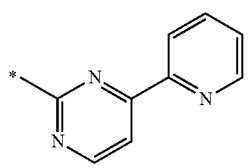
6-192 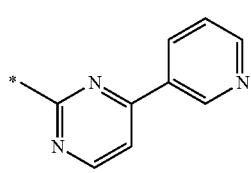
6-193 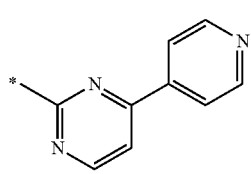
6-194 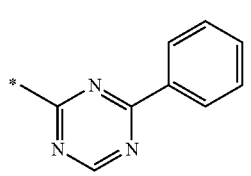
6-195 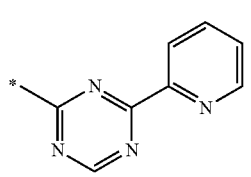
6-196 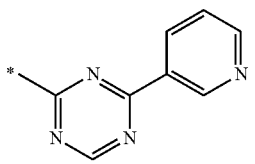
6-197 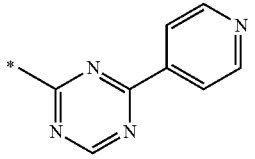
6-198 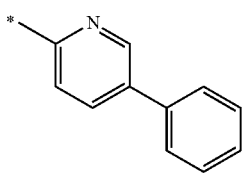
6-199 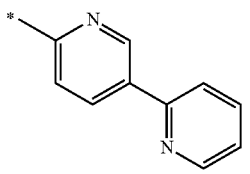
6-200 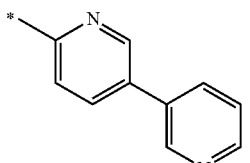
6-201 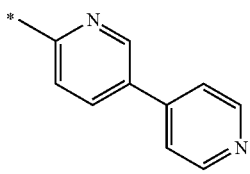
6-202 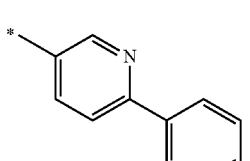
6-203 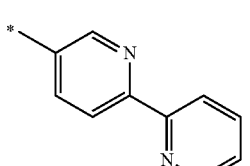
6-204 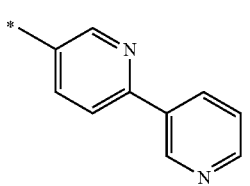

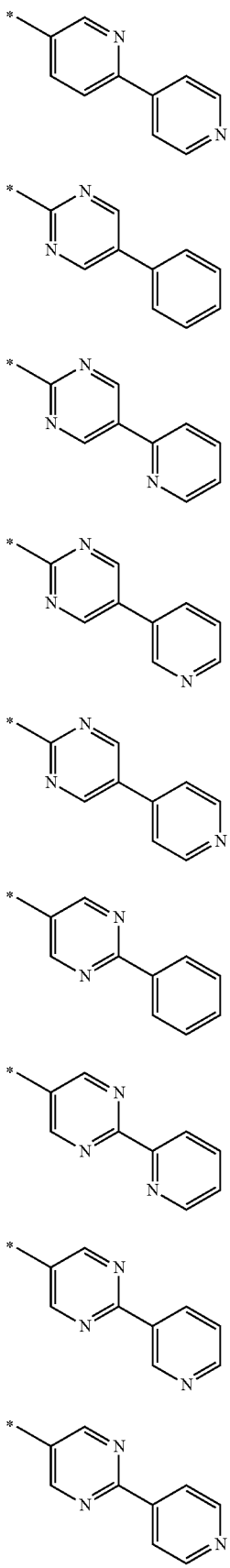
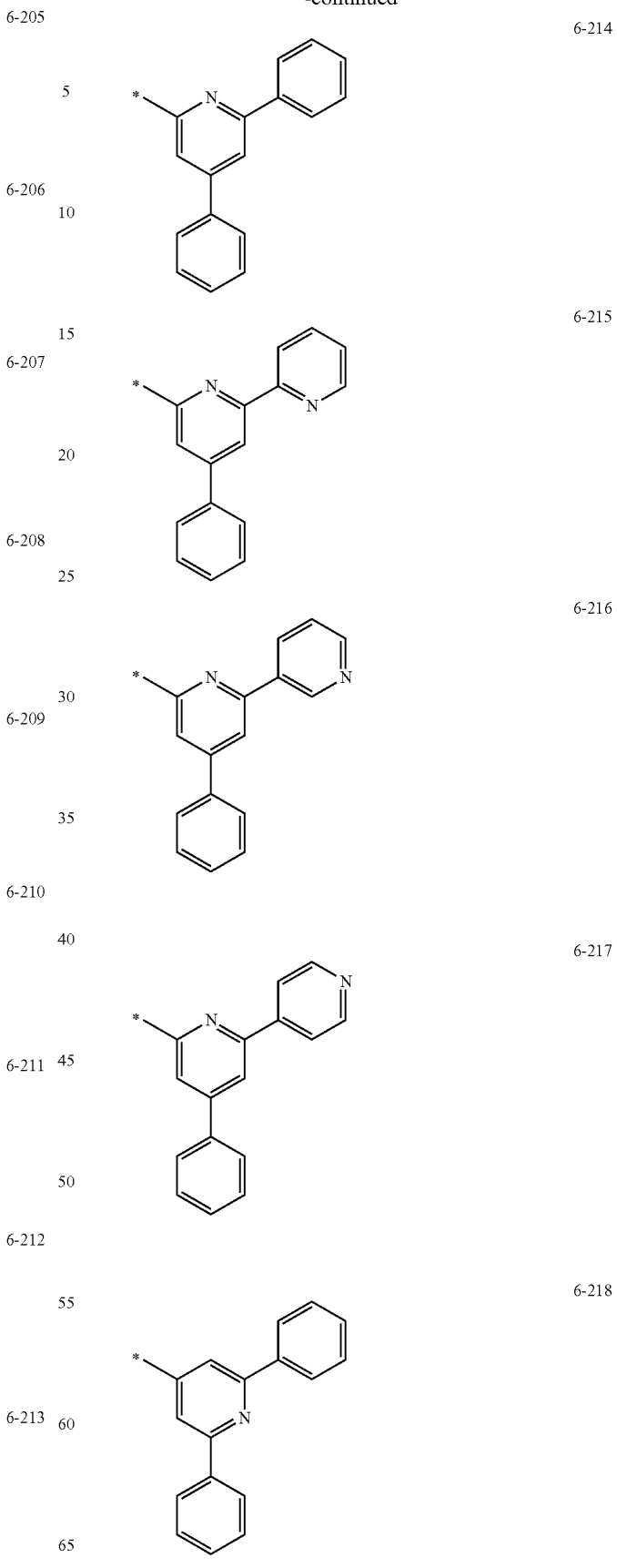

-continued
6-219
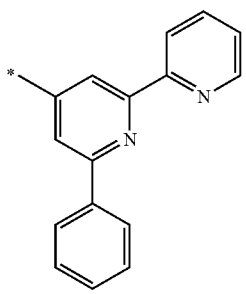
6-220
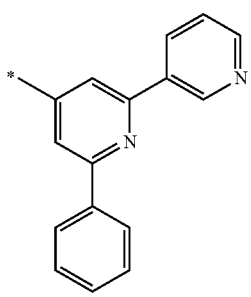
6-221
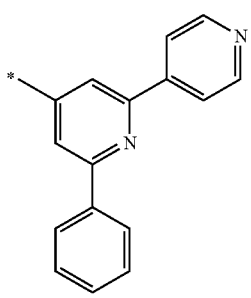
6-222
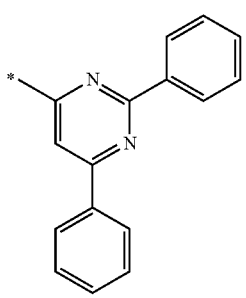
6-223
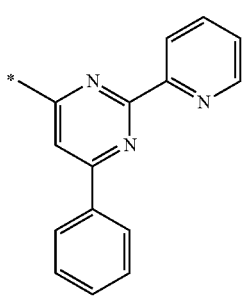
-continued
6-224
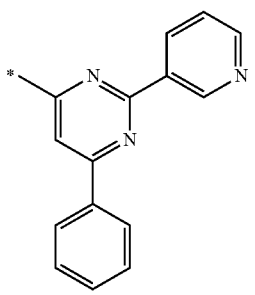
6-225
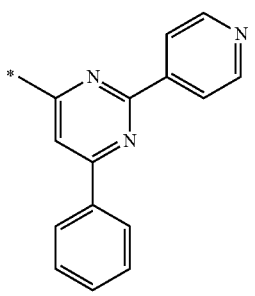
6-226
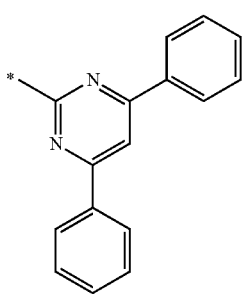
6-227
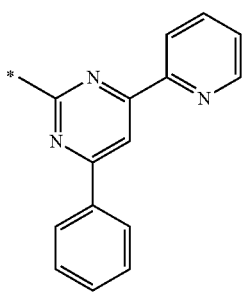
6-228
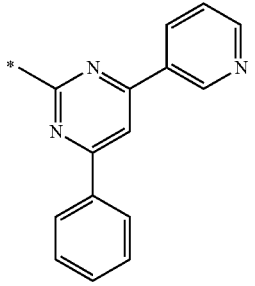

6-229
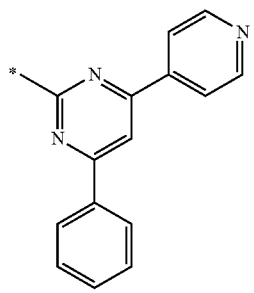
6-230
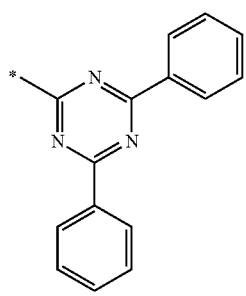
6-231
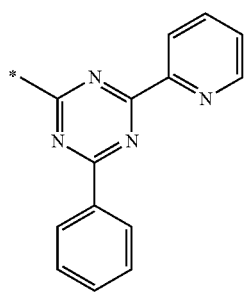
6-232
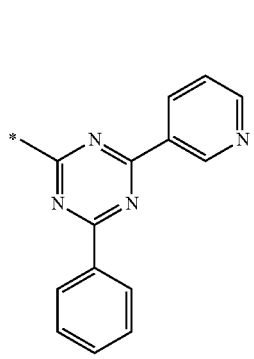
6-233
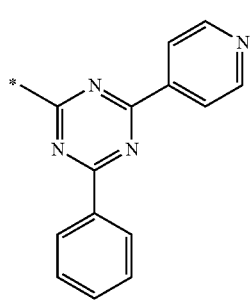
6-234
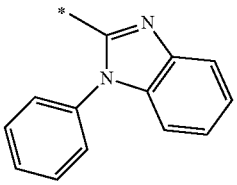
6-235
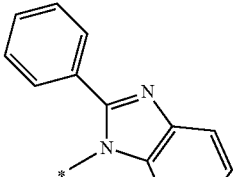
6-236
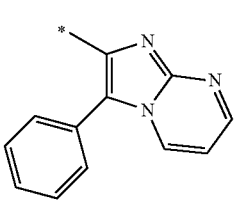
6-237
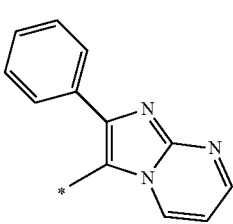
6-238
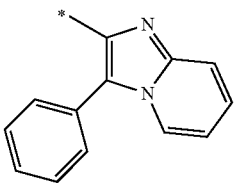
6-239
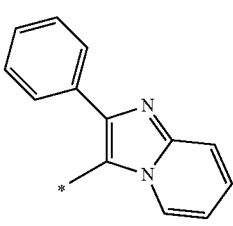
6-240
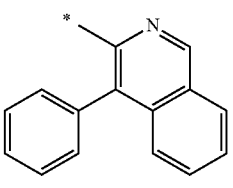

325
-continued
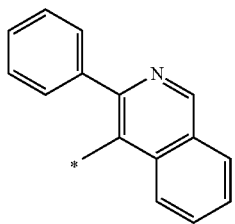
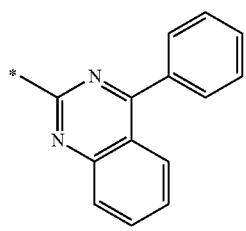
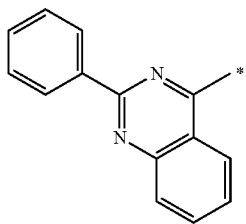
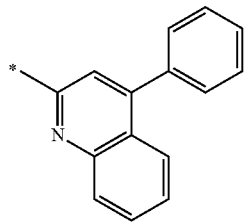
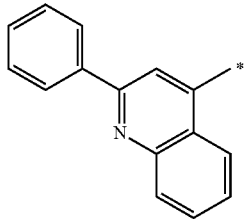
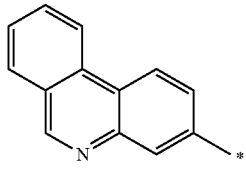
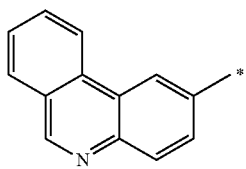
326
-continued
6-241
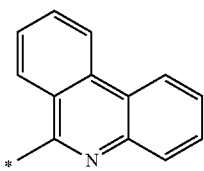
6-242
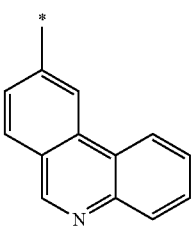
6-243
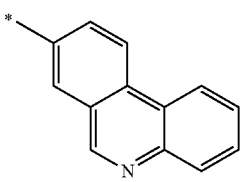
6-244
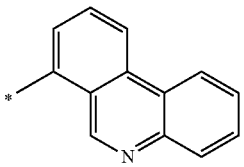
6-245
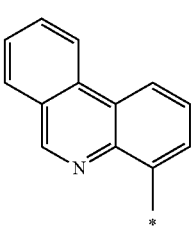
6-246
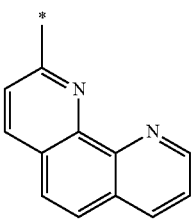
6-247
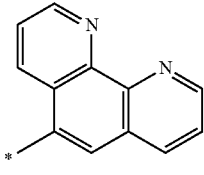
6-248
6-249
6-250
6-251
6-252
6-253
6-254
6-255

-continued

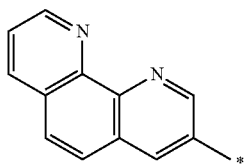
6-256

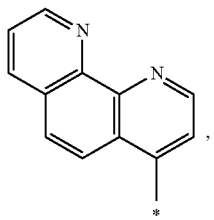
6-257 in Formulae 6-1 to 6-257,
t-Bu indicates a tert-butyl group,
Ph indicates a phenyl group,
1-Naph indicates a 1-naphthyl group,
2-Naph indicates a 2-naphthyl group, and
* indicates a binding site to a neighboring atom.

13. The condensed cyclic compound of claim 1, wherein the condensed cyclic compound represented by Formula 1 is represented by Formula 1-1:

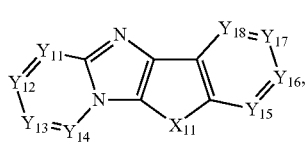
<Formula 1-1> in Formula 1-1,
$Y_{11}$ to $Y_{18}$ are each independently selected from N, $C(R_x)$, and $C(R_y)$, provided that at least one of $Y_{11}$ to $Y_{18}$ is $C(R_y)$,
$R_x$ is selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$),
$R_y$ is a group represented by *-($L_{11}$)$_{a11}$-($Ar_{11}$)$_{c11}$,
$X_{11}$, $L_{11}$, a11, $Ar_{11}$, c11, and $Q_1$ to $Q_3$ are the same as described in connection with Formula 1, and
* indicates a binding site to a neighboring atom.

13. The condensed cyclic compound of claim 12, wherein
$Y_{11}$ is $C(R_y)$, and $Y_{12}$ to $Y_{18}$ are each independently selected from N, $C(R_x)$, and $C(R_y)$;
$Y_{12}$ is $C(R_y)$, and $Y_{11}$ and $Y_{13}$ to $Y_{18}$ are each independently selected from N, $C(R_x)$, and $C(R_y)$;
$Y_{13}$ is $C(R_y)$, and $Y_{11}$, $Y_{12}$, and $Y_{14}$ to $Y_{18}$ are each independently selected from N, $C(R_x)$, and $C(R_y)$;
$Y_{14}$ is $C(R_y)$, and $Y_{11}$ to $Y_{13}$ and $Y_{15}$ to $Y_{18}$ are each independently selected from N, $C(R_x)$, and $C(R_y)$;
$Y_{15}$ is $C(R_y)$, and $Y_{11}$ to $Y_{14}$ and $Y_{16}$ to $Y_{18}$ are each independently selected from N, $C(R_x)$, and $C(R_y)$;
$Y_{16}$ is $C(R_y)$, and $Y_{11}$ to $Y_{15}$, $Y_{17}$, and $Y_{18}$ are each independently selected from N, $C(R_x)$, and $C(R_y)$;
$Y_{17}$ is $C(R_y)$, and $Y_{11}$ to $Y_{16}$ and $Y_{18}$ are each independently selected from N, $C(R_x)$, and $C(R_y)$; or
$Y_{18}$ is $C(R_y)$, and $Y_{11}$ to $Y_{17}$ are each independently selected from N, $C(R_x)$, and $C(R_y)$.

14. The condensed cyclic compound of claim 1, wherein the condensed cyclic compound represented by Formula 1 is represented by one of Formulae 1-11 to 1-18, 1-21 to 1-27, 1-31 to 1-37, 1-41 to 1-47, 1-51 to 1-57, 1-61 to 1-67, 1-71 to 1-77, and 1-81 to 1-87:

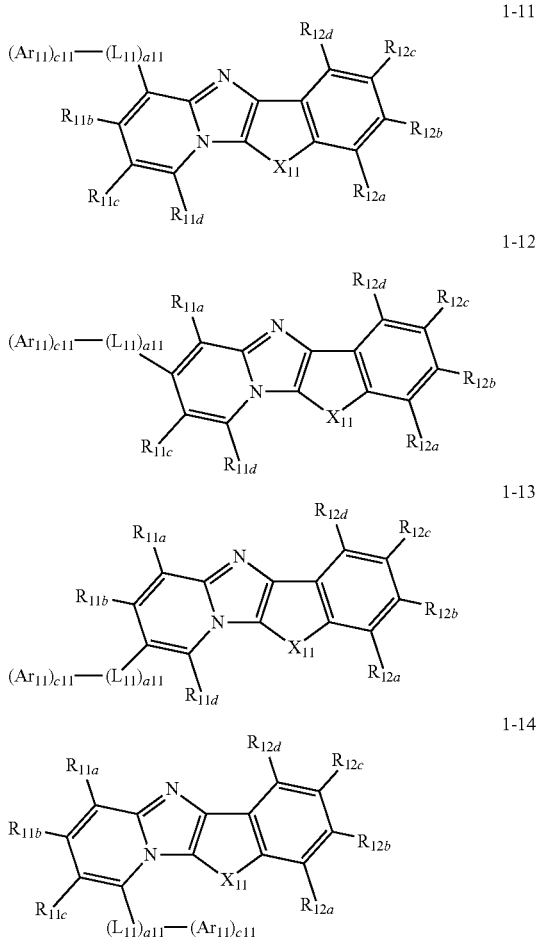

1-15
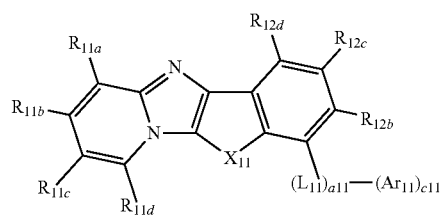
1-16
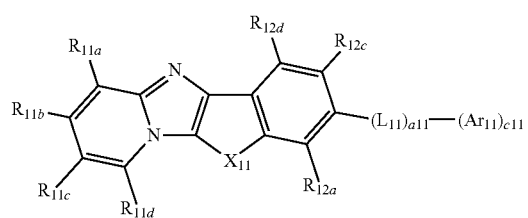
1-17
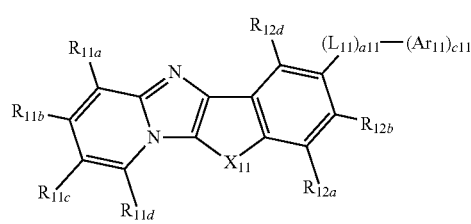
1-18
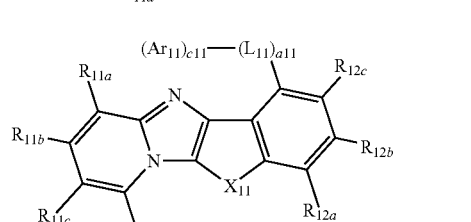
1-21
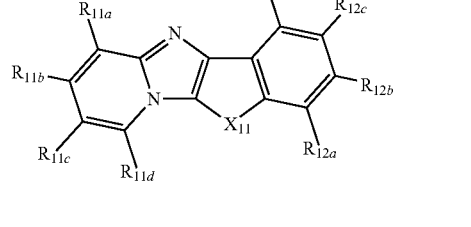
1-22
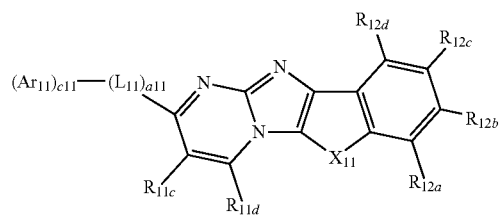
1-23
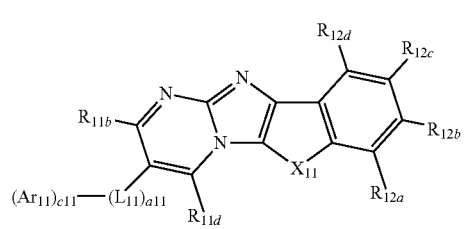
1-24
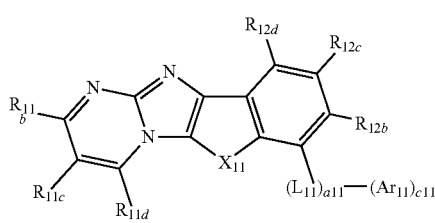
1-25
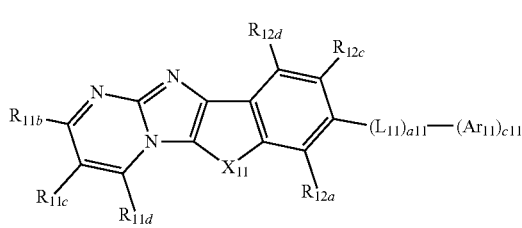
1-26
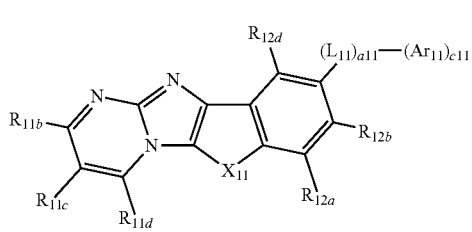
1-27
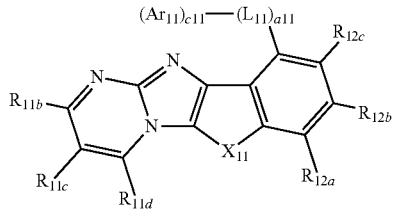
1-31
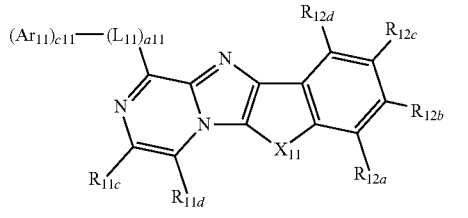
1-32
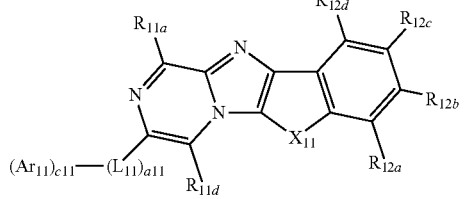
1-33
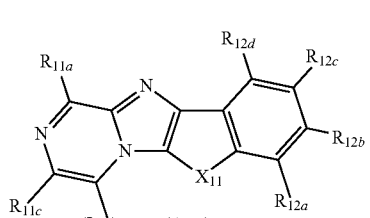

1-34
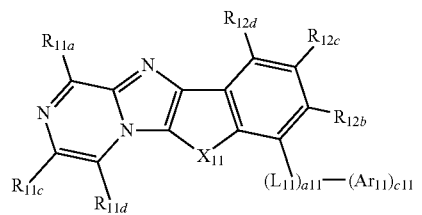
1-35
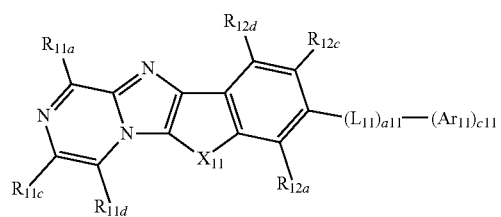
1-36
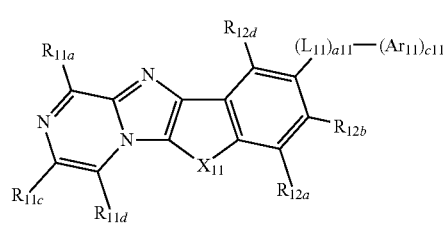
1-37
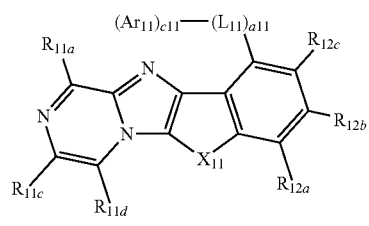
1-41
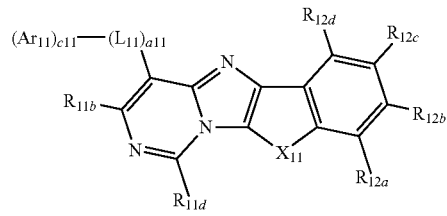
1-42
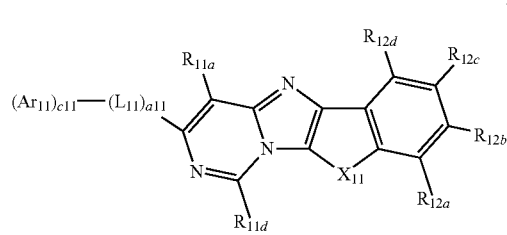
1-43
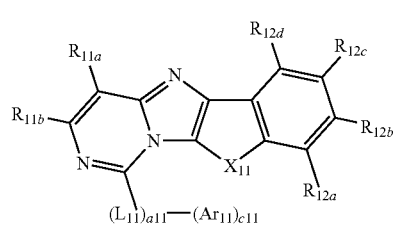
1-44
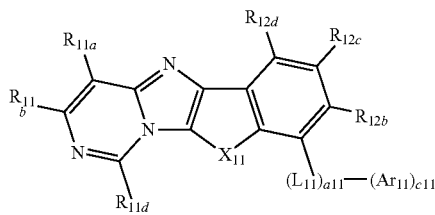
1-45
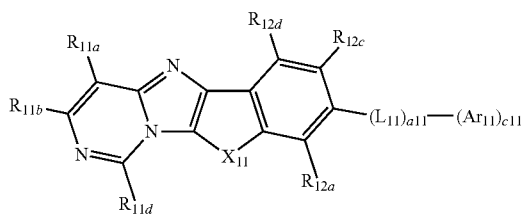
1-46
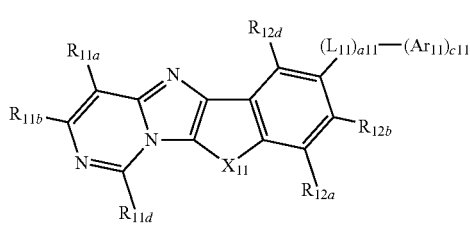
1-47
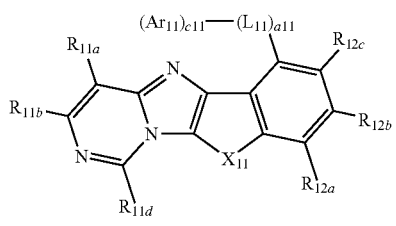
1-51
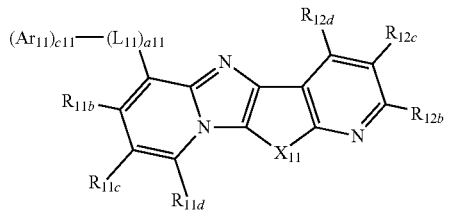
1-52
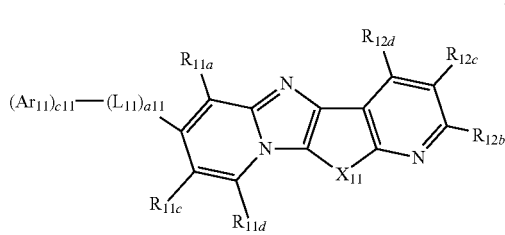
1-53
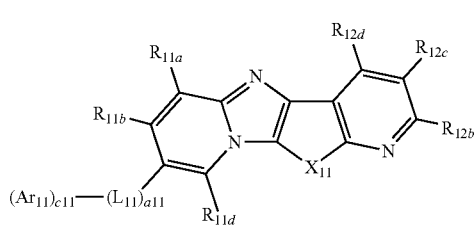

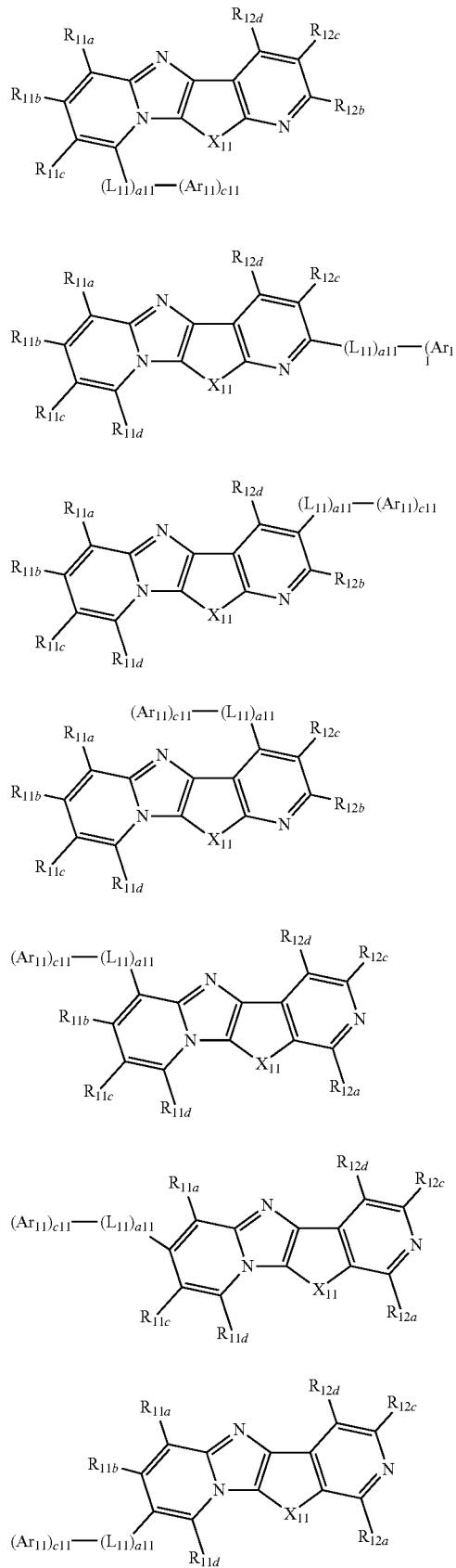
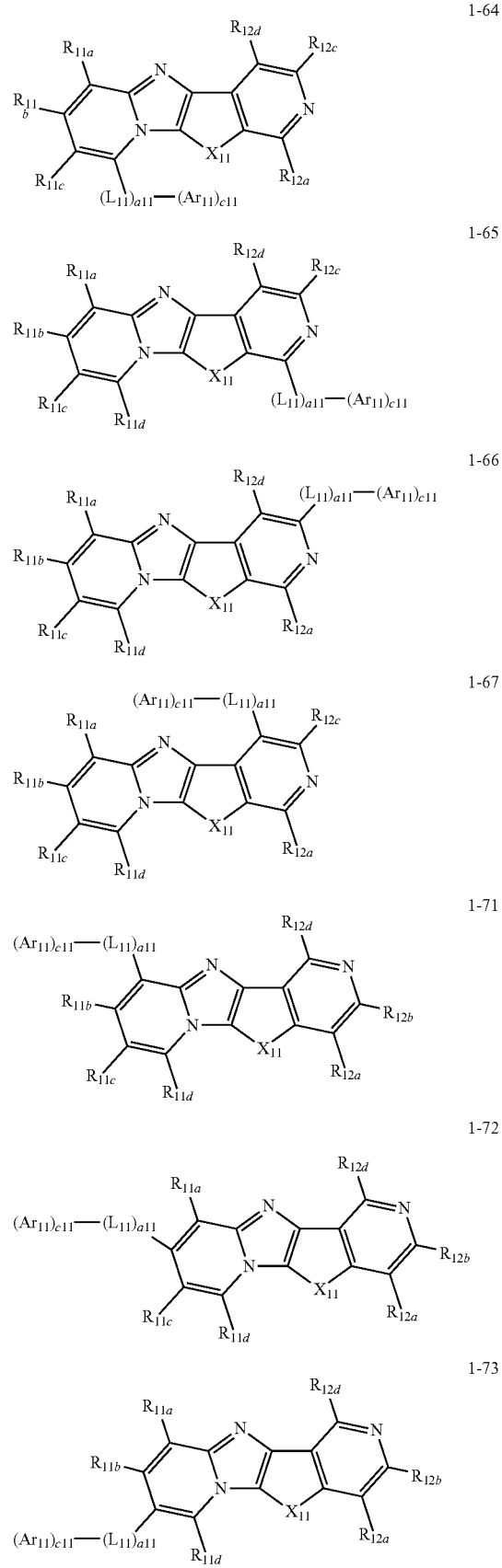

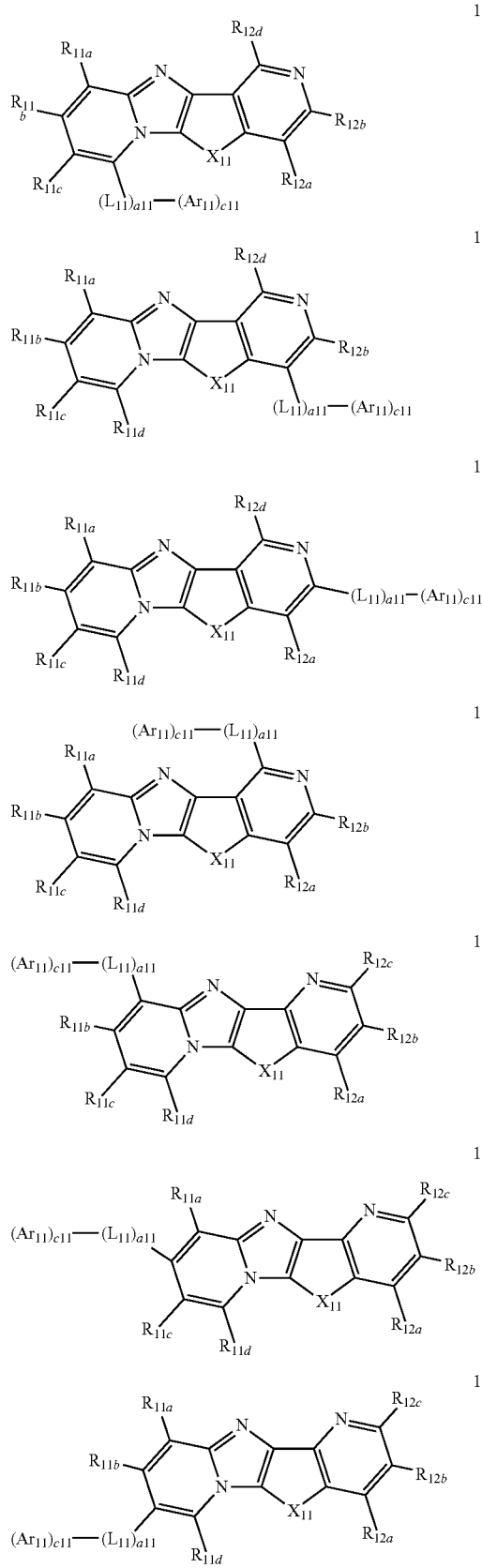

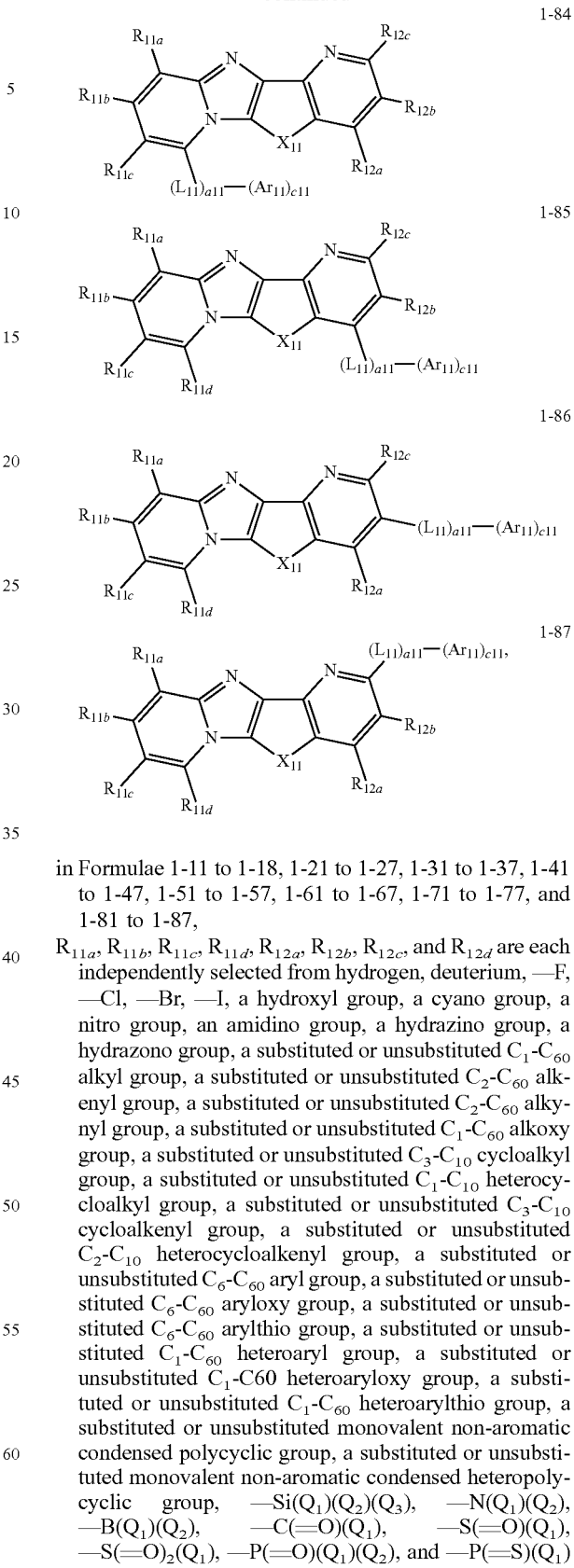

in Formulae 1-11 to 1-18, 1-21 to 1-27, 1-31 to 1-37, 1-41 to 1-47, 1-51 to 1-57, 1-61 to 1-67, 1-71 to 1-77, and 1-81 to 1-87, $R_{11a}$, $R_{11b}$, $R_{11c}$, $R_{11d}$, $R_{12a}$, $R_{12b}$, $R_{12c}$, and $R_{12d}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and $X_{11}$, $L_{11}$, a11, $Ar_{11}$, c11, and $Q_1$ to $Q_3$ are the same as described in connection with Formula 1.

15. The condensed cyclic compound of claim 14, wherein $R_{11a}$, $R_{11b}$, $R_{11c}$, $R_{11d}$, $R_{12a}$, $R_{12b}$, $R_{12c}$, and $R_{12d}$ are each independently selected from:
hydrogen, deuterium, —F, —Cl, —Br, —I, a cyano group, a methyl group, an ethyl group, an n-propyl group, an iso-propyl group, an n-butyl group, an iso-butyl group, a sec-butyl group, and a tert-butyl group;
a methyl group, an ethyl group, an n-propyl group, an iso-propyl group, an n-butyl group, an iso-butyl group, a sec-butyl group, and a tert-butyl group, each substituted with at least one selected from deuterium, —F, —Cl, —Br, —I, and a cyano group; and
a phenyl group, a naphthyl group, and a pyridinyl group.

16. The condensed cyclic compound of claim 1, wherein the condensed cyclic compound represented by Formula 1 is selected from Compounds 1 to 211:

1

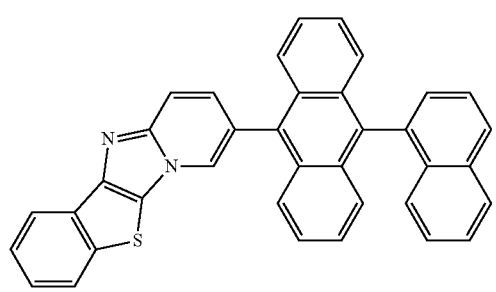

2

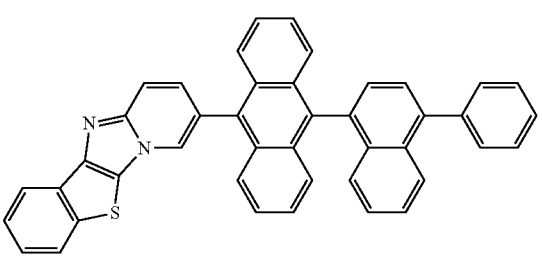

3

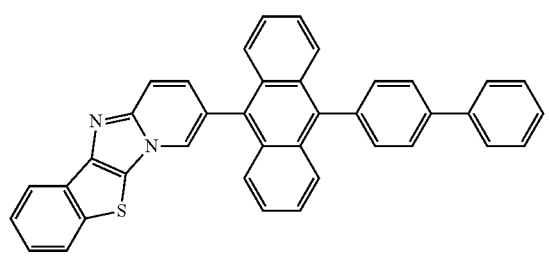

4

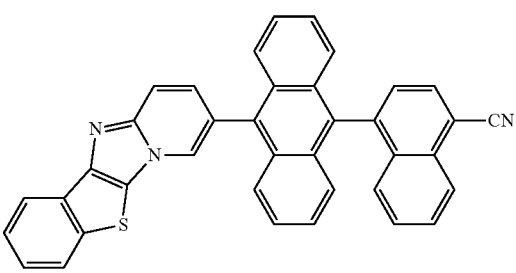

5

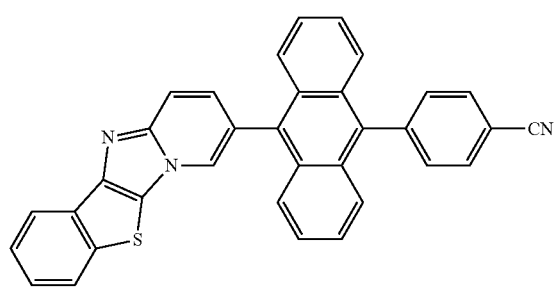

6

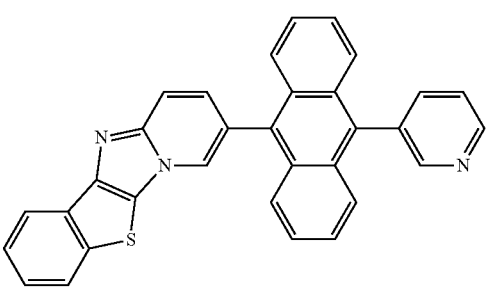

7

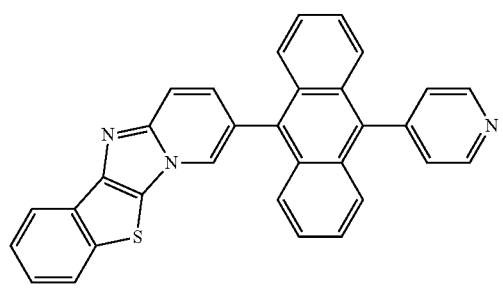

8

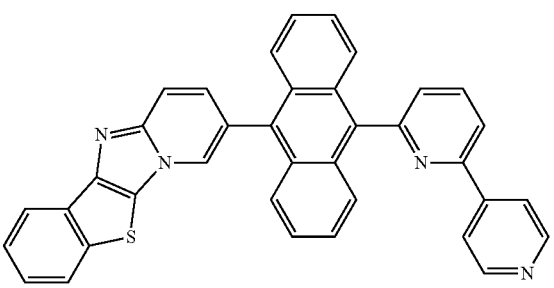

-continued
9
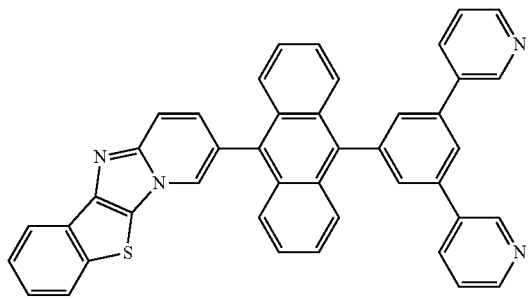
10
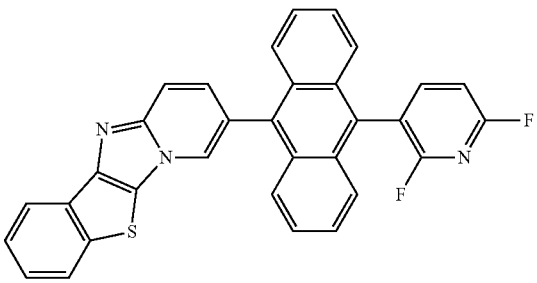
11
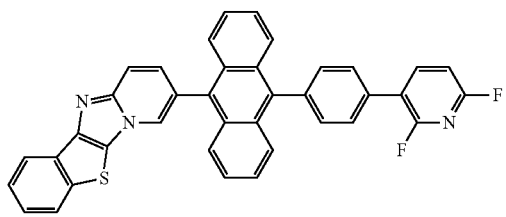
12
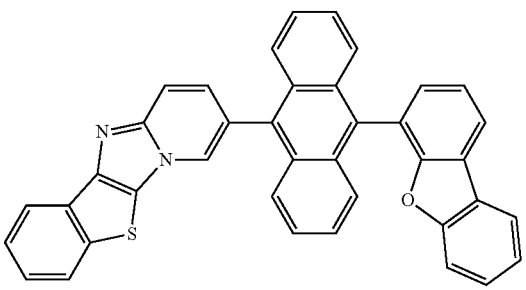
13
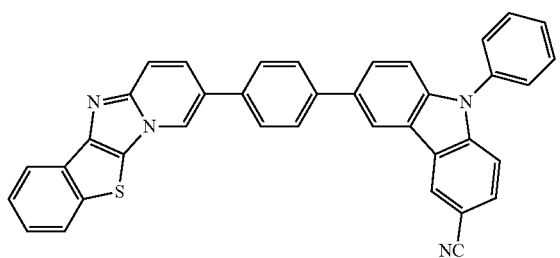
14
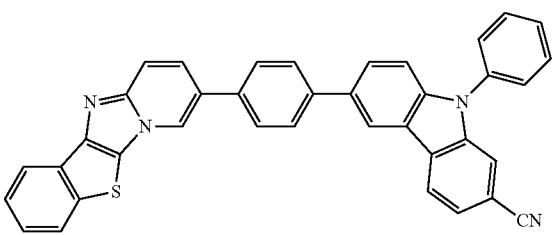
15
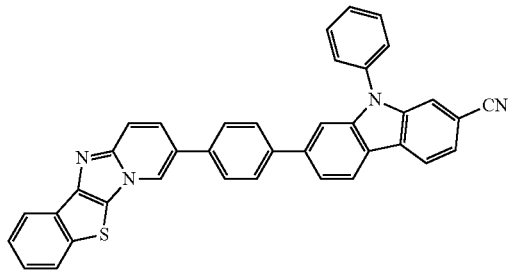
16
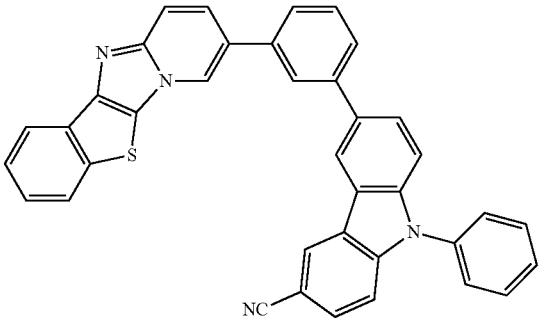
17
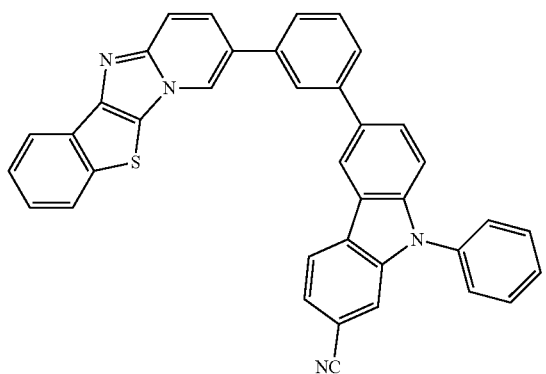
18
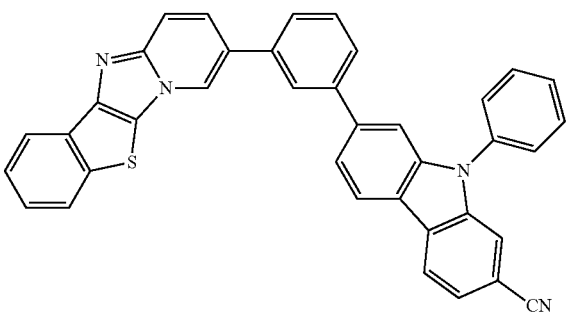

-continued
19
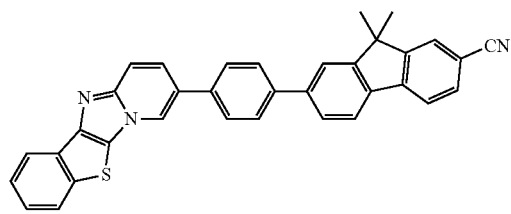
20
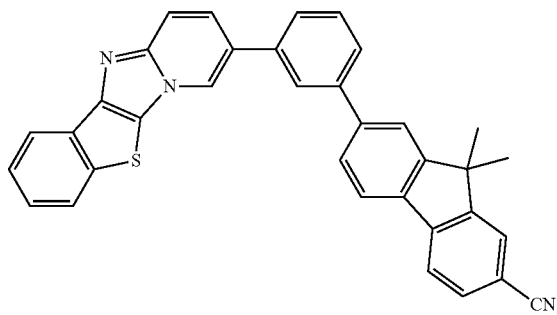
21
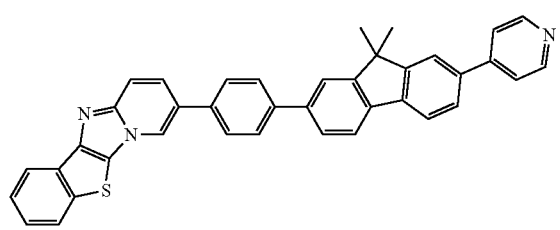
22
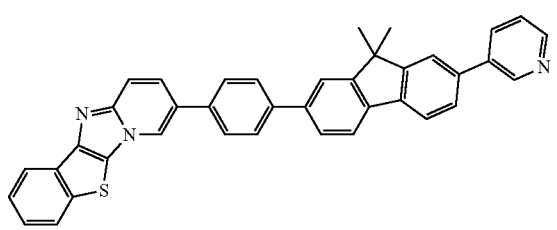
23
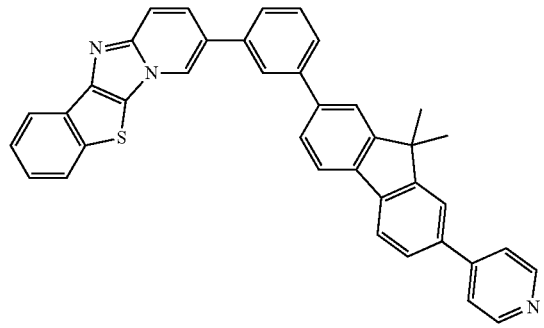
24
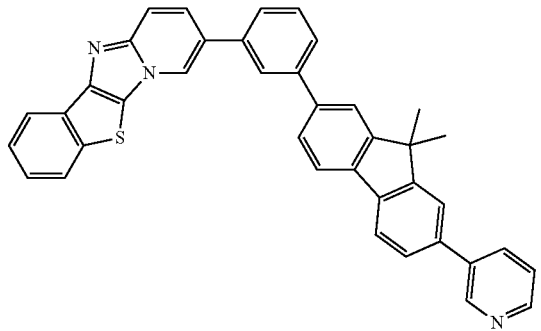
25
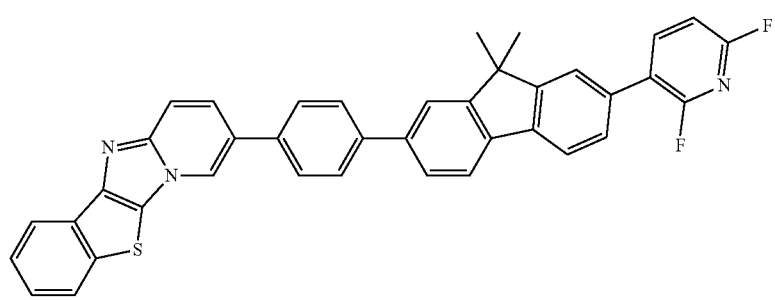
26
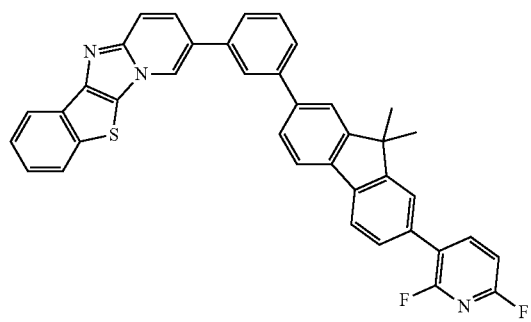
27
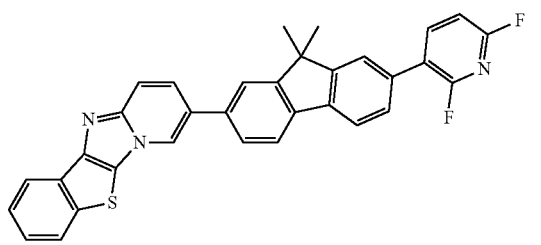

28
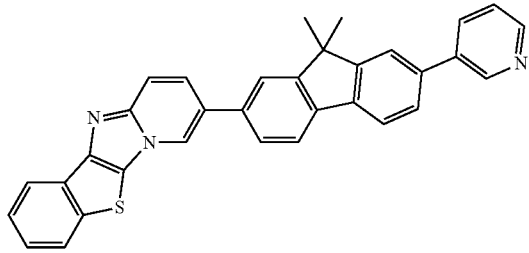
29
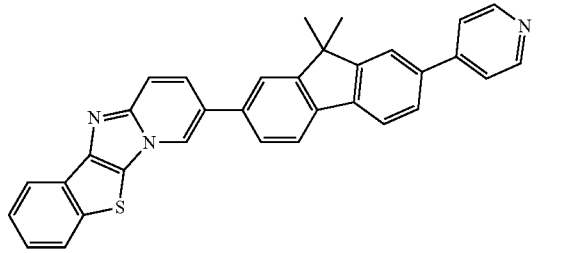
30
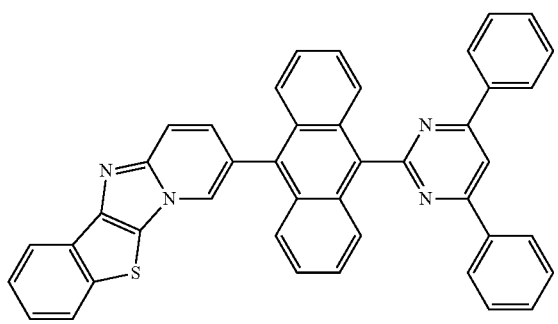
31
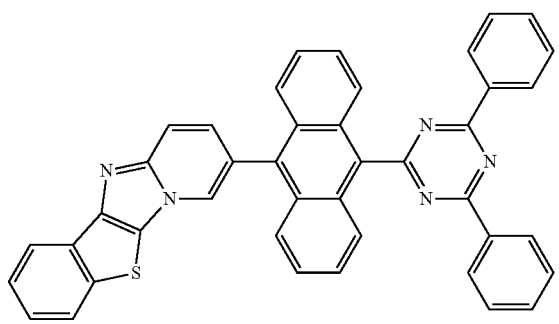
32
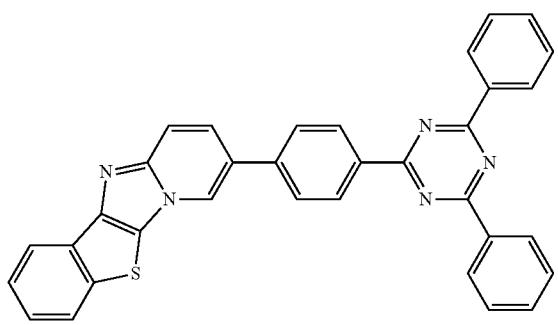
33
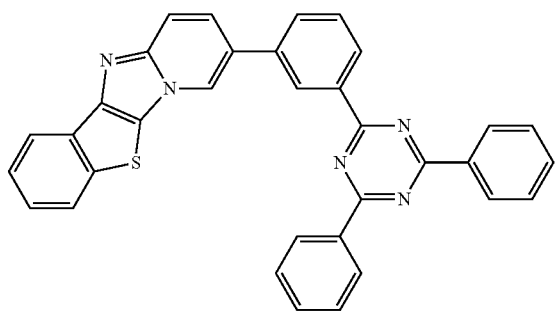
34
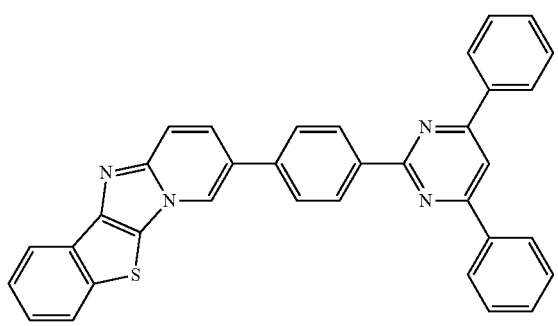
35
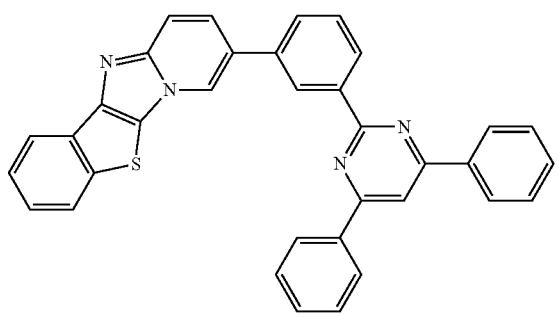
36
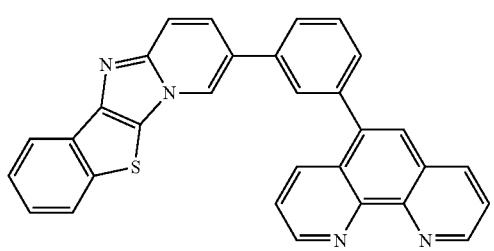
37
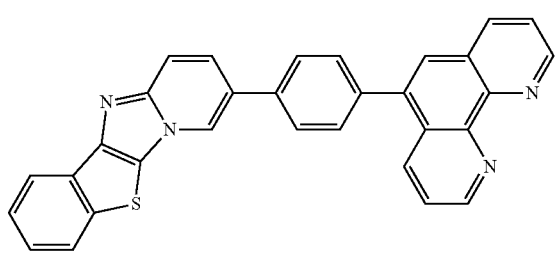

-continued
38
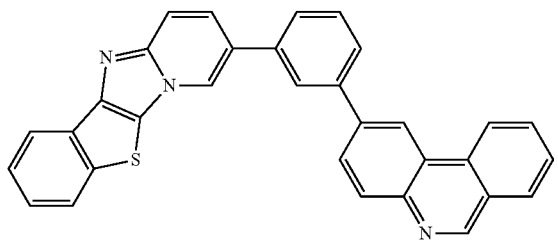
39
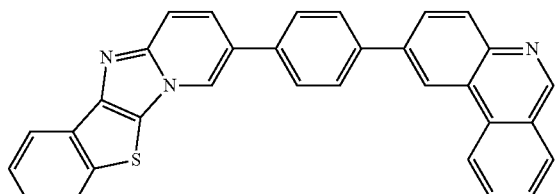
40
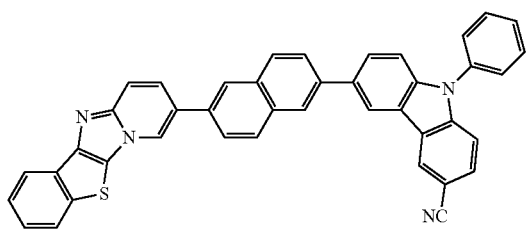
41
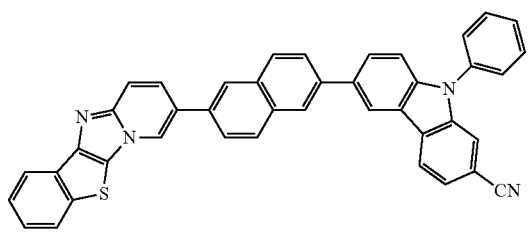
42
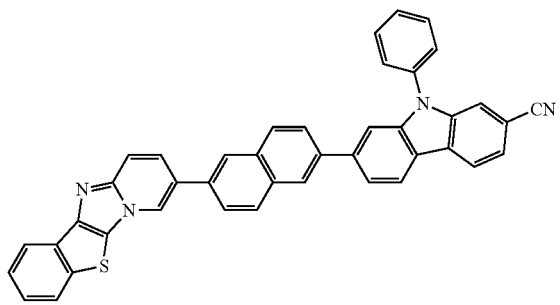
43
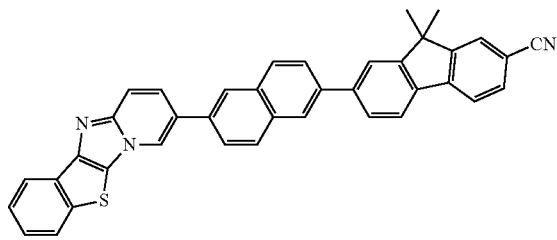
44
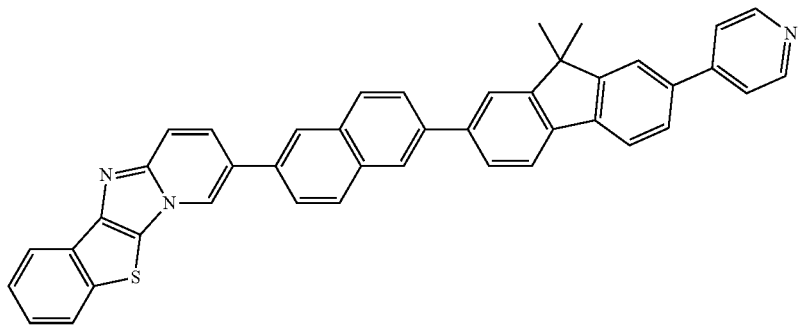
45
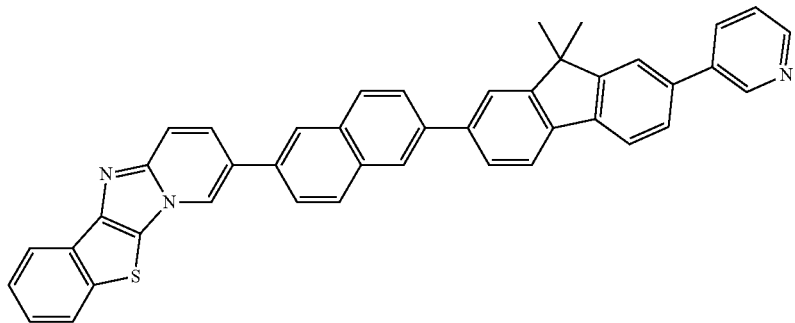

-continued
46
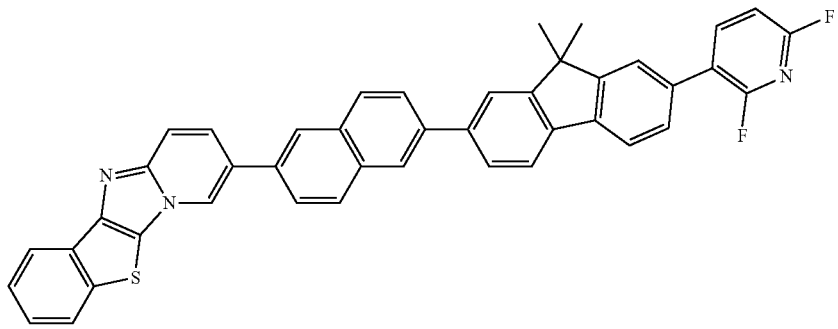
47
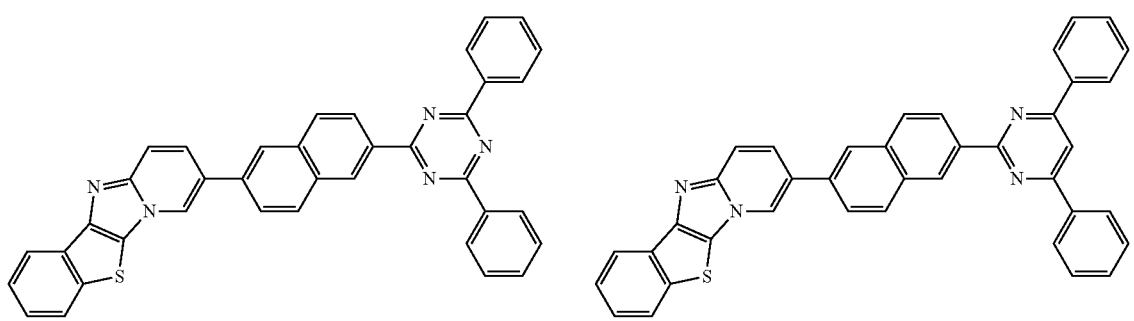
48
49
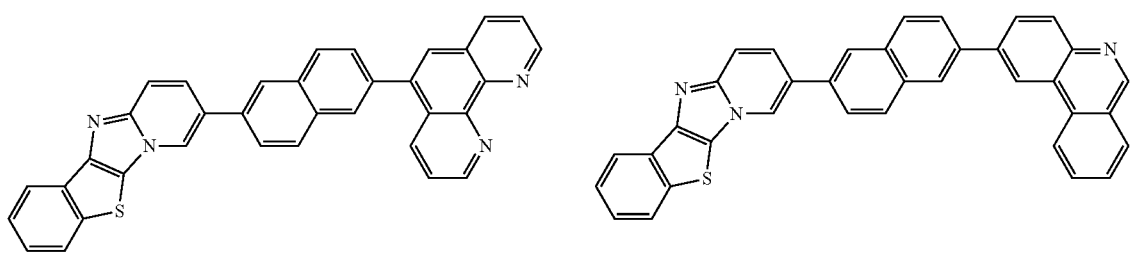
50
51
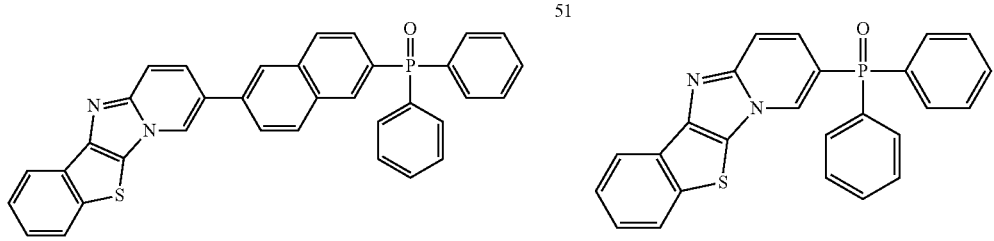
52
53
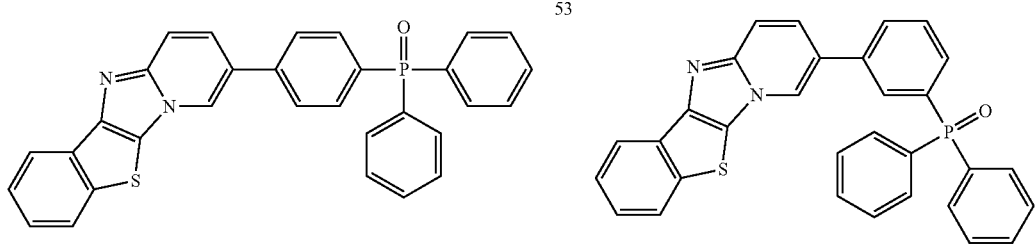
54

-continued
55
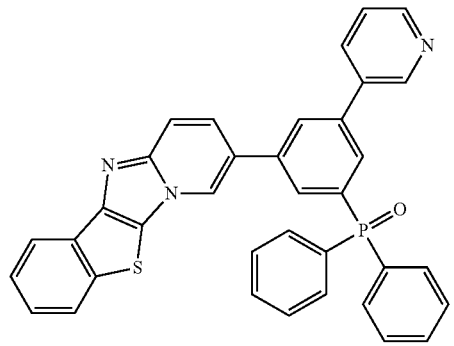
56
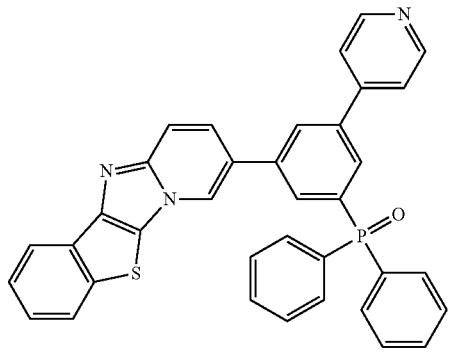
57
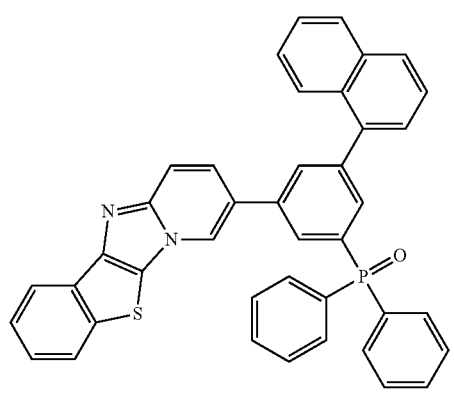
58
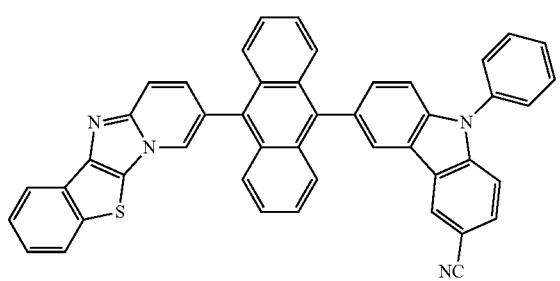
59
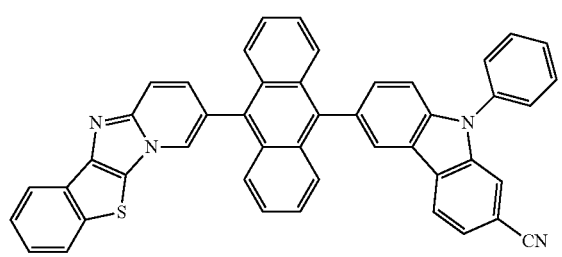
60
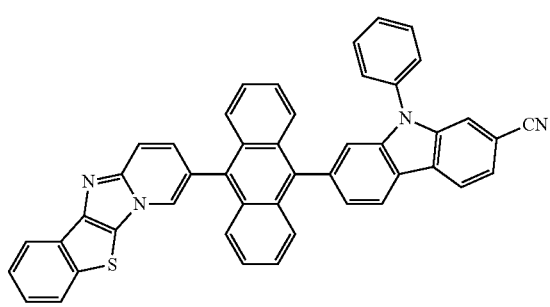
61
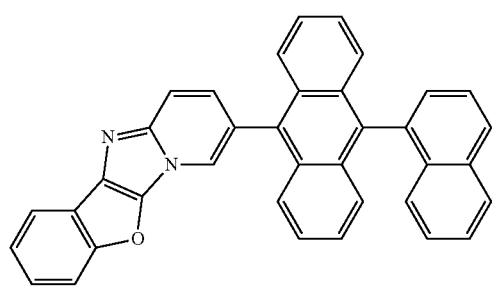
62
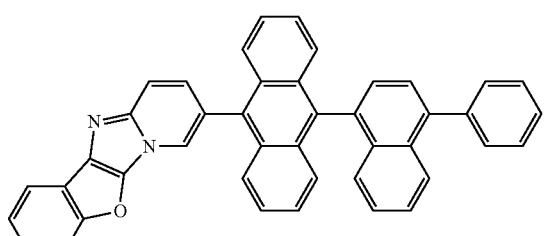

-continued
63
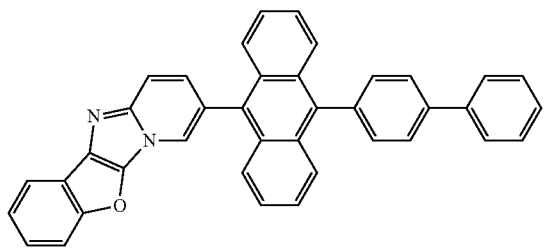
64
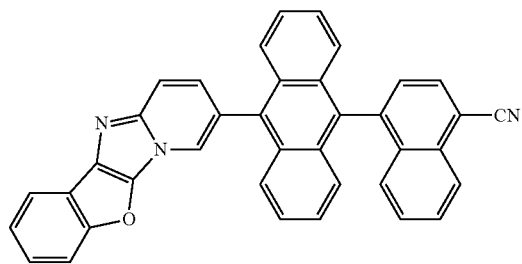
65
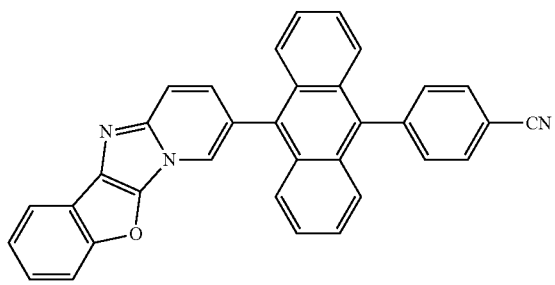
66
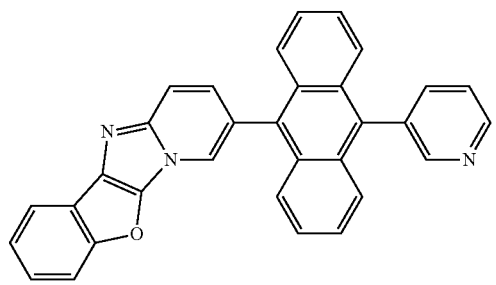
67
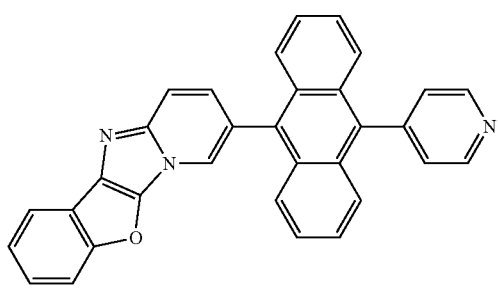
68
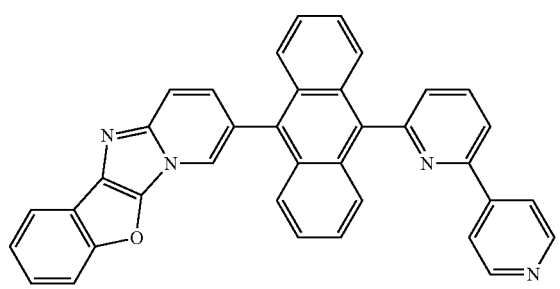
69
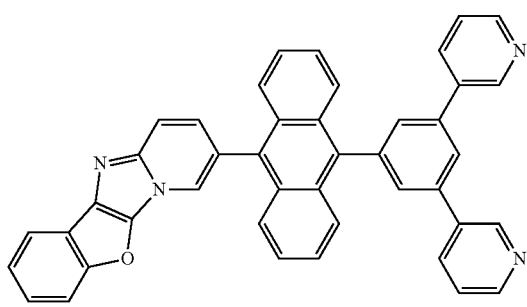
70
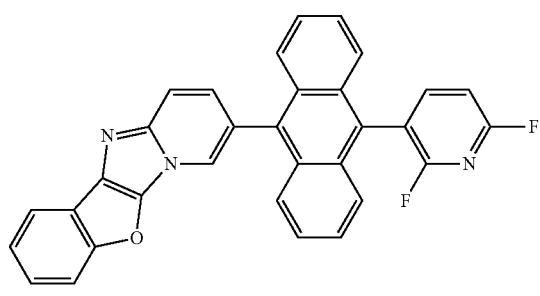
71
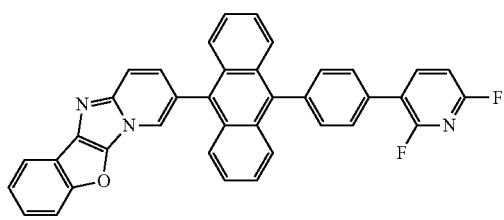
72
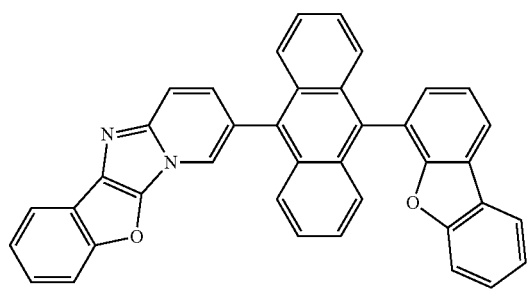

-continued
73
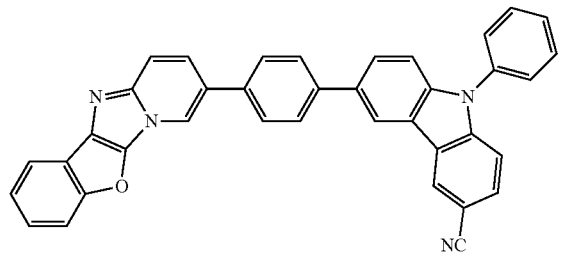
74
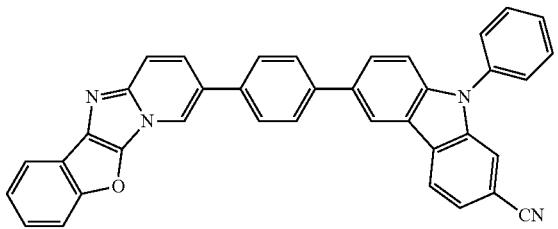
75
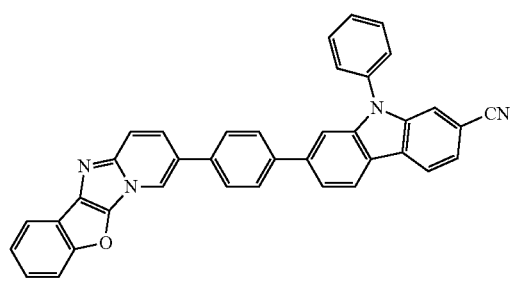
76
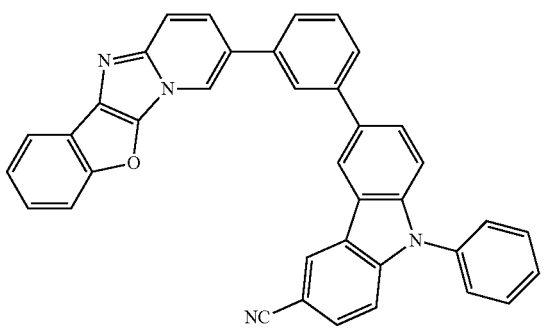
77
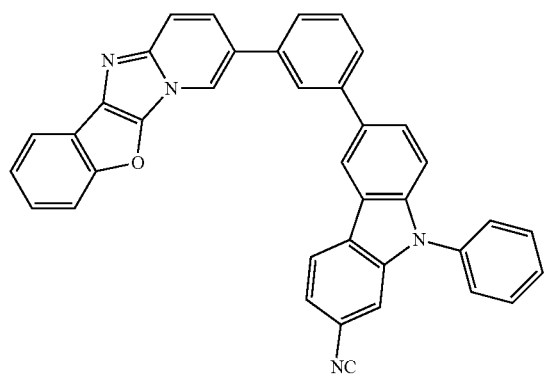
78
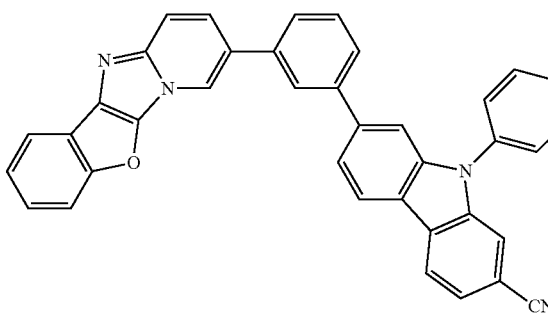
79
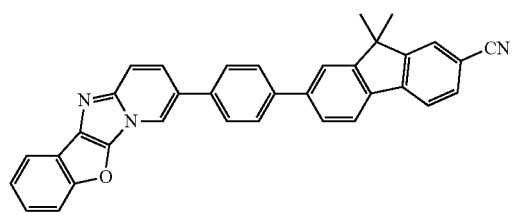
80
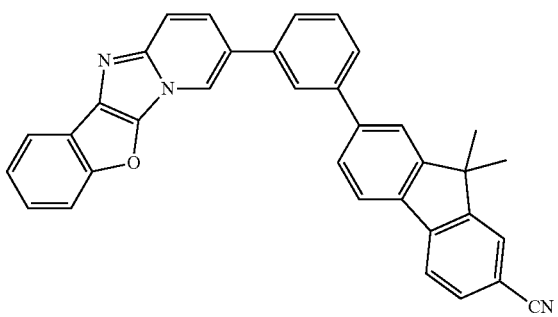
81
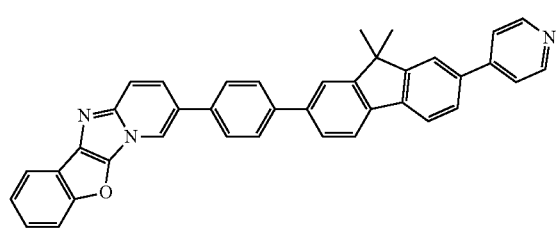
82
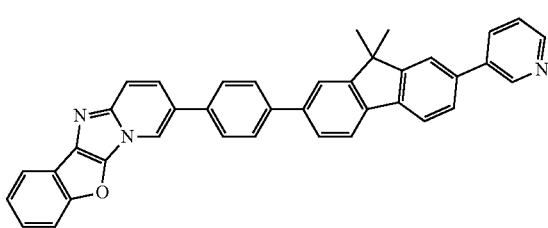

-continued
83
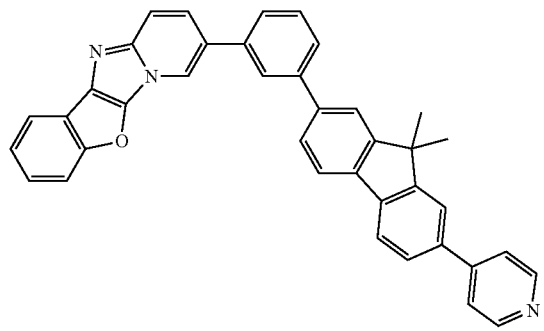
84
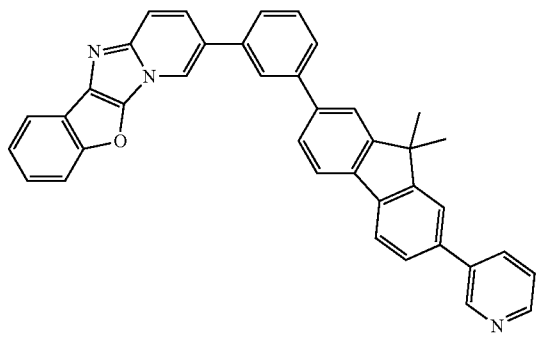
85
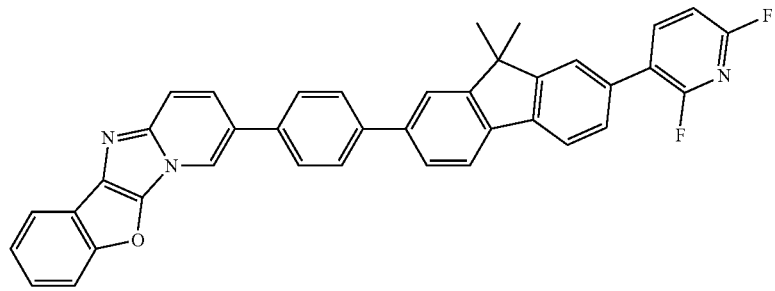
86
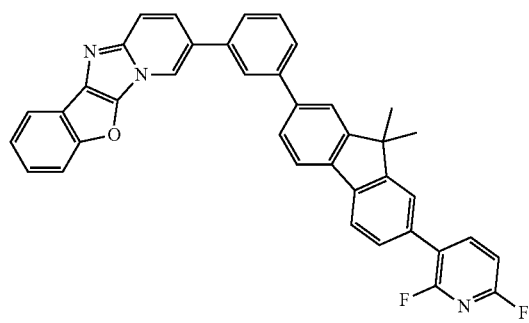
87
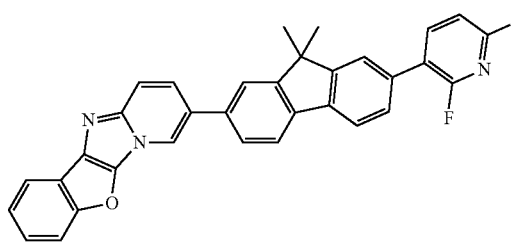
88
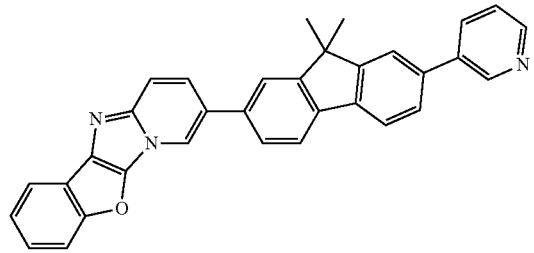
89
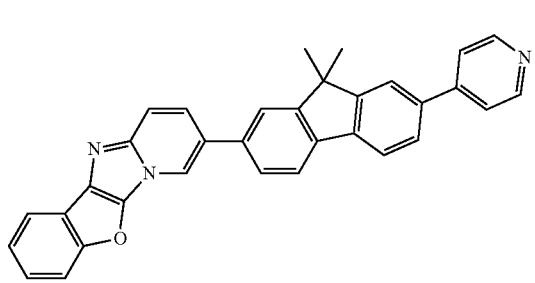
90
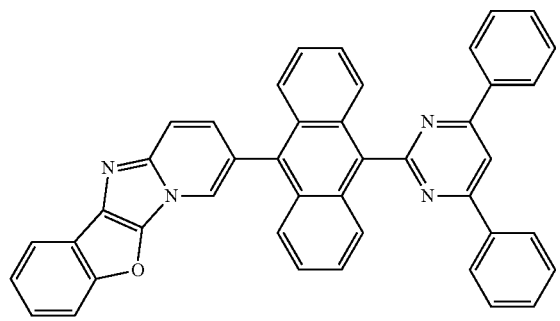
91
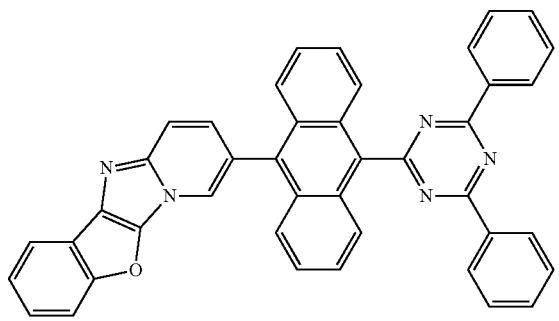

-continued
92
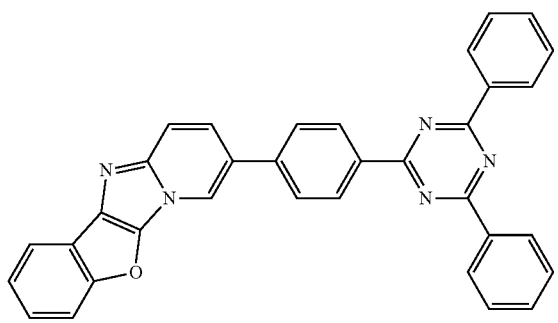
93
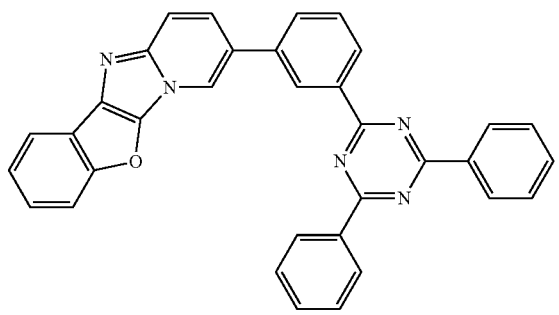
94
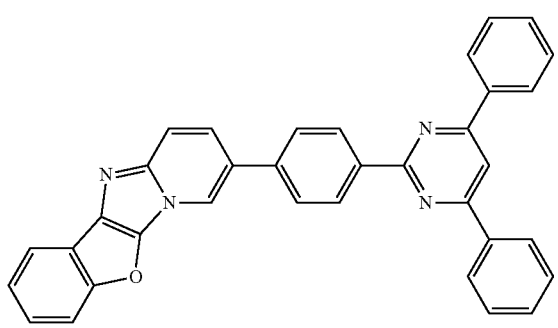
95
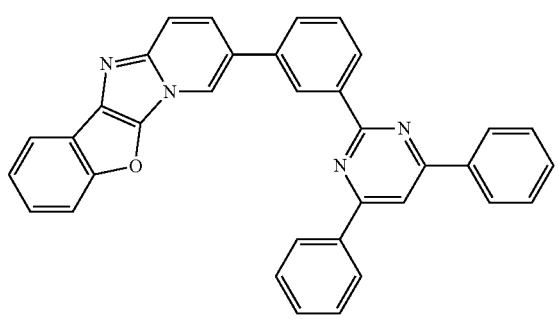
96
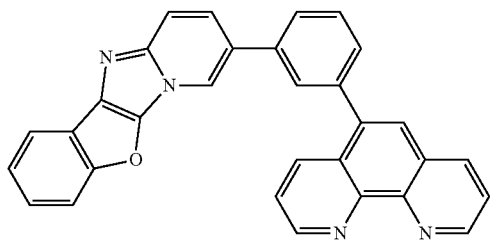
97
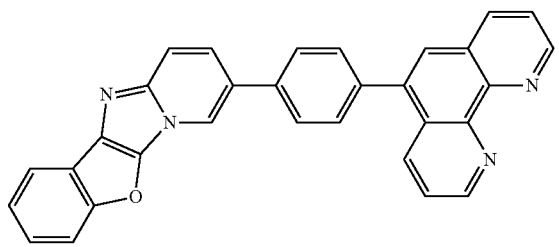
98
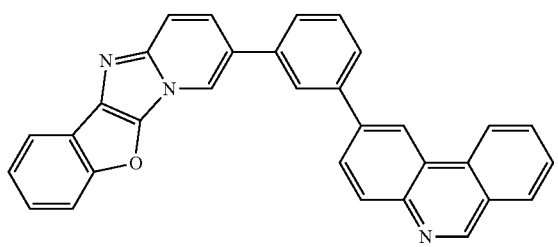
99
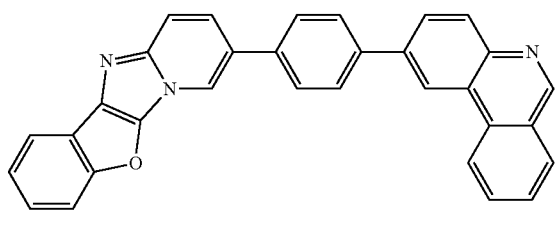
100
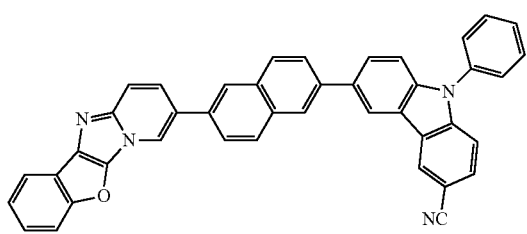
101
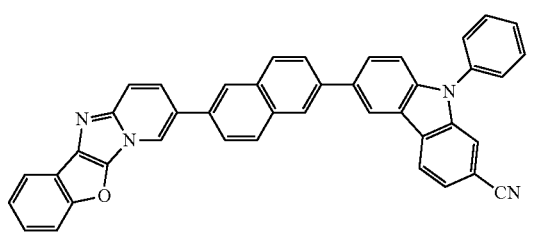

-continued
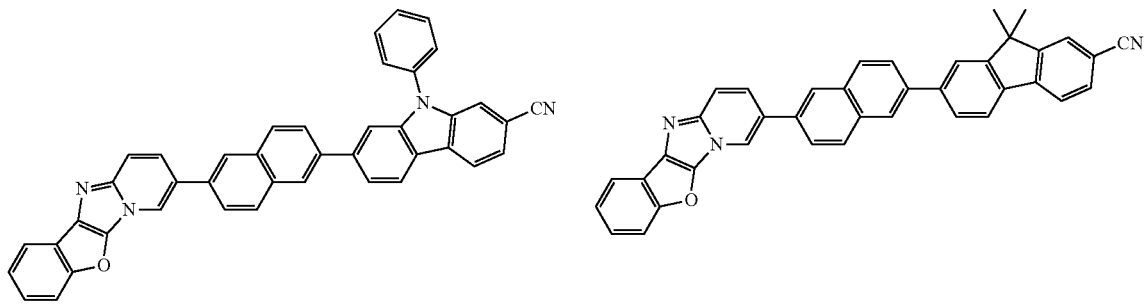
102
103
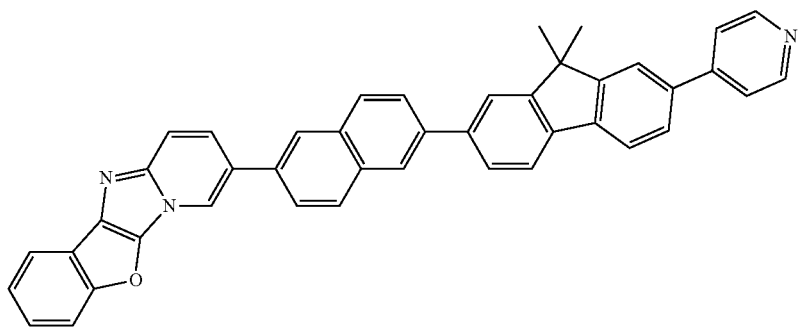
104
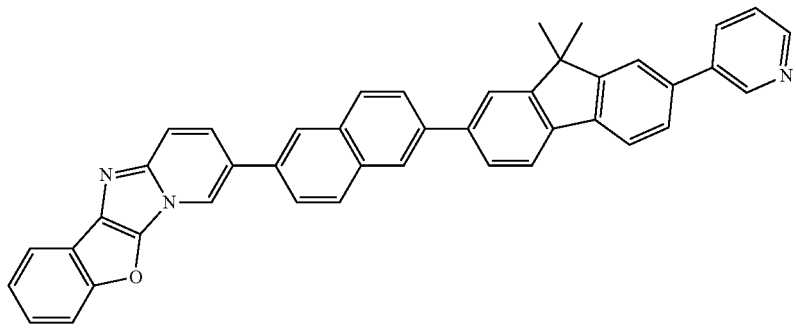
105
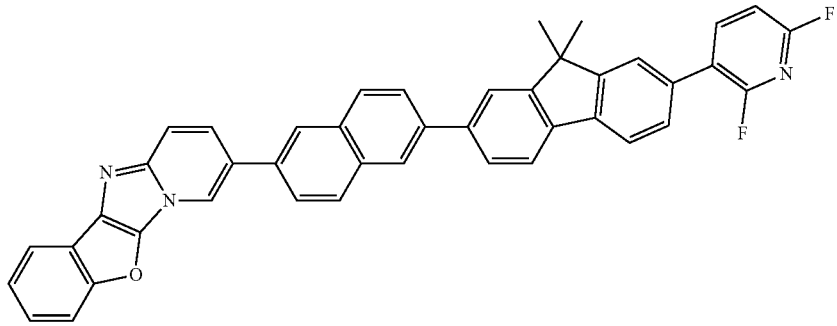
106

-continued
107 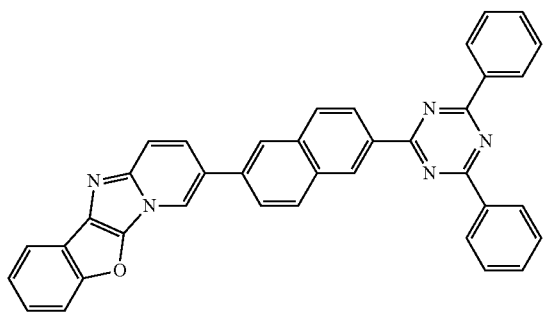 108 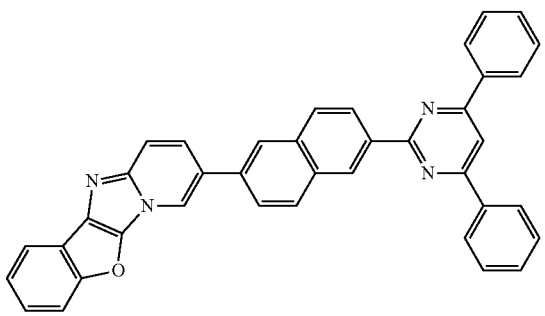
109 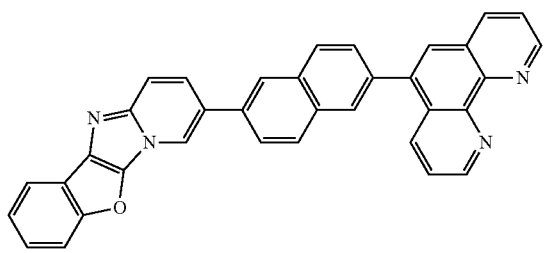 110 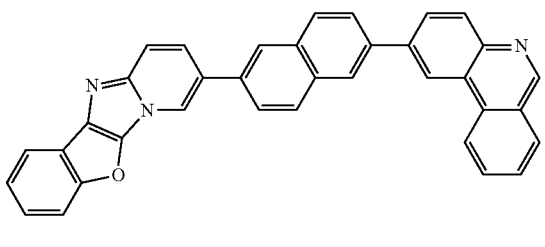
111 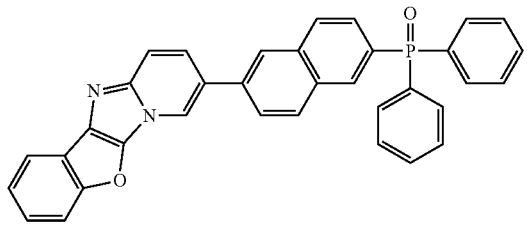 112 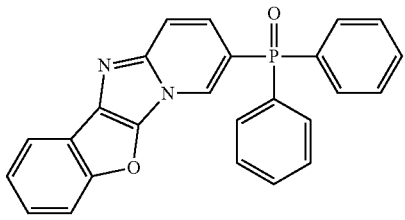
113 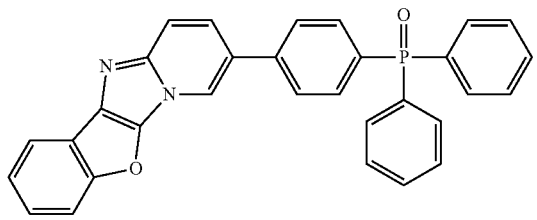 114 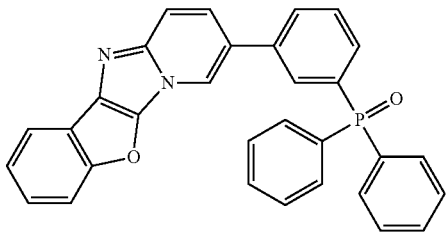
115 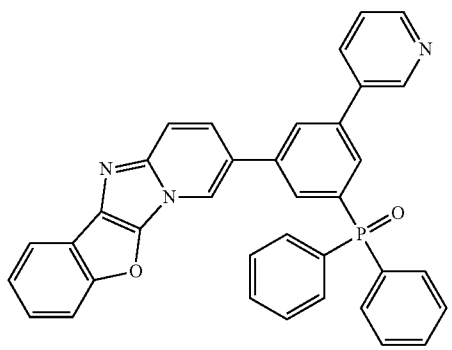 116 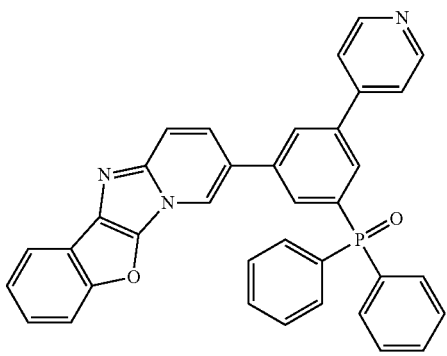

-continued
117
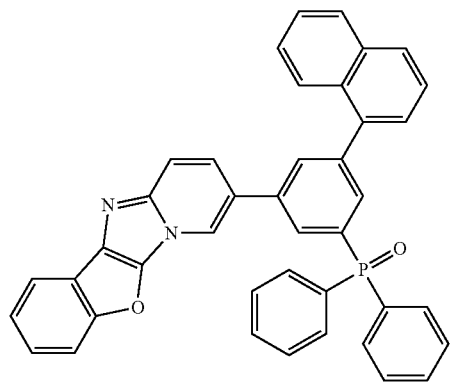
118
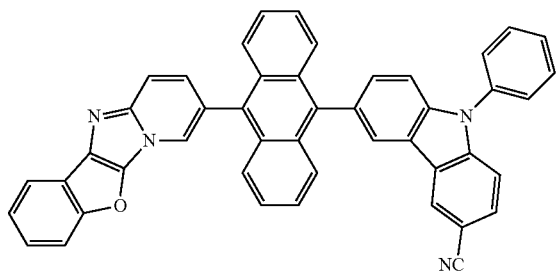
119
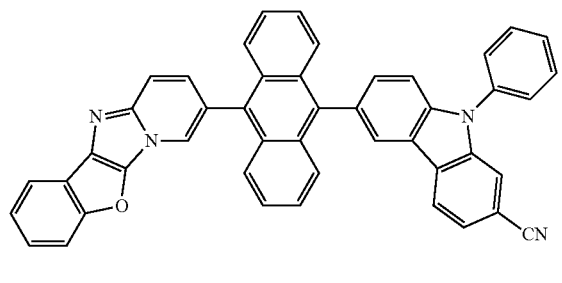
120
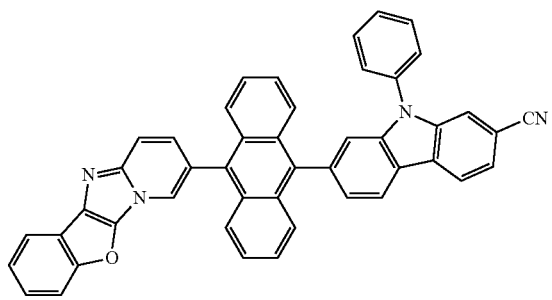
121
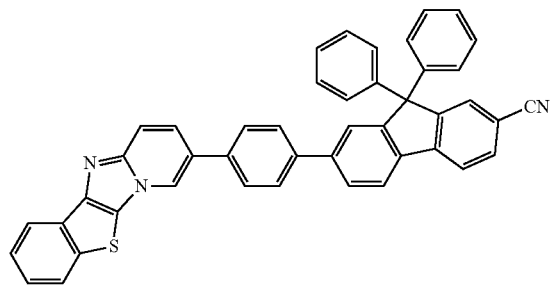
122
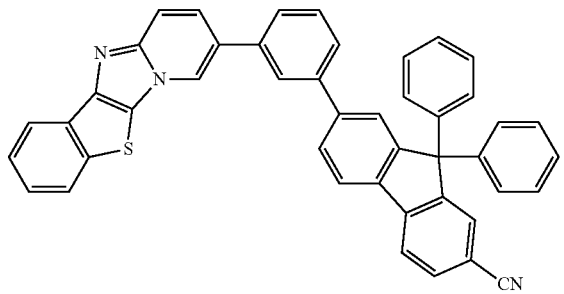
123
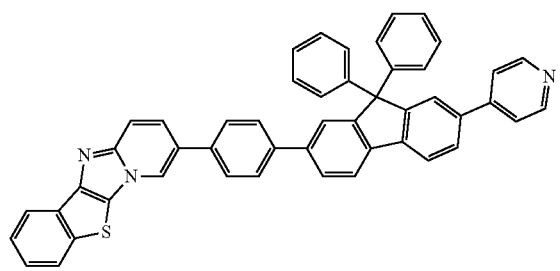
124
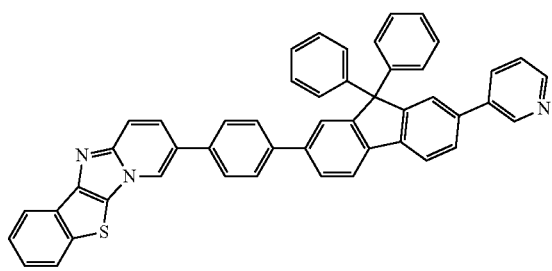

-continued
125
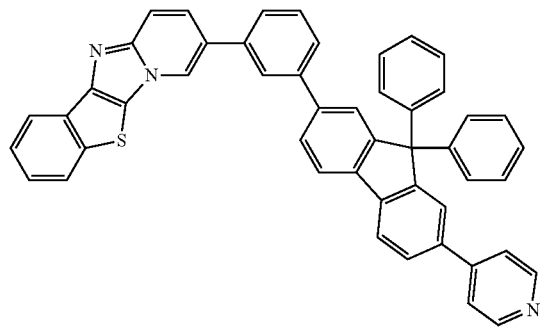
126
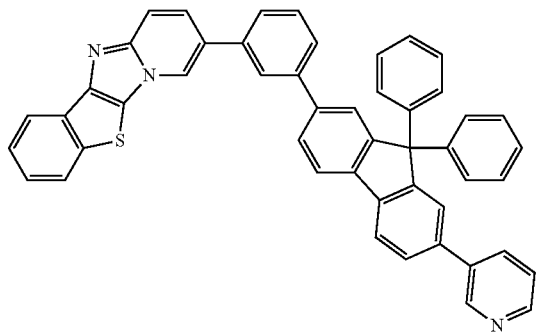
127
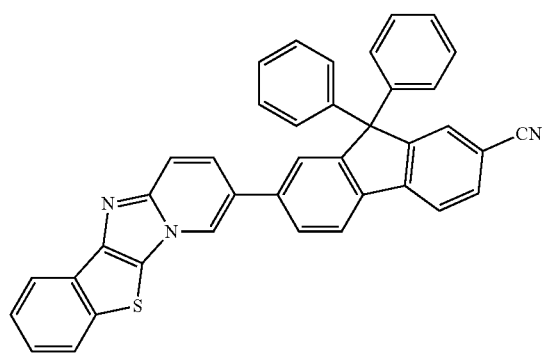
128
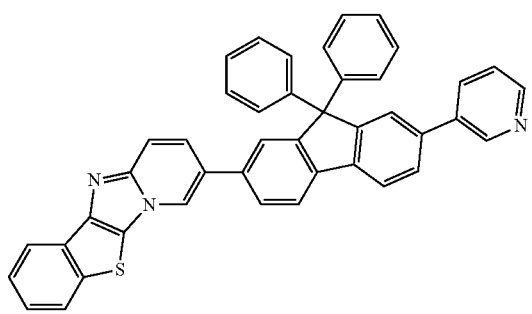
129
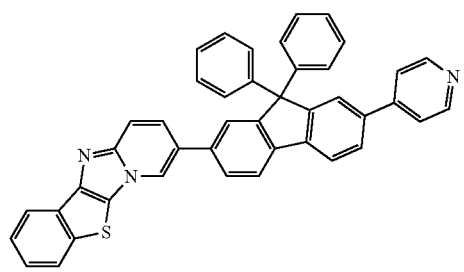
130
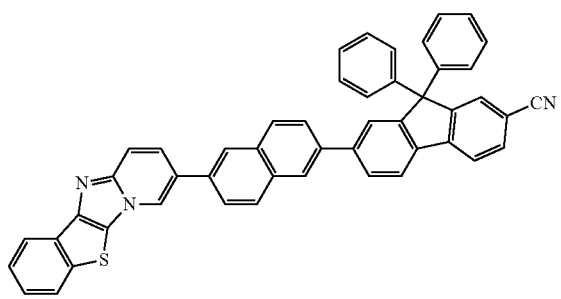
131
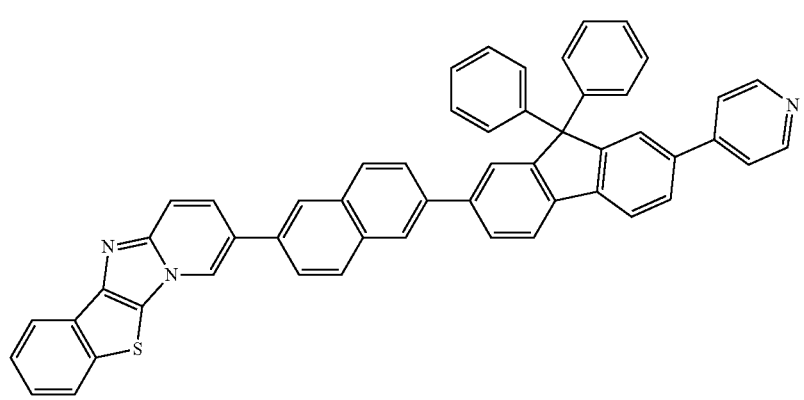

132
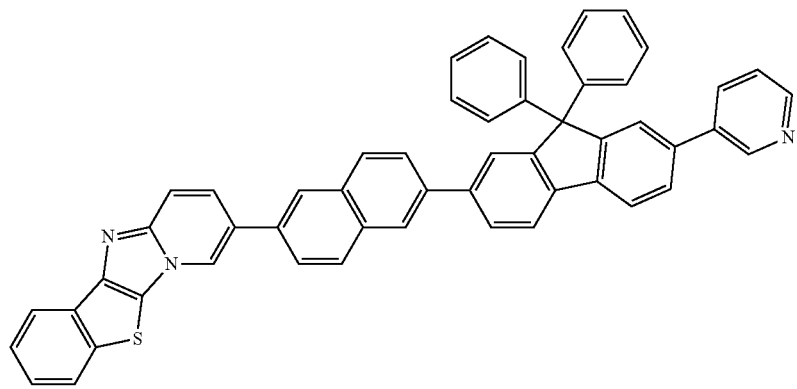
133 134
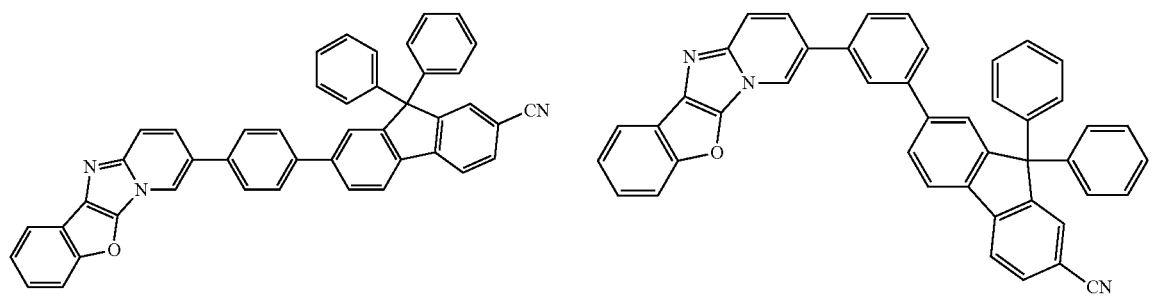
135 136
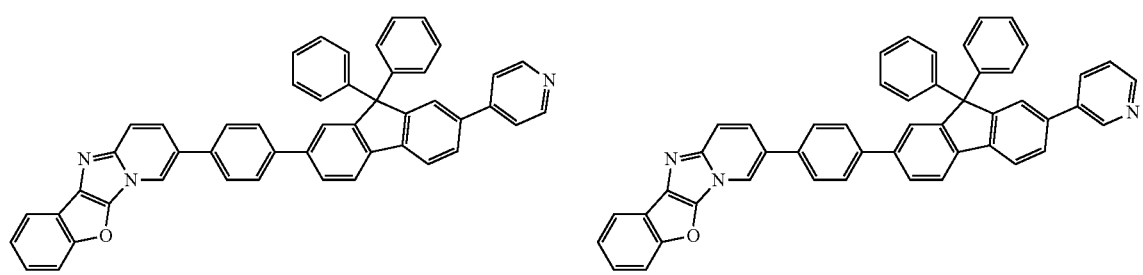
137 138
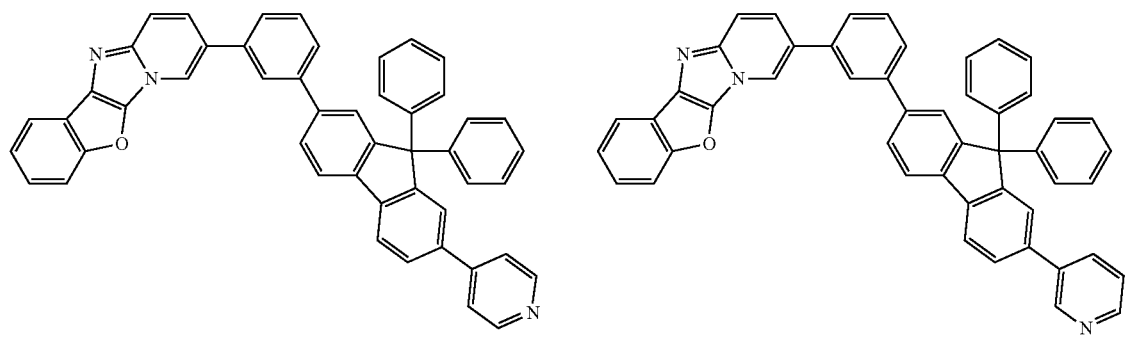

-continued
139 140
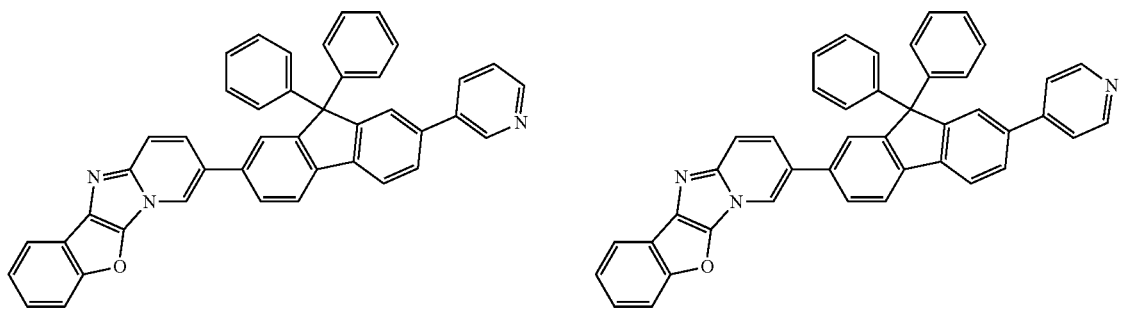
141
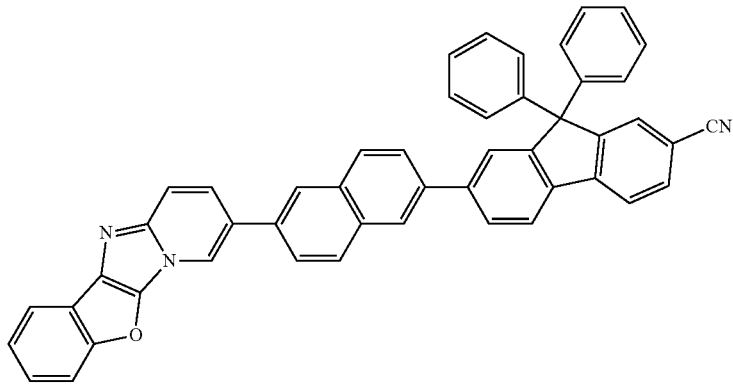
142
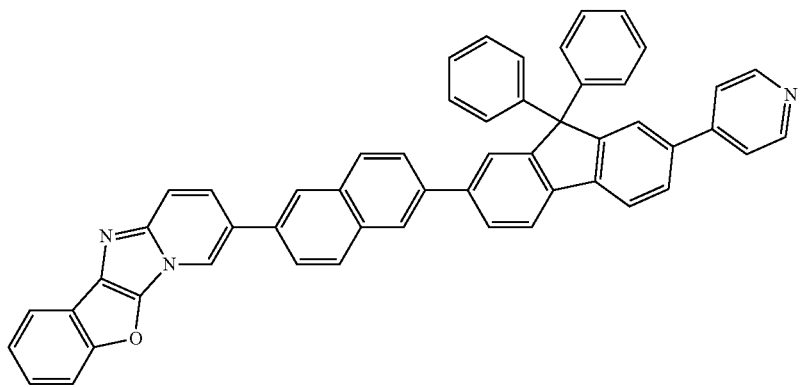
143
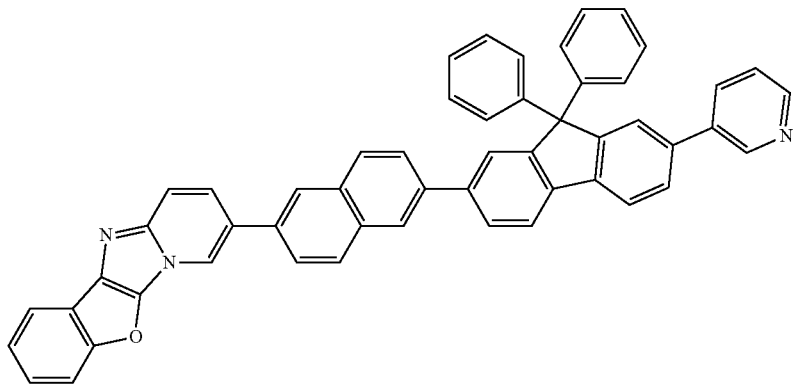

-continued
144
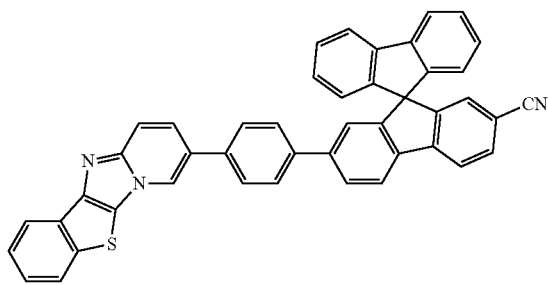
145
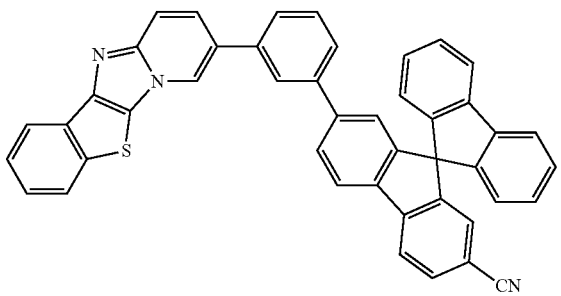
146
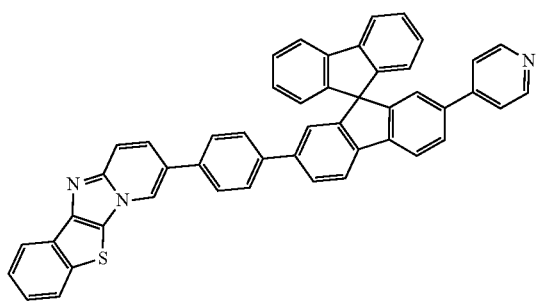
147
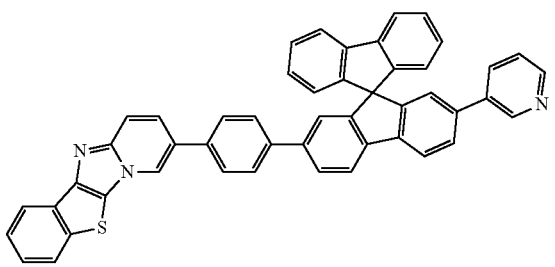
148
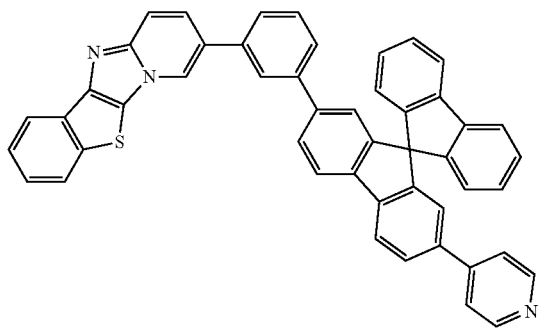
149
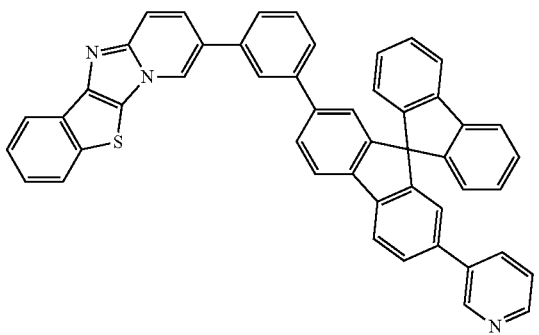
150
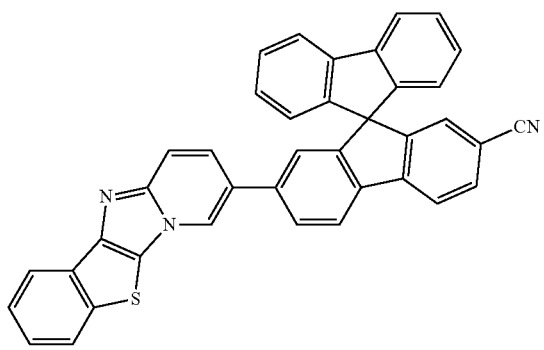
151
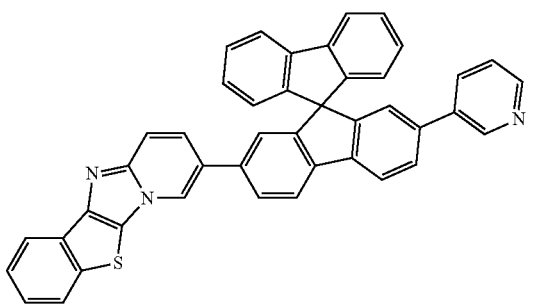

-continued
152
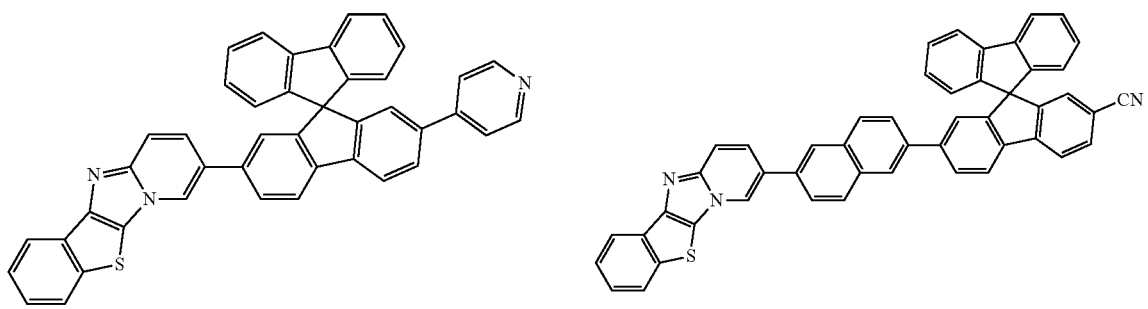
153
154
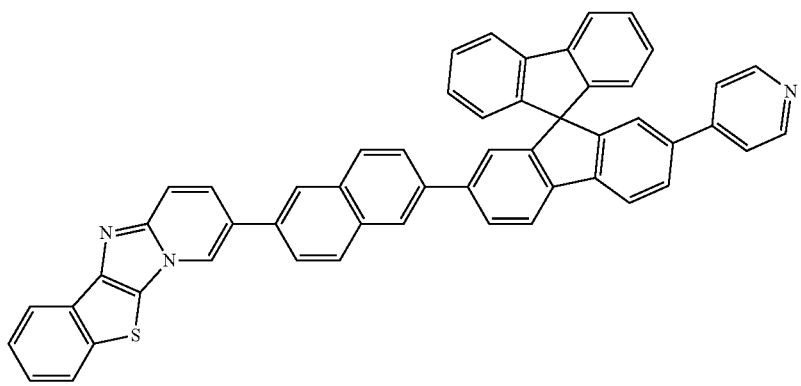
155
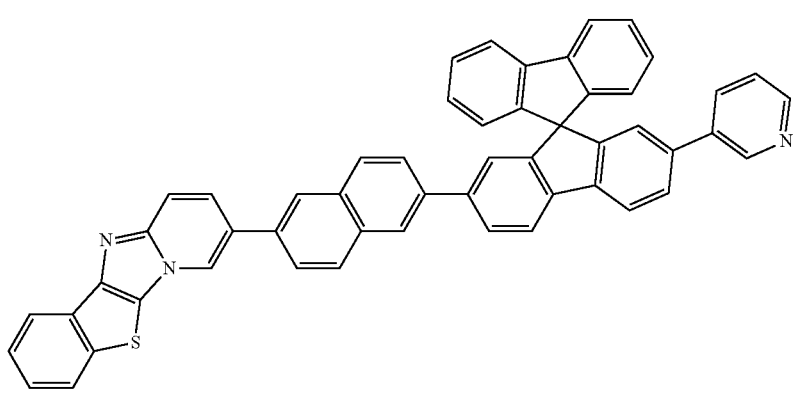
156
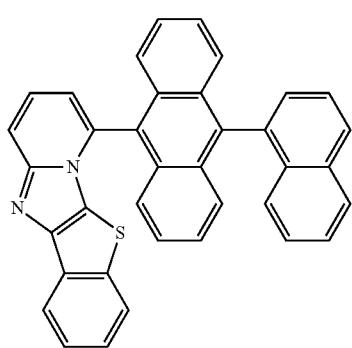
157
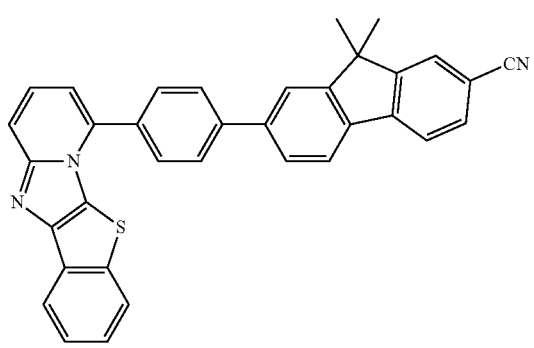

-continued
158
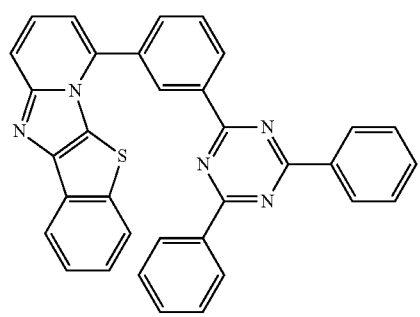
159
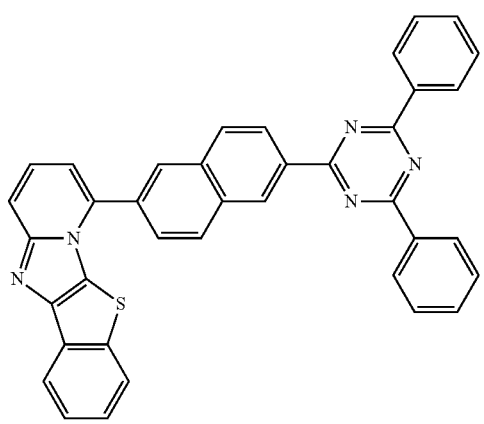
160
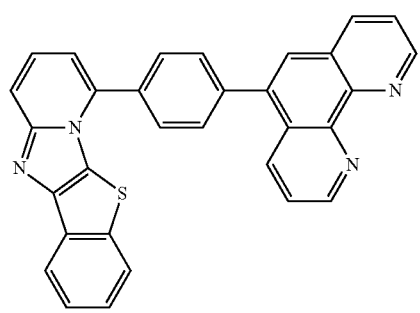
161
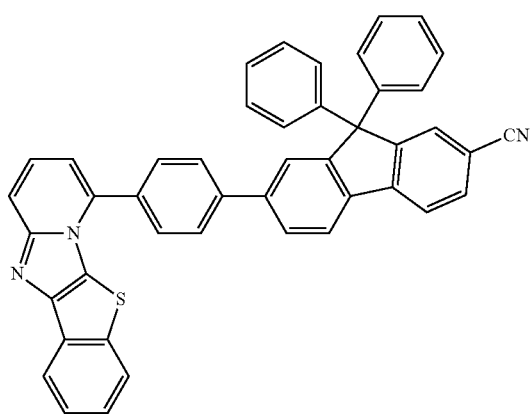
162
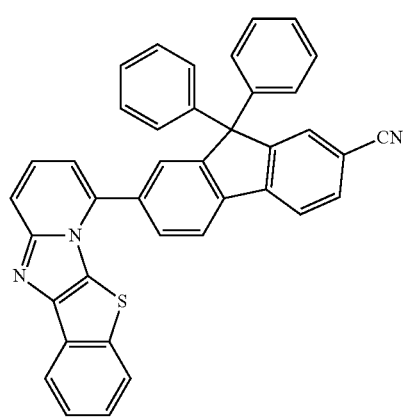
163
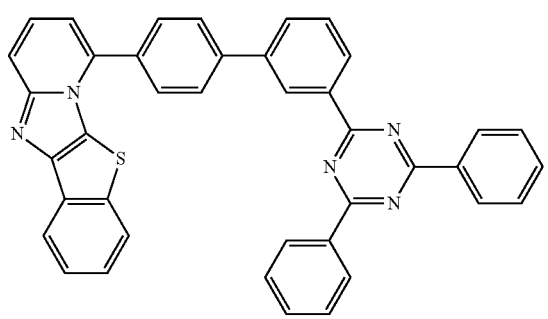

164
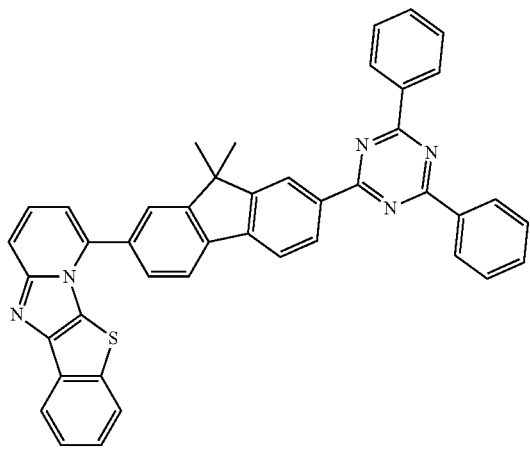
165
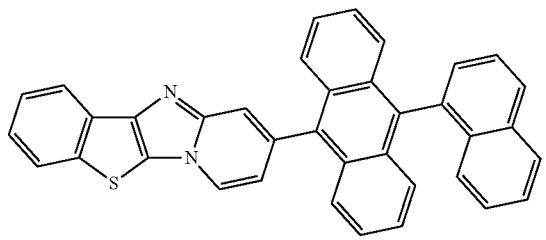
166
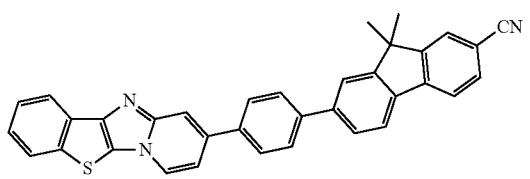
167
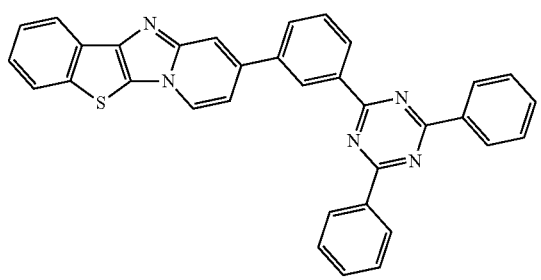
168
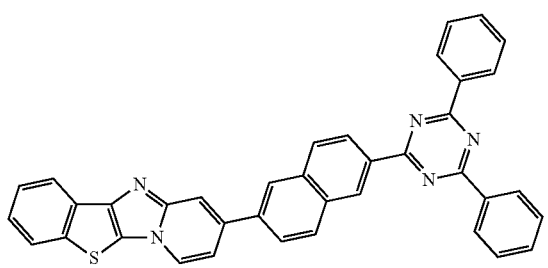
169
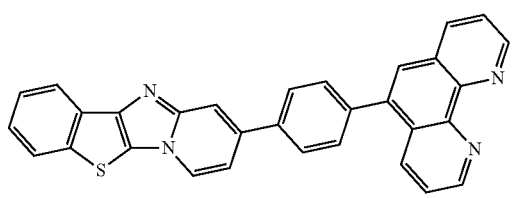
170
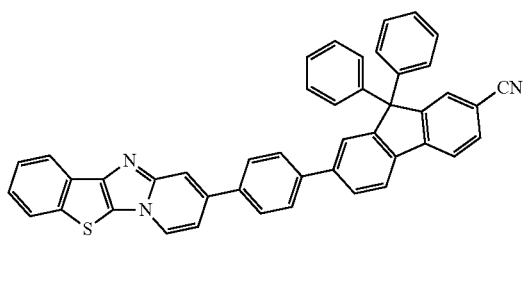
171
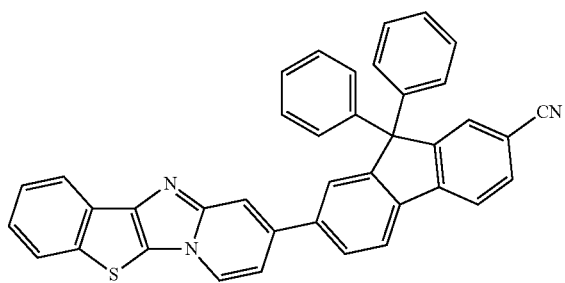

-continued
172
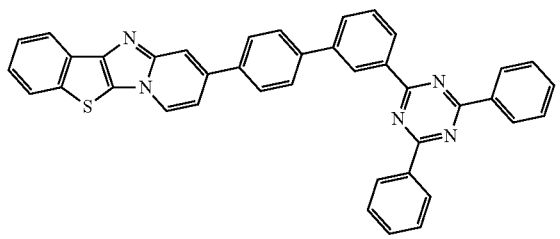
173
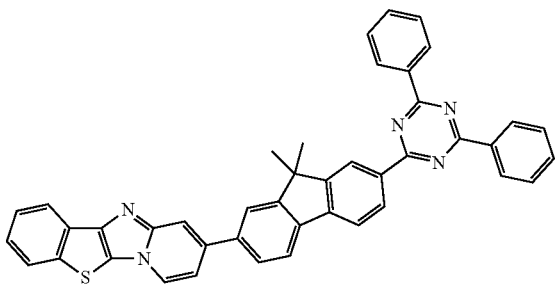
174
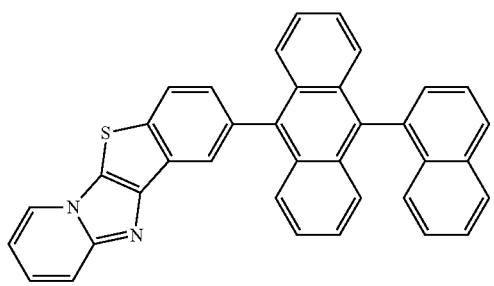
175
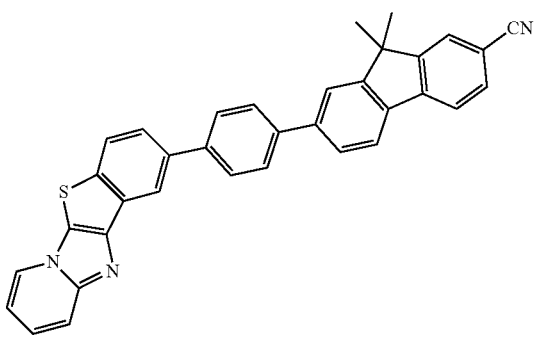
176
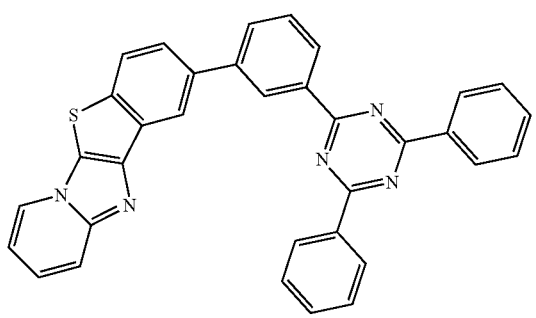
177
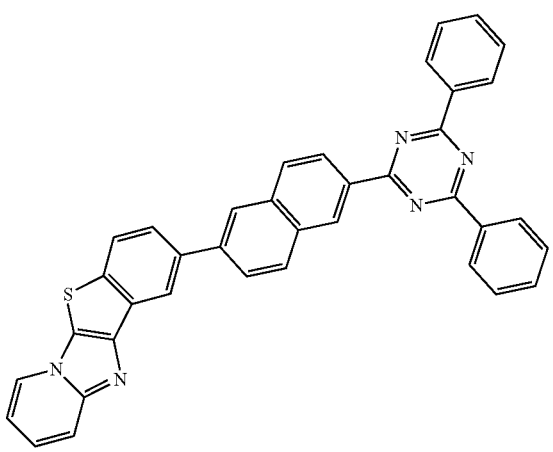
178
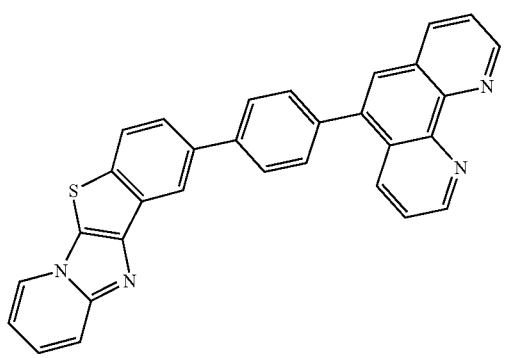
179
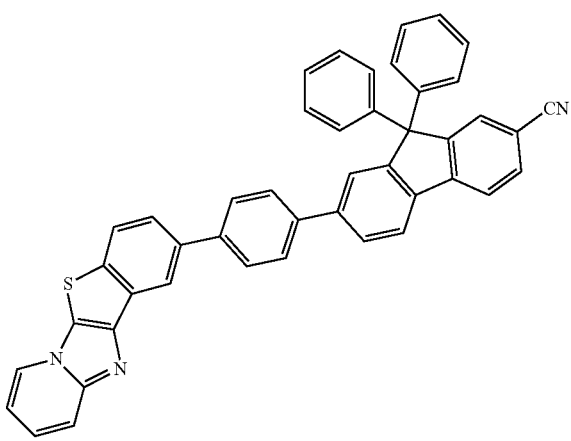

-continued
180
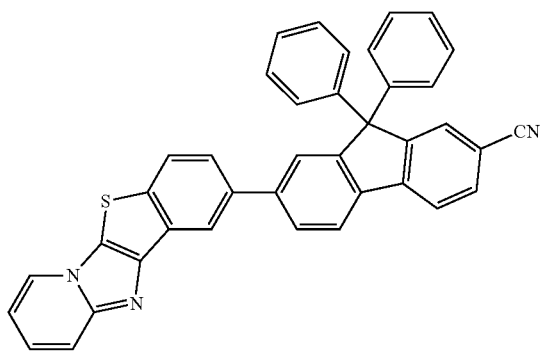
181
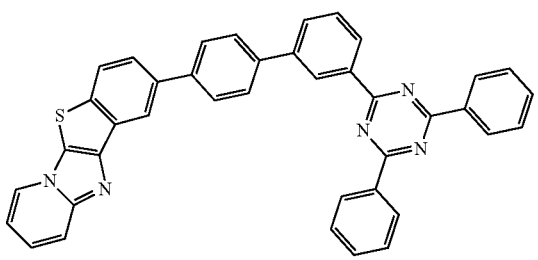
182
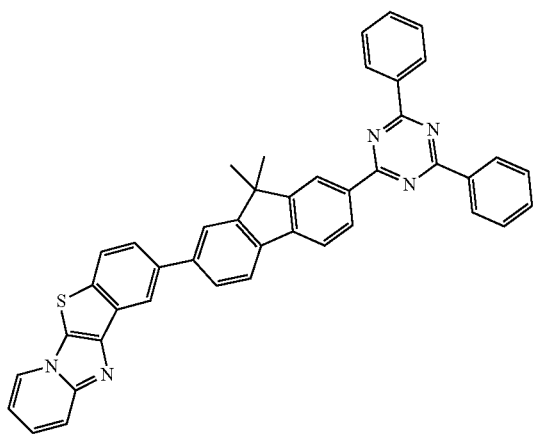
183
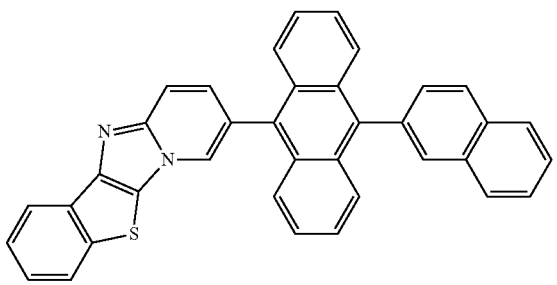
184
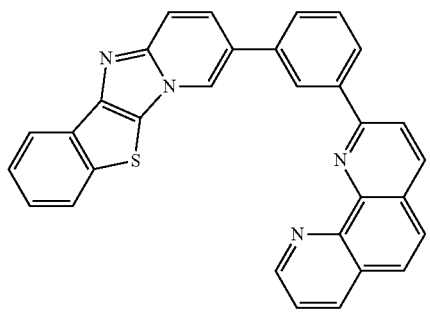
185
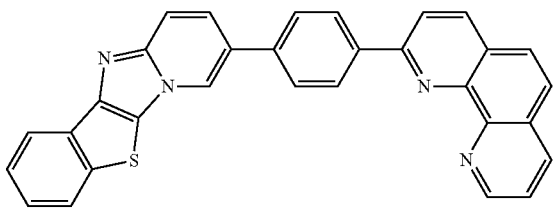
186
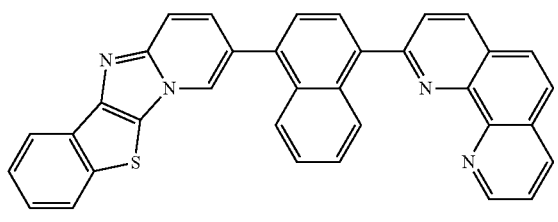
187
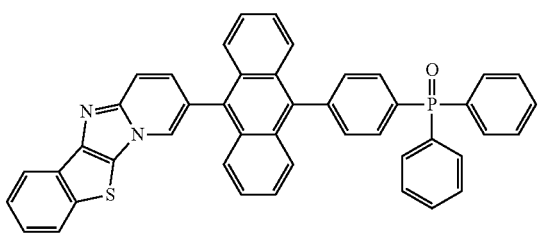

-continued
188
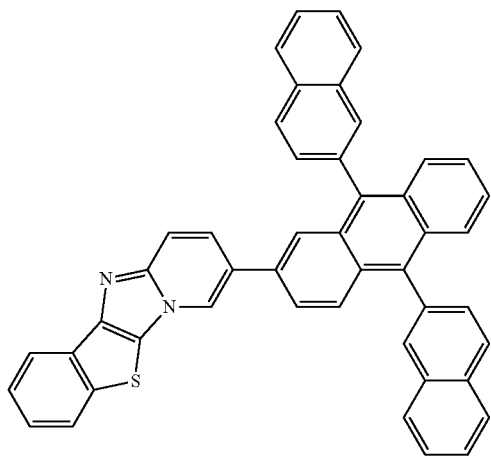
189
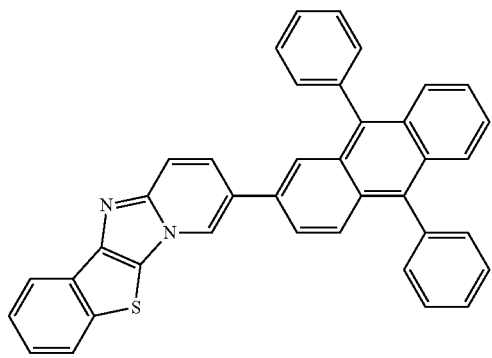
190
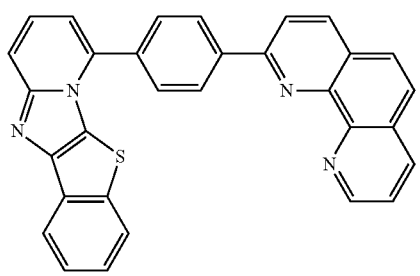
191
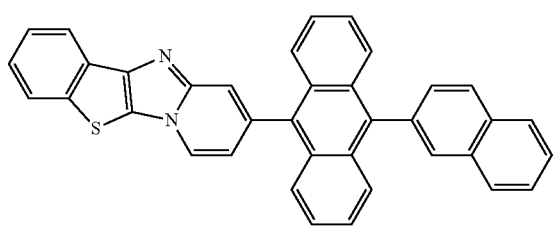
192
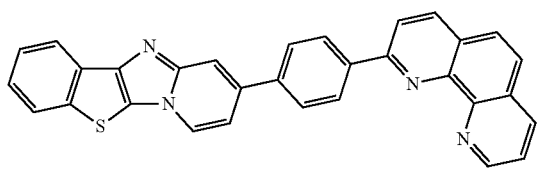
193
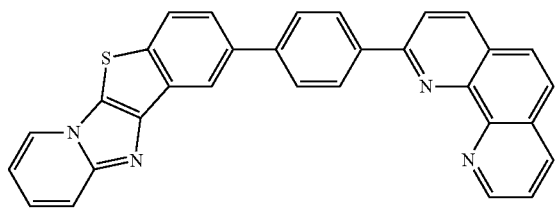
194
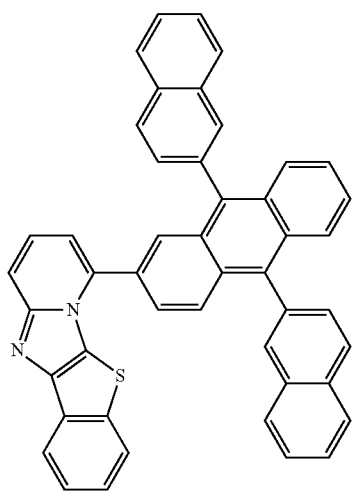
195
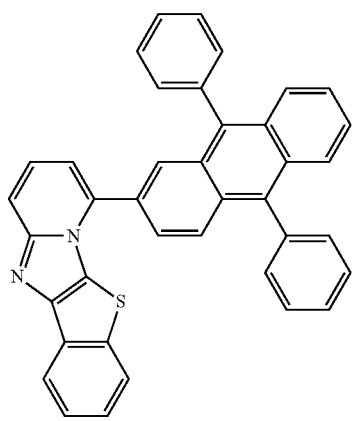

-continued
196
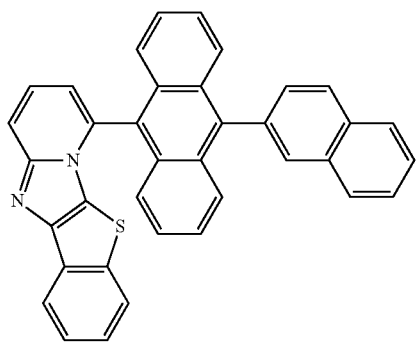
197
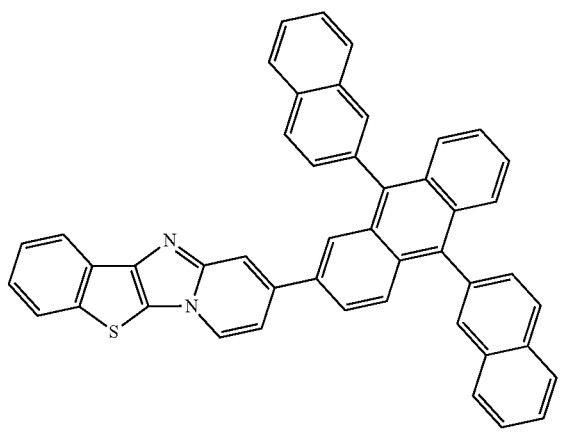
198
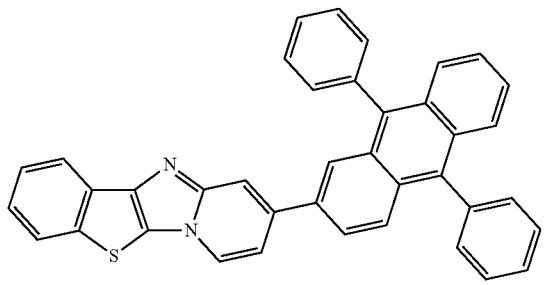
199
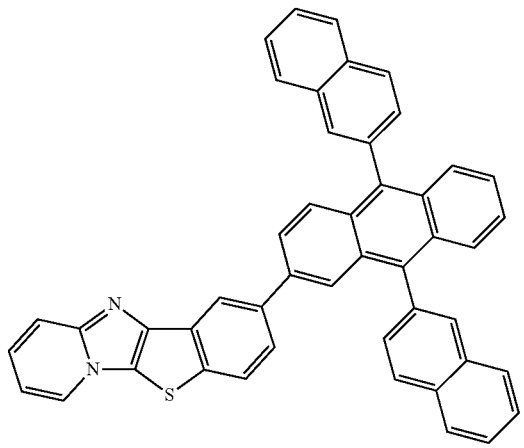
200
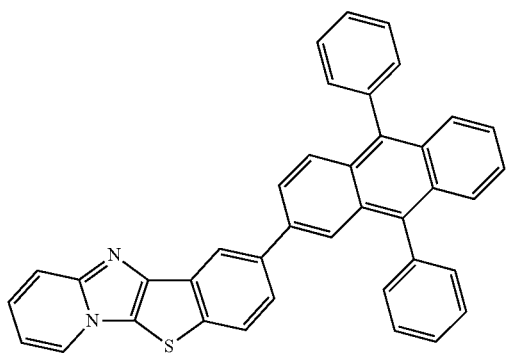
201
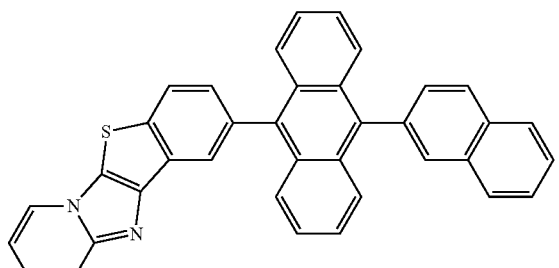

-continued
202
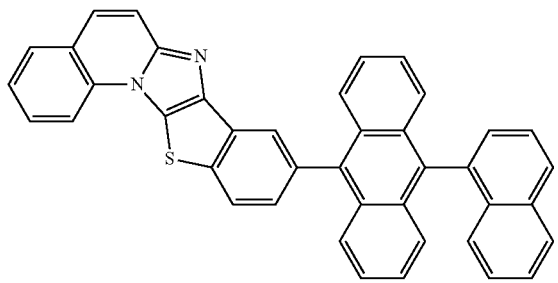
203
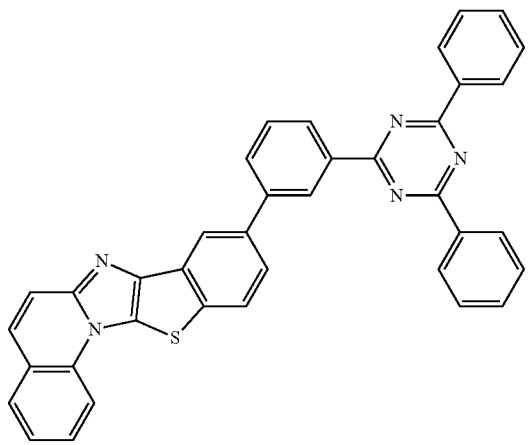
204
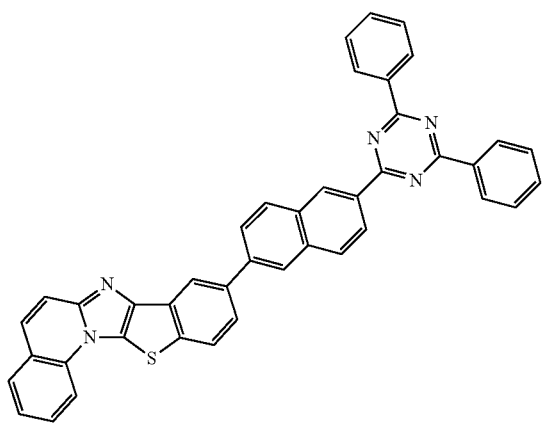
205
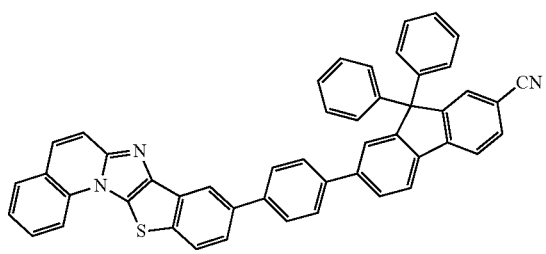
206
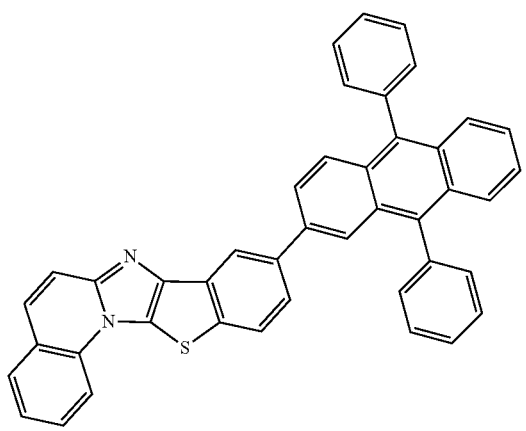
207
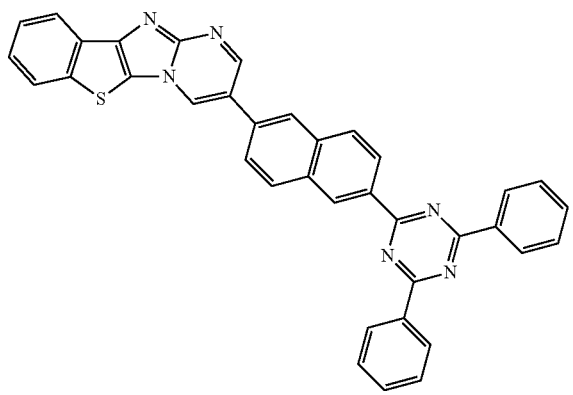

208

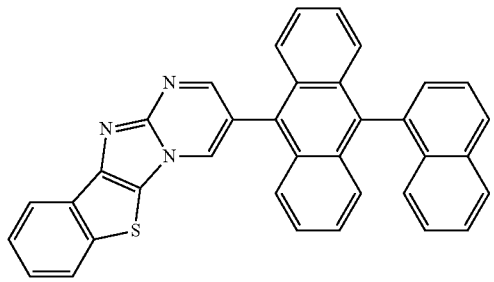

209

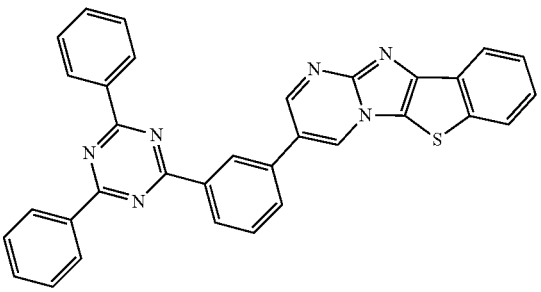

210

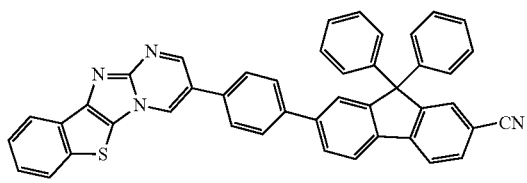

211

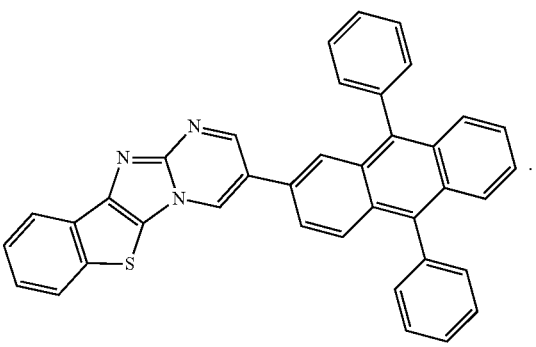

17. An organic light-emitting device comprising:
a first electrode;
a second electrode; and
an organic layer disposed between the first electrode and the second electrode, the organic layer comprising an emission layer and a condensed cyclic compound represented by Formula 1:

<Formula 1>

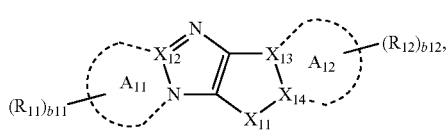

in Formula 1,
$A_{11}$ is a $C_1$-$C_{60}$ heterocyclic group,
$A_{12}$ is a $C_5$-$C_{60}$ carbocyclic group or a $C_1$-$C_{60}$ heterocyclic group,
$X_{11}$ is O or S,
$X_{12}$ is C,
$X_{13}$ is selected from N, C, and C($R_{13}$),
$X_{14}$ is selected from N, C, and C($R_{14}$),
$X_{13}$ and $X_{14}$ are linked via a single bond or a double bond,
$R_{11}$ and $R_{12}$ are each independently selected from a group represented by *-$(L_{11})_{a11}$-$(Ar_{11})c_{11}$, hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), and at least one of $R_{11}$ and $R_{12}$ is a group represented by *-$(L_{11})_{a11}$—$(Ar_{11})c_{11}$,
b11 and b12 are each independently selected from 1, 2, 3, 4, 5, 6, 7, 8, 9, and 10,
$L_{11}$ is selected from a single bond, a substituted or unsubstituted $C_5$-$C_{60}$ carbocyclic group, and a substituted or unsubstituted $C_1$-$C_{60}$ heterocyclic group,
a11 is selected from 0, 1, 2, 3, and 4,
$Ar_{11}$ is selected from —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)($Q_1$), —S(=O)$_2$($Q_1$), —P(=O)($Q_1$)($Q_2$), and —P(=S)($Q_1$)($Q_2$), c11 is selected from 1, 2, 3, 4, 5, and 6, $R_{13}$, $R_{14}$, and $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, and a substituted or unsubstituted monovalent non-aromatic condensed heteropolycyclic group, and

* indicates a binding site to a neighboring atom.

18. The organic light-emitting device of claim 17, wherein the first electrode is an anode, the second electrode is a cathode, the organic layer further comprises an electron transport region between the second electrode and the emission layer, and the electron transport region comprises the condensed cyclic compound.

19. An organic light-emitting device comprising:

a first electrode;

a second electrode; and an organic layer disposed between the first electrode and the second electrode, the organic layer comprising a condensed cyclic compound, wherein the condensed cyclic compound comprises a multicyclic structure including a bicyclic structure of two fused 5-member heterocyclic rings, one of the two fused 5-member heterocyclic rings comprises two N atoms as hetero atoms, other one of the two fused 5-member heterocyclic rings comprises O atom or S atom as a hetero atom, the multicyclic structure comprises tetracyclic structure or higher order polycyclic structure, at least one hydrogen of the multicyclic structure is substituted with F, Cl, Br, I, a hydroxyl group, a cyano group, a nitro group, an amidino group, a hydrazino group, a hydrazono group and an organic substituent group, and the organic substituent group comprises at least one C atom and optionally comprises at least one of N, S, O, P, Si, B, F, Cl, Br, and I atoms.

20. The organic light-emitting device of claim 19, wherein the two fused 5-member heterocyclic rings are two fused 5-member heteroaryl rings, the multicyclic structure is a tetracyclic structure comprising 4 fused aromatic rings, at least one hydrogen of the multicyclic structure is substituted with a group represented by *-($L_{11}$)$_{a11}$-($Ar_{11}$)$c_{11}$, $L_{11}$ is selected from a single bond, a substituted or unsubstituted $C_5$-$C_{60}$ carbocyclic group, and a substituted or unsubstituted $C_1$-$C_{60}$ heterocyclic group, a11 is selected from 0, 1, 2, 3, and 4, $Ar_{11}$ is selected from —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_0$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_1$)($Q_2$), —B($Q_1$)($Q_2$), —C(=O)($Q_1$), —S(=O)$_2$($Q_1$), —S(=O)$_2$($Q_1$), —P(=O)($Q_1$)($Q_2$), and —P(=S)($Q_1$)($Q_2$), c11 is selected from 1, 2, 3, 4, 5, and 6, $Q_1$ to $Q_3$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted $C_1$-$C_{60}$ heteroaryloxy group, a substituted or unsubstituted $C_1$-$C_{60}$ heteroarylthio group, a substituted or unsubstituted monovalent non-aromatic condensed polycyclic group, and a substituted or unsubstituted monovalent non-aromatic condensed heteropolycyclic group, and

* indicates a binding site to a neighboring atom.

* * * * *